(12) United States Patent
Halim et al.

(10) Patent No.: US 8,546,389 B2
(45) Date of Patent: Oct. 1, 2013

(54) VIRAL POLYMERASE INHIBITORS

(75) Inventors: Rosliana Halim, Notting Hill (AU);
Michael Harding, Notting Hill (AU);
Richard Hufton, Notting Hill (AU);
Craig James Morton, Notting Hill (AU); Saba Jahangiri, Notting Hill (AU); Brett Raymond Pool, Notting Hill (AU); Tyrone Pieter Jeynes, Notting Hill (AU); Alistair George Draffan, Notting Hill (AU); Barbara Frey, Notting Hill (AU); Michael John Lilly, Notting Hill (AU)

(73) Assignee: Biota Scientific Management Pty Ltd., Notting Hill, Victoria (AU)

( * ) Notice: Subject to any disclaimer, the term of this patent is extended or adjusted under 35 U.S.C. 154(b) by 0 days.

(21) Appl. No.: 13/278,021

(22) Filed: Oct. 20, 2011

(65) Prior Publication Data
US 2012/0142686 A1    Jun. 7, 2012

Related U.S. Application Data

(60) Provisional application No. 61/394,994, filed on Oct. 20, 2010.

(51) Int. Cl.
| | | |
|---|---|---|
| A61K 31/5377 | (2006.01) | |
| A61K 31/416 | (2006.01) | |
| A61K 31/41 | (2006.01) | |
| A61K 31/4178 | (2006.01) | |
| A61K 31/4523 | (2006.01) | |
| A61K 31/4427 | (2006.01) | |
| A61K 31/497 | (2006.01) | |
| A61K 31/427 | (2006.01) | |
| A61K 31/422 | (2006.01) | |
| A61K 31/501 | (2006.01) | |
| A61K 31/4245 | (2006.01) | |
| C07D 413/04 | (2006.01) | |
| C07D 231/56 | (2006.01) | |
| C07D 257/04 | (2006.01) | |
| C07D 233/54 | (2006.01) | |
| C07D 211/00 | (2006.01) | |
| C07D 401/02 | (2006.01) | |
| C07D 417/02 | (2006.01) | |
| C07D 261/06 | (2006.01) | |
| C07D 403/02 | (2006.01) | |
| C07D 413/02 | (2006.01) | |
| C07D 271/08 | (2006.01) | |

(52) U.S. Cl.
USPC ............. 514/234.5; 514/252.06; 514/255.05; 514/322; 514/338; 514/364; 514/365; 514/378; 514/381; 514/397; 514/406; 544/140; 544/238; 544/405; 546/199; 546/275.7; 548/110; 548/125; 548/181; 548/240; 548/250; 548/311.7; 548/362.5

(58) Field of Classification Search
USPC .................... 514/234.5, 252.06, 255.05, 322, 514/338, 364, 365, 378, 381, 397, 406; 544/140, 238, 405; 546/199, 275.7; 548/110, 548/125, 181, 240, 250, 311.7, 362.5
See application file for complete search history.

(56) References Cited

U.S. PATENT DOCUMENTS

| | | |
|---|---|---|
| 7,265,152 B2 | 9/2007 | Saha et al. |
| 8,198,449 B2 * | 6/2012 | Pracitto et al. ............... 546/121 |
| 2010/0184800 A1 | 7/2010 | Pracitto et al. |

FOREIGN PATENT DOCUMENTS

| | | |
|---|---|---|
| WO | WO 2004/041201 | 5/2004 |
| WO | WO 2010/030538 | 3/2010 |
| WO | WO2011/112186 | 9/2011 |

OTHER PUBLICATIONS

International Search Report for PCT Application No. PCT/AU2011/001336 dated Jan. 13, 2012.
Written Opinion of the International Searching Authority for PCT Application No. PCT/AU2011/001336 dated Jan. 13, 2012.
CAPlus Online Abstract Accession No. 2011:1158685, Mar. 1, 2012.
CAPlus Online Abstract Accession No. 2010:914099, Jul. 23, 2010.

* cited by examiner

*Primary Examiner* — Samantha Shterengarts
(74) *Attorney, Agent, or Firm* — Klarquist Sparkman, LLP

(57) ABSTRACT

The present invention relates to viral polymerase inhibitors of formula (I), salts, N-oxides, solvates, hydrates, racemates, enantiomers or isomers thereof, processes for their preparation and their use in the treatment of Flaviviridae viral infections such as Hepatitis C virus (HCV) infections:

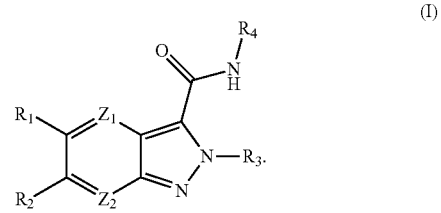

37 Claims, 1 Drawing Sheet

VIRAL POLYMERASE INHIBITORS

CROSS-REFERENCE TO RELATED APPLICATION

This application claims the benefit of priority of U.S. Provisional Application No. 61/394,994, filed Oct. 20, 2010, which is herein incorporated by reference in its entirety.

FIELD

The present invention relates to viral polymerase inhibitors, in particular inhibitors of viral polymerases within the Flaviviridae family such as hepatitis C virus (HCV), processes for their preparation and their use in the treatment of Flaviviridae viral infections such as Hepatitis C virus (HCV) infections.

BACKGROUND

The Flaviviridae are a group of positive single-stranded RNA viruses with a genome size from 9-15 kb. The Flaviviridae consist of various genera including: Hepaciviruses (this genus contains only one species, the Hepatitis C virus (HCV), which is composed of many genotypes and subtypes); Flaviviruses (this genus includes the Dengue virus, Japanese Tick-Borne and the Yellow Fever virus and there are some additional Flaviviruses that are unclassified) and Pestiviruses (this genus includes three serotypes of bovine viral diarrhoea virus, but no known human pathogens).

Hepatitis C virus (HCV) is a major cause of viral hepatitis and has infected more than 200 million people worldwide. Hepatitis C virus has a positive-strand RNA genome enclosed in a nucleocapsid and lipid envelope. The HCV genome is approximately 9.6 kb in length and encodes a polyprotein of about 3,000 amino acids. There are at least six major genotypes, which have different geographic distributions. In the United States (US), for example, genotypes 1a and 1b account for about 75% of cases, and genotypes 2 and 3 for 10-20% of cases. Significant differences are observed in the geographic distribution of HCV genotypes. For example, in Europe genotypes 2 and 3 comprise up to one half of cases whereas genotype 3 is thought to dominate in India. In addition, varied genotype distributions can be observed between countries in a particular region as well as in different areas of a given nation. In the US, HCV is the most common chronic blood-borne infection, affecting approximately 3.2 million persons. After infection with HCV, approximately 75-85% of people develop chronic infection, whilst 60-70% develop chronic liver disease. Of these, 5-20% go on to develop cirrhosis over a period of 20-30 years, and, finally, 1-5% succumb to the consequences of chronic infection (liver cancer/cirrhosis).

Until recently, the only treatment option for HCV was 24 or 48 weeks of combination therapy consisting of weekly injections of pegylated interferon (peg-IFN) and oral ribavirin for 24 or 48 weeks. The best treatment response is seen in patients with HCV genotypes 2 and 3, in whom sustained viral response (SVR) rates of approximately 80% can be achieved with 24 weeks of therapy. Patients with HCV genotype 1 remain the most difficult to treat, with SVR rates of approximately 40% after 48 weeks of therapy. In addition to the low response rates, combination peg-IFN/ribavirin therapy is limited by serious side effects, including fatigue, influenza-like symptoms, depression and suicide with peg-IFN, and haemolytic anaemia with ribavirin. Furthermore, peg-IFN/ribavirin therapy is contra-indicated in patients who have depression, anaemia, HCV-related decompensated cirrhosis, alcohol/substance abuse and autoimmune disorders or who are pregnant.

New treatment options for HCV became available in May 2011 with the US launch of the first direct-acting antiviral (DAA) HCV drugs, telaprevir (Vertex Pharmaceuticals) and boceprevir (Merck). Both drugs are protease inhibitors and are approved for the treatment of chronic HCV genotype 1 infection in combination with peg-IFN and ribavirin. Pivotal phase 3 trials demonstrated that the addition of telaprevir or boceprevir to peg-IFN/RBV therapy achieved shortened durations of therapy and potent viral suppression, with SVR rates approaching 75% in genotype 1 treatment-naive patients and 30% to 85% in treatment-experienced patients.

However, addition of a third drug to the treatment regimen has resulted in increased adverse events. Telaprevir is associated with an increased incidence of rash and anaemia, while boceprevir is associated with anaemia and dysgeusia. Triple therapy with telaprevir or boceprevir and peg-IFN/ribavirin remains unsuitable for those intolerant to or with contraindications to peg-IFN/ribavirin therapy.

Due to the limited tolerability, efficacy, side effects, genotype coverage and concern over the emergence of resistance there is an ongoing need to find alternative agents for the treatment of HCV. The majority of compounds that are currently in development have a limited spectrum of activity against the various HCV genotypes and, in many cases, are only active against HCV genotypes 1b and/or 1a.

The HCV genome possesses structural (core) and non-structural (NS2, NS3, NS4A, NS4B, NS5A and NS5B) proteins. The non-structural proteins are involved in viral genomic replication, with the initial synthesis of RNA carried out by NS5B RNA dependent RNA polymerase. The NS5B protein is a key target for anti-HCV therapy, as it is essential for HCV replication and has no human host equivalent. This protein has been well characterised and is a validated target for drug discovery.

HCV therapy is also anticipated to evolve towards oral multidrug therapy, in which combinations of different DAA drugs with complementary mechanisms of action serve to increase viral suppression and delay or prevent the emergence of resistance.

Accordingly, there remains on ongoing need for HCV agents, particularly with targeted mechanisms of action such as NS5B inhibitors. There is also an unmet need for HCV agents with cross-genotypic activity against genotypes 1, 2 and 3.

SUMMARY

The inventors have found a new class of antiviral compounds for the treatment of HCV infections.

More specifically, compounds of the invention demonstrate activity as NS5B inhibitors against multiple HCV genotypes, specifically 1a, 1b, 2a and 3a.

Compounds of the present invention are therefore considered to be useful in treating and preventing hepatitis C infections when used on their own or in combination with one or more other antiviral agents such as ribavirin, an antiviral nucleoside, polymerase inhibitor, protease inhibitor and/or inhibitor of viral entry, assembly or egress. The combination may also additionally comprise at least one immunomodulatory agent for example an interferon or interferon derivative and/or an inhibitor of inosine-5'-monophosphate dehydrogenase (IMPDH).

It is also believed that compounds of the invention will be efficacious in combination with at least one other DAA with a different mechanism of action and a complementary resistance profile (for example an NS5a inhibitor, a nucleoside or nucleotide NS5b inhibitor or a NS3 protease inhibitor) thereby offering an alternative treatment regime for patients not eligible for or treatable with the recently approved triple combination therapy.

Accordingly, in a first aspect there is provided a compound of formula (I), salts, N-oxides, solvates, hydrates, racemates, enantiomers or isomers thereof:

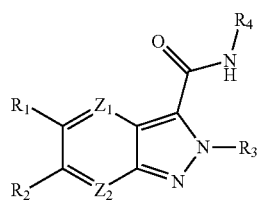

(I)

wherein
$Z_1$ and $Z_2$ are each independently selected from C—H, C-halo, C—$C_{1-4}$alkyl, C—$C_{1-4}$alkylhalo, C—$C_{1-4}$alkoxy, C—$C_{1-4}$alkoxyhalo and N;
$R_1$ is selected from H, $C_{1-6}$alkyl, $C_{2-6}$alkenyl, $C_{2-6}$alkynyl, $C_{1-6}$alkoxy, halo, $C_{1-4}$alkylhalo, $C_{1-4}$alkoxyhalo, $C_{3-7}$cycloalkyl, $C_{3-7}$cycloalkenyl, 5-6-membered heterocyclyl and 5-6 membered heteroaryl and wherein alkyl, alkenyl, alkynyl, alkoxy, cycloalkyl, heterocyclyl and heteroaryl in each occurrence may be optionally substituted;
$R_2$ is selected from halo, $C_{1-6}$alkyl, $C_{2-6}$alkenyl, $NO_2$, $N(R_5)_2$, $NR_5R_6$, $NR_6(SO_2R_5)$, $SO_2N(R_8)_2$, $SR_8$, $C(R_5)_2SO_2R_8$, $NR_5C(=O)R_8$, optionally substituted aryl, optionally substituted aryl-$R_7$, optionally substituted heterocyclyl, optionally substituted heterocyclyl-$R_7$, optionally substituted heteroaryl and optionally substituted heteroaryl-$R_7$;
$R_3$ is selected from aryl, aryl-X-aryl, aryl-X-heteroaryl, heteroaryl, heteroaryl-X-heteroaryl, and heteroaryl-X-aryl wherein X is $[C(R_5)_2]_p$, O, S, S(=O), $SO_2$, $NR_5$, C=O, $CF_2$, C(=O)$NR_5$ or $NR_5C(=O)$ wherein p is 1, 2 or 3 and wherein aryl and heteroaryl in each occurrence may be optionally substituted and further wherein aryl is preferably phenyl and heteroaryl is preferably 5-6-membered heteroaryl;
$R_4$ is H, $C_{1-4}$alkyl, $C_{2-4}$alkenyl, $C_{2-4}$alkynyl, or $C_{3-7}$cycloalkyl preferably $C_{1-4}$alkyl;
$R_5$ in each occurrence is independently H or optionally substituted $C_{1-6}$alkyl;
$R_6$ is selected from H, $C_{1-6}$alkyl, $C_{2-6}$alkenyl, $C_{2-6}$alkynyl, $C_{1-6}$alkoxy, $C_{1-6}$alkylhalo, $C_{1-6}$alkoxyhalo, $R_8$, $C_{1-6}$alkyl-$R_8$, $C_{1-6}$alkyl-$OR_8$, $C_{1-6}$alkyl-$SR_8$, $C_{1-6}$alkyl-S(=O)$R_8$, $C_{1-6}$alkyl-$SO_2R_8$, $C_{1-6}$alkyl-N($R_8$)$_2$, $C_{1-6}$alkyl-C(=O)—$R_8$, $C_{1-6}$alkyl-O(C=O)—$R_8$, $C_{1-6}$alkyl-C(=O)O—$R_8$, $C_{1-6}$alkyl-C(=O)N($R_8$)$_2$, $C_{1-6}$alkyl-$NR_5C$(=O)—$R_8$, $C_{1-6}$alkyl-$NR_5SO_2$—$R_8$, $C_{1-6}$alkyl-$SO_2NR_5$—$R_8$ and $C_{1-6}$alkyl-C(=O)$NR_5SO_2R_8$ and wherein alkyl, alkenyl, alkynyl, alkoxy, aryl, cycloalkyl, heterocyclyl and heteroaryl in each occurrence of $R_6$ may be optionally substituted;
$R_8$ in each occurrence is independently H, an optionally an optionally substituted $C_{1-6}$alkyl, an optionally substituted $C_{2-6}$alkenyl, an optionally substituted ($C_{1-6}$alkyl)$_q$-aryl, an optionally substituted ($C_{1-6}$alkyl)$_q$-$C_{3-7}$cycloalkyl, an optionally substituted ($C_{1-6}$alkyl)$_q$-5-6-membered heterocyclyl or an optionally substituted ($C_{1-6}$alkyl)$_q$-5-6-membered heteroaryl, preferably each $R_8$ is independently H or an optionally substituted $C_{1-6}$alkyl;

q is 0 or 1; and
$R_7$ is selected from optionally substituted ($C_{1-6}$alkyl)$_q$-N($R_5$)$_2$, optionally substituted ($C_{1-6}$alkyl)$_q$-aryl, optionally substituted ($C_{1-6}$alkyl)$_q$-5-6-membered heteroaryl, optionally substituted ($C_{1-6}$alkyl)$_q$-$NR_5C$(=O)—($C_{1-6}$alkyl)$_q$-aryl, optionally substituted ($C_{1-6}$alkyl)$_q$-C(=O)$NR_5$—($C_{1-6}$alkyl)$_q$-aryl, optionally substituted ($C_{1-6}$alkyl)$_q$-C(=O)$NR_5$—($C_{1-6}$alkyl)$_q$-5-6-membered heteroaryl and optionally substituted ($C_{1-6}$alkyl)$_q$-$NR_5C$(=O)—($C_{1-6}$alkyl)$_q$-5-6-membered heteroaryl.

According to a second aspect there is provided a method for making the compounds of formula (I) defined above wherein $R_2$ is $NR_6(SO_2R_5)$ comprising reacting a compound of formula (II) with a halogenated-$R_6$ reagent, such as Br—$R_6$, F—$R_6$, Cl—$R_6$ or I—$R_6$ (provided that $R_6$ is not H):

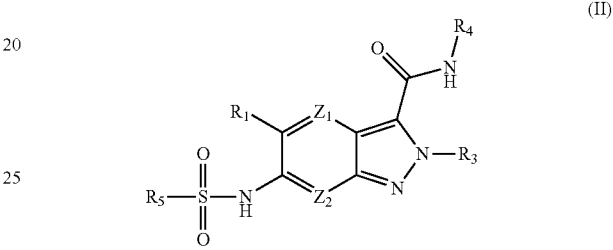

(II)

wherein
$Z_1$, $Z_2$, $R_1$, $R_3$, $R_4$ and $R_5$ are as defined in formula (I).

According to a third aspect there is provided a method for making the compounds of formula (I) defined above wherein $R_2$ is optionally substituted and selected from aryl, aryl-$R_7$, 5-6-membered heteroaryl and 5-6-membered heteroaryl-$R_7$ comprising reacting a compound of general formula (I) wherein $R_2$ is a H, halo, triflate, boronic acid or boronic acid ester in a palladium (0)- or palladium (II)-mediated coupling reaction with a suitably substituted coupling partner containing aryl, aryl-$R_7$, 5-6-membered heteroaryl or 5-6-membered heteroaryl-$R_7$.

The compounds of formula (I) are inhibitors of HCV. In particular, the compounds of formula (I) inhibit RNA synthesis by the RNA dependent RNA polymerase of HCV (the NS5B protein encoded by HCV). NS5B inhibitors have been clinically validated as potential antiviral agents for the treatment of HCV infection.

According to a fourth aspect, there is provided a pharmaceutical agent comprising the compound of formula (I) or salts, N-oxides, solvates, hydrates, racemates, enantiomers or isomers thereof as defined above, optionally in combination with another HCV antiviral agent.

There is also provided use of the compound of formula (I) or salts, N-oxides, solvates, hydrates, racemates, enantiomers or isomers thereof as defined above as a pharmaceutical agent, optionally in combination with another HCV antiviral agent.

There is further provided the compound of formula (I) or salts, N-oxides, solvates, hydrates, racemates, enantiomers or isomers thereof as defined above for use as a pharmaceutical agent, optionally in combination with another HCV antiviral agent.

The pharmaceutical agent may be an antiviral agent.

According to a fifth aspect, there is provided a viral polymerase inhibitor in particular a HCV polymerase inhibitor such as a NS5B inhibitor comprising the compound of formula (I) or salts, N-oxides, solvates, hydrates, racemates, enantiomers or isomers thereof as defined above, optionally in combination with another HCV antiviral agent.

There is also provided use of the compound of formula (I) or salts, N-oxides, solvates, hydrates, racemates, enantiomers or isomers thereof as defined above as a viral polymerase inhibitor in particular a HCV polymerase inhibitor such as a NS5B inhibitor, optionally in combination with another HCV antiviral agent.

There is further provided the compound of formula (I) or salts, N-oxides, solvates, hydrates, racemates, enantiomers or isomers thereof as defined above for use as a viral polymerase inhibitor in particular a HCV polymerase inhibitor such as a NS5B inhibitor, optionally in combination with another HCV antiviral agent.

The compound of formula (I) or salts, N-oxides, solvates, hydrates, racemates, enantiomers or isomers thereof as may be administered in the form of a pharmaceutical composition together with a pharmaceutically acceptable carrier, optionally in combination with another HCV antiviral agent.

According to a sixth aspect, there is provided a pharmaceutical composition comprising the compound of formula (I) or salts, N-oxides, solvates, hydrates, racemates, enantiomers or isomers thereof and a pharmaceutically acceptable carrier.

According to one embodiment, the pharmaceutical composition additionally comprises a therapeutically effective amount of one or more antiviral agents such as at least one other HCV antiviral agent.

According to a seventh aspect, there is provided a method for the treatment of a Flaviviridae viral infection such as a HCV infection which comprises administering an effective amount of the compound of formula (I) or salts, N-oxides, solvates, hydrates, racemates, enantiomers or isomers thereof as defined above or the pharmaceutical composition defined above, optionally in combination with another HCV antiviral agent to a subject in need thereof.

There is also provided use of the compound of formula (I) or salts, N-oxides, solvates, hydrates, racemates, enantiomers or isomers thereof as defined above or the pharmaceutical composition as defined above in the manufacture of a medicament for use in the treatment of a Flaviviridae viral infection such as a HCV infection, optionally in combination with another HCV antiviral agent.

There is further provided use of the compound of formula (I) or salts, N-oxides, solvates, hydrates, racemates, enantiomers or isomers thereof as defined above or the pharmaceutical composition as defined above, optionally in combination with another HCV antiviral agent in the treatment of a Flaviviridae viral infection such as a HCV infection.

There is still further provided the compound of the formula (I) or salts, N-oxides, solvates, hydrates, racemates, enantiomers or isomers thereof as defined above or the pharmaceutical composition defined above, optionally in combination with another HCV antiviral agent for use in the treatment of a Flaviviridae viral infection such as a HCV infection.

According to an eighth aspect, there is provided a method of inhibiting the RNA-dependent RNA polymerase activity of the enzyme NS5B, encoded by HCV, comprising exposing the enzyme NS5B to an effective amount of the compound of formula (I) or salts, N-oxides, solvates, hydrates, racemates, enantiomers or isomers thereof as defined above, optionally in combination with another HCV antiviral agent.

According to a ninth aspect, there is provided a method of inhibiting HCV replication comprising exposing a cell infected with HCV to an effective amount of the compound of formula (I) or pharmaceutically acceptable salts, N-oxides, solvates, hydrates, racemates, enantiomers or isomers thereof as defined above, optionally in combination with another HCV antiviral agent.

DETAILED DESCRIPTION

Figure 1:
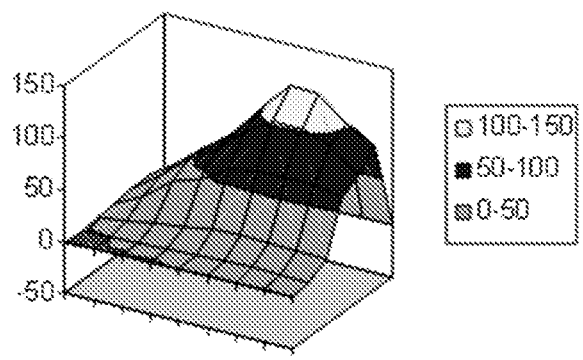
FIG. 1 is a 3D synergy plot which shows the synergistic activity of Compound 175 in combination with a nucleoside NS5b inhibitor (4-amino-7-(2-C-methyl-β-D-ribofuranosyl)-pyrrolo[2,1-f][1,2,4]triazine) in accordance with an embodiment of the invention where the Z axis represents the percentage replicon inhibition for the combination with the compounds being represented on the X and Y axis.

The present invention relates to compounds of formula (I) which inhibit viral polymerases and are useful in the treatment of Flaviviridae viral infections, particularly, hepatitis C(HCV).

Compounds

The present invention relates to compounds of formula (I), salts, N-oxides, solvates, hydrates, racemates, enantiomers or isomers thereof as defined above.

In one embodiment of formula (I), $Z_1$ and $Z_2$ are each C—H thereby forming a fused phenyl ring.

In another embodiment, $R_1$ is H.

In yet another embodiment $R_1$ is selected from optionally substituted $C_{1-6}$alkyl preferably $C_{1-4}$alkyl particularly methyl, ethyl, n-propyl and iso-propyl; optionally substituted $C_{2-3}$alkenyl preferably ethenyl, propenyl and iso-propenyl optionally substituted with $C_{1-4}$alkyl (preferably methyl) and/or hydroxy; $C_{2-3}$alkynyl optionally substituted with hydroxy; optionally substituted $C_{1-3}$alkoxy (preferably methoxy) optionally substituted with cyano and/or halo particularly F; halo particularly Br and I; $C_{1-3}$alkylhalo; $C_{1-3}$alkoxyhalo particularly $OCHF_2$; 5-6-membered heterocyclyl, particularly dihydropyranyl, optionally substituted with $C_{1-3}$alkyl preferably methyl; 5-6 membered heteroaryl, particularly thiazolyl, optionally substituted with $C_{1-3}$alkyl preferably methyl; $C_{5-6}$cycloalkenyl particularly cyclopentenyl and $C_{3-6}$cycloalkyl particularly cyclopentyl and cyclopropyl.

In a particularly preferred embodiment $R_1$ is selected from optionally substituted $C_{1-4}$alkyl, optionally substituted $C_{1-3}$alkoxy, halo and optionally substituted $C_{3-6}$cycloalkyl. Cyclopropyl is particularly preferred.

In one embodiment $R_2$ is selected from $NR_6(SO_2R_5)$, $SO_2N(R_8)_2$, $C(R_5)_2SO_2R_8$, $NR_5C(=O)R_8$, optionally substituted aryl, optionally substituted aryl-$R_7$, optionally substituted heterocyclyl, optionally substituted heterocyclyl-$R_7$, optionally substituted heteroaryl and optionally substituted heteroaryl-$R_7$. More preferably $R_2$ is selected from $NR_6(SO_2R_5)$, $SO_2N(R_8)_2$, $C(R_5)_2SO_2R_8$, $NR_5C(=O)R_8$, optionally substituted phenyl, optionally substituted 5-6-membered heterocyclyl, and optionally substituted 5-6-membered heteroaryl wherein $R_8$ in each occurrence is H or an optionally an optionally substituted $C_{1-6}$alkyl, an optionally substituted aryl, an optionally substituted $C_{3-8}$cycloalkyl, an optionally substituted heterocyclyl or an optionally substituted heteroaryl.

In one embodiment $R_2$ is optionally substituted and selected from aryl, aryl-$R_7$, 5-6-membered heterocyclyl, 5-6-membered heteroaryl and 5-6-membered heteroaryl-$R_7$, and in the case of optionally substituted aryl or aryl-$R_7$, more preferably a substituted phenyl or phenyl-$R_7$. In a particular embodiment when $R_2$ is phenyl-$R_7$ then $R_7$ is an optionally substituted $(C_{1-3}$alkyl$)_q$-$NR_5C(=O)$—$(C_{1-3}$alkyl$)_q$-aryl or an optionally substituted $(C_{1-3}$alkyl$)_q$-$C(=O)NR_5$—$(C_{1-3}$alkyl$)_q$-aryl, more particularly an optionally substituted $(C_{1-3}$alkyl$)_q$-$NR_5C(=O)$—$(C_{1-3}$alkyl$)_q$-phenyl. When $R_2$ is an optionally substituted 5-6-membered heteroaryl or an optionally substituted 5-6-membered heteroaryl-$R_7$ then particularly preferred 5-membered heteroaryl include imidazolyl, thiazolyl and oxazolyl and 6-membered heteroaryl include pyridinyl, pyridazinyl, pyrimidinyl and pyrazinyl. Optionally substituted 5-membered heteroaryl are particularly preferred wherein suitable optional substituents include $C_{1-3}$alkyl preferably methyl or ethyl optionally substituted with OH. When $R_2$ is an optionally substituted 5-6-membered heterocyclyl, 5-membered heterocyclyl are particularly preferred including dioxidothiazolidine and dioxidothiadiazolidine optionally substituted with $C_{1-3}$alkyl and pyrrolidinyl optionally substituted with oxo (=O), $C(=O)C_{1-3}$alkyl and/or benzyl.

In another embodiment, $R_2$ is selected from $NR_6(SO_2R_5)$, $SO_2N(R_8)_2$, $C(R_5)_2SO_2R_8$ and $NR_5C(=O)R_8$.

In one embodiment when $R_2$ is $SO_2N(R_8)_2$ particularly preferred $R_8$ are independently selected from H and optionally substituted $C_{1-3}$alkyl, particularly methyl and ethyl wherein suitable optional substituents include OH.

In one embodiment when $R_2$ is $C(R_5)_2SO_2R_8$ particularly preferred $R_5$ are independently selected from H and optionally substituted $C_{1-3}$alkyl particularly ethyl and propyl wherein suitable optional substituents include OH and $CO_2C_{1-3}$alkyl and particularly preferred $R_8$ is $C_{1-3}$alkyl most preferably methyl.

In one embodiment when $R_2$ is $NR_5C(=O)R_8$ particularly preferred $R_5$ is $C_{1-3}$alkyl particularly ethyl and particularly preferred $R_8$ is $C_{1-3}$alkyl optionally substituted with $CO_2C_{1-3}$alkyl or heteroaryl such as furanyl.

Most preferably $R_2$ is $NR_6(SO_2R_5)$.

In a particularly preferred embodiment $R_2$ is $NR_6(SO_2R_5)$ where $R_5$ is $C_{1-6}$alkyl (preferably $C_{1-3}$alkyl) or $C_{1-3}$alkyl substituted with halo (preferably F). Preferably $R_5$ is methyl, $CF_3$ or $CHF_2$ most preferably $R_5$ is methyl.

In a further preferred embodiment when $R_2$ is $NR_6(SO_2R_5)$ then $R_6$ is optionally substituted 5-6-membered heterocyclyl (preferably pyrrolidinyl or piperidinyl wherein suitable optional substituents include methylsulfonyl) or optionally substituted $C_{1-6}$alkyl. Preferably $R_6$ is optionally substituted $C_{1-6}$alkyl, more preferably $C_{1-3}$alkyl. Even more preferably $R_6$ is —$(CH_2)_n$—$R_{10}$ wherein n is an integer selected from 0, 1, 2 or 3, preferably 1, 2 or 3 most preferably 2 or 3 and $R_{10}$ is selected from H, $C_{1-3}$alkyl, $C_{2-3}$alkenyl, $C_{1-3}$alkoxy such as methoxy, halo, $C_{1-3}$haloalkyl such as $CHF_2$ and $CF_3$, $C_{1-3}$haloalkoxy such as $OCHF_2$ and $OCF_3$, OH, $OR_{11}$, $C_{1-3}$alkylOH, $CH(C_{1-3}$alkylOH$)_2$, $CO_2H$, $CH(CO_2H)_2$, $CO_2R_{11}$, $CH(CO_2C_{1-3}$alkyl$)_2$, $OC(=O)H$, $OC(=O)R_{11}$, $SR_{11}$, $S(=O)R_{11}$, $SO_2R_{11}$, $SO_2NH_2$, $SO_2NHR_{11}$, $SO_2N(R_{11})_2$, $NHSO_2R_{11}$, $NR_{11}SO_2R_{11}$ CN, $NH_2$, $NHR_{11}$, $N(R_{11})_2$, NHC(=O)H, $NHC(=O)R_{11}$, $NR_{11}C(=O)R_{11}$, $C(=O)NH_2$, $C(=O)NHR_{11}$, $C(=O)N(R_{11})_2$, $C(=O)NHSO_2R_{11}$, $C(=O)NR_{11}SO_2R_{11}$, $C_{3-7}$cycloalkyl preferably $C_{3-6}$cycloalkyl, aryl preferably phenyl, heterocyclyl preferably 5-6-membered heterocyclyl and heteroaryl preferably 5-6-membered heteroaryl; wherein each $R_{11}$ is independently selected from $C_{1-3}$alkyl, $C_{3-6}$cycloalkyl, $C_{3-6}$cycloalkenyl, phenyl, $C_{1-3}$alkylphenyl, 5-6-membered heterocyclyl, 5-6-membered heteroaryl and $C_{1-3}$alkyl 5-6-membered heteroaryl; and wherein each alkyl, cycloalkyl, aryl, heterocyclyl, heteroaryl or —$(CH_2)$— moiety when present may be further optionally substituted.

In a further embodiment $R_{10}$ is selected from H, $C_{2-3}$alkenyl, $C_{1-3}$alkoxy, halo, $CHF_2$, $CF_3$, OH, $CH(CH_2OH)_2$, $CO_2H$, $CH(CO_2H)_2$, $CO_2C_{1-3}$alkyl, $CH(CO_2C_{1-3}$alkyl$)_2$, $OC(=O)$phenyl, $OC(=O)_{5-6}$ membered heteroaryl, $SC_{1-3}$alkyl, $S(=O)C_{1-3}$alkyl, $SO_2C_{1-3}$alkyl, $SO_2NH_2$, $SO_2NHC_{1-3}$alkyl, $SO_2N(C_{1-3}$alkyl$)_2$, $NHSO_2C_{1-3}$alkyl, $NC_{1-3}$alkyl$SO_2C_{1-3}$alkyl, $NHSO_2C_{1-3}$alkylphenyl, $NC_{1-3}$alkyl$SO_2C_{1-3}$alkylphenyl, CN, $NH_2$, $NHC_{1-3}$alkyl, $NHC_{1-3}$alkylaryl, $NHC_{1-3}$alkylheteroaryl, $N(C_{1-3}$alkyl$)_2$, NHC(=O)$R_{11}$, $NC_{1-3}$alkyl$C(=O)R_{11}$, $C(=O)NH_2$, $C(=O)NHC_{1-3}$alkyl, $C(=O)N(C_{1-3}$alkyl$)_2$, $C(=O)NHSO_2C_{1-3}$alkyl, $C(=O)NHSO_2$-phenyl, $C(=O)NHSO_2$-5-6-membered heteroaryl, $C(=O)NC_{1-3}$alkyl$SO_2C_{1-3}$alkyl, $C(=O)NC_{1-3}$alkyl$SO_2$-phenyl, $C(=O)NC_{1-3}$alkyl$SO_2$-5-6-membered heteroaryl, $C_{3-6}$cycloalkyl, phenyl, 5-6-membered heterocyclyl and 5-6-membered heteroaryl; wherein $R_{11}$ is independently selected from $C_{1-3}$alkyl, $C_{3-6}$cycloalkyl, phenyl, benzyl, 5-6-membered heteroaryl and $C_{1-3}$alkyl-5-6-membered heteroaryl; and wherein each alkyl, cycloalkyl, aryl, heterocyclyl, heteroaryl or —$(CH_2)$— moiety when present may be further optionally substituted.

In still a further embodiment $R_{10}$ is selected from H, $C_{2-3}$alkenyl (optionally substituted with OH), methoxy, halo particularly F, $CHF_2$, $CF_3$, OH, $CH(CH_2OH)_2$, $CO_2H$, $CH(CO_2H)_2$, $CO_2CH_3$ (optionally substituted with $OC(=O)$ $C_{1-4}$alkyl), $CO_2$-ethyl, $CO_2$propyl (including n-propyl and iso-propyl optionally substituted with methyl), $CO_2$-phenyl, $CH(CO_2C_{1-3}$alkyl$)_2$, $OC(=O)$phenyl (optionally substituted with $CO_2H$), $OC(=O)$-6-membered heteroaryl, $SCH_3$, $S(=O)CH_3$, $SO_2CH_3$, $SO_2NH_2$, $NHSO_2CH_3$, $N(CH_3)$ $SO_2CH_3$, $NHSO_2$-benzyl (optionally substituted with halo), $N(CH_3)SO_2$-benzyl (optionally substituted with halo), CN, $NH_2$, $NHCH_3$, $N(CH_3)_2$, NHbenzyl (optionally substituted with $C_{1-3}$alkoxy particularly methoxy), $NHCH_2$-6-membered-heteroaryl, $NHC(=O)C_{1-3}$alkyl (optionally substituted with halo, $NH_2$, $NH(C_{1-3}$alkyl), $N(C_{1-3}$alkyl$)_2$, $CO_2H$, $CO_2C_{1-3}$alkyl, $CF_3$, $C_{1-3}$alkoxy particularly methoxy, $CONH_2$, $CONHC_{1-3}$alkyl, $C_{3-6}$cycloalkyl, phenyl, 5-6-membered heterocyclyl and/or 5-6-membered heteroaryl), $NHC(=O)C_{2-3}$alkenyl, $NHC(=O)C_{3-6}$cycloalkyl (optionally substituted with $CO_2H$ and/or $CO_2C_{1-3}$alkyl), $NHC(=O)$ $C_{3-6}$ cycloalkenyl (optionally substituted with $CO_2H$), NHC(=O)phenyl (optionally substituted with halo particularly F, $C_{1-3}$alkoxy particularly methoxy, $CO_2C_{1-3}$alkyl and/or $CONHC_{1-3}$alkyl), $NHC(=O)_{5-6}$-membered heterocyclyl (optionally substituted with oxo (=O) and/or $C_{1-3}$alkyl), $NHC(=O)_{5-6}$-membered heteroaryl (optionally substituted with oxo (=O), $C_{1-3}$alkoxy preferably methoxy, $C_{1-3}$alkyl preferably methyl and/or morpholino), $C(=O)NH_2$, $C(=O)NHC_{1-3}$alkyl, $C(=O)N(C_{1-3}$alkyl$)_2$, $C(=O)NHSO_2C_{1-2}$alkyl (optionally substituted with F), $C(=O)NHSO_2$-phenyl (optionally substituted with halo), $C(=O)NHSO_2$-5-6-membered heteroaryl, $C(=O)NHSO_2NHCH_3$, $C(=O)NHSO_2N(CH_3)_2$, $C_{3-6}$cycloalkyl, phenyl, 5-6-membered heterocyclyl and 5-6-membered heteroaryl; wherein each alkyl, cycloalkyl, aryl, heterocyclyl, heteroaryl or —$(CH_2)$— moiety when present may be further optionally substituted. Particularly preferred $C_{3-6}$cycloalkyl include cyclopropyl, cyclobutyl, cyclopentyl and cyclohexyl and may be unsaturated for example cyclopentenyl or cyclohexenyl. Particularly preferred 5-membered heterocyclyl include O and/or N containing 5-membered heterocyclyls such as tetrahydrofuranyl, imidazolinyl and pyrrolidinyl. Particularly preferred 6-membered heterocyclyl include O and/or N containing 6-membered heterocyclyls such as tetrahydropyranyl, piperidinyl, morpholinyl and dioxanyl. Particularly preferred 5-membered heteroaryl include O, N and/or S containing 5-membered heteroaryls such as oxazoyl, oxadiazolyl, isoxazolyl, furanyl, thiophenyl, thiazolyl, imidazolyl, pyrazolyl and tetrazolyl. Particularly preferred 6-membered heteroaryl include N containing 6-membered heteroaryl such as pyridinyl, pyridazinyl, pyrimidinyl and pyrazinyl.

In one embodiment, $R_3$ is optionally substituted and is selected from phenyl, phenyl-X-phenyl, phenyl-X-heteroaryl, heteroaryl, heteroaryl-X-heteroaryl, and heteroaryl-X-phenyl wherein heteroaryl is a 5-membered or 6-membered heteroaryl (with 6-membered heteroaryl being selected from pyridyl, pyridazinyl, pyrimidinyl and pyrazinyl being particularly preferred with pyridyl being most preferred). Optionally substituted phenyl, phenyl-X-phenyl, phenyl-X-6-membered heteroaryl, 6-membered heteroaryl, 6-membered heteroaryl-X-6-membered heteroaryl, and 6-membered heteroaryl-X-phenyl are preferred with optionally substituted phenyl, 6-membered heteroaryl, phenyl-X-phenyl and 6-membered heteroaryl-X-phenyl being even more preferred. Optionally substituted phenyl and phenyl-X-phenyl are particularly preferred. Suitable optional substituents for $R_3$ include but are not limited to 1 or more, preferably 1 or 2 and most preferably in the case of phenyl and 6-membered heteroaryl, a para-substituent, in each case independently selected from halo; $C_{1-6}$alkyl preferably $C_{1-3}$alkyl including methyl, ethyl, propyl and iso-propyl, particularly methyl; $C_{2-6}$alkenyl preferably $C_{2-3}$alkenyl including ethenyl, propenyl and iso-propenyl; $C_{1-6}$alkoxy preferably $C_{1-4}$alkoxy including methoxy, $CH_2OCH(CH_3)_2$ and $OCH_2CH(CH_3)_2$; aryloxy including benzyloxy; $C_{1-6}$alkylamino including $NHC_{1-6}$alkyl and $N(C_{1-6}alkyl)_2$ such as for example $NHCH(CH_3)_2$ and $NHCH_2CH(CH_3)_2$; and $C_{3-6}$cycloalkyl particularly cyclopropyl.

In another embodiment, X is O, S or $NR_5$. Preferably X is O, NH or N—$C_{1-3}$alkyl more preferably O or NH.

In a further embodiment, $R_4$ is $C_{1-3}$alkyl, preferably methyl.

In a still further embodiment of formula (I) there is provided a compound of formula (Ia), salts, N-oxides, solvates, hydrates, racemates, enantiomers or isomers thereof

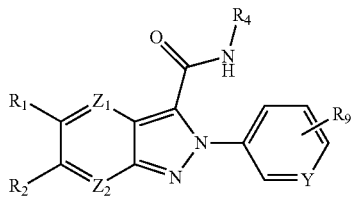

(Ia)

wherein
$Z_1$ and $Z_2$ are each CH;
Y is CH or N;
$R_1$ is H, $C_{3-6}$cycloalkyl such as cyclopropyl; $C_{1-6}$alkyl such as methyl, ethyl, n-propyl and iso-propyl; halo or $C_{1-6}$alkoxy such as $C_{1-4}$alkoxy such as methoxy; ethoxy, n-propoxy and iso-propoxy;

$R_2$ is $NR_6(SO_2R_5)$, $SO_2N(R_8)_2$, $C(R_5)_2SO_2$, $NR_5C(=O)R_8$, optionally substituted phenyl (including optionally substituted phenyl-$R_7$), optionally substituted 5-6-membered heterocyclyl or optionally substituted 5-6-membered heteroaryl;
$R_6$ is selected from H, optionally substituted $C_{1-6}$alkyl and optionally substituted 5-6-membered heterocyclyl, preferably $R_6$ is optionally substituted $C_{1-6}$alkyl more particularly —$(OH_2)_n$—$R_{10}$ wherein n and $R_{10}$ are as previously defined above;
$R_5$ is H or optionally substituted $C_{1-6}$alkyl, preferably $C_{1-3}$alkyl optionally substituted with halo such as $CF_3$ or $CHF_2$; more preferably methyl, $CF_3$ or $CHF_2$; most preferably methyl;
$R_8$ is H or optionally substituted $C_{1-6}$alkyl;
$R_9$ is H or one or more, preferably 1, 2 or 3 more preferably 1 or 2 substituents independently selected from halo; $C_{1-6}$alkyl preferably $C_{1-3}$alkyl particularly methyl; $C_{2-6}$alkenyl preferably $C_{2-3}$alkenyl including ethenyl, propenyl and iso-propenyl; $C_{1-3}$alkylhalo; $C_{1-6}$alkoxy preferably $C_{1-4}$alkoxy including methoxy, $CH_2OCH(CH_3)_2$ and $OCH_2CH(CH_3)_2$; $C_{1-6}$alkylamino including $NHC_{1-6}$alkyl and $N(C_{1-6}alkyl)_2$ such as, for example, $NCH_2CH(CH_3)_2$; $C_{3-6}$cycloalkyl particularly cyclopropyl; and X-optionally substituted phenyl particularly optionally substituted O-phenyl or optionally substituted NH-phenyl; and in a particularly preferred embodiment $R_9$ is in the para-position; and
X is O or $NR_5$, preferably O, NH or N—$C_{1-3}$alkyl more preferably O or NH.

The term "$C_{1-6}$alkyl" refers to optionally substituted straight chain or branched chain hydrocarbon groups having from 1 to 6 carbon atoms. Examples include methyl (Me), ethyl (Et), propyl (Pr), isopropyl (i-Pr), butyl (Bu), isobutyl (i-Bu), sec-butyl (s-Bu), tert-butyl (t-Bu), pentyl, neopentyl, hexyl and the like. Unless the context requires otherwise, the term "$C_{1-6}$alkyl" also encompasses alkyl groups containing one less hydrogen atom such that the group is attached via two positions i.e. divalent. "$C_{1-4}$alkyl" and "$C_{1-3}$alkyl" including methyl, ethyl, propyl, isopropyl, n-butyl, iso-butyl, sec-butyl and tert-butyl are preferred with methyl being particularly preferred.

The term "$C_{2-6}$alkenyl" refers to optionally substituted straight chain or branched chain hydrocarbon groups having at least one double bond of either E or Z stereochemistry where applicable and 2 to 6 carbon atoms. Examples include vinyl, 1-propenyl, 1- and 2-butenyl and 2-methyl-2-propenyl. Unless the context requires otherwise, the term "$C_{2-6}$alkenyl" also encompasses alkenyl groups containing one less hydrogen atom such that the group is attached via two positions i.e. divalent. "$C_{2-4}$alkenyl" and "$C_{2-3}$alkenyl" including ethenyl, propenyl and butenyl are preferred with ethenyl being particularly preferred.

The term "$C_{2-6}$alkynyl" refers to optionally substituted straight chain or branched chain hydrocarbon groups having at least one triple bond and 2 to 6 carbon atoms. Examples include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl and the like. Unless the context indicates otherwise, the term "$C_{2-6}$alkynyl" also encompasses alkynyl groups containing one less hydrogen atom such that the group is attached via two positions i.e. divalent. $C_{2-3}$alkynyl is preferred.

The term "$C_{3-8}$cycloalkyl" refers to non-aromatic cyclic groups having from 3 to 8 carbon atoms, including cyclopropyl, cyclobutyl, cyclopentyl, cyclohexyl, cycloheptyl and cyclooctyl. It will be understood that cycloalkyl groups may be saturated such as cyclohexyl or unsaturated such as cyclohexenyl. $C_{3-6}$cycloalkyl such as cyclopropyl, cyclobutyl, cyclopentyl, cyclopentenyl, cyclohexyl and cyclohexenyl are preferred.

The terms "hydroxy" and "hydroxyl" refer to the group —OH.

The term "oxo" refers to the group =O.

The term "$C_{1-6}$alkoxy" refers to an alkyl group as defined above covalently bound via an O linkage containing 1 to 6 carbon atoms, such as methoxy, ethoxy, propoxy, isoproxy, butoxy, tert-butoxy and pentoxy. "$C_{1-4}$alkoxy" and "$C_{1-3}$alkoxy" including methoxy, ethoxy, propoxy and butoxy are preferred with methoxy being particularly preferred.

The term "$C_{1-6}$alkylhalo" refers to a $C_{1-6}$alkyl which is substituted with one or more halogens. $C_{1-3}$alkylhalo groups are preferred, such as for example, —$CHF_2$ and —$CF_3$.

The term "$C_{1-6}$alkoxyhalo" refers to a $C_{1-6}$alkoxy which is substituted with one or more halogens. $C_{1-3}$alkoxyhalo groups are preferred, such as for example, —$OCHF_2$ and —$OCF_3$.

The term "carboxylate" or "carboxyl" refers to the group —$COO^-$ or —COOH.

The term "ester" refers to a carboxyl group having the hydrogen replaced with, for example a $C_{1-6}$alkyl group ("carboxyl$C_{1-6}$alkyl" or "alkylester"), an aryl or aralkyl group ("arylester" or "aralkylester") and so on. $CO_2C_{1-3}$alkyl groups are preferred, such as for example, methylester ($CO_2Me$), ethylester ($CO_2Et$) and propylester ($CO_2Pr$) and includes reverse esters thereof (e.g. —OCOMe, —OCOEt and —OCOPr).

The term "cyano" refers to the group —CN.

The term "nitro" refers to the group —$NO_2$.

The term "amino" refers to the group —$NH_2$.

The term "substituted amino" or "secondary amino" refers to an amino group having a hydrogen replaced with, for example a $C_{1-6}$alkyl group ("$C_{1-6}$alkylamino"), an aryl or aralkyl group ("arylamino", "aralkylamino") and so on. $C_{1-3}$alkylamino groups are preferred, such as for example, methylamino (NHMe), ethylamino (NHEt) and propylamino (NHPr).

The term "disubstituted amino" or "tertiary amino" refers to an amino group having the two hydrogens replaced with, for example a $C_{1-6}$alkyl group, which may be the same or different ("dialkylamino"), an aryl and alkyl group ("aryl (alkyl)amino") and so on. Di($C_{1-3}$alkyl)amino groups are preferred, such as for example, dimethylamino ($NMe_2$), diethylamino ($NEt_2$), dipropylamino ($NPr_2$) and variations thereof (e.g. N(Me)(Et) and so on).

The term "acyl" or "aldehyde" refers to the group —C(=O)H.

The term "substituted acyl" or "ketone" refers to an acyl group having a hydrogen replaced with, for example a $C_{1-6}$alkyl group ("$C_{1-6}$alkylacyl" or "alkylketone" or "ketoalkyl"), an aryl group ("arylketone"), an aralkyl group ("aralkylketone") and so on. $C_{1-3}$alkylacyl groups are preferred.

The term "amido" or "amide" refers to the group —C(O)$NH_2$.

The term "aminoacyl" refers to the group —NHC(O)H.

The term "substituted amido" or "substituted amide" refers to an amido group having a hydrogen replaced with, for example a $C_{1-6}$alkyl group ("$C_{1-6}$alkylamido" or "$C_{1-6}$alkylamide"), an aryl ("arylamido"), aralkyl group ("aralkylamido") and so on. $C_{1-3}$alkylamide groups are preferred, such as for example, methylamide (—C(O)NHMe), ethylamide (—C(O)NHEt) and propylamide (—C(O)NHPr) and includes reverse amides thereof (e.g. —NHMeC(O)—, —NHEtC(O)— and —NHPrC(O)—).

The term "disubstituted amido" or "disubstituted amide" refers to an amido group having the two hydrogens replaced with, for example a $C_{1-6}$alkyl group ("di($C_{1-6}$alkyl)amido" or "di($C_{1-6}$alkyl)amide"), an aralkyl and alkyl group ("alkyl(aralkyl)amido") and so on. Di($C_{1-3}$alkyl)amide groups are preferred, such as for example, dimethylamide (—C(O)$NMe_2$), diethylamide (—C(O)$NEt_2$) and dipropylamide ((—C(O)$NPr_2$) and variations thereof (e.g. —C(O)N(Me)Et and so on) and includes reverse amides thereof.

The term "thiol" refers to the group —SH.

The term "$C_{1-6}$alkylthio" refers to a thiol group having the hydrogen replaced with a $C_{1-6}$alkyl group. $C_{1-3}$alkylthio groups are preferred, such as for example, thiolmethyl, thiolethyl and thiolpropyl.

The term "thioxo" refers to the group =S.

The term "sulfinyl" refers to the group —S(=O)H.

The term "substituted sulfinyl" or "sulfoxide" refers to a sulfinyl group having the hydrogen replaced with, for example a $C_{1-6}$alkyl group ("$C_{1-6}$alkylsulfinyl" or "$C_{1-6}$alkylsulfoxide"), an aryl ("arylsulfinyl"), an aralkyl ("aralkyl sulfinyl") and so on. $C_{1-3}$alkylsulfinyl groups are preferred, such as for example, —SOmethyl, —SOethyl and —SOpropyl.

The term "sulfonyl" refers to the group —$SO_2H$.

The term "substituted sulfonyl" refers to a sulfonyl group having the hydrogen replaced with, for example a $C_{1-6}$alkyl group ("sulfonyl$C_{1-6}$alkyl"), an aryl ("arylsulfonyl"), an aralkyl ("aralkylsulfonyl") and so on. Sulfonyl$C_{1-3}$alkyl groups are preferred, such as for example, —$SO_2Me$, —$SO_2Et$ and —$SO_2Pr$.

The term "sulfonylamido" or "sulfonamide" refers to the group —$SO_2NH_2$.

The term "substituted sulfonamido" or "substituted sulphonamide" refers to an sulfonylamido group having a hydrogen replaced with, for example a $C_{1-6}$alkyl group ("sulfonylamido$C_{1-6}$alkyl"), an aryl ("arylsulfonamide"), aralkyl ("aralkylsulfonamide") and so on. Sulfonylamido$C_{1-3}$alkyl groups are preferred, such as for example, —$SO_2NHMe$, —$SO_2NHEt$ and —$SO_2NHPr$ and includes reverse sulfonamides thereof (e.g.—$NHSO_2Me$, —$NHSO_2Et$ and —$NHSO_2Pr$).

The term "disubstituted sulfonamido" or "disubstituted sulphonamide" refers to an sulfonylamido group having the two hydrogens replaced with, for example a $C_{1-6}$alkyl group, which may be the same or different ("sulfonylamidodi($C_{1-6}$alkyl)"), an aralkyl and alkyl group ("sulfonamido(aralkyl)alkyl") and so on. Sulfonylamidodi($C_{1-3}$alkyl) groups are preferred, such as for example, —$SO_2NMe_2$, —$SO_2NEt_2$ and —$SO_2NPr_2$ and variations thereof (e.g. —$SO_2N(Me)Et$ and so on) and includes reserve sulfonamides thereof.

The term "sulfate" refers to the group OS(O)$_2$OH and includes groups having the hydrogen replaced with, for example a $C_{1-6}$alkyl group ("alkylsulfates"), an aryl ("arylsulfate"), an aralkyl ("aralkylsulfate") and so on. $C_{1-3}$ sulfates are preferred, such as for example, OS(O)$_2$OMe, OS(O)$_2$OEt and OS(O)$_2$OPr.

The term "sulfonate" refers to the group $SO_3H$ and includes groups having the hydrogen replaced with, for example a $C_{1-6}$alkyl group ("alkylsulfonate"), an aryl ("arylsulfonate"), an aralkyl ("aralkylsulfonate") and so on. $C_{1-3}$ sulfonates are preferred, such as for example, $SO_3Me$, $SO_3Et$ and $SO_3Pr$.

The term "aryl" refers to a carbocyclic (non-heterocyclic) aromatic ring or mono-, bi- or tri-cyclic ring system. The aromatic ring or ring system is generally composed of 6 to 10 carbon atoms. Examples of aryl groups include but are not limited to phenyl, biphenyl, naphthyl and tetrahydronaphthyl.

6-membered aryls such as phenyl are preferred. The term "alkylaryl" refers to $C_{1-6}$alkylaryl such as benzyl.

The term "alkoxyaryl" refers to $C_{1-6}$alkyloxyaryl such as benzyloxy.

The term "heterocyclyl" refers to a moiety obtained by removing a hydrogen atom from a ring atom of a heterocyclic compound which moiety has from 3 to 10 ring atoms (unless otherwise specified), of which 1, 2, 3 or 4 are ring heteroatoms each heteroatom being independently selected from O, S and N.

In this context, the prefixes 3-, 4-, 5-, 6-, 7-, 8-, 9- and 10-membered denote the number of ring atoms, or range of ring atoms, whether carbon atoms or heteroatoms. For example, the term "3-10 membered heterocyclyl", as used herein, pertains to a heterocyclyl group having 3, 4, 5, 6, 7, 8, 9 or 10 ring atoms. Examples of heterocyclyl groups include 5-6-membered monocyclic heterocyclyls and 9-10 membered fused bicyclic heterocyclyls.

Examples of monocyclic heterocyclyl groups include, but are not limited to, those containing one nitrogen atom such as aziridine (3-membered ring), azetidine (4-membered ring), pyrrolidine (tetrahydropyrrole), pyrroline (e.g., 3-pyrroline, 2,5-dihydropyrrole), 2H-pyrrole or 3H-pyrrole (isopyrrole, isoazole) or pyrrolidinone (5-membered rings), piperidine, dihydropyridine, tetrahydropyridine (6-membered rings), and azepine (7-membered ring); those containing two nitrogen atoms such as imidazoline, pyrazolidine (diazolidine), imidazoline, pyrazoline (dihydropyrazole) (5-membered rings), piperazine (6-membered ring); those containing one oxygen atom such as oxirane (3-membered ring), oxetane (4-membered ring), oxolane (tetrahydrofuran), oxole (dihydrofuran) (5-membered rings), oxane (tetrahydropyran), dihydropyran, pyran (6-membered rings), oxepin (7-membered ring); those containing two oxygen atoms such as dioxolane (5-membered ring), dioxane (6-membered ring), and dioxepane (7-membered ring); those containing three oxygen atoms such as trioxane (6-membered ring); those containing one sulfur atom such as thiirane (3-membered ring), thietane (4-membered ring), thiolane (tetrahydrothiophene) (5-membered ring), thiane (tetrahydrothiopyran) (6-membered ring), thiepane (7-membered ring); those containing one nitrogen and one oxygen atom such as tetrahydrooxazole, dihydrooxazole, tetrahydroisoxazole, dihydroisoxazole (5-membered rings), morpholine, tetrahydrooxazine, dihydrooxazine, oxazine (6-membered rings); those containing one nitrogen and one sulfur atom such as thiazoline, thiazolidine (5-membered rings), thiomorpholine (6-membered ring); those containing two nitrogen and one oxygen atom such as oxadiazine (6-membered ring); those containing one oxygen and one sulfur such as: oxathiole (5-membered ring) and oxathiane (thioxane) (6-membered ring); and those containing one nitrogen, one oxygen and one sulfur atom such as oxathiazine (6-membered ring).

Heterocyclyls also encompass aromatic heterocyclyls and non-aromatic heterocyclyls. Such groups may be substituted or unsubstituted.

The term "aromatic heterocyclyl" may be used interchangeably with the term "heteroaromatic" or the term "heteroaryl" or "hetaryl". The heteroatoms in the aromatic heterocyclyl group may be independently selected from N, S and O.

"Heteroaryl" is used herein to denote a heterocyclic group having aromatic character and embraces aromatic monocyclic ring systems and polycyclic (e.g. bicyclic) ring systems containing one or more aromatic rings. The term aromatic heterocyclyl also encompasses pseudoaromatic heterocyclyls. The term "pseudoaromatic" refers to a ring system which is not strictly aromatic, but which is stabilized by means of delocalization of electrons and behaves in a similar manner to aromatic rings. The term aromatic heterocyclyl therefore covers polycyclic ring systems in which all of the fused rings are aromatic as well as ring systems where one or more rings are non-aromatic, provided that at least one ring is aromatic. In polycyclic systems containing both aromatic and non-aromatic rings fused together, the group may be attached to another moiety by the aromatic ring or by a non-aromatic ring.

Examples of heteroaryl groups are monocyclic and bicyclic groups containing from five to ten ring members. The heteroaryl group can be, for example, a five membered or six membered monocyclic ring or a bicyclic structure formed from fused five and six membered rings or two fused six membered rings or two fused five membered rings. Each ring may contain up to about four heteroatoms typically selected from nitrogen, sulphur and oxygen. The heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Aromatic heterocyclyl groups may be 5-membered or 6-membered mono-cyclic aromatic ring systems.

Examples of 5-membered monocyclic heteroaryl groups include but are not limited to furanyl, thienyl, pyrrolyl, oxazolyl, oxadiazolyl (including 1,2,3 and 1,2,4 oxadiazolyls and furazanyl i.e. 1,2,5-oxadiazolyl), thiazolyl, isoxazolyl, isothiazolyl, pyrazolyl, imidazolyl, triazolyl (including 1,2,3,1,2,4 and 1,3,4 triazolyls), oxatriazolyl, tetrazolyl, thiadiazolyl (including 1,2,3 and 1,3,4 thiadiazolyls) and the like.

Examples of 6-membered monocyclic heteroaryl groups include but are not limited to pyridinyl, pyrimidinyl, pyridazinyl, pyrazinyl, triazinyl, pyranyl, oxazinyl, dioxinyl, thiazinyl, thiadiazinyl and the like. Examples of 6-membered aromatic heterocyclyls containing nitrogen include pyridyl (1 nitrogen), pyrazinyl, pyrimidinyl and pyridazinyl (2 nitrogens).

Aromatic heterocyclyl groups may also be bicyclic or polycyclic heteroaromatic ring systems such as fused ring systems (including purine, pteridinyl, napthyridinyl, 1H thieno[2,3-c] pyrazolyl, thieno[2,3-b]furyl and the like) or linked ring systems (such as oligothiophene, polypyrrole and the like). Fused ring systems may also include aromatic 5-membered or 6-membered heterocyclyls fused to carbocyclic aromatic rings such as phenyl, napthyl, indenyl, azulenyl, fluorenyl, anthracenyl and the like, such as 5-membered aromatic heterocyclyls containing nitrogen fused to phenyl rings, 5-membered aromatic heterocyclyls containing 1 or 2 nitrogens fused to phenyl ring.

A bicyclic heteroaryl group may be, for example, a group selected from: a) a benzene ring fused to a 5- or 6-membered ring containing 1, 2 or 3 ring heteroatoms; b) a pyridine ring fused to a 5- or 6-membered ring containing 1, 2 or 3 ring heteroatoms; c) a pyrimidine ring fused to a 5- or 6-membered ring containing 1 or 2 ring heteroatoms; d) a pyrrole ring fused to a 5- or 6-membered ring containing 1, 2 or 3 ring heteroatoms; e) a pyrazole ring fused to a 5- or 6-membered ring containing 1 or 2 ring heteroatoms; f) an imidazole ring fused to a 5- or 6-membered ring containing 1 or 2 ring heteroatoms; g) an oxazole ring fused to a 5- or 6-membered ring containing 1 or 2 ring heteroatoms; h) an isoxazole ring fused to a 5- or 6-membered ring containing 1 or 2 ring heteroatoms; i) a thiazole ring fused to a 5- or 6-membered ring containing 1 or 2 ring heteroatoms; j) an isothiazole ring fused to a 5- or 6-membered ring containing 1 or 2 ring heteroatoms; k) a thiophene ring fused to a 5- or 6-membered ring containing 1, 2 or 3 ring heteroatoms; l) a furan ring fused to a 5- or 6-membered ring containing 1, 2 or 3 ring heteroatoms; m) a cyclohexyl ring fused to a 5- or 6-membered ring containing 1, 2 or 3 ring heteroatoms; and n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), benzodioxole and pyrazolopyridine (e.g. pyrazolo[1,5-a]pyridine) groups. A further example of a six membered ring fused to a five membered ring is a pyrrolopyridine group such as a pyrrolo[2,3-b]pyridine group.

Particular examples of bicyclic heteroaryl groups containing two fused six membered rings include but are not limited to quinoline, isoquinoline, chroman, thiochroman, chromene, isochromene, isochroman, benzodioxan, quinolizine, benzoxazine, benzodiazine, pyridopyridine, quinoxaline, quinazoline, cinnoline, phthalazine, naphthyridine and pteridine groups.

Examples of heteroaryl groups containing an aromatic ring and a non-aromatic ring include tetrahydronaphthalene, tetrahydroisoquinoline, tetrahydroquinoline, dihydrobenzothiophene, dihydrobenzofuran, 2,3-dihydro-benzo[1,4]dioxine, benzo[1,3]dioxole, 4,5,6,7-tetrahydrobenzofuran, indoiine, isoindoline and indane groups.

Examples of aromatic heterocyclyls fused to carbocyclic aromatic rings may therefore include but are not limited to benzothiophenyl, indolyl, isoindolyl, benzofuranyl, isobenzofuranyl, benzimidazolyl, indazolyl, benzoxazolyl, benzisoxazolyl, isobenzoxazoyl, benzothiazolyl, benzisothiazolyl, quinolinyl, isoquinolinyl, quinoxalinyl, quinazolinyl, cinnolinyl, benzotriazinyl, phthalazinyl, carbolinyl and the like.

The term "non-aromatic heterocyclyl" encompasses optionally substituted saturated and unsaturated rings which contain at least one heteroatom selected from the group consisting of N, S and O.

Non-aromatic heterocyclyls may be 3-7 membered monocyclic rings.

Examples of 5-membered non-aromatic heterocyclyl rings include 2H-pyrrolyl, 1-pyrrolinyl, 2-pyrrolinyl, 3-pyrrolinyl, pyrrolidinyl, 1-pyrrolidinyl, 2-pyrrolidinyl, 3-pyrrolidinyl, tetrahydrofuranyl, tetrahydrothiophenyl, pyrazolinyl, 2-pyrazolinyl, 3-pyrazolinyl, pyrazolidinyl, 2-pyrazolidinyl, 3-pyrazolidinyl, imidazolidinyl, 3-dioxalanyl, thiazolidinyl, isoxazolidinyl, 2-imidazolinyl and the like.

Examples of 6-membered non-aromatic heterocyclyls include piperidinyl, piperidinonyl, pyranyl, dihyrdopyranyl, tetrahydropyranyl, 2H pyranyl, 4H pyranyl, thianyl, thianyl oxide, thianyl dioxide, piperazinyl, diozanyl, 1,4-dioxinyl, 1,4-dithianyl, 1,3,5-triozalanyl, 1,3,5-trithianyl, 1,4-morpholinyl, thiomorpholinyl, 1,4-oxathianyl, triazinyl, 1,4-thiazinyl and the like.

Examples of 7-membered non-aromatic heterocyclyls include azepanyl, oxepanyl, thiepanyl and the like.

Non-aromatic heterocyclyl rings may also be bicyclic heterocyclyl rings such as linked ring systems (for example uridinyl and the like) or fused ring systems. Fused ring systems include non-aromatic 5-membered, 6-membered or 7-membered heterocyclyls fused to carbocyclic aromatic rings such as phenyl, napthyl, indenyl, azulenyl, fluorenyl, anthracenyl and the like. Examples of non-aromatic 5-membered, 6-membered or 7-membered heterocyclyls fused to carbocyclic aromatic rings include indolinyl, benzodiazepinyl, benzazepinyl, dihydrobenzofuranyl and the like.

The term "halo" refers to fluoro, chloro, bromo or iodo.

Unless otherwise defined, the term "optionally substituted" or "optional substituent" as used herein refers to a group which may or may not be further substituted with 1, 2, 3, 4 or more groups, preferably 1, 2 or 3, more preferably 1 or 2 groups selected from the group consisting of $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl, heterocyclyl and heteroaryl and groups containing them may be further optionally substituted. Preferred optional substituents include $C_{1-4}$alkyl, $C_{2-4}$alkenyl, $C_{2-4}$alkynyl, $C_{3-8}$cycloalkyl, hydroxyl, oxo, $C_{1-4}$alkoxy, halo, $C_{1-4}$alkylhalo (such as $CF_3$ and $CHF_2$), $C_{1-4}$alkoxyhalo, carboxyl, esters, amino, substituted amino, disubstituted amino, ketones, amides, substituted amides, disubstituted amides, sulphonyl, substituted sulphonyl, aryl, ar$C_{1-6}$alkyl, heterocyciyl and heteroaryl, wherein each alkyl, alkenyl, alkynyl, cycloalkyl, aryl, heterocyclyl and heteroaryl and the group containing them may be further optionally substituted Optional substituents in the case of heterocycles containing N may also include but are not limited to $C_{1-6}$alkyl i.e. N—$C_{1-3}$alkyl, more preferably methyl particularly N-methyl.

It will be understood that suitable derivatives of aromatic heterocyclyls containing nitrogen include N-oxides thereof.

The compounds of the invention may also be prepared as salts which are pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulfuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, trihalomethanesulfonic, toluenesulfonic, benzenesulfonic, isethionic, salicylic, sulphanilic, aspartic, glutamic, edetic, stearic, palmitic, oleic, lauric, pantothenic, tannic, ascorbic, valeric and orotic acids. Salts of amine groups may also comprise quaternary ammonium salts in which the amino nitrogen atom carries a suitable organic group such as an alkyl, alkenyl, alkynyl or aralkyl moiety.

The salts may be formed by conventional means, such as by reacting the free base form of the compound with one or more equivalents of the appropriate acid.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, alcohols such as methanol, ethanol or isopropyl alcohol, DMSO, acetonitrile, dimethyl formamide (DMF) and the like with the solvate forming part of the crystal lattice by either non-covalent binding or by occupying a hole in the crystal lattice. Hydrates are formed when the solvent is water, alcoholates are formed when the solvent is alcohol. Solvates of the compounds of the present invention can be conveniently prepared or formed during the processes described herein. In general, the solvated forms are considered equivalent to the unsolvated forms for the purposes of the compounds and methods provided herein.

It will be understood that compounds of formula (I) may possess a chiral centre and may therefore exist as an isomer such as a racemate or an R- or S-enantiomer. The compounds may therefore be used as a purified enantiomer or diastereomer, or as a mixture of any ratio thereof.

This invention also encompasses prodrugs of the compounds of formula (I).

The term "pro-drug" is used herein in its broadest sense to include those compounds which are converted in vivo to the compound of formula (I). Use of the prodrug strategy optimises the delivery of the drug to its site of action. In one embodiment, compounds of formula (I) having free amino, amido, hydroxyl, or carboxylic acid groups can be converted into prodrugs. Prodrugs include compounds wherein carbonates, carbamates, amide and alkyl esters which are covalently bonded to the above substituents of compounds of the present invention through a carbonyl carbon prodrug sidechain. Prodrugs may also include N-oxides of ring nitrogen atoms in formula (I).

Viral Polymerase Inhibition

The ability of the compounds of formula (I) to inhibit RNA synthesis by the RNA dependent RNA polymerase of HCV (NS5B) can be demonstrated by any assay capable of measuring RNA dependent RNA polymerase activity. A suitable assay is described in the examples.

While the invention is described with particular reference to compounds having inhibitory activity against a HCV NS5B polymerase, it will be understood that other polymerases can, if desired, be substituted in whole or in part for the HCV polymerase herein described. For example, one microbial polymerase target is HCV NS5B which is the viral RNA-dependent RNA polymerase (RdRp) that is responsible for viral replications. HCV NS5B protein, is released from a polyprotein and is involved in the synthesis of double-stranded RNA from a single-stranded viral RNA genome. It is believed that the replication and/or reproduction of HCV virus may be inhibited or prevented through the inhibition of NS5B and suppress or prevent the formation of the double-stranded HCV RNA.

To demonstrate that the compounds of formula (I) act by specific inhibition of NS5B, the compounds may be tested for the lack of inhibitory activity in an assay measuring the activity of an RNA-dependent RNA polymerase other than HCV polymerase or in a DNA dependent RNA polymerase assay.

Pharmaceutical Compositions

The invention also provides a pharmaceutical composition comprising a compound of formula (I) and a pharmaceutically acceptable carrier.

The pharmaceutical composition may further comprise or be administered in combination with one or more other antiviral agents such as Ribavirin (Copegus® or Rebetol®), an antiviral nucleoside inhibitor of NS5b polymerase (such as 4-amino-7-(2-C-methyl-β-D-ribofuranosyl)-pyrrolo[2,1-f][1,2,4]triazine; PSI-7977; PSI-938; RG7128 or mericitabine; IDX-184; INX-189 and other such agents that may be developed) a non-nucleoside inhibitor of NS5b polymerase (such as GS-9190 or tegobuvir; PF-868554 or filibuvir; VX-222; IDX-375; ABT-072; ABT-333; ANA-598 or setrobuvir; B1207127; JTK-853; GS-9669; and other such agents that may be developed), a NS3/4a protease inhibitor (such as telaprevir or Incivek®; boceprevir or Victrelis®; BI-201335; TMC-435; RG-7227 or danoprevir; MK-7009 or vaniprevir; GS-9451; GS-9256; BMS-650032; ACH-1625; ACH-2684; MK-5172; ABT-450; IDX-320; SCH-900518 and other such agents that may be developed), an NS5a inhibitor (such as BMS-790052 (daclatasvir); GS-5885; ABT-267; PPI-461; ACH-2928; GSK2336805 and other such agents that may be developed) and/or inhibitor of viral entry, assembly or egress. The composition may also additionally comprise at least one immunomodulatory agent for example an interferon or interferon derivative such as interferon alpha 2B (such as Intron® A interferon available from Schering Corp., Kenilworth, N.J.), pegylated interferon alpha 2A (such as Pegasys® available from Hoffmann-LaRoche, Nutley, N.J.), pegylated interferon alpha 2B (such as Peg-Intron® available from Schering Corp., Kenilworth, N.J.), consensus interferon (such as interferon alphacon-1, or Infergen® available from Valeant Pharmaceuticals, Costa Mesa, Calif.), interferon alpha 2A, recombinant interferon alpha 2A (such as Roferon® available from Hoffmann-LaRoche, Nutley, N.J.), or lymphoblastoid interferon tau, and/or an inhibitor of inosine-5'-monophosphate dehydrogenase (IMPDH) and other large or small molecules known to modulate host immune responses.

Accordingly, in one embodiment of the pharmaceutical composition, the other antiviral agent is Ribavarin optionally in combination with peg/IFN.

In another embodiment, the other antiviral agent is an NS5b inhibitor, more particularly a nucleoside inhibitor such as the bicyclic nucleosides and nucleotides of the general formula described in WO2010/002877, for example, 4-amino-7-(2-C-methyl-β-D-ribofuranosyl)-pyrrolo[2,1-f][1,2,4]triazine.

In yet another embodiment, the other antiviral agent is an NS3/4a protease inhibitor such as telaprevir (VX-950) or Incivek®; boceprevir or Victrelis®; BI-201335; TMC-435; RG-7227 or danoprevir; MK-7009 or vaniprevir; GS-9451; GS-9256; BMS-650032; ACH-1625; ACH-2684; MK-5172; ABT-450; IDX-320; SCH-900518, particularly telaprevir (VX-950).

In still another embodiment, the other antiviral agent is an NS5a inhibitor such as BMS-790052 (daclatasvir); GS-5885; ABT-267; PPI-461; ACH-2928; GSK2336805, particularly BMS-790052 (daclatasvir).

It will be understood that combined administration of the compounds of the invention with the other antiviral agent may be concurrent, sequential or separate administration.

The term "composition" is intended to include the formulation of an active ingredient with conventional carriers and excipients, and also with encapsulating materials as the carrier, to give a capsule in which the active ingredient (with or without other carriers) is surrounded by the encapsulation carrier. Any carrier must be "pharmaceutically acceptable" meaning that it is compatible with the other ingredients of the composition and is not deleterious to a subject. The compositions of the present invention may contain other therapeutic agents as described above, and may be formulated, for example, by employing conventional solid or liquid vehicles or diluents, as well as pharmaceutical additives of a type appropriate to the mode of desired administration (for example, excipients, binders, preservatives, stabilizers, flavours, etc.) according to techniques such as those well known in the art of pharmaceutical formulation (See, for example, Remington: *The Science and Practice of Pharmacy,* 21st Ed., 2005, Lippincott Williams & Wilkins).

The pharmaceutical composition includes those suitable for oral, rectal, nasal, topical (including buccal and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For preparing pharmaceutical compositions from the compounds of the present invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compositions according to the present invention may thus be formulated for parenteral administration (e.g. by injection, for example bolus injection or continuous infusion) and may be presented in unit dose form in ampoules, prefilled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Pharmaceutical forms suitable for injectable use include sterile injectable solutions or dispersions, and sterile powders for the extemporaneous preparation of sterile injectable solutions. They should be stable under the conditions of manufacture and storage and may be preserved against oxidation and the contaminating action of microorganisms such as bacteria or fungi.

The solvent or dispersion medium for the injectable solution or dispersion may contain any of the conventional solvent or carrier systems for the compounds, and may contain, for example, water, ethanol, polyol (for example, glycerol, propylene glycol and liquid polyethylene glycol, and the like), suitable mixtures thereof, and vegetable oils.

Pharmaceutical forms suitable for injectable use may be delivered by any appropriate route including intravenous, intramuscular, intracerebral, intrathecal, epidural injection or infusion.

Sterile injectable solutions are prepared by incorporating the active compounds in the required amount in the appropriate solvent with various other ingredients such as these enumerated above, as required, followed by filtered sterilization. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile-filtered solution of the active ingredient plus any additional desired ingredients.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like.

The amount of active compound in therapeutically useful compositions should be sufficient that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound (s) may be incorporated into sustained-release preparations and formulations, including those that allow specific delivery of the active peptide to specific regions of the gut.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Pharmaceutically acceptable carriers and/or diluents include any and all solvents, dispersion media, coatings, antibacterial and antifungal agents, isotonic and absorption delaying agents and the like.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension.

In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas.

The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g. gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the dosage unit forms are dictated by and directly dependent on (a) the unique characteristics of the active material and the particular therapeutic effect to be achieved, and (b) the limitations inherent in the art of compounding such an active material for the treatment of a HCV viral infection in living subjects having a diseased condition in which bodily health is impaired.

The invention also includes the compounds in the absence of carrier where the compounds are in unit dosage form.

Compositions comprising compounds of the invention formulated for oral delivery either alone or in combination with another HCV antiviral agent are particularly preferred.

Methods of Treatment

The compounds of formula (I) may be used in the treatment of a Flaviviridae viral infection such as a HCV infection.

Generally, the term "treatment" means affecting a subject, tissue or cell to obtain a desired pharmacological and/or physiological effect and includes: (a) inhibiting the viral infection, i.e. arresting its development or further development; (b) relieving or ameliorating the effects of the viral infection, i.e. cause regression of the effects of the viral infection; (c) reducing the incidence or the viral infection or (d) preventing the infection from occurring in a subject, tissue or cell predisposed to the viral infection disease or at risk thereof, but has not yet been diagnosed with a protective pharmacological and/or physiological effect so that the viral infection does not develop or occur in the subject, tissue or cell.

The prevention of hepatitis C means, for example, administration of a pharmaceutical agent to a subject found to carry a HCV by a test and the like but without a symptom of infection, or to a subject who shows an improved disease state of hepatitis after a treatment of hepatitis C, but who still carries a HCV and is associated with a risk of recurrence of hepatitis.

The term "subject" as used herein refers to any animal, in particular mammals such as humans having a disease or condition which requires treatment with the compound of formula (I).

The term "administering" refers to providing the compound or pharmaceutical composition of the invention to a subject suffering from or at risk of the diseases or conditions to be treated or prevented.

The term "viral infection" refers to the introduction of a virus into cells or tissues, e.g., hepatitis C virus (HCV). In general, the introduction of a virus is also associated with replication. Viral infection may be determined by measuring virus antibody titer in samples of a biological fluid, such as blood, using, e.g., enzyme immunoassay. Other suitable diagnostic methods include molecular based techniques, such as RT-PCR, direct hybrid capture assay, nucleic acid sequence based amplification, and the like. A virus may infect an organ, e.g., liver, and cause disease, e.g., hepatitis, cirrhosis, chronic liver disease and hepatocellular carcinoma.

The term "Flaviviridae virus" refers to a virus of the family Flaviviridae, which family includes the Hepacivirus Flavivirus and Pestivirus or hepatitis C-like virus genera. A representative species of the genus of hepatitis C-like viruses is hepatitis C virus.

Dosages

The term "therapeutically effective amount" refers to the amount of the compound of formula (I) that will elicit the biological or medical response of a subject, tissue or cell that is being sought by the researcher, veterinarian, medical doctor or other clinician.

In the prevention or treatment of HCV infections or diseases an appropriate dosage level will generally be about 0.01 to 500 mg per kg subject body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. The dosage may be selected, for example to any dose within any of these ranges, for therapeutic efficacy and/or symptomatic adjustment of the dosage to the subject to be treated It will be understood that the specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the subject undergoing therapy.

It will further be understood that when the compounds of the invention are to be administered in combination with one or more HCV antiviral agents the dosage forms and levels may be formulated for either concurrent, sequential or separate administration or a combination thereof.

General Methods

It will be understood that unless otherwise defined each moiety having a substitutable hydrogen such as for example, alkyl, alkenyl, alkynyl, alkoxy, cycloalkyl, cycloalkenyl, heterocyclyl, aryl and heteroaryl, in each occurrence as described in the general schemes and methods which follow may be optionally substituted.

It will also be understood that the particular examples which are described herein may undergo further functionalisation using methods known in the art, for example, compounds comprising amino groups or acid groups may undergo reduction amination or amide couplings respectively to form further examples of compounds of the invention.

Method A

The arylaldehyde was nitrated using a mixture of fuming nitric acid and sulfuric acid to give a mixture of mono-, di- and tri-nitrated products. The mono-nitrohaloarylaldehyde was separated by conventional separation techniques (e.g. column chromatography) and again subjected to the nitrating conditions described above to give the corresponding dinitroarylhaloarylaldehyde. The dinitroarylhaoloaldehyde was reacted with a suitably substituted boronic acid or boronic acid derivative in the presence of a suitable catalyst (e.g. tetrakistriphenylphosphinepalladium(0)) and a suitable base (e.g. sodium carbonate) in a suitable solvent (e.g. toluene) as described by Miyaura and. Suzuki (see Miyaura, N.; Suzuki, A. J. Chem. Soc., Chem. Commun. 1979, 866-867) to give the corresponding dinitroaldehyde. The dinitroaldehyde was then reacted with a primary aryl- or alkyamine (e.g. 4-bromoaniline) in the presence of a cyanide source (e.g. sodium cyanide) and acetic acid and acetic anhydride to give the corresponding nitrocyanoindazole-N-oxide. The nitrocyanoindazole-N-oxide can be converted to the corresponding nitrocyanoindazole by treatment with a reagent such as phosphorus (III) trichloride. The cyano group of the nitrocyanoindazole can then be hydrolysed to the corresponding nitroindazole carboxylic acid (e.g. using sodium hydroxide in aqueous ethanol), which can then be coupled to an amine using standard peptide coupling conditions (e.g. HATU/DIPEA/acetonitrile) to give the a nitroindazoleamide. The nitroindazoleamide can then be reduced to the corresponding nitroindazoleamine using standard conditions normally associated with the reduction of an arylnitro-group to an aniline (e.g iron in the presence of an aqueous alcoholic solvent).

Scheme 1:

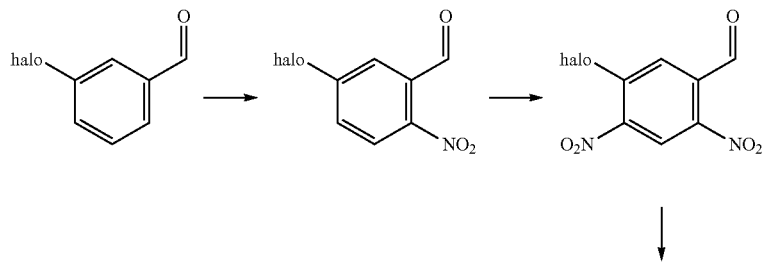

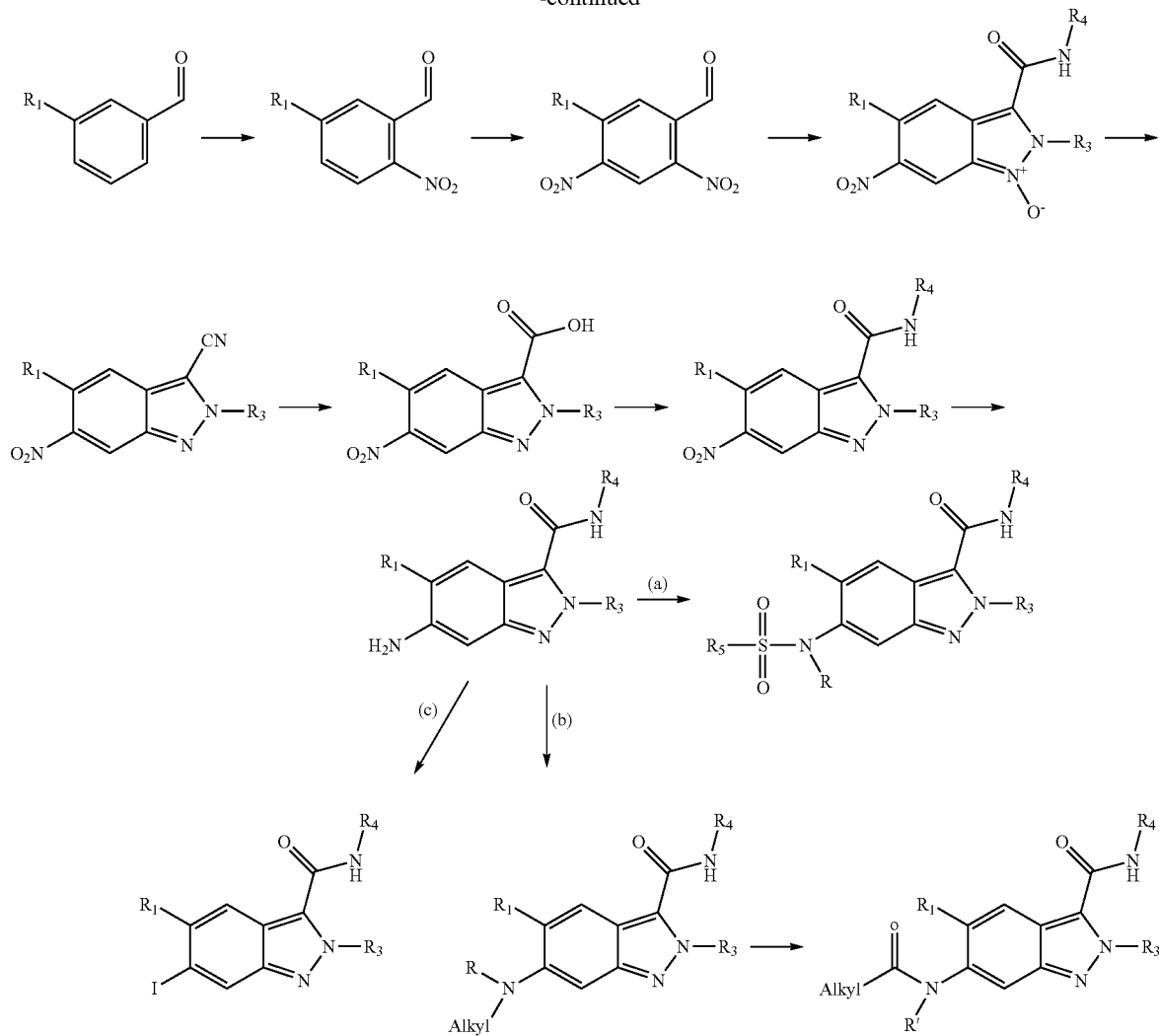

where $R_1$ may be, for example, $C_{3-6}$cycloalkyl such as cyclopropyl, $C_{1-6}$alkyl including methyl, ethyl, n-propyl and iso-propyl, halo or $C_{1-6}$alkoxy including methoxy, ethoxy, n-propoxy and iso-propoxy; $R_3$ may be, for example, optionally substituted aryl or optionally substituted heteroaryl; $R_4$ may be, for example, H or $C_{1-6}$alkyl; $R_5$ may be, for example, $C_{1-6}$alkyl including methyl, ethyl, n-propyl and iso-propyl preferably methyl or $C_{1-3}$alkylhalo (i.e. $C_{1-3}$alkyl substituted with halo such as $CF_3$ or $CHF_2$); R may be, for example, H or $C_{1-6}$alkyl and R' may be, for example, $C_{1-6}$alkyl or heteroaryl.

Route (a): The amino analogue was first converted to the bis-sulfonyl analogue using standard sulfonylation conditions with an activated sulfonic acid (e.g. methanesulfonyl chloride) and base (e.g. DIPEA) in an organic solvent (e.g. dichloromethane). The bis-sulfonyl analogue then underwent hydrolysis using base (e.g. potassium hydroxide) in aqueous alcoholic solvent (e.g. ethanol) to give the desired sulfonamide. Alternatively, the amino analogue was converted directly to the desired sulphonamide by reaction with the activated sulfonic acid (e.g. difluoromethanesulfonyl chloride) in a basic organic solvent (e.g pyridine).

Route (b): Starting from the amino analogue, standard reductive amination conditions using an aldehyde (e.g. acetaldehyde) and a reducing agent (e.g. sodium borohydride) in alcoholic solvent (e.g. methanol) gave the alkylated amine. The alkylated amine was then subjected to standard acylation conditions using an activated acid (e.g. acetyl chloride) and base (e.g. DIPEA) in an organic solvent (e.g. dichloromethane) to give the desired amide.

Route (c): The amino analogue was subjected to standard diazotisation conditions using nitrite (e.g. sodium nitrite) in aqueous acid (e.g. hydrochloric acid) followed by the addition of halide salt (e.g. potassium iodide) to give the desired halide adduct.

Method B

The haloindazole was reacted with a suitably substituted vinyl boronic acid or boronic acid derivative in the presence of a suitable catalyst (e.g. palladium (II) acetate) and a suitable base (e.g. potassium phosphate) and a suitable ligand (tricyclohexylphosphine) in suitable solvents (e.g. toluene and water) to give the corresponding vinylindzole. The olefinic portion of the vinylindazole was then reduced to the corresponding alkylindazole using hydrogen gas and a suitable catalyst, (e.g. palladium on carbon) and a suitable solvent (e.g. ethanol). Alkylation of the sulfonamide group contained within this intermediate was achieved by treatment with an alkyl halide (e.g. 3-bromo-1-propanol) and a base (e.g. potassium carbonate) in a suitable solvent (e.g. acetonitrile).

Scheme 2:

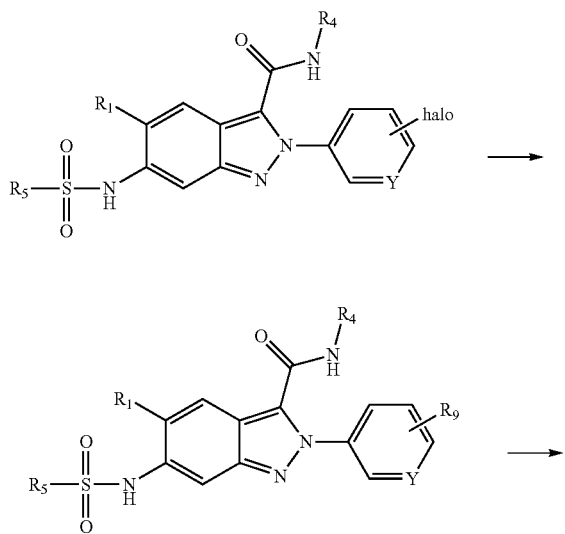

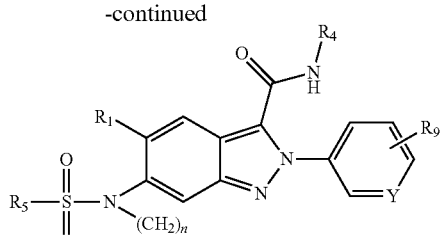

where $R_1$ may be, for example, $C_{3-6}$cycloalkyl such as cyclopropyl, $C_{1-6}$alkyl including methyl, ethyl, n-propyl and iso-propyl, halo, or $C_{1-6}$alkoxy including methoxy, ethoxy, n-propoxy and iso-propoxy; $R_4$ may be, for example, H or $C_{1-6}$alkyl; $R_5$ may be, for example, $C_{1-6}$alkyl including methyl, ethyl, n-propyl and iso-propyl preferbably methyl or $C_{1-6}$alkylhalo (i.e. $C_{1-3}$alkyl substituted with halo such as $CF_3$ or $CHF_2$); $R_9$ may be, for example, H or one or more substituents each independently selected from halo, $C_{1-6}$alkyl, $C_{1-3}$alkylhalo, $C_{1-6}$alkoxy, $NHC_{1-6}$alkyl, $N(C_{1-6}alkyl)_2$, optionally substituted O-phenyl or optionally substituted NH-phenyl; R may be, for example, OH, $C_{1-6}$alkyl, $C_{3-6}$cycloalkyl $C_{1-6}$alkoxy, $NHC_{1-6}$alkyl, $N(C_{1-6}alkyl)_2$, or 5-6-membered heterocyclyl; Y may be CH or N; n may be an integer selected from 0, 1, 2, 3, 4, 5 and 6 and each —$(CH_2)$— may be optionally substituted.

Method C

The sulfonamide analogue was alkylated by treating with an alkyl halide (e.g. 3-bromo-1-propanol) and base (e.g. potassium carbonate) in a suitable solvent (e.g. acetonitrile).

Scheme 3:

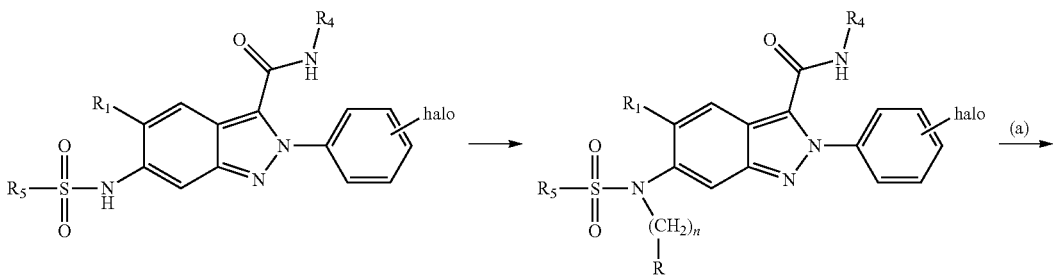

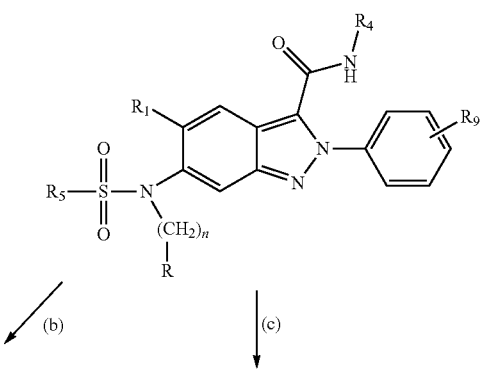

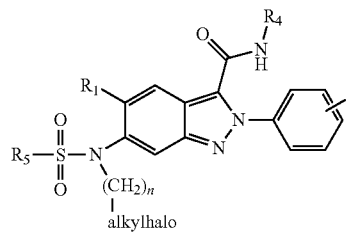

where $R_1$ may be, for example, $C_{3-6}$cycloalkyl such as cyclopropyl, $C_{1-6}$alkyl including methyl, ethyl, n-propyl and iso-propyl, halo or $C_{1-6}$alkoxy including methoxy, ethoxy, n-propoxy and iso-propoxy; $R_4$ may be, for example, H or $C_{1-6}$alkyl; $R_5$ may be, for example, $C_{1-6}$alkyl including methyl, ethyl, n-propyl and iso-propyl preferably methyl or $C_{1-3}$alkylhalo (i.e. $C_{1-3}$alkyl substituted with halo such as $CF_3$ or $CHF_2$); $R_9$ may be, for example, H or one or more substituents each independently selected from halo, $C_{1-6}$alkyl, $C_{1-3}$alkylhalo, $C_{1-6}$alkoxy, $NHC_{1-6}$alkyl, $N(C_{1-6}$alkyl$)_2$, optionally substituted O-phenyl or optionally substituted NH-phenyl; R may be H, OH, halo, $C_{1-6}$alkyl, $C_{3-6}$cycloalkyl, $C_{1-6}$alkoxy, $NHC_{1-6}$alkyl, $N(C_{1-6}$alkyl$)_2$, aryl, 5-6-membered heterocyclyl and 5-6-membered heteroaryl; X may be CH or N; n may be an integer selected from 0, 1, 2, 3, 4, 5 and 6 and each —(CH$_2$)— may be optionally substituted.

Route (a): The halide analogue was subjected to standard coupling conditions with a coupling partner (e.g. 2-fluoroaniline) using base (e.g. cesium carbonate), ligand (e.g. 2,2'-bis(diphenylphosphino)-1,1'-binaphthalene) and catalyst (e.g. palladium acetate) in organic solvent (e.g. toluene) to afford the coupled product.

Route (b): The hydroxy analogue was oxidised under standard conditions using an oxidant (e.g Dess-Martin periodinane) in an organic solvent (e.g. dichloromethane) to give the aldehyde adduct. The aldehyde was halogenated using a halide source (e.g. Deoxo-Fluor) in organic solvent (e.g. dichloromethane).

Route (c): The hydroxyl analogue was halogenated using a halide source (e.g. Deoxo-Fluor) in organic solvent (e.g. dichloromethane).

Method D

The phthalimide analogue was prepared in either of the following ways: by alkylation with an alkyl halide (e.g. N-(2-bromoethyl)phthalamide and base (e.g. potassium carbonate) in a suitable solvent; or by a Mitsunobu reaction with an acidic component (e.g. phthalimide), phosphine (e.g. triphenyl phosphine), and azodicarboxylate (e.g. diisopropyl azodicarboxylate). This intermediate was hydrolysed (e.g. hydrazine hydrate) in a suitable solvent (e.g. ethanol) to afford the amino intermediate.

Scheme 4:

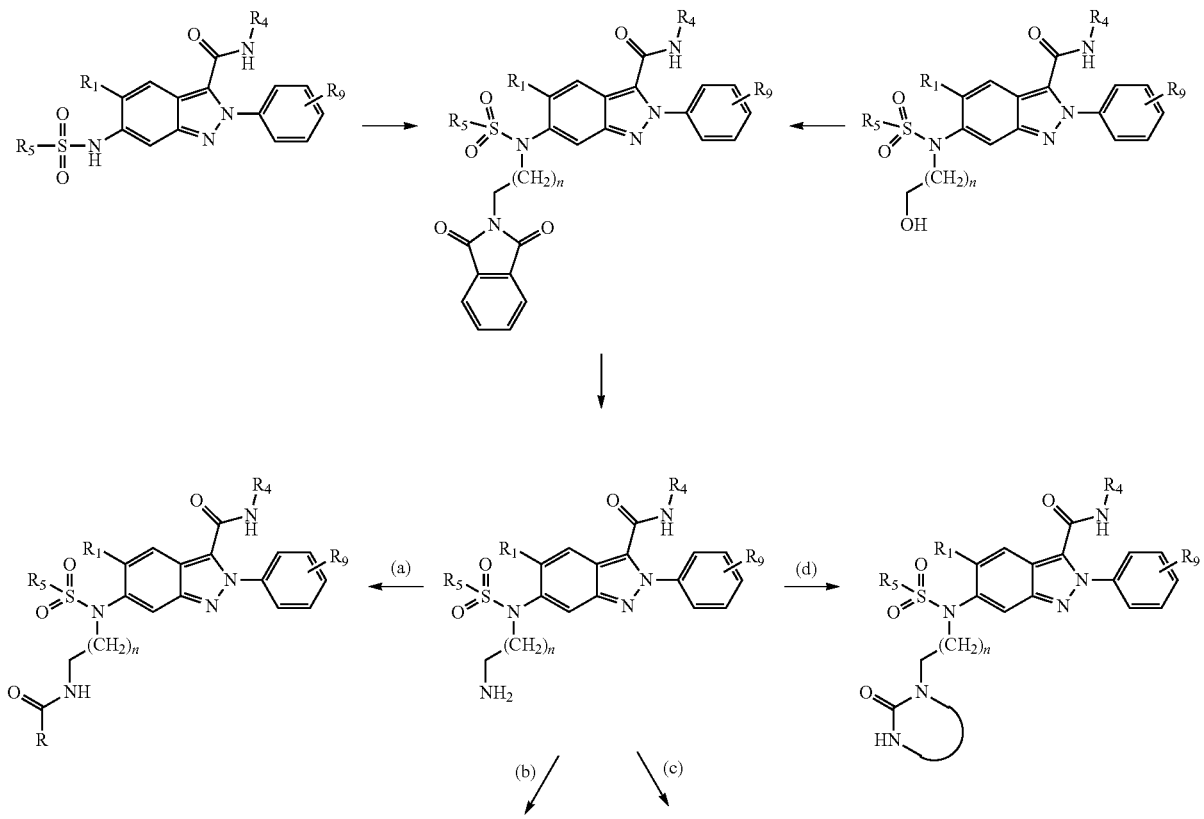

-continued

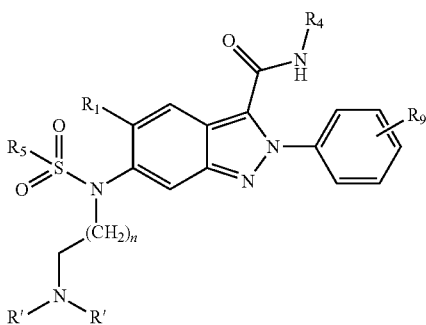

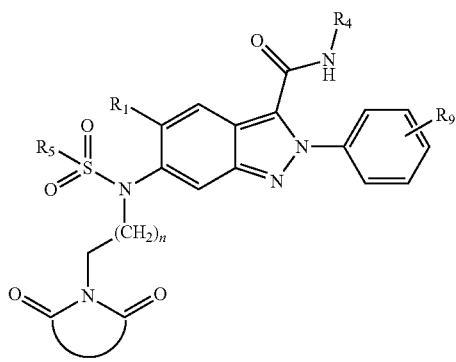

where $R_1$ may be, for example, $C_{3-6}$cycloalkyl such as cyclopropyl, $C_{1-6}$alkyl including methyl, ethyl, n-propyl and iso-propyl, halo, or $C_{1-6}$alkoxy including methoxy, ethoxy, n-propoxy and iso-propoxy; $R_4$ may be, for example, H or $C_{1-6}$alkyl; $R_5$ may be, for example, $C_{1-6}$alkyl including methyl, ethyl, n-propyl and iso-propyl preferably methyl or $C_{1-3}$alkylhalo (i.e. $C_{1-3}$alkyl substituted with halo such as $CF_3$ or $CHF_2$); $R_9$ may be, for example, H or one or more substituents each independently selected from halo, $C_{1-6}$alkyl, $C_{1-3}$alkylhalo, $C_{1-6}$alkoxy, $NHC_{1-6}$alkyl, $N(C_{1-6}alkyl)_2$, optionally substituted O-phenyl or optionally substituted NH-phenyl; R may be $C_{1-6}$alkyl, $C_{2-6}$alkenyl, $C_{3-6}$cycloalkyl, $C_{1-6}$alkoxy, $NHC_{1-6}$alkyl, $N(C_{1-6}alkyl)_2$, or 5-6-membered heterocyclyl, aryl, or 5-6-membered heteroaryl; each R' may be H, $C_{1-6}$alkyl or $SO_2C_{1-6}$alkyl; n may be an integer selected from 0, 1, 2, 3, 4, 5 and 6 and each ——$(CH_2)$—— may be optionally substituted.

Route (a): The amine intermediate was subjected to standard amide coupling conditions for example, using an acid (e.g. tetrazole acetic acid), an amide coupling reagent (e.g. HATU) and base (e.g. DIPEA) in an organic solvent (e.g. DMF) or an anhydride in pyridine or an acid chloride in pyridine to give the desired amide.

Route (b): The amine or sulfonylamide intermediate was treated with standard reductive amination conditions using an aldehyde (e.g. formaldehyde) and reducing agent (e.g. sodium cyanoborohydride) in an alcoholic solvent (e.g. methanol) to yield the desired alkylated adduct.

Route (c): The amine intermediate was subjected to standard amide coupling conditions with a diacid (e.g. succinic acid) using an amide coupling reaganet (e.g. HATU) and base (e.g. DIPEA) in an organic solvent (e.g. DMF). The resultant amide was treated with a base (e.g. potassium carbonate), an alkyl halide (e.g. methyl iodide) and an alcohol (e.g. methanol) in an organic solvent (e.g acetonitrile) to yield the desired cyclic diamide adduct.

Route (d): The amine intermediate was treated with a halide substitued isocyanate (e.g. 2-chloroethyl isocyanate) in an organic solvent (e.g. dichloromethane) to yield the urea adduct. This adduct was stirred in an organic solvent (e.g. ethanol) with base (e.g. sodium hydroxide) to yield the cyclic urea adduct.

Method E

The sulfonamide analogue was prepared by reacting the alkyl amino analogue with a sulfonyl chloride (e.g. 4-fluorophenyl)sulfonyl chloride) and base (e.g. DIPEA) in a suitable solvent (e.g. DMF).

Scheme 5:

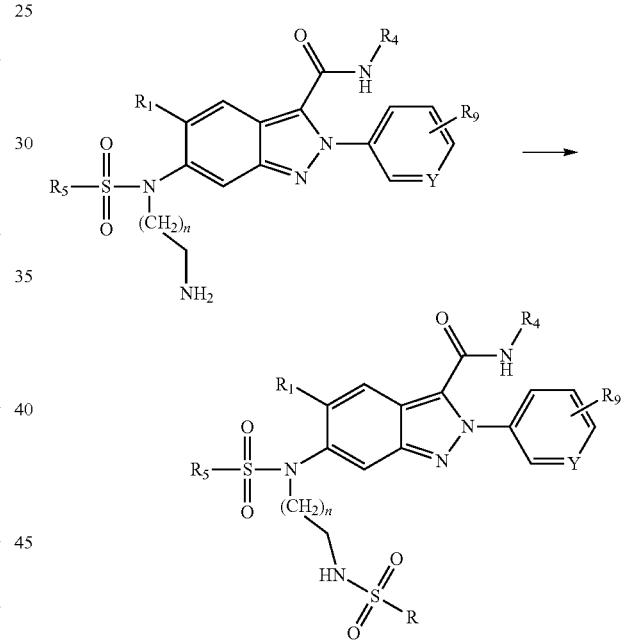

where $R_1$ may be, for example, $C_{3-6}$cycloalkyl such as cyclopropyl, $C_{1-6}$alkyl including methyl, ethyl, n-propyl and iso-propyl, halo, or $C_{1-6}$alkoxy including methoxy, ethoxy, n-propoxy and iso-propoxy; $R_4$ may be, for example, H or $C_{1-6}$alkyl; $R_5$ may be, for example, $C_{1-6}$alkyl including methyl, ethyl, n-propyl and iso-propyl preferably methyl or $C_{1-3}$alkylhalo (i.e. $C_{1-3}$alkyl substituted with halo such as $CF_3$ or $CHF_2$); $R_9$ maybe, for example, H or one or more substituents each independently selected from halo, $C_{1-6}$alkyl, $C_{1-3}$alkylhalo, $C_{1-6}$alkoxy, $NHC_{1-6}$alkyl, $N(C_{1-6}alkyl)_2$, optionally substituted O-phenyl or optionally substituted NH-phenyl; R may be $C_{1-6}$alkyl, $C_{3-6}$cycloalkyl $C_{1-6}$alkoxy, $NHC_{1-6}$alkyl, $N(C_{1-6}alkyl)_2$, or 5-6-membered heterocyclyl, aryl, or 5-6-membered heteroaryl; n may be an integer selected from 0, 1, 2, 3, 4, 5 and 6 and each ——$(CH_2)$—— may be optinally substituted.

Method F

In an alternative method to general Methods B and C, compounds having a sulphonamide alkyl-OH group were synthesised as follows. Alkylation of the sulfonamide was carried out by treating with an optionally substituted alkyl halide (e.g. 2-(bromoethoxy)(tert-butyl)dimethylsilane), base (e.g. potassium carbonate) in a suitable solvent (e.g. DMF). Where the alkyl halide contained a protecting group, the corresponding unprotected analogue could be achieved by deprotection (e.g. ammonium fluoride) in a suitable solvent (e.g. methanol/water).

Scheme 6:

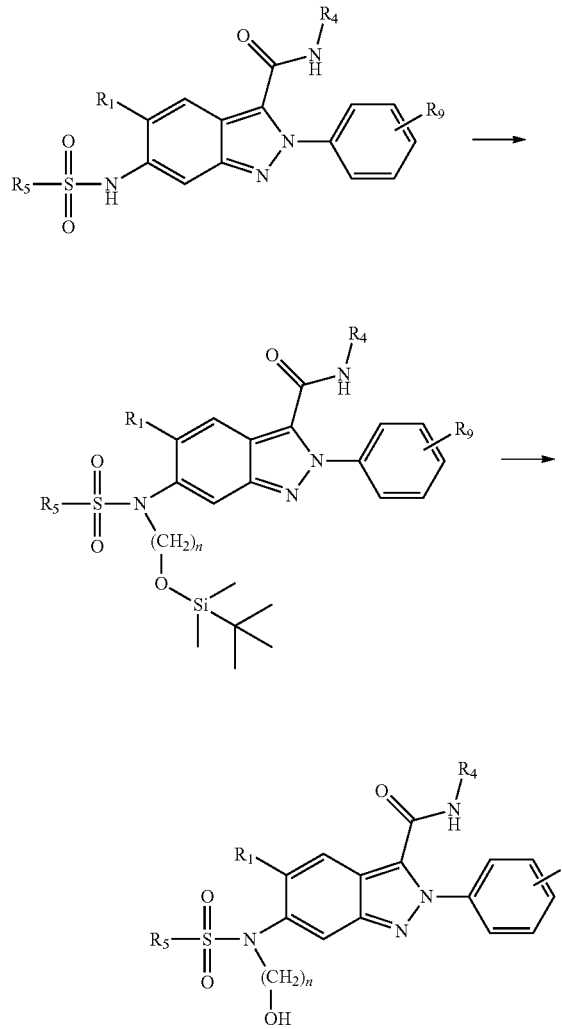

where $R_1$ may be, for example, $C_{3-6}$cycloalkyl such as cyclopropyl, $C_{1-6}$alkyl including methyl, ethyl, n-propyl and iso-propyl, halo or $C_{1-6}$alkoxy including methoxy, ethoxy, n-propoxy and iso-propoxy; $R_4$ may be, for example, H or $C_{1-6}$alkyl; $R_5$ may be, for example, $C_{1-6}$alkyl including methyl, ethyl, n-propyl and iso-propyl preferably methyl or $C_{1-3}$alkylhalo (i.e. $C_{1-3}$alkyl substituted with halo such as $CF_3$ or $CHF_2$); $R_9$ may be, for example, H or one or more substituents each independently selected from halo, $C_{1-6}$alkyl, $C_{1-3}$alkylhalo, $C_{1-6}$alkoxy, $NHC_{1-6}$alkyl, $N(C_{1-6}$alkyl$)_2$, optionally substituted O-phenyl or optionally substituted NH-phenyl; n may be an integer selected from 0, 1, 2, 3, 4, 5 and 6 and each ⸺$(CH_2)$⸺ may be optionally substituted.

Method G

Alkylation of the sulfonamide to the corresponding alkoxy analogue was carried out using a suitable alkyl halide (e.g. 2-bromo-propan-1-ol), base (e.g. potassium carbonate) in a suitable solvent (e.g. acetonitrile). Esterification of the alcohol formed was achieved by treatment with either an anhydride (e.g. phthalic anhydride) and base (e.g. pyridine) or coupling with a carboxylic acid (e.g. acetic acid), coupling agent (e.g. N,N-dicyclohexylcarbodiimide) and base (e.g. 4-DMAP) in a suitable solvent (e.g. DMF).

Scheme 7:

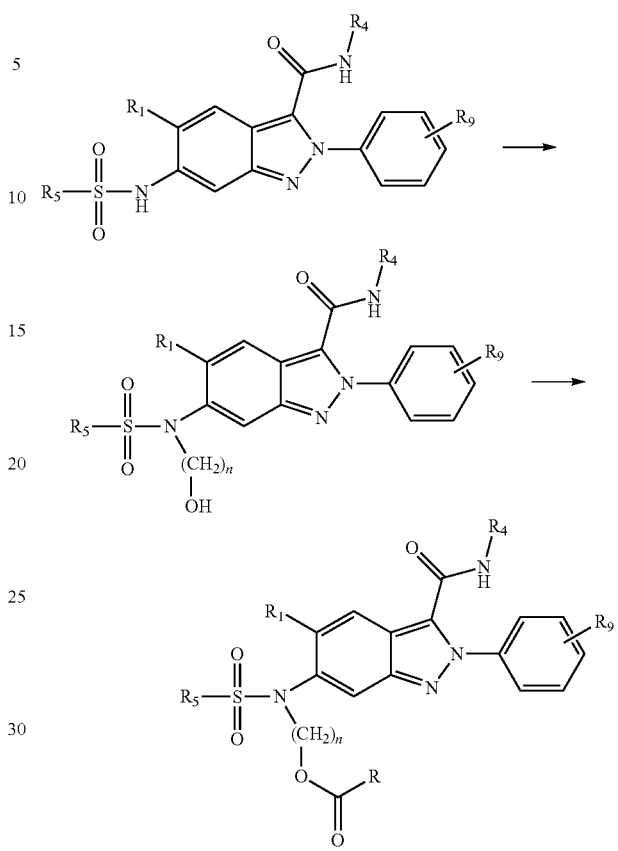

where $R_1$ may be, for example, $C_{3-6}$cycloalkyl such as cyclopropyl, $C_{1-6}$alkyl including methyl, ethyl, n-propyl and iso-propyl, halo or $C_{1-6}$alkoxy including methoxy, ethoxy, n-propoxy and iso-propoxy; $R_4$ may be, for example, H or $C_{1-6}$alkyl; $R_5$ may be, for example, $C_{1-6}$alkyl including methyl, ethyl, n-propyl and iso-propyl preferably methyl or $C_{1-3}$alkylhalo (i.e. $C_{1-3}$alkyl substituted with halo such as $CF_3$ or $CHF_2$); $R_9$ may be, for example, H or one or more substituents each independently selected from halo, $C_{1-6}$alkyl, $C_{1-3}$alkylhalo, $C_{1-6}$alkoxy, $NHC_{1-6}$alkyl, $N(C_{1-6}$alkyl$)_2$, optionally substituted O-phenyl or optionally substituted NH-phenyl; R may be, for example, $C_{1-6}$alkyl, $C_{3-6}$ cycloalkyl, $C_{1-6}$alkoxy, $NHC_{1-6}$alkyl, $N(C_{1-6}$alkyl$)_2$, 5-6-memebered heterocyclyl, aryl, or 5-6-membered heteroaryl; n may be an integer selected from 0, 1, 2, 3, 4, 5 and 6 and each ⸺$(CH_2)$⸺ may be optionally substituted.

Method H

The azide was prepared from the corresponding amino intermediate by diazotization (e.g. with sodium nitrite and dilute hydrochloric acid) followed by the addition of a suitable azide source (e.g. sodium azide). Amide coupling was carried out using a primary or secondary amine (e.g. 4-fluoroaniline), coupling reagent (e.g. HATU), and a base (e.g. DIPEA) in an organic solvent (e.g. DMF). Cyclisation of this intermediate was achieved (e.g. $POCl_3$). Conversion to the amide group was effected in a number of steps by cyanation (e.g. sodium cyanide in DMF), followed by hydrolysis to the amide (e.g. sodium hydroxide in aqueous ethanol), further hydrolysis to the carboxylic acid (e.g. conc. $H_2SO_4$ in water) and finally amide coupling (e.g. methylamine, HATU, DIPEA in DMF). The arylhalide was reacted with a suitably substituted boronic acid or boronic acid derivative (e.g. 3-aminophenylboronic acid) in the presence of a suitable catalyst (e.g. tetrakistriphenylphosphinepalladium(0)) and a suitable base (e.g. cesium carbonate) in a suitable solvent (e.g. ethanol) as described by Miyaura and. Suzuki (see Miyaura, N.; Suzuki, A. J. Chem. Soc., Chem. Commun.

1979, 866-867) to give the corresponding coupled product. This intermediate can be further functionalized through standard transformations, e.g. amide coupling.

Scheme 8:

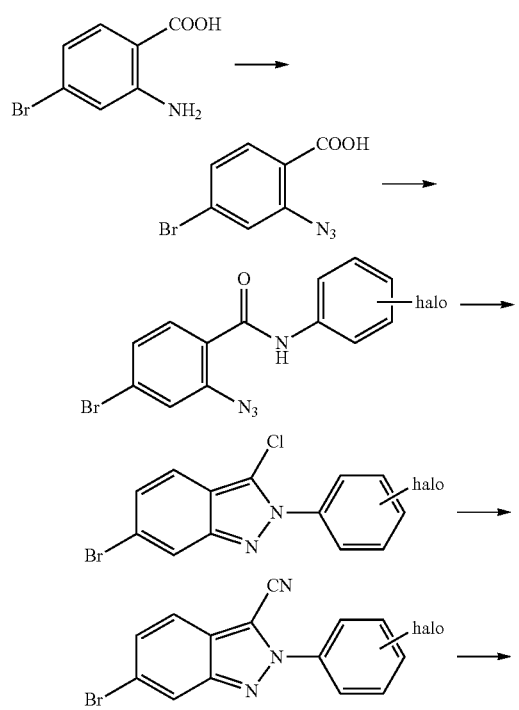

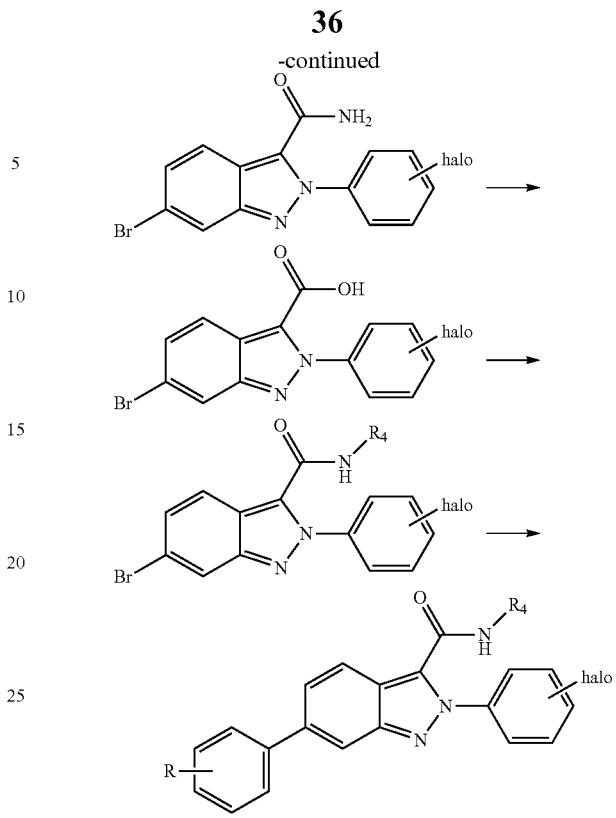

where $R_4$ may be, for example, H or $C_{1-6}$alkyl and R may be an optional substituent and in the case of $NH_2$ may be further reacted under amide coupling conditions to provide an $NHC(\!\!=\!\!O)R'$ group where $R'$ may be selected from, for example, $C_{1-6}$alkyl, aryl, $C_{1-6}$alkylaryl and may be further optionally substituted.

Method I

Scheme 9:

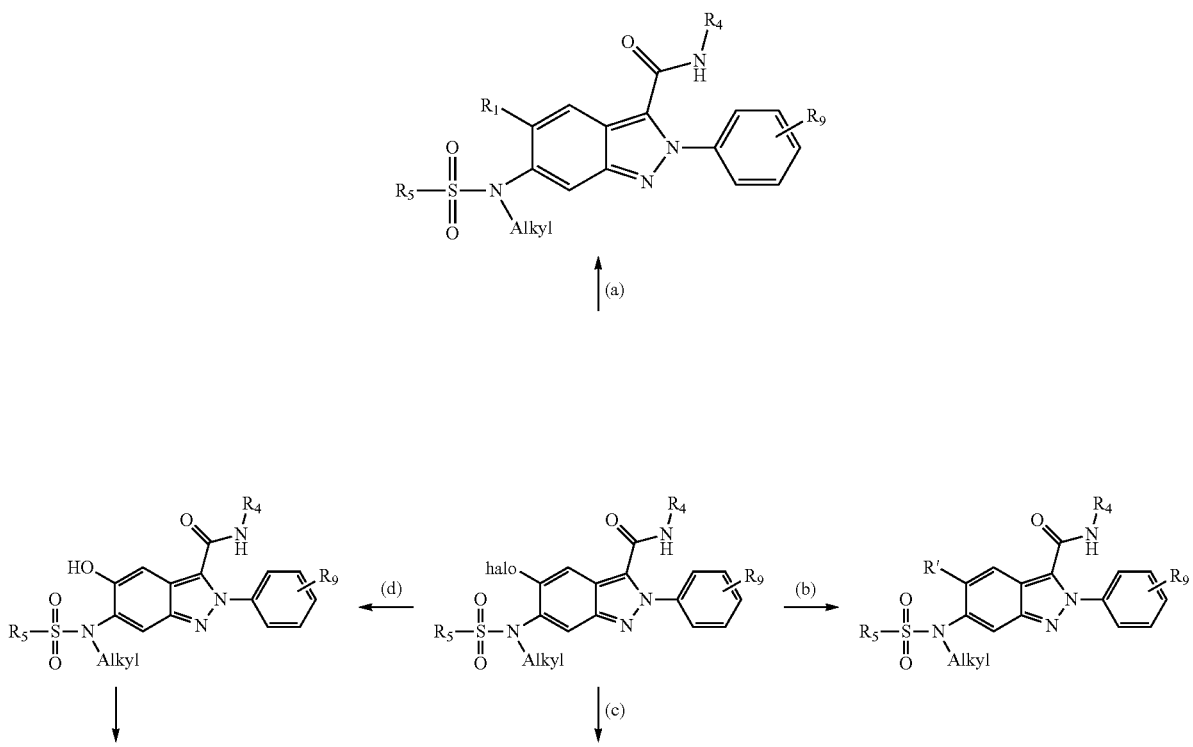

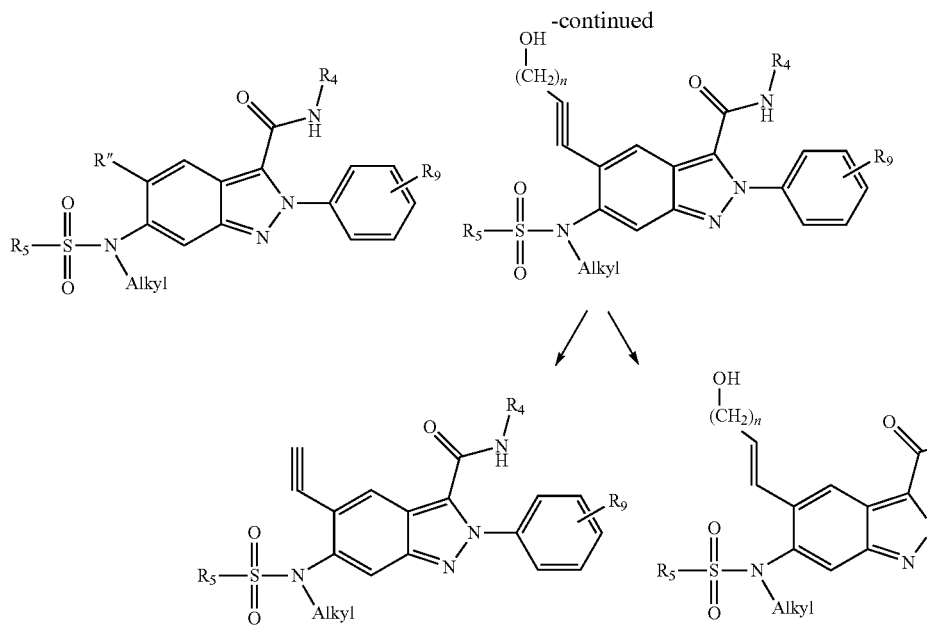

where $R_1$ may be, for example, $C_{3-6}$cycloalkyl such as cyclopropyl, $C_{1-6}$alkyl including methyl, ethyl, n-propyl and iso-propyl, halo, or $C_{1-6}$alkoxy including methoxy, ethoxy, n-propoxy and iso-propoxy; $R_4$ may be, for example, H or $C_{1-6}$alkyl; $R_5$ may be, for example, $C_{1-6}$alkyl including methyl, ethyl, n-propyl and iso-propyl preferably methyl or $C_{1-3}$alkylhalo (i.e. $C_{1-3}$alkyl substituted with halo such as $CF_3$ or $CHF_2$); $R_9$ may be, for example, H or one or more substituents each independently selected from halo, $C_{1-6}$alkyl, $C_{1-3}$alkylhalo, $C_{1-6}$alkoxy, $NHC_{1-6}$alkyl, $N(C_{1-6}$alkyl$)_2$, optionally substituted O-phenyl or optionally substituted NH-phenyl; R may be, for example, H, $C_{1-6}$alkyl, $C_{2-6}$alkenyl; R' may be, for example, $C_{3-6}$cycloalkyl, $C_{3-6}$cycloalkenyl, 5-6-membered heterocyclyl or 5-6-membered heteroaryl; each R" may be $C_{1-6}$alkyl, $C_{1-6}$alkoxy (optionally substituted with CN or halo such as $OCH_2CN$ and $OCHF_2$), $NHC_{1-6}$alkyl or $N(C_{1-6}$alkyl$)_2$; n may be an integer selected from 0, 1, 2, 3, 4, 5 and 6 and each —(CH$_2$)— may be optionally substituted.

Route (a): The aryl halide intermediate was reacted with a suitably substituted boronic acid or boronic acid derivative (e.g vinyl boronic acid) using a base (e.g. cesium carbonate) and a catalyst (e.g. PdCl$_2$(dppf).CH$_2$Cl$_2$) in aqueous organic solvent (e.g. 1,4-dioxane) to give the alkene adduct. This then underwent standard hydrogenation conditions in an organic solvent (e.g methanol) with a catalyst (e.g. 10% palladium on carbon) under a hydrogen atmosphere to give the alkyl adduct.

Route (b): The aryl halide intermediate was reacted with a suitably substituted boronic acid or boronic acid derivative (e.g cyclopentenyl boronic acid) using a base (e.g. cesium carbonate) and a catalyst (e.g. PdCl$_2$(dppf).CH$_2$Cl$_2$) in aqueous organic solvent (e.g. 1,4-dioxane) to give the alkene adduct. This then underwent standard hydrogenation conditions in an organic solvent (e.g methanol) with a catalyst (e.g. 10% palladium on carbon) under a hydrogen atmosphere to give the cycloalkyl adduct.

Route (c): The aryl halide intermediate was subjected to a Sonogashira reaction by treating with a terminal alkyne (e.g. propargyl alcohol) using base (e.g. cesium carbonate), ligand (e.g. 2'-dicyclohexylphosphino-2,6-di-isopropyl-4-sulfonato-1,1'-biphenyl hydrate sodium salt) and catalyst (e.g. PdCl$_2$(MeCN)$_2$) in aqueous organic solvent (e.g. acetonitrile) to yield the alkyne adduct. The alkyne adduct was then subjected to hydrogenation conditions using a catalyst (e.g. Lindlar catalyst) and quinoline in an organic solvent (e.g. ethyl acetate) under an atmosphere of hydrogen to give the reduced species. The propargyl alcohol adduct from the Sonogashira reaction was also treated with an oxidant (e.g. manganese dioxide) and base (e.g. potassium hydroxide) in an organic solvent (e.g. diethyl ether) to yield the terminal alkyne adduct.

Route (d): The aryl halide was treated with base (e.g. potassium hydroxide), ligand (e.g. t-butyl-XPhos) and catalyst (e.g. Pd$_2$(dba)$_3$) in aqueous organic solvent (e.g. dioxane) to give the phenol adduct. The phenol adduct was reacted with an alkylating reagent (e.g. sodium chlorodifluoroacetate), and base (e.g. potassium carbonate) in aqueous organic solvent (e.g. DMF) to give the alkylated adduct.

Method J

In an alternative method to general Methods B and C, compounds having a sulphonamide alkyl-OH group were synthesised as follows. Carbonylation was carried out on the aryl halide using a carbonylating agent (e.g. carbon monoxide), base (e.g. triethylamine), catalyst (e.g. Pd(OAc)$_2$), ligand (e.g. 1,3-bis(diphenylphosphino)propane), and reducing agent (e.g. triethylsilane) in a suitable solvent (e.g. DMF). This intermediate was converted to the alkoxide by treatment with a suitable alcohol (e.g. 2-propanol), acid (e.g. trifluoroacetic acid), and a reducing agent (e.g. triethylsilane) in a suitable solvent (e.g. nitromethane). Alkylation of the sulfonamide group was carried out using an alkylhalide (e.g. 3-bromopropanol) and base (e.g. potassium carbonate) in a suitable solvent (e.g. DMF).

Scheme 10:

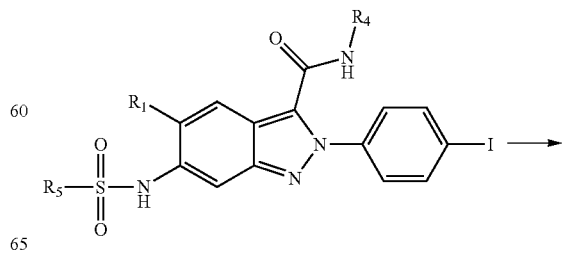

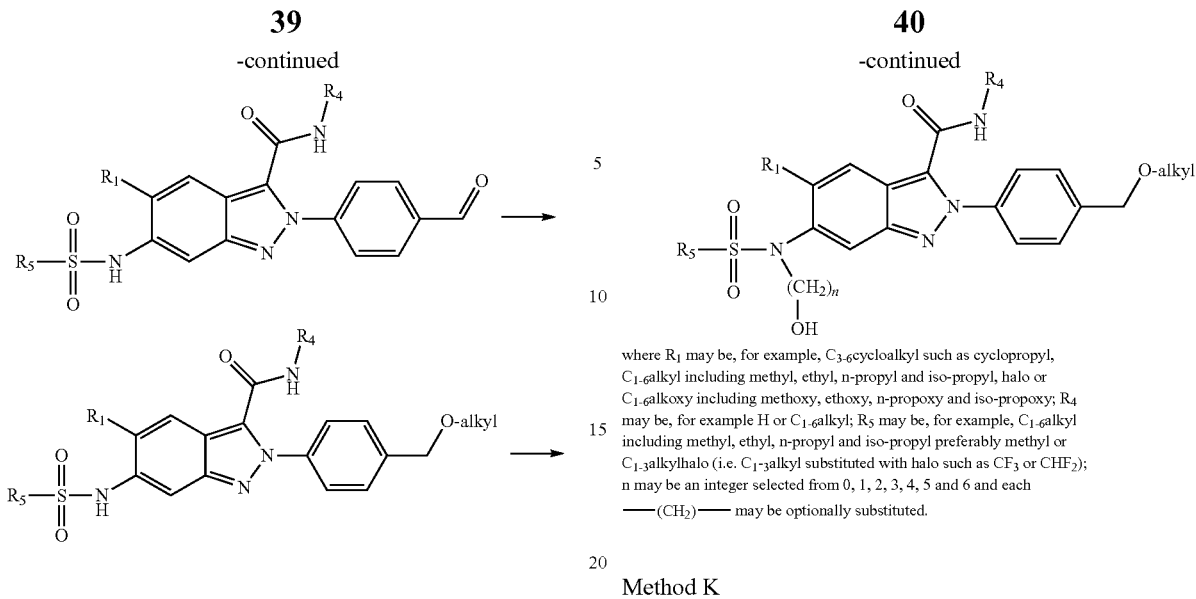

where $R_1$ may be, for example, $C_{3-6}$cycloalkyl such as cyclopropyl, $C_{1-6}$alkyl including methyl, ethyl, n-propyl and iso-propyl, halo or $C_{1-6}$alkoxy including methoxy, ethoxy, n-propoxy and iso-propoxy; $R_4$ may be, for example H or $C_{1-6}$alkyl; $R_5$ may be, for example, $C_{1-6}$alkyl including methyl, ethyl, n-propyl and iso-propyl preferably methyl or $C_{1-3}$alkylhalo (i.e. $C_{1-3}$alkyl substituted with halo such as $CF_3$ or $CHF_2$); n may be an integer selected from 0, 1, 2, 3, 4, 5 and 6 and each —(CH$_2$)— may be optionally substituted.

Method K

Scheme 11:

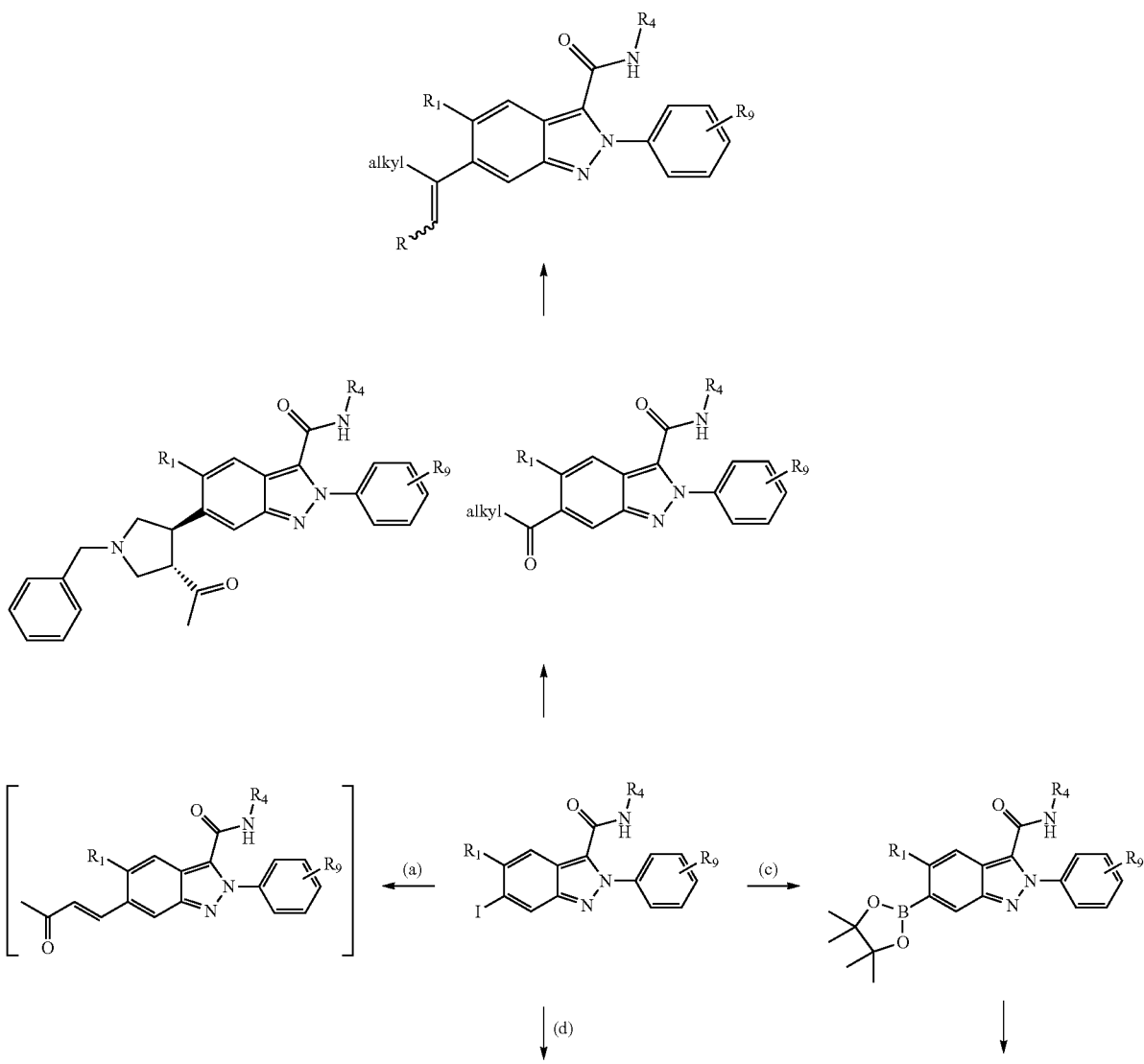

41        42
-continued
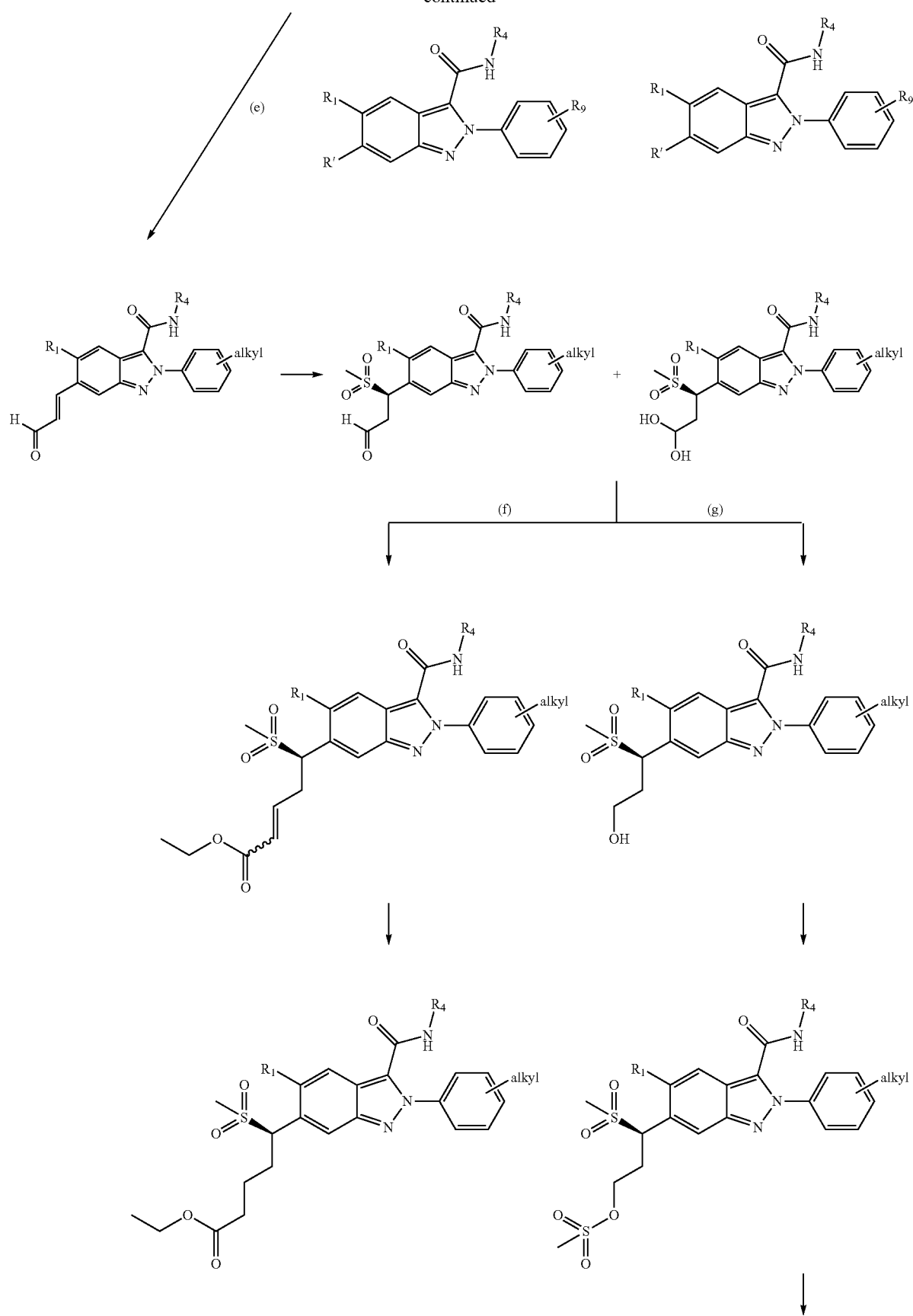

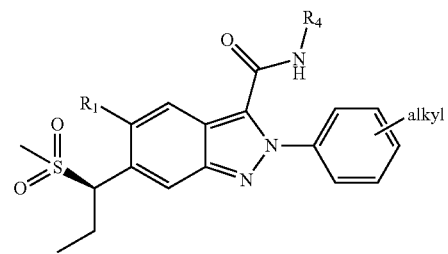

where R₁ may be, for example, $C_{3-6}$cycloalkyl such as cyclopropyl, $C_{1-6}$alkyl including methyl, ethyl, n-propyl and iso-propyl, halo, or $C_{1-6}$alkoxy including methoxy, ethoxy, n-propoxy and iso-propoxy; R₄ may be, for example, H or $C_{1-6}$alkyl; R₉ may be, for example, H or one or more substituents each independently selected from halo, $C_{1-6}$alkyl, $C_{1-3}$alkylhalo, $C_{1-6}$alkoxy, $NHC_{1-6}$alkyl, $N(C_{1-6}$alkyl$)_2$, optionally substituted O-phenyl or optionally substituted NH-phenyl; R may be, for example, $CO_2C_{1-6}$alkyl or OH; and R' may be, for example, 5-6-membered heteroaryl.

Route (a): The iodo intermediate was submitted to a Heck reaction by reacting with an alkene (e.g. but-3-en-2-one) using a base (e.g. potassium carbonate) and a catalyst (e.g. palladium acetate) in an organic solvent (e.g. DMF) to yield the alkene intermediate. The alkene intermediate was treated with N-(methoxymethyl)-1-phenyl-N-(trimethylsilylmethyl)methanamine and acid (e.g. trifluoroacetic acid) in an organic solvent (e.g. DCM) to give the pyrrolidine analogue.

Route (b): The iodo intermediate was reacted with lithium chloride, base (e.g. DIPEA), activated acid (e.g. acetic anhydride) and catalyst (e.g. Pd₂(dba)₃) in an organic solvent (e.g. DMF) to give the ketone analogue. The ketone analogue was treated with an ylide (e.g. the ylide generated from sodium hydride and triethylphosphonoacetate) to give the α,β-unsaturated ester. The α,β-unsaturated ester was treated with a reducing agent (e.g. diisobutylaluminium hydride) to give the hydroxyl analogue.

Route (c): The iodo intermediate was reacted with bis(pinacolato)diboron, base (e.g. potassium acetate) and catalyst (e.g. Pd(dppf)₂Cl₂.CH₂Cl₂) in an organic solvent (e.g DMSO) to yield the boronic pinacol ester. The boronic pinacol ester underwent standard Suzuki reaction with a heteroarylhalide (e.g. 2,4,5-tribromo-1-ethyl-1H-imidazole) using base (e.g. sodium carbonate) and catalyst (e.g. Pd(PPh₃)₄) in aqueous organic solvent (e.g. 1,4-dioxane) to give the heteroaryl analogue. The dibromoheteroaryl analogue was treated with catalyst (e.g. 10% palladium on carbon) in an organic solvent (e.g. methanol) under an atmosphere of hydrogen to give the desired heteroaryl analogue.

Route (d): The iodo intermediate was subjected to a Suzuki reaction by reacting with a heteroaryl boronic acid or boronic acid derivative (e.g. 3,5-dimethylisoxazole-4-boronic acid) using base (e.g. sodium carbonate) and catalyst (e.g. Pd(PPh₃)₄) in aqueous organic solvent (e.g. 1,4-dioxane) to give the heteroaryl analogue.

Route (e): The iodo intermediate was submitted to a Heck reaction with an α,β unsaturated aldehyde (e.g. acrolein) using base (e.g. potassium carbonate), benzyl(triethyl)ammonium chloride and catalyst (e.g. palladium acetate) in an organic solvent (e.g. DMF) to yield the α,β unsaturated aldehyde intermediate. The α,β unsaturated aldehyde was reacted with an aqueous solution of sodium methanesulfinate and acid (e.g. hydrochloric acid) in an organic solvent (e.g 1,4-dioxane) to give a mixture of the aldehyde sulfone analogue and the diol sulfone analogue.

Route (f): The mixture of the aldehyde sulfone analogue and the diol sulfone analogue was treated with an ylide (e.g. ethyl(triphenyl-λ⁵-phosphanylidene)acetate) in an organic solvent (e.g. DCM) to afford the α,β unsaturated ester. The α,β unsaturated ester was treated with catalyst (e.g. 10% palladium on carbon) in an organic solvent (e.g. methanol) under an atmosphere of hydrogen to yield the ester analogue.

Route (g): The mixture of the aldehyde sulfone analogue and the diol sulfone analogue underwent reduction using a reducing agent (e.g. sodium borohydride) in aqueous organic solvent (e.g. 1,4-dioxane) to afford the hydroxy analogue. The hydroxy analogue was treated with an activated sulfonic acid (e.g. methanesulfonyl chloride) and base (e.g. DIPEA) in an organic solvent (e.g. dichloromethane) to yield the sulfonate. The sulfonate was treated with reducing agent (e.g. lithium triethylborohydride) in an organic solvent (e.g. THF) to afford the desired alkyl analogue.

Method L

Treating the aryl amine analogue with a thiol (e.g. benzyl mercaptan), base (e.g. DIPEA), catalyst (e.g. Pd₂(dba)₃) and ligand (e.g. Xantphos), in a suitable solvent (e.g. 1,4-dioxane) afforded the thio intermediate. This intermediate was converted to the sulfonyl halide by treatment with an oxidizing agent (e.g. iodosobenzene) and acid (e.g. concentrated hydrochloric acid) in a suitable solvent (e.g. dichloromethane). The intermediate was treated with a primary or secondary amine (e.g. ethylamine) and base (e.g. triethylamine) in an organic solvent (e.g. DCM) to afford the sulfonamide analogue.

Scheme 12:

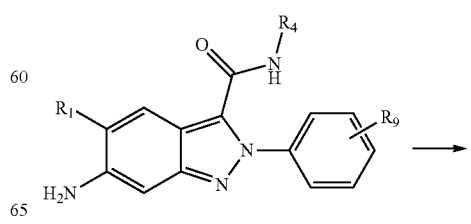

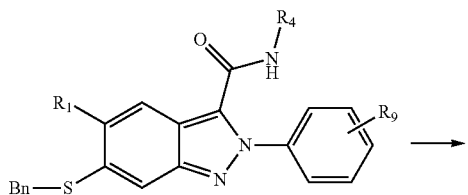

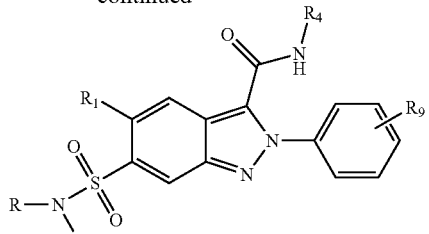

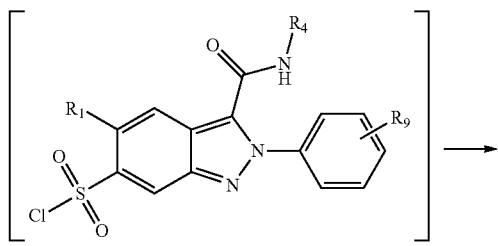

where $R_1$ may be, for example, $C_{3-6}$cycloalkyl such as cyclopropyl, $C_{1-6}$alkyl including methyl, ethyl, n-propyl and iso-propyl, halo or $C_{1-6}$alkoxy including methoxy, ethoxy, n-propoxy and iso-propoxy; $R_4$ may be, for example H or $C_{1-6}$alkyl; $R_5$ may be, for example, $C_{1-6}$alkyl including methyl, ethyl, n-propyl and iso-propyl preferably methyl or $C_{1-3}$alkylhalo (i.e. $C_{1-3}$alkyl substituted with halo such as $CF_3$ or $CHF_2$);

n may be an integer selected from 0, 1, 2, 3, 4, 5 and 6 and each —(CH$_2$)— may be optionally substituted.

Method M

The sulfonamide analogue was alkylated by treatment with a suitable ester substituted alkyl halide (e.g. ethyl 4-bromobutyrate) and base (e.g. potassium carbonate) in an organic solvent (e.g. acetonitrile) to afford an ester intermediate. This intermediate was hydrolysed under basic conditions (e.g. lithium hydroxide) in an appropriate solvents (e.g aqueous 1,4-dioxane/methanol) to afford the corresponding acid. Alternatively this acid may be prepared by the oxidation of a suitably substituted alkyloxy analogue with an oxidizing agent (e.g. periodic acid) in a solvent (e.g. acetonitrile) followed by additional oxidation using an oxidizing agent (e.g. pyridinium chlorochromate) to afford the corresponding acid.

Scheme 13:
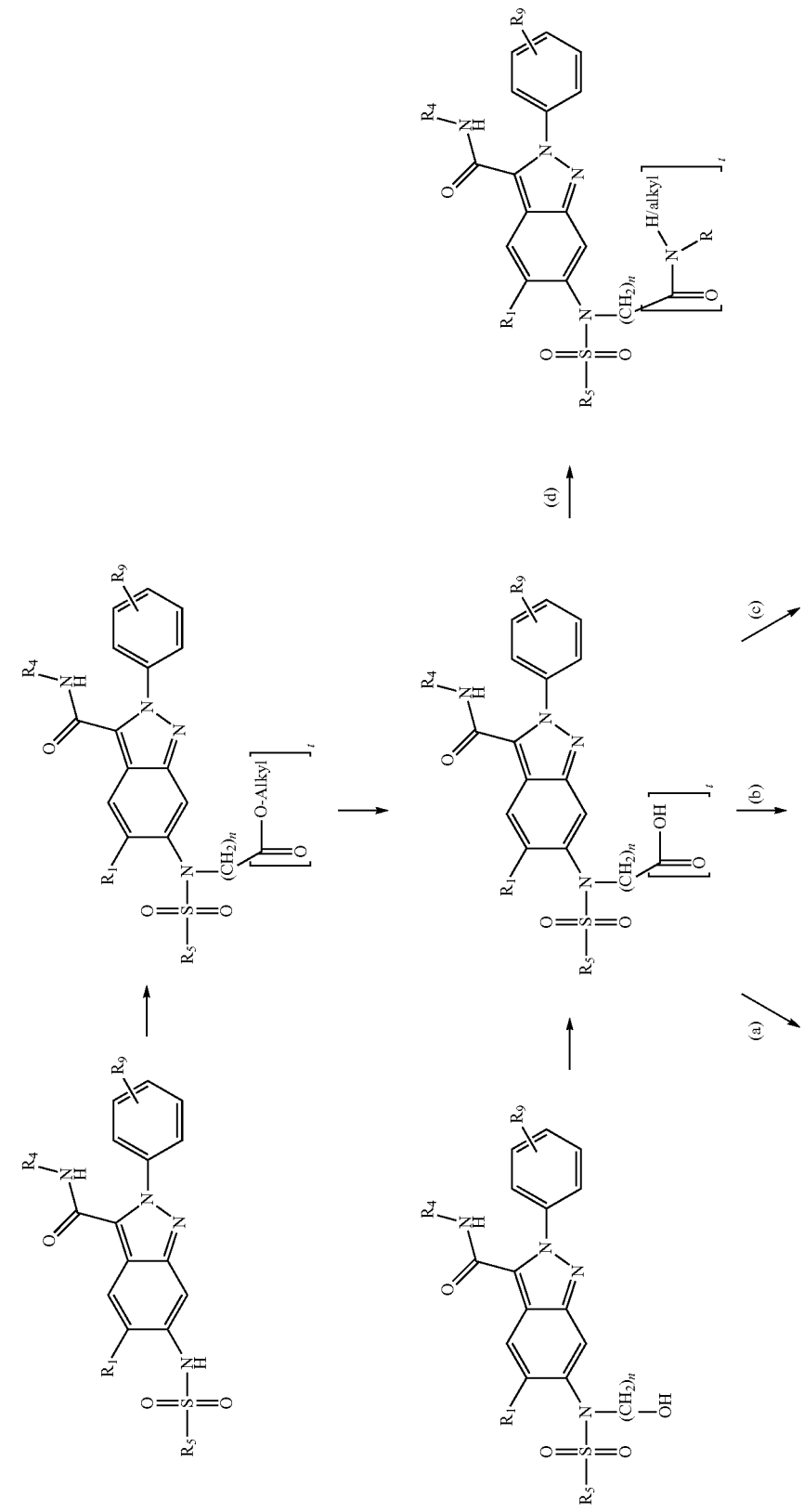

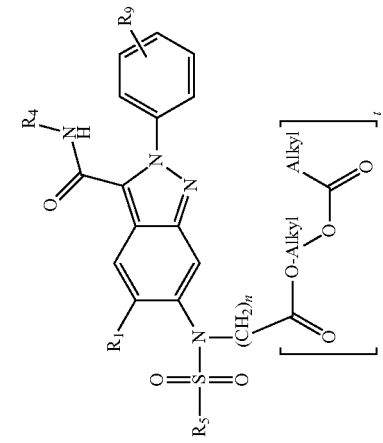

-continued

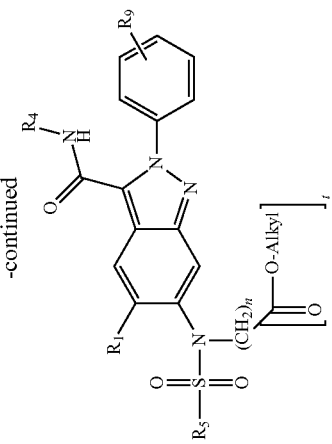

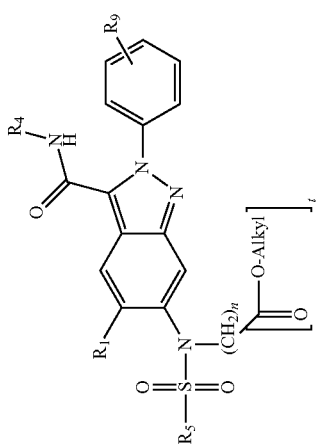

where $R_1$ may be, for example, $C_{3-6}$cycloalkyl such as cyclopropyl, $C_{1-6}$alkyl including methyl, ethyl, n-propyl and iso-propyl, halo or $C_{1-6}$alkoxy including methoxy, ethoxy, n-propoxy and iso-propoxy; $R_4$ may be, for example, H or $C_{1-6}$alkyl; $R_5$ may be, for example, $C_{1-6}$alkyl including methyl, ethyl, n-propyl and iso-propyl preferably methyl or $C_{1-3}$alkylhalo (i.e. $C_{1-3}$alkyl substituted with halo such as $CF_3$ or $CHF_2$); $R_9$ may be, for example, H or one or more substituents each independently selected from halo, $C_{1-6}$alkyl, $C_{1-3}$alkylhalo, $C_{1-6}$alkoxy, $NHC_{1-6}$alkyl, $N(C_{1-6}$alkyl$)_2$, optionally substituted O-phenyl or optionally substituted NH-phenyl; R may be, for example, R may be H, $C_{1-6}$alkyl, $SO_2C_{1-6}$alkyl, $SO_2N(C_{1-3}$alkyl$)$, $SO_2$aryl or $SO_2$-5-6- membered heteroaryl; t is 1 or 2; n may be an integer selected from 0, 1, 2, 3, 4, 5 and 6 and each —$(CH_2)$— may be optionally substituted.

Route (a): The acid analogue was subjected to acidic (e.g. sulphuric acid) esterification conditions in an alcohol (e.g. butanol) to give the corresponding ester.

Route (b): The acid analogue was subjected to standard esterification conditions using an aryl alcohol (e.g. phenol), coupling agent (e.g. HATU), and base (e.g. DIPEA) in an organic solvent (DMF) to afford the corresponding ester.

Route (c): The acid analogue was treated with an alkyl halide (e.g. chloromethyl pivalate) and a base (DIPEA) in the presence of sodium iodide to afford the corresponding ester.

Route (d): The acid analogue was subjected to standard amide coupling conditions with an amine (e.g. isopropylamine), coupling reagent (e.g. HATU) and a base (e.g. DIPEA) in an organic solvent (e.g. DMF) to afford the corresponding amide.

Method N

The dihydroxy analogue was prepared from the corresponding protected diol following suitable deprotection (e.g. trifluoroacetic acid) in a solvent (e.g. aqueous THF/methanol mixture). The dihydroxy analogue was then converted to the cyclic carbonate by treating with an appropriately substituted carbonyl compound (e.g. carbonyldiimidazole) in an organic solvent (e.g. dichloromethane).

Scheme 14:

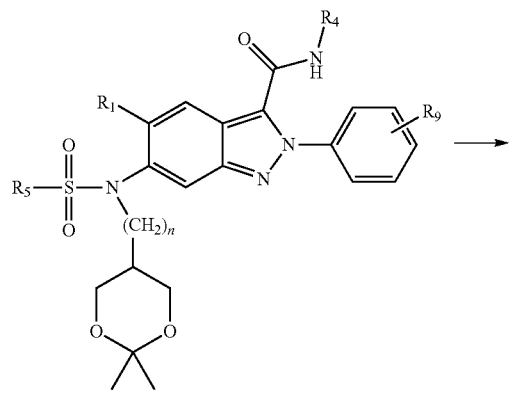

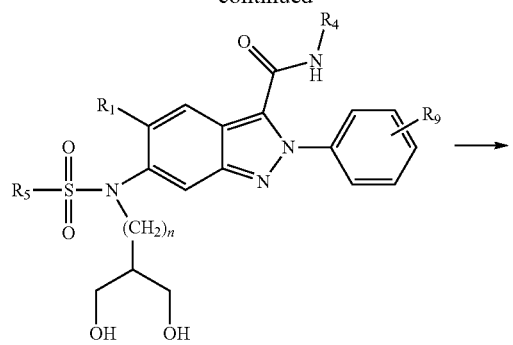

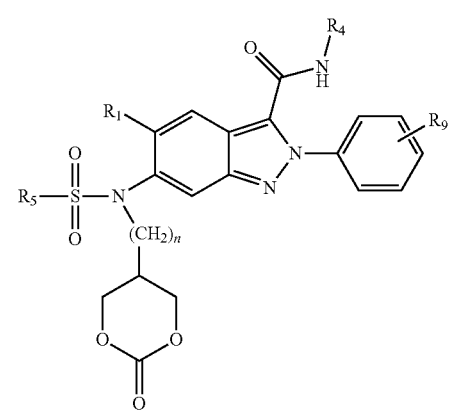

where $R_1$ may be, for example, $C_{3-6}$cycloalkyl such as cyclopropyl, $C_{1-6}$alkyl including methyl, ethyl, n-propyl and iso-propyl, halo or $C_{1-6}$alkoxy including methoxy, ethoxy, n-propoxy and iso-propoxy; $R_4$ may be, for example H or $C_{1-6}$alkyl; $R_5$ may be, for example, $C_{1-6}$alkyl including methyl, ethyl, n-propyl and iso-propyl preferably methyl or $C_{1-3}$alkylhalo (i.e. $C_{1-3}$alkyl substituted with halo such as $CF_3$ or $CHF_2$); $R_9$ may be halo; n may be an integer selected from 0, 1, 2, 3, 4, 5 and 6 and each —(CH$_2$)— may be optionally substituted.

Method O

Scheme 15:

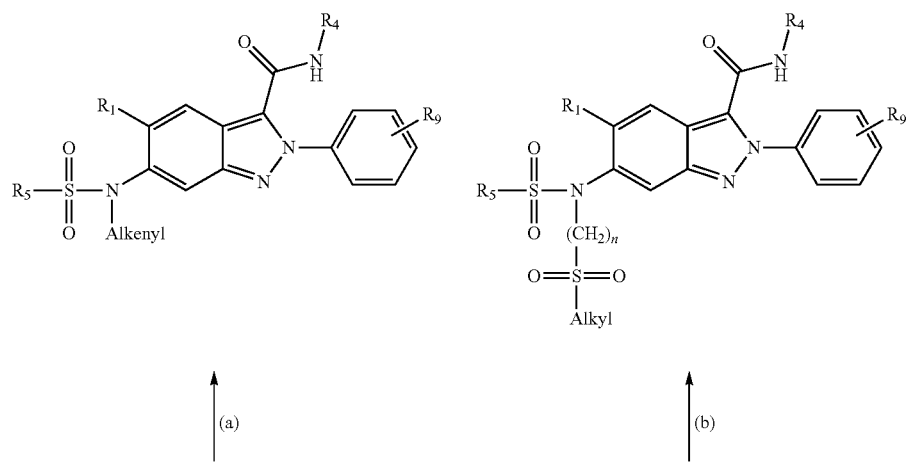

-continued

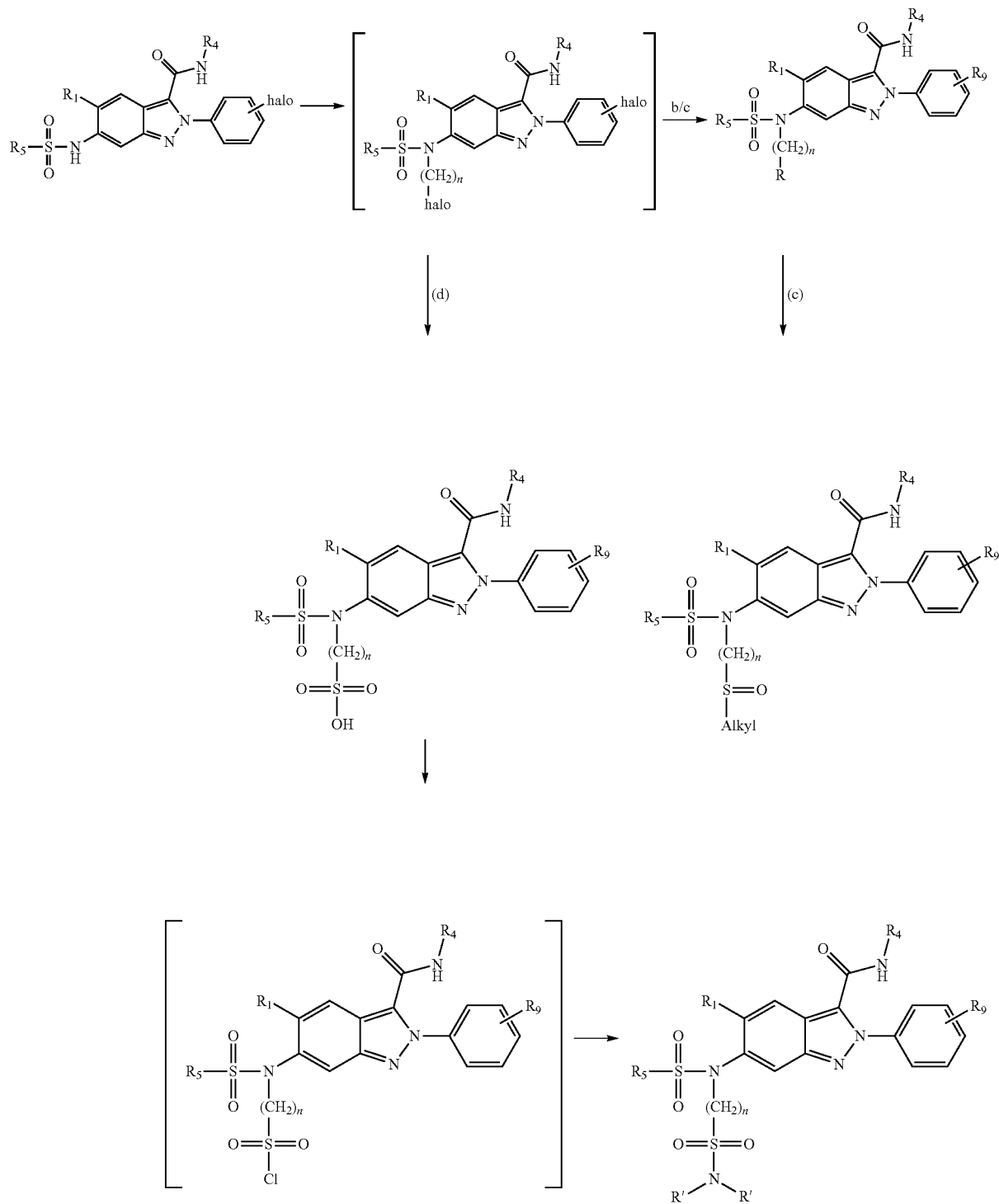

where $R_1$ may be, for example, $C_{3-6}$cycloalkyl such as cyclopropyl, $C_{1-6}$alkyl including methyl, ethyl, n-propyl and iso-propyl, halo or $C_{1-6}$alkoxy including methoxy, ethoxy, n-propoxy and iso-propoxy; $R_4$ may be, for example H or $C_{1-6}$alkyl; $R_5$ may be, for example, $C_{1-6}$alkyl including methyl, ethyl, n-propyl and iso-propyl preferably methyl or $C_{1-3}$alkylhalo (i.e. $C_{1-3}$alkyl substituted with halo such as $CF_3$ or $CHF_2$); $R_9$ may be, for example, H or one or more substituents each independently selected from halo, $C_{1-6}$alkyl, $C_{1-3}$alkylhalo, $C_{1-6}$alkoxy, $NHC_{1-6}$alkyl, $N(C_{1-6}alkyl)_2$, optionally substituted O-phenyl or optionally substituted NH-phenyl; R may be, for example, SH, $SC_{1-6}$alkyl or $C_{1-6}$alkoxy; each R' may be independently H or $C_{1-6}$alkyl; n may be an integer selected form 0, 1, 2, 3, 4, 5 and 6 and each ——(CH2)—— may be optionally substituted.

Route (a): The sulfonamide analogue was alkylated with a a suitable dihaloalkane (e.g. 1,3-dibromopropane) using a suitable solvent (e.g. acetonitrile) and base (e.g. potassium carbonate) to give a bromoalkylsulfonamide. This intermediate was then treated with a suitable base (e.g. sodium hydride) in an appropriate solvent (e.g. THF) to give the alkenylsulfonamide analogue.

Route (b): The bromoalkylsulfonamide intermediate was prepared as described above in Method O, Route (a). This intermediate was then treated with an appropriate metalthioalkoxide (e.g sodium thiomethoxide) or metalalkoxide (e.g. sodium methoxide) in a suitable solvent (e.g. methanol) to give the corresponding alkylhioether or alkyl ether respectively. The alkylthioether described above (i.e. X=S) can be oxidised to the corresponding sulfone by treatment with a suitable oxidizing agent (e.g. oxone).

Route (c): The alkylthioether was prepared as described above in Method O, Route (b) and oxidised to the corresponding sulfoxide analogue using a suitable oxidising agent (e.g. sodium periodate).

Route (d): The bromoalkylsulfonamide intermediate was prepared as described above in Method O, Route (a) and then treated with a suitable sulfonylating agent (e.g. sodium sulfite) to give the corresponding sulfonic acid. The sulfonic acid was then converted to the corresponding sulfonyl chloride using a standard dehydrating/chlorinating agent (e.g. phosphorus oxychloride). The sulfonylchloride can then be treated with ammonia or a primary/secondary amine to give the corresponding sulfonamide.

Method P

Scheme 16:

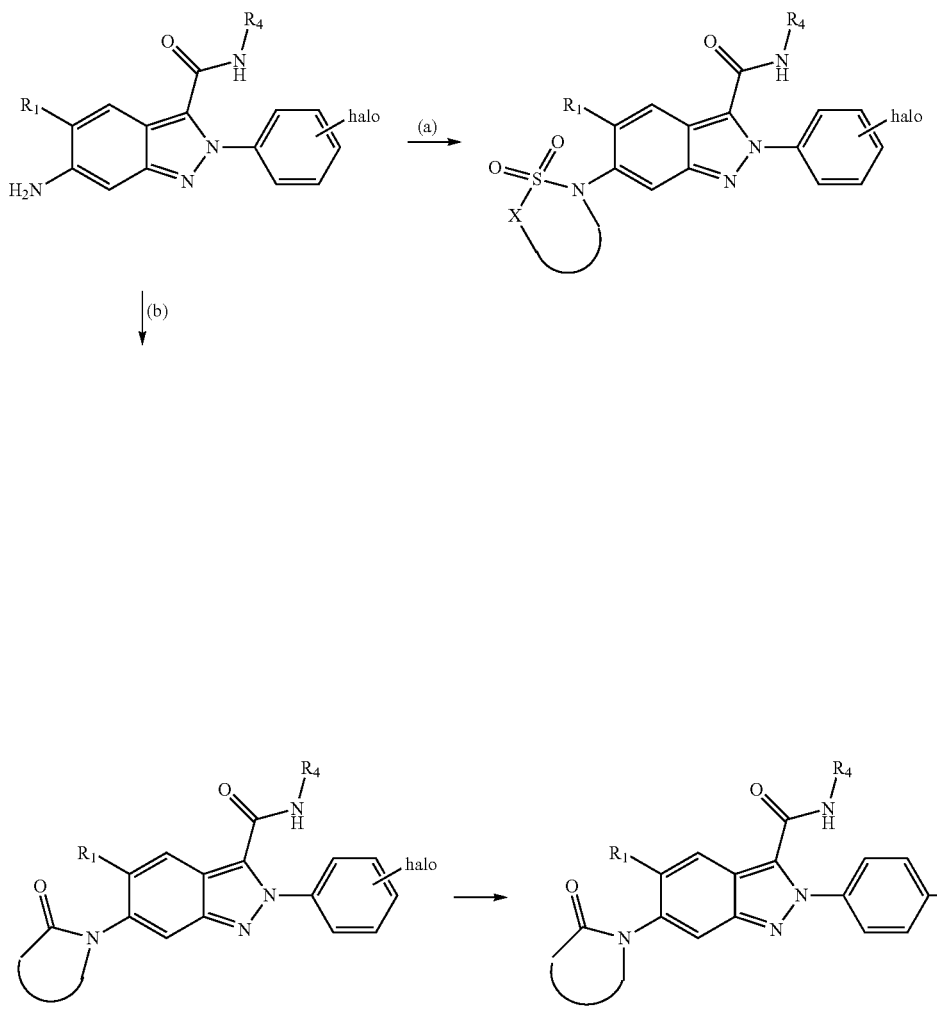

where $R_1$ may be, for example, $C_{3-6}$cycloalkyl such as cyclopropyl, $C_{1-6}$alkyl including methyl, ethyl, n-propyl and iso-propyl, halo, or $C_{1-6}$alkoxy including methoxy, ethoxy, n-propoxy and iso-propoxy; $R_4$ may be, for example, H or $C_{1-6}$alkyl; and X may be, for example, CH, $CH_2$, $CHC_{1-6}$alkyl, NH or $NC_{1-6}$alkyl.

Route (a): The aryl amino analogue was treated with a haloalkyl sulfamoyl chloride (e.g. N-(2-chloroethyl)-sulfamoyl chloride) or haloalkyl sulfonyl chloride (e.g. 3-chloropropylsulfonyl chloride) and a base (e.g. triethylamine) in an organic solvent (e.g. DCM). Cyclisation of the intermediate with a base (e.g. potassium carbonate) in an organic solvent (e.g. DMSO) afforded the corresponding cyclic sulfamide or cyclic sulfonamide analogues respectively.

Route (b): The aryl amino analogue was N-acylated using a haloalkyl acid halide (e.g. 4-bromobutyrylchloride) and a suitable base/activating agent (e.g. 4-DMAP) in an organic solvent (e.g. DCM). The resultant acyclic intermediate was treated with a base (e.g. sodium hydride) in a suitable solvent (e.g. DMF) to give the corresponding cyclic lactam. Where this intermediate contained a haloaryl group, coupling of this with a primary or secondary amine (e.g. isobutylamine), a base (e.g. tert-butoxide), catalyst (e.g. $Pd_2(dba)_3$), and ligand (e.g. (2-biphenyl)di-tert-butylphosphine) in an appropriate solvent (e.g. 1,4-dioxane) gave the corresponding coupled product.

Method Q tic acid) in an organic solvent (DCM) was carried out. The resultant amine was sulfonylated with a suitable sulfonylating agent (e.g. methanesulfonyl chloride), in the presence of a base (e.g. DIPEA) in an organic solvent (e.g. DCM) to afford the corresponding sulfonamide product.

Method R

The sulfonamide analogue was alkylated using an alkyl halide (e.g. bromoethane) and base (e.g. potassium carbonate) in a suitable solvent (e.g. acetonitrile). Deprotection (e.g. boron trifluoride) in a suitable solvent (e.g. dichloromethane) gave the pyridone intermediate which was treated with an appropriate triflating agent (e.g. triflic anhydride) and base (e.g. triethylamine) in a suitable solvent (e.g. dichloromethane) to afford the corresponding triflate intermediate. This intermediate was treated with a primary or secondary amine (e.g. isobutylamine) in a suitable solvent (e.g. 1,4-dioxane) to give the corresponding alkylamino analogue.

Scheme 17:

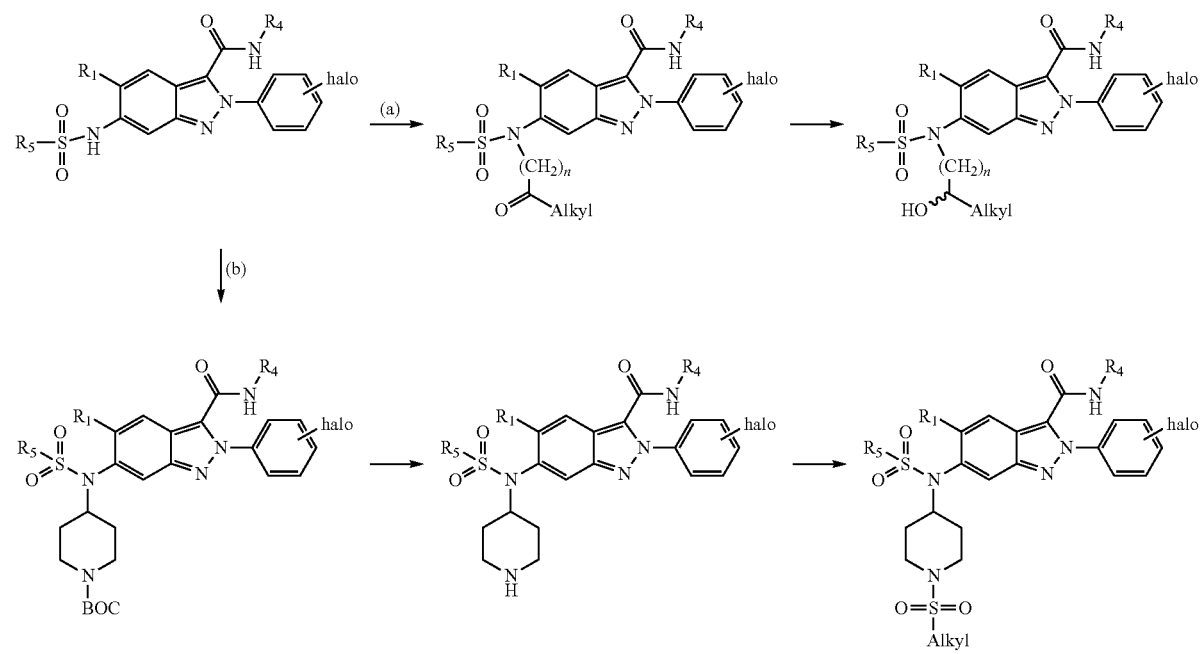

where $R_1$ may be, for example, $C_{3-6}$cycloalkyl such as cyclopropyl, $C_{1-6}$alkyl including methyl, ethyl, n-propyl and iso-propyl, halo, or $C_{1-6}$alkoxy including methoxy, ethoxy, n-propoxy and iso-propoxy; $R_4$ may be, for example, H or $C_{1-6}$alkyl; $R_5$ may be, for example, $C_{1-6}$alkyl including methyl, ethyl, n-propyl and iso-propyl preferably methyl or $C_{1-3}$alkylhalo (i.e. $C_{1-3}$alkyl substituted with halo such as $CF_3$ or $CHF_2$); $R_9$ may be for example, H or one or more substituents each independently selected from halo, $C_{1-6}$alkyl, $C_{1-3}$alkylhalo, $C_{1-6}$alkoxy, $NHC_{1-6}$alkyl, $N(C_{1-6}$alkyl$)_2$, optionally substituted O-phenyl, or optionally substituted NH-phenyl; n may be in integer selected from 0, 1, 2, 3, 4, 5 and 6 and each —($CH_2$)— may be optionally substituted.

Route (a): The aryl sulfonamide analogue was alkylated by treating with a suitable haloalkyl ketone (e.g. chloroacetone) and a base (e.g. potassium carbonate) in an organic solvent (e.g ACN). The resultant keto-intermediate was reduced to the corresponding racemic alcohol using a reducing agent (e.g. sodium borohydride) in a suitable organic solvent (e.g. a mixture of tetrahydrofuran and MeOH).

Route (b): The aryl sulfonamide analogue was alkylated by treating with a halogenated heterocycle (e.g. N-Boc-4-bromopiperidine) and a base (e.g. potassium carbonate) in an organic solvent (e.g. ACN). Where the resultant adduct contained an N-protecting group, deprotection (e.g. trifluoroace- Scheme 18:

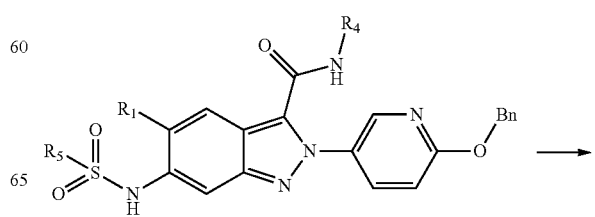

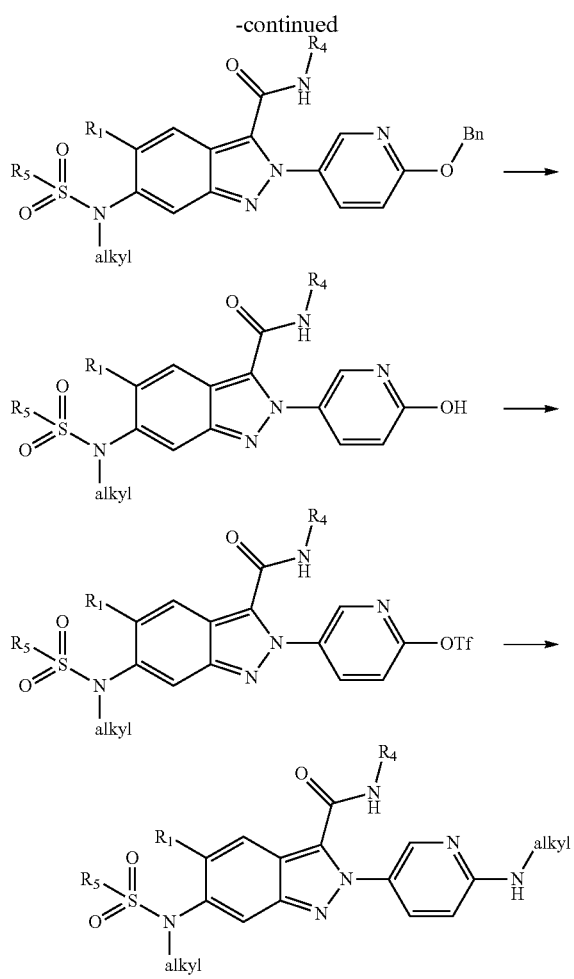

where $R_1$ may be, for example,
$R_1$ may be, for example, $C_{3-6}$cycloalkyl such as cyclopropyl, $C_{1-6}$alkyl including methyl, ethyl, n-propyl and iso-propyl, halo or $C_{1-6}$alkoxy including methoxy, ethoxy, n-propoxy and iso-propoxy; $R_4$ may be, for example, H or $C_{1-6}$alkyl; $R_5$ may be, for example, $C_{1-6}$alkyl including methyl, ethyl, n-propyl and iso-propyl preferably methyl or $C_{1-3}$alkylhalo (i.e. $C_{1-3}$alkyl substituted with halo such as $CF_3$ or $CHF_2$); and R may be $C_{1-6}$alkyl.

EXAMPLES

The invention will now be described without limitation by reference to the examples which follow.
Synthetic Methods $^1$H NMR spectra were recorded on either a Bruker Avance DRX 400, AC 200 or AM 300 spectrometer. Spectra were recorded in deuterated solvents (CDCl$_3$, MeOD, DMSO, CD$_3$CN, or Acetone) using the residual solvent peak as a reference. Chemical shifts are reported on the δ scale in parts per million (ppm) using the following conventions to assign the multiplicity: s (singlet), d (doublet), t (triplet), q (quartet), p (pentet), m (multiplet) and prefixed br (broad). Mass spectra (ESI) were recorded on either a Micromass Platform QMS or Thermo Finnigan LCQ Advantage spectrometer. Flash chromatography was performed on 40-63 μm silica gel 60 (Merck No. 9385). Automated flash chromatography was performed either on a Combi-Flash™ purification system using Combi-Flash™ silica gel columns or on a Biotage SP4 purification system using either GraceResolv™ silica gel cartridges, Grace Reveleris™ C-18 reverse phase silica gel cartridges or Biotage SNAP™ C-18 reverse phase silica gel cartridges. Preparative HPLC was carried out using either a Gilson 322 pump with a Gilson 215 liquid handler and a HP1100 PDA detector or an Agilent 1200 Series mass detected preparative LCMS using a Varian XRs C-18 100×21.2 mm column. Unless otherwise specified, the HPLC systems employed Phenomenex C8(2) columns using either ACN or ACN containing 0.06% TFA in water, water containing 0.1% TFA or water containing 0.1% formic acid.

During the reactions a number of the moieties may need to be protected. Suitable protecting groups are well known in industry and have been described in many references such as Protecting Groups in Organic Synthesis, Greene T W, Wiley-Interscience, New York, 1981.

The abbreviations used in the Examples are as follows unless indicated otherwise:

| | |
|---|---|
| Ac: | acetyl |
| ACN: | acetonitrile |
| conc.: | concentrated |
| dba: | dibenzylideneacetone |
| DCM: | dichloromethane |
| DIPEA: | N,N-diisopropylethylamine |
| DMF: | N,N-dimethylformamide |
| DMSO: | dimethylsulfoxide |
| dppf: | 1,1'-bis(diphenylphosphino)ferrocene |
| ESI: | electrospray ionisation |
| EtOAc | ethyl acetate |
| h: | hour(s) |
| HATU: | 2-(7-Aza-1H-benzotriazole-1-yl)-1,1,3,3-tetramethyluronium hexafluorophosphate |
| HPLC: | high performance liquid chromatography |
| LCMS: | liquid chromatography coupled mass spectrometry |
| MeOH: | methanol |
| min: | minute(s) |
| MS: | mass spectrometry |
| NMR: | nuclear magnetic resonance |
| PyBOP: | benzotriazol-1-yl-oxytripyrrolidinophosphonium hexafluorophosphate |
| s: | second(s) |
| SM: | starting material |
| RT: | room temperature |
| THF: | tetrahydrofuran |
| TFA: | trifluoroacetic acid |
| TLC: | thin-layer chromatography |

Method A Examples

Route (a): 2-(4-bromophenyl)-5-cyclopropyl-N-methyl-6-[(methylsulfonyl)amino]-2H-indazole-3-carboxamide (1)

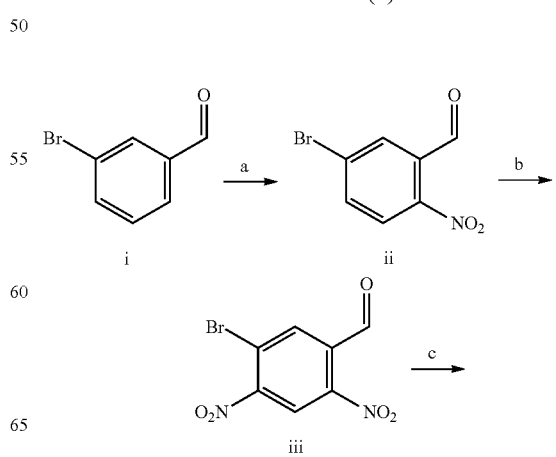

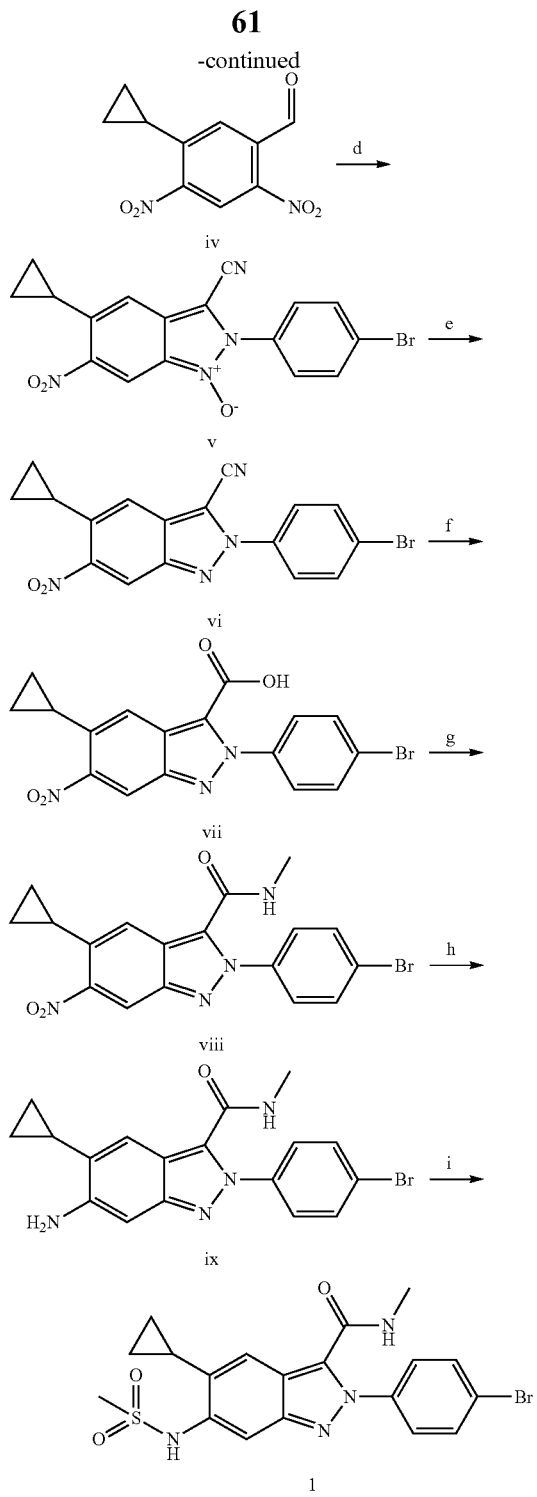

Step a: To an ice cold conc. sulphuric acid (400 mL) was added fuming nitric acid (200 mL) and to this solution was added 3-bromobenzaldehyde (i) (100 g, 0.540 mol) dropwise within 15 min. The reaction mixture was stirred for 10 min at same temperature at which time TLC showed complete reaction. The reaction mixture was quenched in ice water and filtered to afford a mixture of products which was purified by flash column chromatography eluting with EtOAc/hexane (1-5%) to give 5-bromo-2-nitrobenzaldehyde (ii) as white solid (60 g, 48%).

Step b: To ice cold conc. sulphuric acid (360 mL) was added fuming nitric acid (180 mL) and to this solution was added compound (ii) (60 g, 0.26 mol) within 15 min. The reaction mixture was stirred for 10 min at same temperature then at RT for 30 min, at 45° C. for 2 h and finally at 50° C. for 3 h at which time TLC showed complete reaction. The reaction mixture was quenched in ice water and extracted with chloroform to give a mixture of products which was separated by flash column chromatography eluting with EtOAc/hexane (5-30%). The desired 5-bromo-2,4-dinitrobenzaldehyde (iii) was isolated as white solid (5.1 g, 7%).

Step c: To a stirred solution of compound (iii) (3 g, 10.9 mmol) in toluene (75 mL) was added a solution of sodium carbonate (2.29 g, 21.8 mmol) in water (15 mL) and the mixture was purged with nitrogen for 10 min. Cyclopropyl boronic acid (1.4 g, 16.4 mmol) and tetrakis(triphenylphosphine)palladium(0) (0.25 g, 0.22 mmol) were added and the reaction mixture was heated at reflux for 6 h (monitored by TLC). The reaction was then cooled to RT and diluted with EtOAc. The aqueous and organic layers were separated. Concentration of the solvent gave the crude product which was purified by column chromatography to give 5-cyclopropyl-2,4-dinitrobenzaldehyde (iv) (2 g, 78%).

Step d: To a stirred suspension of compound (iv) (6.2 g, 0.026 mol) in acetic acid (120 mL) was added 4-bromoaniline (9.28 g, 0.054 mol) and the reaction mixture was heated to 60° C. to get a clear solution. To this was added sodium cyanide portionwise (6.2 g, 0.127 mol) and the reaction mixture was stirred at 60° C. for 5 min. Acetic anhydride (1.9 mL, 0.020 mol) was added and the reaction mixture was stirred for 5 min at the same temperature. Sodium cyanide (6.2 g, 0.127 mol) was then added at the same temperature at which time the product precipitated out. The reaction mixture was stirred for 30 min at this temperature and diluted with water (50 mL), filtered and washed with ethanol to give 2-(4-bromophenyl)-5-cyclopropyl-6-nitro-2H-indazole-3-carbonitrile 1-oxide (v) (4.1 g, 39%).

Step e: To a stirred solution of compound (v) (4.1 g, 0.010 mol) in chloroform (40 mL) was added phosphorus trichloride (4.1 mL, 0.047 mol) and the reaction mixture was heated to 60° C. for 1 h (monitored by TLC and LCMS). The reaction mixture was quenched in ice water and the product was extracted into DCM (2×80 mL). Concentration of solvent gave the crude product, to which was added ethanol and filtered to give 2-(4-bromophenyl)-5-cyclopropyl-6-nitro-2H-indazole-3-carbonitrile (vi) (3.3 g, 84%).

Step f: To a stirred suspension of compound (vi) (3.3 g, 8.6 mmol) in ethanol (35 mL) was added aqueous NaOH (3.44 g, 86 mmol) and the reaction mixture was heated to 90° C. and maintained for 15 h when TLC and LCMS showed the absence of SM and formation of product. Concentration of the solvent gave a crude residue which was dissolved in water and filtered. The filtrate was acidified with dilute HCl at which time the product precipitated and was filtered to give the crude product which was purified by acid-base treatment to give 2-(4-bromophenyl)-5-cyclopropyl-6-nitro-2H-indazole-3-carboxylic acid (vii) (2.2 g, 63%).

Step g: To a stirred solution of compound (vii) (2.2 g, 5.5 mmol) in pyridine (45 mL) was added methyl amine (8.2 mL, 2 M solution in THF, 16 mmol). The reaction mixture was cooled to 0° C. and POCl₃ (2.88 g, 19 mmol) was added dropwise at the same temperature. After 1 h TLC and LCMS showed the absence of SM and formation of product. The reaction mixture was quenched in ice water and the precipitate was filtered and crystallized from MeOH to give 2-(4-bromophenyl)-5-cyclopropyl-N-methyl-6-nitro-2H-indazole-3-carboxamide (viii) (1.25 g, 55%). ESI-MS m/z calculated for [M+H]⁺: 415.04/417.04; found: 415.15/417.15.

Step h: To a suspension of compound (viii) (500 mg, 1.20 mmol) in a mixture of ethanol (30 mL) and water (6 mL) was added ammonium chloride (450 mg, 8.43 mmol) followed by iron powder (470 mg, 8.43 mmol). The mixture was heated to 80° C. and stirred vigorously for 90 min. After cooling to RT, 5% MeOH in DCM solution (50 mL) was added to the reaction mixture. The resulting suspension was filtered through celite and washed with MeOH. The filtrate was concentrated in vacuo to give a yellow solid which was then suspended in water (40 mL) and filtered. The solid was collected and dried to give 6-amino-2-(4-bromophenyl)-5-cyclopropyl-N-methyl-2H-indazole-3-carboxamide (ix) (320 mg, 68%) as a yellow solid. ESI-MS m/z calculated for [M+H]⁺: 385.07/387.06; found: 385.12/387.10.

Step i: To a suspension of compound (ix) (320 mg, 0.83 mmol) in DCM (20 mL) was added DIPEA (0.43 mL, 2.49 mmol) followed by methanesulfonyl chloride (0.32 mL, 4.15 mmol) and the reaction mixture was stirred at RT for 3 h (monitored by LCMS). The mixture was diluted with DCM (20 mL), washed with saturated ammonium chloride (20 mL), brine (20 mL) and dried (MgSO₄). The solvent was removed in vacuo to give a yellow solid. This material was taken up in ethanol (20 mL) and treated with powdered potassium hydroxide (210 mg, 3.80 mmol) and stirred for 5 min. The mixture was neutralized by addition of 1M aqueous hydrochloric acid and the resulting suspension was concentrated in vacuo to give an orange residue. The residue was taken up in DCM (20 mL), washed with water (20 mL), dried over MgSO₄ and the solvent was removed in vacuo to give 2-(4-bromophenyl)-5-cyclopropyl-N-methyl-6-[(methylsulfonyl)amino]-2H-indazole-3-carboxamide (1) (300 mg, 86%) as yellow solid. ESI-MS m/z calculated for [M+H]⁺: 463.04/465.04; found: 463.05/465.05. ¹H NMR (400 MHz, CDCl₃) δ 7.82 (d, J=0.4 Hz, 1H), 7.68 (d, J=0.5 Hz, 1H), 7.65 (brd, J=8.8 Hz, 2H), 7.47 (d, J=8.8 Hz, 2H), 7.09 (s, 1H), 5.80 (brd, J=4.1 Hz, 1H), 3.13 (s, 3H), 3.00 (d, J=4.9 Hz, 3H), 1.80 (dddd, J=13.6, 8.1, 5.4, 1.3 Hz, 1H), 1.16-0.99 (m, 2H), 0.79-0.67 (m, 2H).

2-(4-bromophenyl)-5-methoxy-N-methyl-6-[(methylsulfonyl)amino]-2H-indazole-3-carboxamide (41)

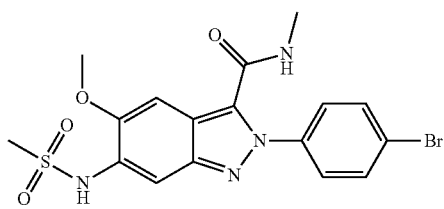 [SMILES: CNC(=O)c1c2cc(OC)c(NS(C)(=O)=O)cc2nn1-c1ccc(Br)cc1]

Starting from anisaldehyde, Compound (41) was prepared in a similar manner to the synthesis of Compound (1), with the following variations: the Suzuki reaction at Step c was not required; the reduction at Step h was performed at an earlier stage in the route (between Step e and Step f); the hydrolysis reaction at Step f required KOH and heating in a sealed vessel at 150° C. for 3 days, instead of NaOH and heating at 90° C. for 15 h; and the amide coupling at Step g was achieved using HATU and DIPEA in DMF instead of POCl₃ in pyridine. ESI-MS m/z [M+H]⁺: 453.0/455.0. ¹H NMR (400 MHz, Acetone) δ 7.77-7.71 (m, 3H), 7.63-7.59 (m, 2H), 7.29 (s, 1H), 4.01 (s, 3H), 3.13 (s, 3H), 2.95 (d, J=4.7 Hz, 3H).

5-bromo-2-(4-fluorophenyl)-N-methyl-6-[(methylsulfonyl)amino]-2H-indazole-3-carboxamide (42)

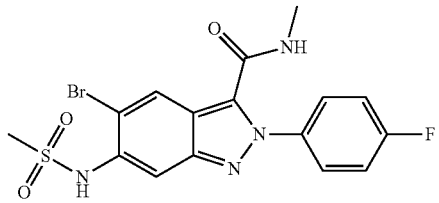 [SMILES: CNC(=O)c1c2cc(Br)c(NS(C)(=O)=O)cc2nn1-c1ccc(F)cc1]

Compound (42), ESI-MS m/z [M+H]⁺: 441.0/443.0. ¹H NMR (400 MHz, DMSO) δ 9.50 (s, 1H), 8.76 (q, J=4.3 Hz, 1H), 8.22 (s, 1H), 7.84 (s, 1H), 7.70-7.61 (m, 2H), 7.48-7.36 (m, 2H), 3.13 (s, 3H), 2.84 (d, J=4.7 Hz, 3H), was prepared in a similar manner to the synthesis of Compound (1), with the following variations: the Suzuki reaction at Step c was not required; and the hydrolysis at Step f was performed as follows.

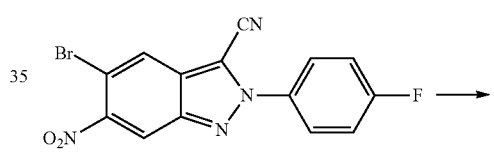

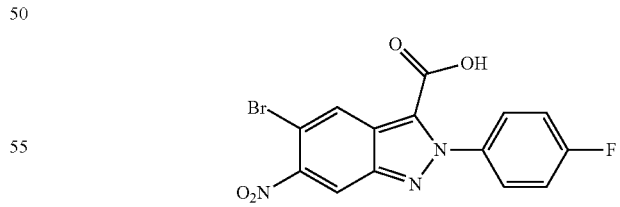

5-bromo-2-(4-fluorophenyl)-6-nitro-2H-indazole-3-carbonitrile (1.03 g, 2.85 mmol) in 70 aqueous sulfuric acid (15 mL) was heated at 85° C. for 17 h. The reaction mixture was cooled to RT, added to water (40 mL) and the precipitate was collected by filtration. The crude material was added to 2 M aqueous sodium hydroxide (40 mL), stirred for 5 min and then filtered. The filtrate was acidified with hydrochloric acid and the precipitate was collected by filtration to give 5-bromo-2-(4-fluorophenyl)-6-nitro-2H-indazole-3-carboxylic acid as a tan solid (0.93 g, 86%).

5-cyclopropyl-2-[6-(4-fluorophenoxy)pyridin-3-yl]-N-methyl-6-[(methylsulfonyl)amino]-2H-indazole-3-carboxamide (43)

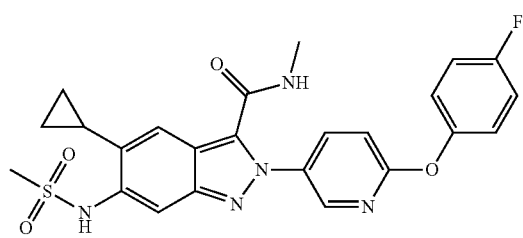 [SMILES: CNC(=O)c1c2cc(C3CC3)c(NS(C)(=O)=O)cc2nn1-c1ccc(Oc2ccc(F)cc2)nc1]

Compound (43) ESI-MS m/z [M+H]$^+$: 496.1 was prepared in a similar manner to the synthesis of Compound (1), with the following variations: 6-(4-fluorophenoxy)pyridin-3-amine was used instead of 4-fluoroaniline at Step d; the hydrolysis at Step f was completed with 70% aqueous sulfuric acid in a similar manner to that used in the synthesis of 5-bromo-2-(4-fluorophenyl)-N-methyl-6-[(methylsulfonyl)amino]-2H-indazole-3-carboxamide; the amide coupling at Step g was achieved using PyBOP in THF instead of POCl$_3$ in pyridine; and the Suzuki reaction at Step c was performed at a later stage in the route (between Step g and Step h) as follows.

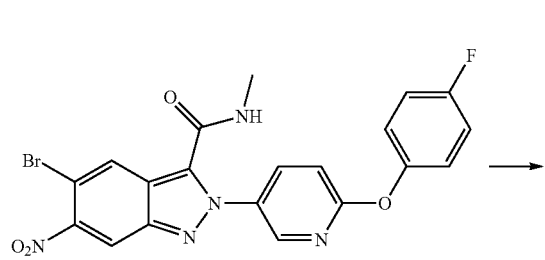

A degassed suspension of 5-bromo-2-[6-(4-fluorophenoxy)pyridin-3-yl]-N-methyl-6-nitro-2H-indazole-3-carboxamide (10 mg, 0.021 mmol), potassium phosphate (35 mg, 0.16 mmol), potassium cyclopropyltrifluoroborate (19 mg, 0.13 mmol) and Pd(dppf)Cl$_2$·CH$_2$Cl$_2$ (3 mg, 0.004 mmol) in toluene (1 mL) and water (0.1 mL) was heated under microwave irradiation at 110° C. for 1 h. The reaction mixture was diluted with EtOAc (3 mL), washed with water (1 mL) and brine (1 mL), then dried (MgSO$_4$) and concentrated to dryness. The residue was purified by flash column chromatography eluting with MeOH/DCM (0-10%) to give 5-cyclopropyl-2-[6-(4-fluorophenoxy)pyridin-3-yl]-N-methyl-6-nitro-2H-indazole-3-carboxamide as a tan solid (7 mg, 73%).

2-(4-chlorophenyl)-5-cyclopropyl-N-methyl-6-[(methylsulfonyl)amino]-2H-indazole-3-carboxamide (44)

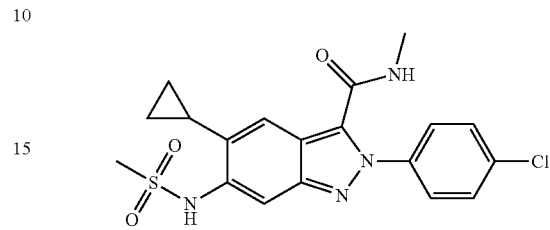

Compound (44) ESI-MS m/z [M+H]$^+$: 419.1, $^1$H NMR (400 MHz, Acetone) δ 7.79 (brs, 1H), 7.66 (s, 1H), 7.61 (brs, 1H), 7.56-7.51 (m, 2H), 7.49 (s, 1H), 7.46-7.41 (m, 2H), 3.02 (s, 3H), 2.81 (d, J=4.7 Hz, 3H), 2.11-2.01 (m, 1H), 0.96-0.90 (m, 2H), 0.66-0.59 (m, 2H), was prepared in a similar manner to the synthesis of Compound (1), with the following variations: 4-chloroaniline was used instead of 4-fluoroaniline at Step d; the amide coupling at Step g was achieved using HATU and DIPEA in DMF instead of POCl$_3$ in pyridine; and the reduction at Step h was performed as follows.

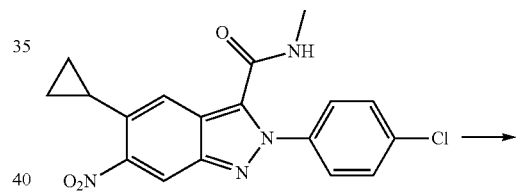

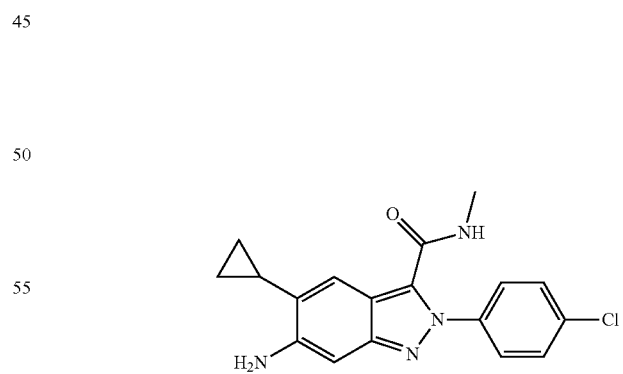

To a solution of 2-(4-chlorophenyl)-5-cyclopropyl-N-methyl-6-nitro-2H-indazole-3-carboxamide (127 mg, 0.34 mmol) in THF (2.5 mL) and MeOH (7.5 mL) was added Raney nickel (20 mg) and the reaction was stirred vigorously under an atmosphere of hydrogen at 60° C. for 2 h. The reaction mixture was diluted with MeOH (40 mL), filtered and then concentrated to dryness to give 6-amino-2-(4-chlorophenyl)-5-cyclopropyl-N-methyl-2H-indazole-3-carboxamide as a tan solid (97 mg, 83%).

5-cyclopropyl-2-(3-fluoro-4-methylphenyl)-N-methyl-6-[(methylsulfonyl)amino]-2H-indazole-3-carboxamide (45)

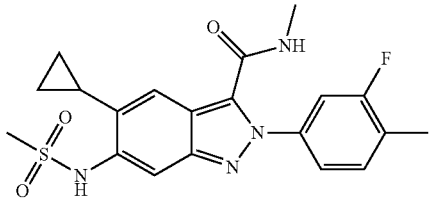

Compound (45) was prepared in a similar manner to the synthesis of Compound (44) with the following variation: 3-fluoro-4-methylaniline was used instead of 4-chloroaniline at Step d. ESI-MS m/z [M+H]$^+$: 417.1, $^1$H NMR (400 MHz, Acetone) δ 7.95 (brs, 1H), 7.81 (s, 1H), 7.75 (brs, 1H), 7.64 (s, 1H), 7.47-7.36 (m, 3H), 3.18 (s, 3H), 2.98 (d, J=4.7 Hz, 3H), 2.37 (d, J=1.9 Hz, 3H), 2.26-2.16 (m, 1H), 1.13-1.06 (m, 2H), 0.81-0.74 (m, 2H).

2-(4-bromo-3-fluorophenyl)-5-cyclopropyl-N-methyl-6-[(methylsulfonyl)amino]-2H-indazole-3-carboxamide (46)

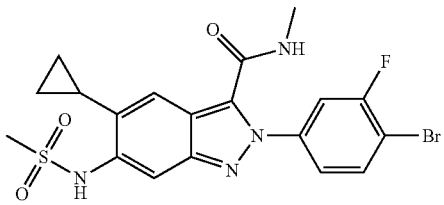 [SMILES: CNC(=O)c1c2cc(C3CC3)c(NS(C)(=O)=O)cc2nn1-c1ccc(Br)c(F)c1]

Compound (46) was prepared in a similar manner to the synthesis of Compound (44) with the following variation: 4-bromo-3-fluoroaniline was used instead of 4-chloroaniline at Step d. ESI-MS m/z [M+H]$^+$: 481.1. $^1$H NMR (400 MHz, DMSO) δ 9.21 (brs, 1H), 8.67 (brs, 1H), 7.96-7.83 (m, 2H), 7.76-7.62 (m, 2H), 7.45-7.30 (m, 2H), 3.10 (s, 3H), 2.90-2.76 (m, 3H), 2.31-2.20 (m, 1H), 1.07-0.92 (m, 2H), 0.80-0.66 (m, 2H).

2-(4-Bromophenyl)-5-cyclopropyl-6-{[(difluoromethyl)sulfonyl]amino}-N-methyl-2H-indazole-3-carboxamide (47)

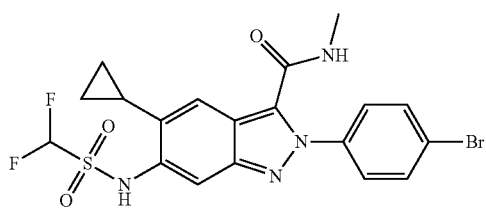 [SMILES: CNC(=O)c1c2cc(C3CC3)c(NS(=O)(=O)C(F)F)cc2nn1-c1ccc(Br)cc1]

ESI-MS m/z calculated for [M+H]$^+$: 499.0/501.0; found: 499.0/501.0. $^1$H NMR (400 MHz, CDCl$_3$) δ 7.78 (s, 1H), 7.70-7.63 (m, 2H), 7.51-7.44 (m, 2H), 7.41 (s, 1H), 6.32 (t, J=53.9 Hz, 1H), 5.76 (br s, 1H), 4.06 (dq, J=14.3, 7.2 Hz, 1H), 3.79 (dq, J=14.2, 7.1 Hz, 1H), 3.01 (d, J=4.9 Hz, 3H), 2.32-2.21 (m, 1H), 1.26 (t, J=7.2 Hz, 3H), 1.19-1.06 (m, 2H), 1.04-0.94 (m, 1H), 0.73-0.62 (m, 1H).

Compound (47) was prepared by the following method: To a suspension of 6-amino-2-(4-bromophenyl)-5-cyclopropyl-N-methyl-2H-indazole-3-carboxamide (20 mg, 0.052 mmol) in neat pyridine (1 mL) at 0° C. was added difluoromethanesulfonyl chloride (60 μL). After 3 d, the reaction was quenched with saturated aqueous ammonium chloride (1 mL) and then extracted with ethyl acetate (3×2 mL). The combined organics were washed with 1M aqueous citric acid (2 mL), brine (2 mL) then dried (MgSO$_4$) and concentrated to dryness to afford crude 2-(4-Bromophenyl)-5-cyclopropyl-6-{[(difluoromethyl)sulfonyl]amino}-N-methyl-2H-indazole-3-carboxamide (18 mg, 69%) which was used without further purification.

Route (b): 6-[Acetyl(ethyl)amino]-2-(4-bromophenyl)-5-cyclopropyl-N-methyl-2H-indazole-3-carboxamide (48)

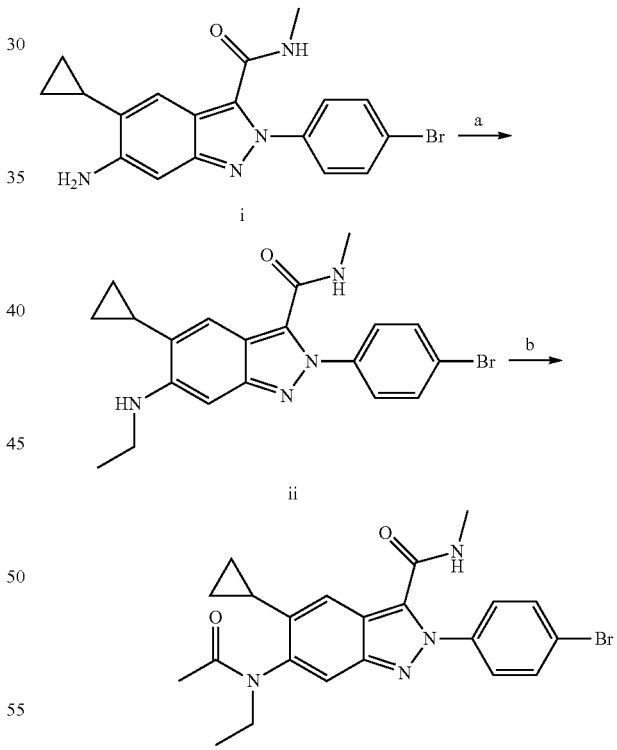

Step a: To a suspension of 6-amino-2-(4-bromophenyl)-5-cyclopropyl-N-methyl-2H-indazole-3-carboxamide (i) (20 mg, 0.052 mmol) in MeOH (0.6 mL) was added acetaldehyde (15 μL 0.27 mmol) at 0° C. Sodium cyanoborohydride (5 mg, 0.078 mmol) was then added and the mixture was stirred at RT for 1 h. The mixture was filtered and the filtrate was concentrated to dryness. The residue was purified by reverse phase flash column chromatography eluting with ACN/water (5-100%) to give 2-(4-bromophenyl)-5-cyclopropyl-6-(ethylamino)-N-methyl-2H-indazole-3-carboxamide (ii) as a white solid (7 mg, 32%).

Step b: To a solution of compound (ii) (6 mg, 0.015 mmol) in DCM was added DIPEA (7 µL, 0.040 mmol), followed by acetyl chloride (7 µL, 0.098 mmol) and the reaction was stirred at RT for 20 min. After concentrating to dryness, the residue was purified by flash column chromatography eluting with MeOH/DCM (0-20%) to give Compound (48) as a white solid (4 mg, 61%). ESI-MS m/z calculated for [M+H]+: 455.1/457.1; found: 455.4/457.4; 1H NMR (400 MHz, CDCl3) δ 7.71-7.63 (m, 2H), 7.56 (brs, 1H), 7.52-7.46 (m, 2H), 7.43 (s, 1H), 5.77 (brs, 1H), 4.32 (dq, J=14.3, 7.2 Hz, 1H), 3.25 (dq, J=14.2, 7.1 Hz, 1H), 3.01 (d, J=4.9 Hz, 3H), 1.96-1.74 (m, 4H), 1.21 (t, J=7.2 Hz, 3H), 1.10-0.97 (m, 2H), 0.86-0.70 (m, 2H).

Route (c): 5-cyclopropyl-2-(4-fluorophenyl)-6-iodo-N-methyl-2H-indazole-3-carboxamide (49)

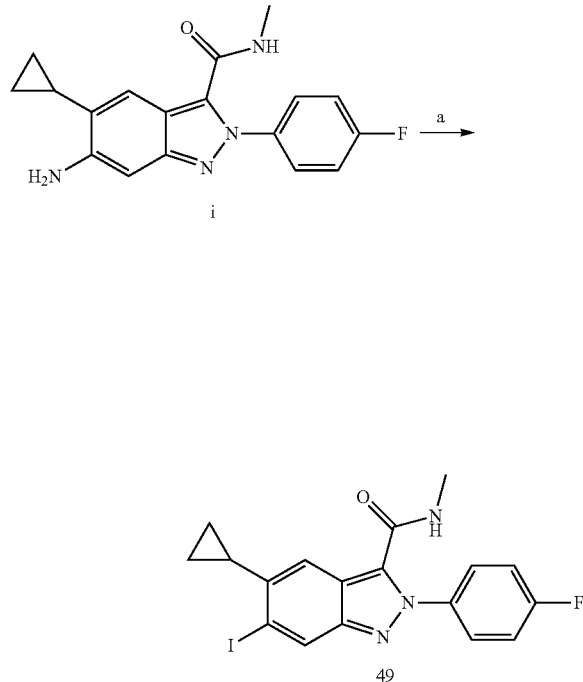

i

49

Step a: To a stirred suspension of 6-amino-5-cyclopropyl-2-(4-fluorophenyl)-N-methyl-2H-indazole-3-carboxamide (i) (0.50 g, 1.54 mmol) in 6 N Hydrochloric acid (25 mL) at −10° C. was added dropwise a solution of sodium nitrite (0.16 g, 2.31 mmol) in water (1 mL) so as to maintain the internal temperature above −5° C. The reaction mixture was stirred for 30 min whereupon a suspension of potassium iodide (1.50 g, 9.06 mmol) in EtOAc:water (1:1 v/v, 50 mL) cooled to 0° C. was added over 30 min. After 1 h, the reaction mixture was diluted with EtOAc (20 mL) and the organic layer was separated and washed with saturated sodium thiosulphate (2×10 mL), brine (10 mL) and dried (MgSO4). The volatiles were removed in vacuo and the residue was then purified by column chromatography eluting with EtOAc/hexane (20-40%) to give Compound (49) as a pale yellow solid (0.16 g, 23%). ESI-MS m/z calculated for [M+H]+: 436.0; found: 436.0; 1H NMR (400 MHz, DMSO) δ 8.66 (brs, 1H), 8.38 (s, 1H), 7.65-7.54 (m, 2H), 7.49-7.31 (m, 3H), 2.87-2.2.73 (m, 3H), 2.10-1.95 (m, 1H), 1.09-0.95 (m, 2H), 0.79-0.67 (m, 2H).

Method B Examples 5-cyclopropyl-2-[4-(4-fluorophenoxy)phenyl]-6-[(2-hydroxyethyl)-(methylsulfonyl)amino]-N-methyl-2H-indazole-3-carboxamide (3)

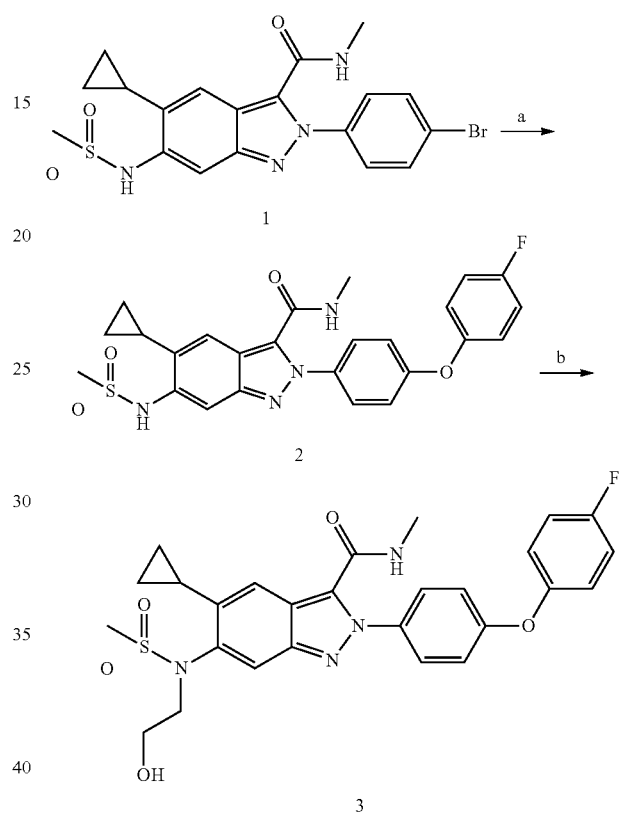

Step a: A mixture of Compound (1) (50 mg, 0.11 mmol), potassium carbonate (30 mg, 0.22 mmol), copper(I) iodide (10 mg, 0.05 mmol), copper (6.9 mg, 0.11 mmol) and 4-fluorophenol (18 mg, 0.16 mmol) in pyridine (1 mL) was heated to 150° C. for 16 h in a sealed-tube. After cooling to RT, MeOH (5 mL) was added and the mixture was filtered through celite and washed with more MeOH. The filtrate was concentrated in vacuo to give a crude mixture which was purified by reverse phase flash column chromatography eluting with ACN/water (10-100%) to give 5-cyclopropyl-2-[4-(4-fluorophenoxy)phenyl]-N-methyl-6-[(methylsulfonyl)amino]-2H-indazole-3-carboxamide (2) (9 mg, 17%) as a pale yellow solid. ESI-MS m/z calculated for [M+H]+: 495.15; found: 495.12.

Step b: To a solution of Compound (2) (13 mg, 26 µmol) in ACN (1 mL) was added potassium carbonate (7.3 mg, 52 µmol) followed by 2-bromoethanol (5.6 µL, 79 µmol). The mixture was then stirred at 80° C. for 16 h (monitored by LCMS). The mixture was cooled to RT, diluted with EtOAc (3 mL), washed with water (1 mL) and brine (2 mL). The organic phase was dried (MgSO4) and the solvent was removed in vacuo. The crude mixture was purified by preparative HPLC to give Compound (3) (4.86 mg, 34%) as a white powder. ESI-MS m/z calculated for [M+H]+: 539.18; found: 539.12;

¹H NMR (400 MHz, CDCl₃) δ 7.80 (s, 1H), 7.52 (brd, J=9.0 Hz, 2H), 7.47 (s, 1H), 7.12-7.02 (m, 6H), 5.79 (brd, J=4.3 Hz, 1H), 4.21-4.00 (m, 1H), 3.85-3.62 (m, 3H), 3.18 (s, 3H), 2.99 (d, J=4.9 Hz, 3H), 2.51-2.27 (m, 1H), 1.06 (ddd, J=11.3, 6.9, 3.1 Hz, 3H), 0.62-0.44 (m, 1H).

5-cyclopropyl-6-[(3-hydroxypropyl)(methylsulfonyl)amino]-N-methyl-2-[4-(propan-2-yl)-phenyl]-2H-indazole-3-carboxamide (50)

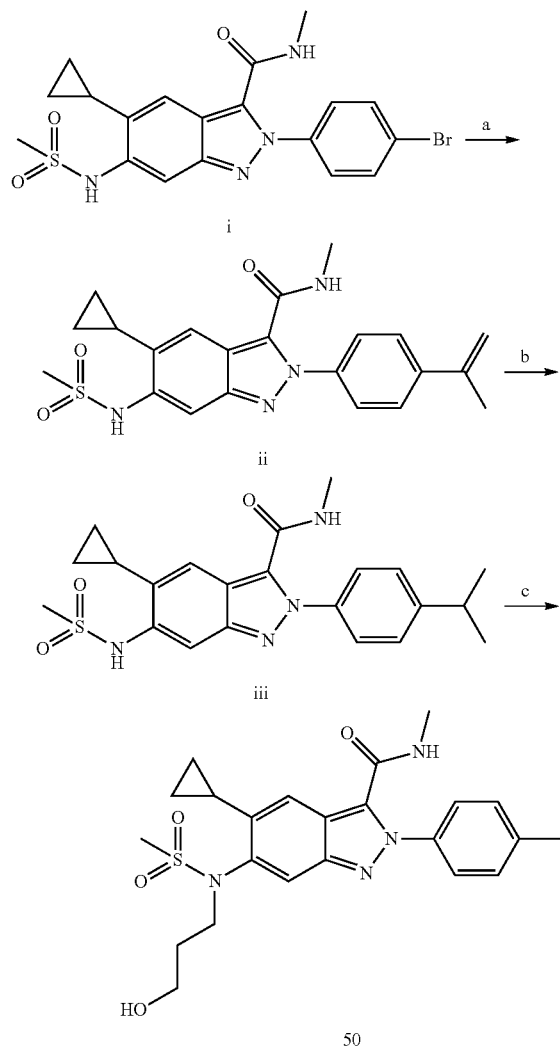

Step a: 2-(4-bromophenyl)-5-cyclopropyl-N-methyl-6-[(methylsulfonyl)amino]-2H-indazole-3-carboxamide (i) (30 mg, 0.065 mmol), 2-isopropenylboronic acid pinacol ester (37 μL, 0.20 mmol), potassium phosphate (55 mg, 0.26 mmol), tricyclohexylphosphine (3.5 mg, 0.013 mmol) and Pd(OAc)₂ (2.1 mg, 0.0094 mmol) had degassed toluene (1 mL) and water (0.1 mL) added and the reaction was heated at 95° C. under argon for 5 h. The reaction mixture was concentrated to dryness and the residue was suspended in DMSO (1 mL), centrifuged, supernatant removed and purified by reverse phase flash column chromatography eluting with ACN/water (0-40-100%) affording 5-cyclopropyl-N-methyl-6-[(methylsulfonyl)amino]-2-[4-(prop-1-en-2-yl)phenyl]-2H-indazole-3-carboxamide (ii) as a white solid (10 mg, 27%).

Step b: To a solution of compound (ii) (10 mg, 0.024 mmol) in MeOH (1 mL) was added 10% palladium on carbon (7 mg). The reaction was stirred vigorously under an atmosphere of hydrogen at RT for 2 h. The reaction mixture was filtered to give 5-cyclopropyl-N-methyl-6-[(methylsulfonyl)amino]-2-[4-(propan-2-yl)phenyl]-2H-indazole-3-carboxamide (iii) as a white solid (10 mg, 99%).

Step c: In a similar manner as outlined in Step b in the synthesis of Compound (3) the desired product was prepared using 3-bromo-1-propanol instead of 2-bromoethanol to afford Compound (50) as a white solid (6.5 mg, 55%). ESI-MS m/z calculated for [M+H]⁺: 485.2; found: 485.2; ¹H NMR (400 MHz, CD₃CN) δ 7.83 (d, J=0.5 Hz, 1H), 7.58-7.49 (m, 2H), 7.47-7.41 (m, 2H), 7.39 (s, 1H), 6.98 (brs, 1H), 4.00-3.72 (m, 2H), 3.69-3.49 (m, 2H), 3.12 (s, 3H), 3.10-2.99 (m, 1H), 2.93 (d, J=4.8 Hz, 3H), 2.65 (brs, 1H), 2.51-2.35 (m, 1H), 1.91-1.61 (m, 2H), 1.33 (d, J=6.9 Hz, 6H), 1.16-0.93 (m, 3H), 0.79-0.54 (m, 1H).

The following compounds were similarly prepared by reference to general Method B and/or the examples previously described.

Method C Examples

Route (a): 5-cyclopropyl-2-{4-[(2-fluorophenyl)amino]phenyl}-6-[(3-hydroxypropyl)(methylsulfonyl)amino]-N-methyl-2H-indazole-3-carboxamide (5)

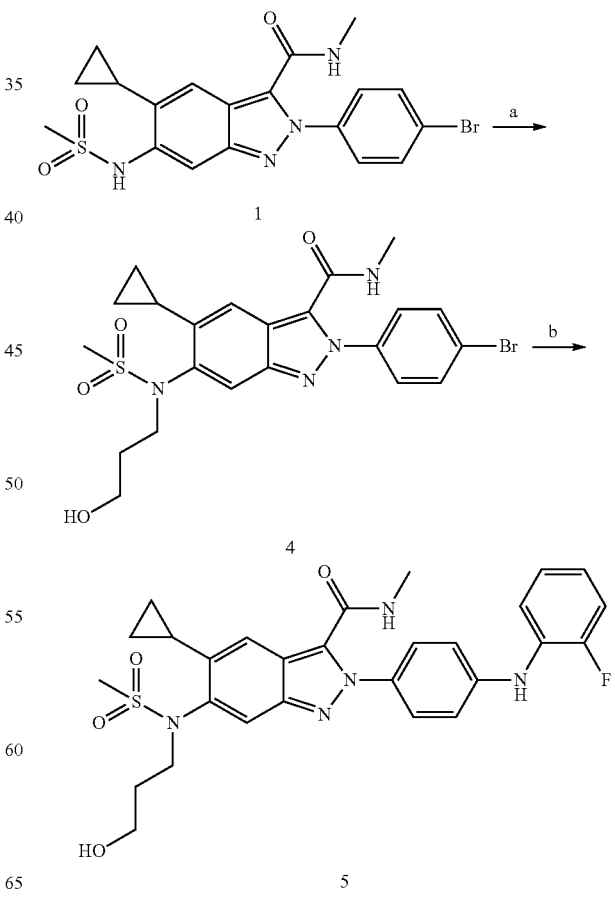

Step a: To a solution of Compound (1) (50 mg, 0.11 mmol) in ACN (4 mL) was added potassium carbonate (30 mg, 0.22 mmol) followed by 3-bromo-1-propanol (38 μL, 0.32 mmol). The mixture was heated to 80° C. and stirred for 16 h at which time no starting material was observed. The mixture was cooled to RT, diluted with EtOAc (10 mL), washed with water (3 mL), brine (3 mL) and dried (MgSO$_4$). The solvent was removed in vacuo to give the crude mixture which was purified by flash column chromatography eluting with EtOAc/hexane (5-100%) to give 2-(4-bromophenyl)-5-cyclopropyl-6-[(3-hydroxypropyl)(methylsulfonyl)amino]-N-methyl-2H-indazole-3-carboxamide (4) (28 mg, 50%). ESI-MS m/z calculated for [M+H]$^+$: 521.09/523.08; found: 521.03/523.03.

Step b: A mixture of Compound (4) (16 mg, 31 μmol), 2-fluoroaniline (4.4 μL, 46 μmol), 2,2'-bis(diphenylphosphino)-1,1'-binaphthalene (4 mg, 6 μmol) and cesium carbonate (30 mg, 92 μmol) in toluene (0.5 mL) and 1,2-dimethoethane (0.2 mL) was placed in a high pressure vial. Nitrogen was bubbled through the mixture for ~20 min. Palladium acetate (0.7 mg, 3 μmol) was then added and the vial was sealed. The mixture was heated to 100° C. and stirred for 16 h. After cooling to RT, the mixture was diluted with EtOAc (10 mL) and filtered through a pad of Celite®. The filtrate was concentrated in vacuo to give a crude mixture which was purified by flash column chromatography eluting with MeOH/DCM (0-20%). Further purification was done by preparative HPLC to give Compound (5) (3.68 mg, 22%) as a pale yellow solid. ESI-MS m/z calculated for [M+H]$^+$: 552.21; found: 552.14. $^1$H NMR (400 MHz, CDCl$_3$) δ 7.73 (s, 1H), 7.52 (s, 1H), 7.49-7.43 (m, 2H), 7.41 (dt, J=8.2, 1.5 Hz, 1H), 7.20-7.07 (m, 4H), 7.04-6.93 (m, 1H), 6.01 (brd, J=1.8 Hz, 1H), 5.71 (brd, J=4.6 Hz, 1H), 4.02-3.63 (m, 4H), 3.07 (s, 3H), 2.95 (d, J=4.9 Hz, 3H), 2.51-2.25 (m, 1H), 1.87-1.74 (m, 2H), 1.13-0.94 (m, 3H), 0.74-0.55 (m, 1H).

2-(4-bromophenyl)-5-cyclopropyl-6-{[(2,3-dihydroxypropyl)(methylsulfonyl)amino}-N-methyl-2H-indazole-3-carboxamide (51)

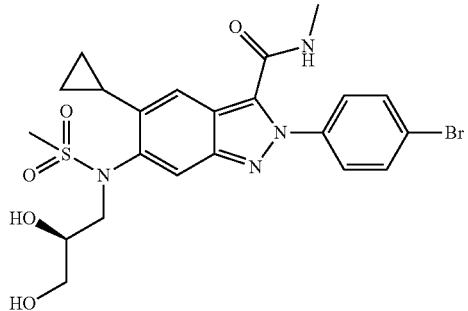 [SMILES: CNC(=O)c1c2cc(C3CC3)c(N(C[C@H](O)CO)S(C)(=O)=O)cc2nn1-c1ccc(Br)cc1]

Step a: 2-(4-Bromophenyl)-5-cyclopropyl-N-methyl-6-{(methylsulfonyl)[(oxiran-2-ylmethyl]amino}-2H-indazole-3-carboxamide was prepared in a similar manner as outlined in Step a in the synthesis of Compound (5) using epichlorohydrin instead of 3-bromo-1-propanol to afford a brown solid which was used directly in the next step.

Step b: To a solution of 2-(4-bromophenyl)-5-cyclopropyl-N-methyl-6-{(methylsulfonyl)[(oxiran-2-ylmethyl]amino}-2H-indazole-3-carboxamide in DCM (0.5 mL) was added trifluoroacetic acid (50 μL) at 0° C. and the mixture was stirred at RT for 16 h. The solution was neutralized with 1 M sodium hydroxide and then vigorously stirred for 5 min and then extracted with DCM (2×1 mL). The combined extracts were dried (MgSO$_4$) and concentrated to dryness. The residue was purified by preparative LCMS (5-20-100% ACN in 0.1% aqueous formic acid) to afford Compound (51) as a white solid. ESI-MS m/z calculated for [M+H]$^+$: 537.1/539.1; found: 537.0/539.0; $^1$H NMR (400 MHz, CDCl$_3$) δ 7.82 (2×s, 1H), 7.66 (d, J=8.5 Hz, 2H), 7.47 (d, J=8.4 Hz, 2H), 7.40 (2×s, 1H), 5.81 (brs, 1H), 4.13-3.51 (m, 5H), 3.20 (s, 2H), 3.11 (s, 1H), 3.01 (d, J=4.8 Hz, 3H), 2.53-2.29 (m, 1H), 1.17-0.99 (m, 3H), 0.72-0.44 (m, 1H).

2-(4-bromophenyl)-5-cyclopropyl-N-methyl-6-{(methylsulfonyl)[1-(methylsulfonyl)pyrrolidin-3-yl]amino}-2H-indazole-3-carboxamide (52)

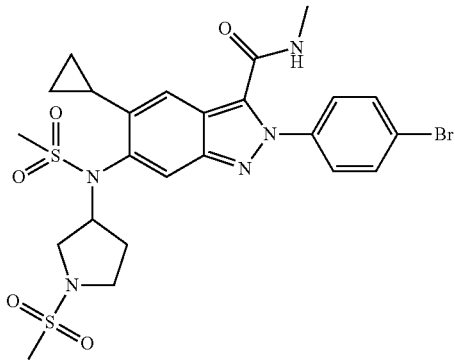 [SMILES: CNC(=O)c1c2cc(C3CC3)c(N(C3CCN(S(C)(=O)=O)C3)S(C)(=O)=O)cc2nn1-c1ccc(Br)cc1]

Step a: tert-Butyl 3-{[2-(4-bromophenyl)-5-cyclopropyl-3-(methylcarbamoyl)-2H-indazol-6-yl](methylsulfonyl)amino}pyrrolidine-1-carboxylate was prepared in a similar manner as outlined in Step a in the synthesis of Compound (5) using tert-butyl 3-bromopyrrolidine-1-carboxylate instead of 3-bromo-1-propanol to afford a tan solid (12 mg, 29%).

Step b: To a solution of tert-butyl 3-{[2-(4-bromophenyl)-5-cyclopropyl-3-(methylcarbamoyl)-2H-indazol-6-yl](methylsulfonyl)amino}pyrrolidine-1-carboxylate (12 mg, 0.019 mmol) in DCM (0.5 mL) was added trifluoroacetic acid (50 μL) and the mixture was stirred at 40° C. for 40 min. The mixture was cooled to RT, washed with saturated aqueous sodium bicarbonate (0.5 mL), dried (MgSO$_4$) and concentrated to dryness. The residue was purified by preparative LCMS (5-100% ACN in 0.1% aqueous formic acid) to afford 2-(4-bromophenyl)-5-cyclopropyl-N-methyl-6-[(methylsulfonyl)(pyrrolidin-3-yl)amino]-2H-indazole-3-carboxamide as a white solid (4.4 mg, 44%).

Step c: To a solution of 2-(4-bromophenyl)-5-cyclopropyl-N-methyl-6-[(methylsulfonyl)(pyrrolidin-3-yl)amino]-2H-indazole-3-carboxamide in DCM at 0° C. was added DIPEA (4 μL, 0.023 mmol), followed by methanesulfonyl chloride (3 μL, 0.039 mmol) and the mixture was stirred at RT for 20 min. The mixture was concentrated to dryness and purified by preparative LCMS (5-40-100% ACN in 0.1% aqueous formic acid) to afford Compound (52) as a white solid (1.4 mg, 36%). ESI-MS m/z calculated for [M+H]$^+$: 610.1/612.1; found: 610.0/612.0; $^1$H NMR (400 MHz, CDCl$_3$) δ 7.72 (2×s, 1H), 7.70-7.64 (m, 2H), 7.51-7.44 (m, 2H), 7.36 (2×s, J=2.6 Hz, 1H), 5.75 (2×d, J=5.0 Hz, 1H), 4.92-4.68 (m, 1H), 3.88-3.68 (m, 1H), 3.54-3.37 (m, 1H), 3.38-3.16 (m, 2H), 3.10 (d, J=4.6

Hz, 3H), 3.00 (2×d, 3H), 2.79 (2×s, 3H), 2.43-2.17 (m, 2H), 2.17-1.82 (m, 1H), 1.21-0.95 (m, 3H), 0.80-0.62 (m, 1H).

5-cyclopropyl-2-(4-cyclopropylphenyl)-6-[(3-hydroxypropyl)(methylsulfonyl)amino]-N-methyl-2H-indazole-3-carboxamide (53)

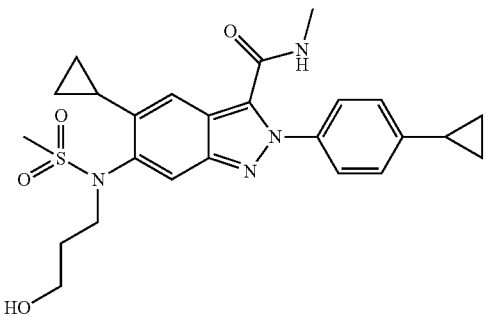 [SMILES: CNC(=O)c1c2cc(C3CC3)c(N(CCCO)S(C)(=O)=O)cc2nn1-c1ccc(C2CC2)cc1]

Step a: To a degassed mixture of 2-(4-bromophenyl)-5-cyclopropyl-6-[(3-hydroxypropyl)(methylsulfonyl)amino]-N-methyl-2H-indazole-3-carboxamide (10 mg, 0.019 mmol), cyclopropylboronic acid (5 mg, 0.058 mmol), potassium phosphate (17 mg, 0.080 mmol) in toluene (0.5 mL) and water (50 µL) were added tricyclohexylphosphine (1 mg, 0.0038 mmol) and Pd(OAc)₂ (0.4 mg, 0.0019 mmol) and the reaction was heated at 100° C. for 2 h. The mixture was concentrated to dryness and purified by preparative LCMS (5-40-100% ACN in 0.1 aqueous formic acid) to afford Compound (53) as a white solid (2.5 mg, 27%). ESI-MS m/z calculated for [M+H]⁺: 483.2; found: 483.2; ¹H NMR (400 MHz, MeOD) δ 7.85 (s, 1H), 7.58-7.43 (m, 2H), 7.39 (s, 1H), 7.28 (d, J=8.5 Hz, 2H), 4.06-3.81 (m, 2H), 3.76-3.57 (m, 2H), 3.17 (s, 3H), 2.94 (s, 3H), 2.54-2.34 (m, 1H), 2.19-1.96 (m, 1H), 1.96-1.68 (m, 2H), 1.21-0.94 (m, 5H), 0.85-0.76 (m, 2H), 0.75-0.59 (m, 1H).

2-(4-Chlorophenyl-1)-5-cyclopropyl-6-[3-hydroxypropyl(methylsulfonyl)amino]-N-methyl-indazole-3-carboxamide (54)

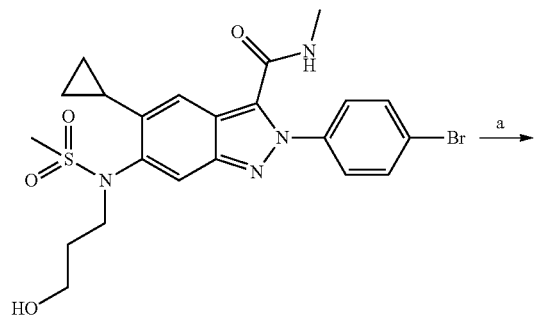

i

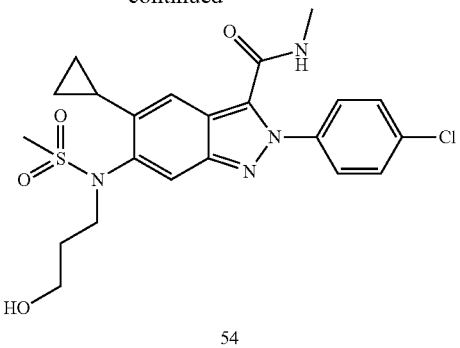

54

Step a: To a solution of 2-(4-bromophenyl)-5-cyclopropyl-6-[3-hydroxypropyl(methylsulfonyl)amino]-N-methyl-indazole-3-carboxamide (i), prepared similarly to Compound (24), (24 mg, 0.046 mmol) in DMF (1 mL) was added nickel chloride (30 mg, 0.23 mmol) and the reaction was heated under microwave irradiation at 200° C. for 20 min. The reaction mixture was partitioned between water (2 mL) and EtOAc (3 mL) and then extracted with EtOAc (2×5 mL). The organic layer was concentrated in vacuo and the residue was purified by reverse phase flash column chromatography eluting with ACN/water (5-40-100%) to afford Compound (54) as a white solid (15 mg, 68%). ESI-MS m/z calculated for [M+H]⁺: 477.1; found: 477.1; ¹H NMR (400 MHz, CD₃CN) δ 7.85 (d, J=0.5 Hz, 1H), 7.68-7.50 (m, 4H), 7.39 (s, 1H), 7.02 (s, 1H), 4.01-3.72 (m, 2H), 3.71-3.46 (m, 2H), 3.13 (s, 3H), 2.93 (d, J=4.8 Hz, 3H), 2.64 (brs, 1H), 2.49-2.35 (m, 1H), 1.89-1.62 (m, 2H), 1.19-0.93 (m, 3H), 0.80-0.48 (m, 1H).

5-cyclopropyl-6-[(3-hydroxypropyl)(methylsulfonyl)amino]-2-(4-methoxyphenyl)-N-methyl-2H-indazole-3-carboxamide (55)

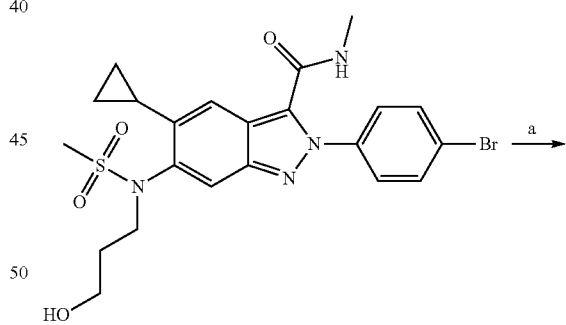

i

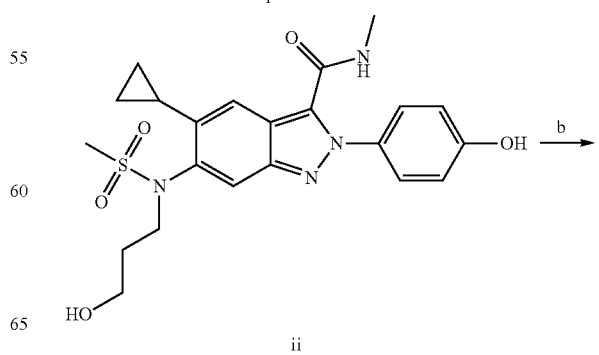

ii

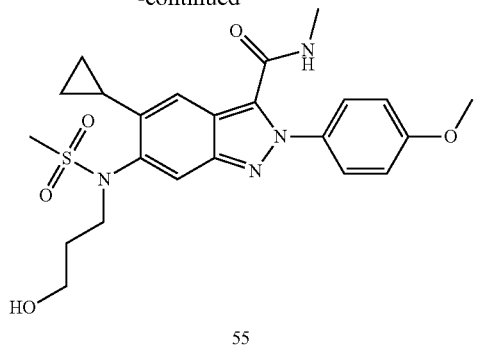

55

Step a: 2-(4-Bromophenyl)-5-cyclopropyl-6-[(3-hydroxypropyl)(methylsulfonyl)amino]-N-methyl-2H-indazole-3-carboxamide (i) (16 mg, 0.031 mmol) in 1,4-dioxane (0.5 mL) had a solution of potassium hydroxide (9 mg, 0.016 mmol) in water (0.5 mL) added and was degassed. tert-Butyl-XPhos (4 mg, 0.009 mmol) and Pd₂(dba)₃ (4 mg, 0.004 mmol) were added and the reaction was heated at 100° C. for 4 h. The mixture was cooled to RT, 1 M hydrochloric acid (0.5 mL) was added and this was then concentrated to dryness. The residue was purified by reverse phase flash column chromatography eluting with ACN/water (5-100%) to afford 5-cyclopropyl-2-(4-hydroxyphenyl)-6-[(3-hydroxypropyl)(methylsulfonyl)amino]-N-methyl-2H-indazole-3-carboxamide (ii) as a white solid (8 mg, 57%).

Step b: To a suspension of compound (ii) (3 mg, 0.007 mmol) and potassium carbonate (3 mg, 0.022 mmol) in DMF (0.25 mL) was added iodomethane (3 μL, 0.048 mmol) and the reaction was stirred at 60° C. for 45 min. The mixture was concentrated to dryness and the residue was purified by reverse phase flash column chromatography eluting with ACN/water (5-100%) to afford Compound (55) as a white solid (2 mg, 65%). ESI-MS m/z calculated for [M+H]⁺: 473.2; found: 473.2; ¹H NMR (400 MHz, Acetone) δ 7.86 (d, J=0.5 Hz, 1H), 7.64 (brs, 1H), 7.62-7.56 (m, 2H), 7.42 (s, 1H), 7.14-7.06 (m, 2H), 3.99-3.85 (m, 5H), 3.71-3.62 (m, 2H), 3.59 (t, J=5.2 Hz, 1H), 3.18 (s, 3H), 2.96 (d, J=4.7 Hz, 3H), 2.52-2.42 (m, 1H), 1.91-1.73 (m, 2H), 1.11-0.94 (m, 3H), 0.64-0.53 (m, 1H).

Routes (b) and (c): 2-(4-Chlorophenyl-5-cyclopropyl-6-[3,3-difluoropropyl(methylsulfonyl)-amino]-N-methyl-indazole-3-carboxamide (56); and 2-(4-chlorophenyl)-5-cyclopropyl-6-[3-fluoropropyl(methylsulfonyl)amino]-N-methyl-2H-indazole-3-carboxamide (57)

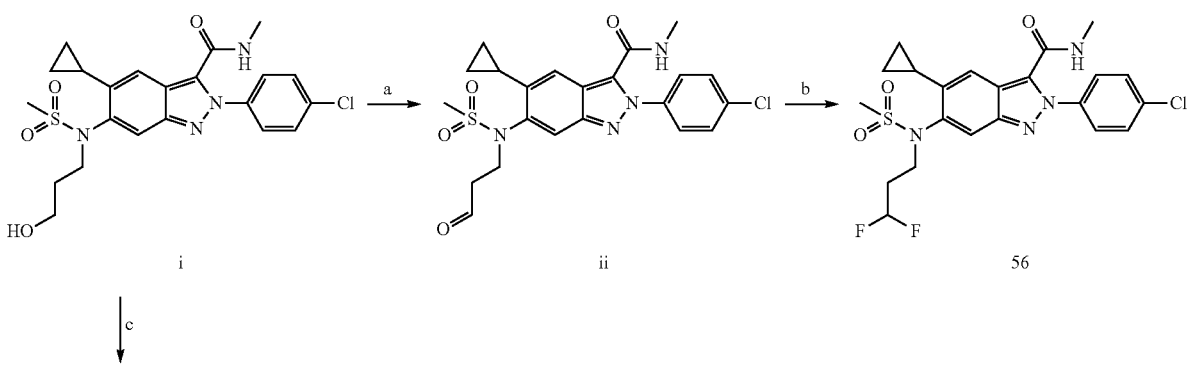

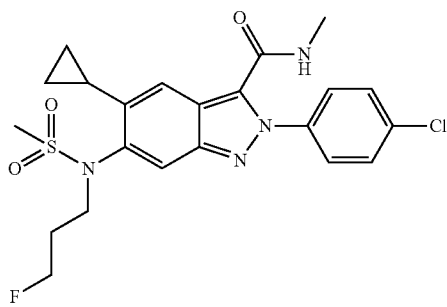

57

Route (b): Step a: To a solution of 2-(4-chlorophenyl)-5-cyclopropyl-6-[3-hydroxypropyl(methylsulfonyl)amino]-N-methyl-indazole-3-carboxamide (i) (16 mg, 0.034 mmol) in DCM (0.8 mL) at 0° C. was added Dess-Martin periodinane (22 mg, 0.051 mmol). The mixture was then stirred at RT for 1 h. Partial conversion to the aldehyde was observed. A further portion of Dess-Martin periodinane (22 mg, 0.051 mmol) was added and the mixture was stirred at RT for 18 h. The mixture was diluted with DCM (2 mL) and washed with saturated aqueous bicarbonate solution (0.5 mL), dried (MgSO$_4$) and concentrated in vacuo. The residue, 2-(4-chlorophenyl)-5-cyclopropyl-N-methyl-6-[methylsulfonyl(3-oxopropyl)amino]indazole-3-carboxamide (ii) was used in the subsequent fluorination step without further purification.

Step b: To a stirred solution of compound (ii) (15 mg, 0.032 mmol) in DCM (1.5 mL) was added Deoxo-Fluor (15 μL, 0.047 mmol) and the mixture was stirred at RT for 1 h. The mixture was diluted with DCM (1 mL) and washed with saturated aqueous sodium bicarbonate (0.5 mL). The organic phase was separated, dried (MgSO$_4$) and the solvent was removed in vacuo. The residue was purified by preparative LCMS (5-50-70-100% ACN in 0.1% aqueous formic acid) to afford Compound (56) as a white solid (2.5 mg, 16%). ESI-MS m/z calculated for [M+H]$^+$: 497.12; found: 497.06; $^1$H NMR (400 MHz, CDCl$_3$) δ 7.80 (s, 1H), 7.65-7.51 (m, 4H), 7.46 (s, 1H), 5.99 (tt, J=56.0, 4.2 Hz, 1H), 5.81 (br s, 1H), 4.10-3.91 (m, 2H), 3.12 (s, 3H), 3.05 (d, J=4.9 Hz, 3H), 2.48-2.37 (m, 1H), 2.37-2.12 (m, 2H), 1.21-1.03 (m, 3H), 0.68-0.59 (m, 1H).

Route (c): Step c: To a solution of compound (i) (13 mg, 0.027 mmol) in DCM (0.5 mL) at 0° C. was added Deoxo-Fluor (15 μL, 0.041 mmol). The mixture was then stirred at RT for 2 h. The mixture was diluted with DCM (2 mL), washed with aqueous sodium bicarbonate solution (2 mL), dried (MgSO$_4$) and concentrated in vacuo. The residue was purified by reverse phase flash column chromatography eluting with EtOAc/hexane (5-100%) to afford Compound (57) as a white solid (8 mg, 65%). ESI-MS m/z calculated for [M+H]$^+$: 479.1; found: 479.1; $^1$H NMR (400 MHz, CDCl$_3$) δ 7.80 (s, 1H), 7.61-7.53 (m, 4H), 7.44 (s, 1H), 5.81 (br s, 1H), 4.68-4.59 (m, 1H), 4.54-4.47 (m, 1H), 4.05-3.88 (m, 2H), 3.12 (s, 3H), 3.05 (d, J=4.9 Hz, 3H), 2.53-2.37 (m, 1H), 2.20-1.94 (m, 2H), 1.21-1.01 (m, 3H), 0.68-0.59 (m, 1H).

Method D Examples

Route (a): 2-(4-bromophenyl)-5-cyclopropyl-N-methyl-6-[(methylsulfonyl){2-[(2H-tetrazol-5-ylacetyl)amino]ethyl}amino]-2H-indazole-3-carboxamide (8)

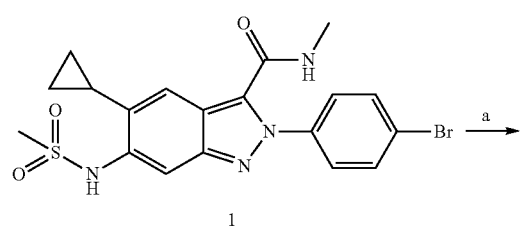

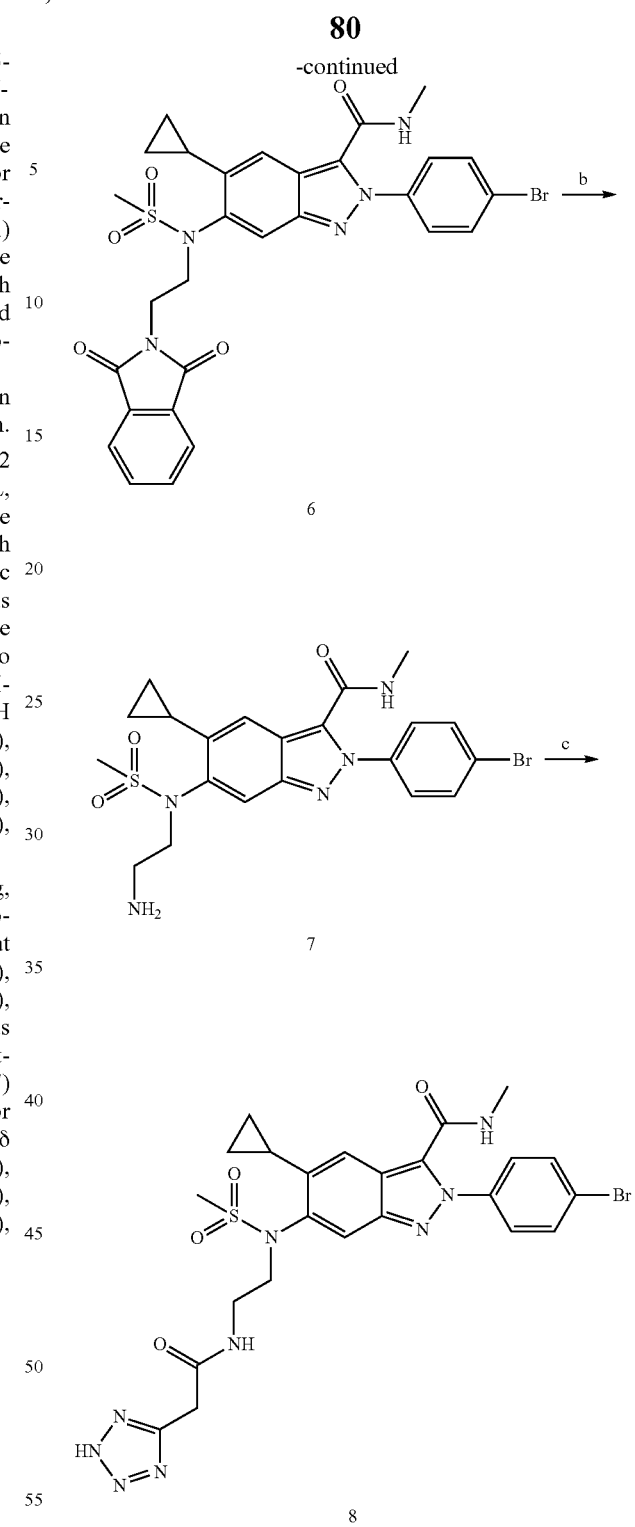

Step a: Intermediate (6) was prepared by alkylation of Compound (1) (210 mg, 0.45 mmol) with N-(2-bromoethyl)phthalimide (230 mg, 0.90 mmol) according to the procedure in Method C, Step a. The crude material was purified by flash column chromatography eluting with EtOAc/hexane (5-80%) to afford 2-(4-bromophenyl)-5-cyclopropyl-6-{[2-(1,3-dioxo-1,3-dihydro-2H-isoindol-2-yl)ethyl](methylsulfonyl)amino}-N-methyl-2H-indazole-3-carboxamide (6) as an off-white solid (22 mg).

Step b: A mixture of Compound (6) (92 mg, 0.14 mmol) and hydrazine hydrate (0.15 mL) in ethanol (7 mL) was stirred at RT for 16 h. The resulting suspension was filtered and the filtrate was concentrated to give a crude oil which then was partitioned between EtOAc (5 mL) and water (2 mL). The organic phase was separated and the aqueous phase was extracted with EtOAc (3×3 mL). The combined organic phase was dried (MgSO$_4$) and the solvent was removed in vacuo to give 6-[(2-aminoethyl)(methylsulfonyl)amino]-2-(4-bromophenyl)-5-cyclopropyl-N-methyl-2H-indazole-3-carboxamide (7) (68 mg, 93%). ESI-MS m/z calculated for [M+H]$^+$: 506.08/508.09; found: 505.88/507.89.

Step c: To a mixture of Compound (7) (34 mg, 67 μmol) and tetrazole acetic acid (10 mg, 81 μmol) in DMF (3 mL) at 0° C. was added HATU (31 mg, 81 μmol) and DIPEA (18 μL, 0.1 mmol). The mixture was stirred at RT for 40 min. Ethyl acetate (5 mL) was added and the mixture was washed with 1M hydrochloric acid and saturated sodium bicarbonate. The combined aqueous phase was neutralised to pH 7 (by addition of 6M hydrochloric acid) and lyophilised. The crude material was then purified by reverse phase flash column chromatography eluting with ACN/water (5-100%) to give Compound (8) (17 mg, 41%). ESI-MS m/z calculated for [M+H]$^+$: 616.11/618.11; found: 615.96/617.96. $^1$H NMR (400 MHz, d$_4$-MeOH) δ 9.42 (s, 1H), 9.27 (d, J=8.7 Hz, 2H), 9.10 (d, J=8.7 Hz, 2H), 8.87 (s, 1H), 5.55-5.37 (m, 2H), 5.37-5.14 (m, 2H), 5.01 (t, J=6.5 Hz, 2H), 4.70 (s, 3H), 4.52 (s, 3H), 3.95-3.73 (m, 1H), 2.69-2.41 (m, 3H), 2.27-2.10 (m, 1H).

4-[(3-{[5-Cyclopropyl-2-{4-[(4-fluorophenyl)amino]phenyl}-3-(methylcarbamoyl)-2H-indazol-6-yl](methylsulfonyl)amino}propyl)amino]-4-oxobutanoic acid (58)

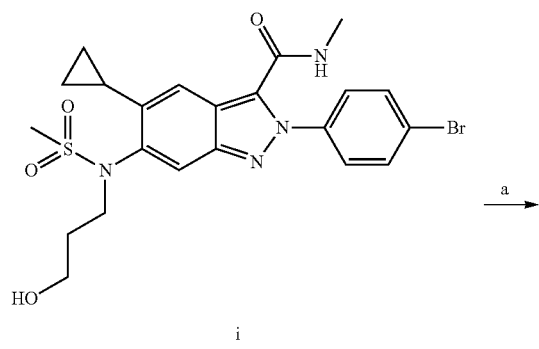

Step a: 5-Cyclopropyl-2-{4-[(4-fluorophenyl)amino]phenyl}-6-[(3-hydroxypropyl)(methylsulfonyl)amino]-N-methyl-2H-indazole-3-carboxamide (ii) was prepared similarly to Compound (5) (Method C, Step b) from 2-(4-bromophenyl)-5-cyclopropyl-6-[(3-hydroxypropyl)(methylsulfonyl)amino]-N-methyl-2H-indazole-3-carboxamide (i) using 4-fluoroaniline instead of 2-fluoroaniline.

Step b: To a solution of compound (ii) (5 mg, 0.009 mmol), triphenylphosphine (3.6 mg, 0.014 mmol) and phthalimide (2.0 mg, 0.014 mmol) in THF (0.5 mL) was added diisopropyl azodicarboxylate (2.7 μL, 0.014 mmol) at 0° C. After the mixture had been stirred at RT for 3.5 h, more triphenylphosphine (3.6 mg, 0.014 mmol), phthalimide (2.0 mg, 0.014 mmol) and DIAD (2.7 μL, 0.014 mmol) were added and stirring was continued at RT for a further 40 min. The solvent was removed in vacuo and the residue was purified by preparative LCMS (5-50-100% ACN in 0.1% aqueous formic acid) to afford 5-cyclopropyl-6-[3-(1,3-dioxoisoindolin-2-yl)propyl-methylsulfonyl-amino]-2-[4-(4-fluoroanilino)phenyl]-N-methyl-indazole-3-carboxamide (iii) as a white solid (20 mg, 81%).

Step c: 6-[3-Aminopropyl(methylsulfonyl)amino]-5-cyclopropyl-2-[4-(4-fluoroanilino)phenyl]-N-methyl-indazole-3-carboxamide (iv) was prepared by hydrolysis of compound (iii) using a similar procedure to Compound (7) (Method D, Step b).

Step d: Compound (58) was prepared in a similar manner to Compound (66) see below (Step c) to afford a white solid (3.7 mg, 58%). ESI-MS m/z calculated for [M+H]$^+$: 651.2; found: 651.1; $^1$H NMR (400 MHz, MeOD) δ 7.81 (s, 1H), 7.39 (brd, J=8.9 Hz, 2H), 7.36 (s, 1H), 7.24-7.12 (m, 2H), 7.12-6.94 (m, 4H), 3.91-3.65 (m, 2H), 3.25 (t, J=6.7 Hz, 2H), 3.14 (s, 3H), 2.93 (s, 3H), 2.55 (dd, J=10.5, 3.9 Hz, 2H), 2.48-2.32 (m, 3H), 1.90-1.67 (m, 2H), 1.16-0.89 (m, 3H), 0.75-0.53 (m, 1H).

6-{[3-(Acetylamino)propyl](methylsulfonyl)amino}-2-(4-bromophenyl)-5-cyclopropyl-N-methyl-2H-indazole-3-carboxamide (59) and 6-{[3-(acetylamino)propyl](methylsulfonyl)amino}-5-cyclopropyl-N-methyl-2-(4-[(2-methylpropyl)amino]phenyl)-2H-indazole-3-carboxamide (60)

calculated for [M+H]$^+$: 562.1/564.1; found: 561.9/563.9; $^1$H NMR (400 MHz, CDCl$_3$) δ 7.74 (s, 1H), 7.70-7.58 (m, 2H), 7.52-7.40 (m, 2H), 7.36 (s, 1H), 5.94 (t, J=5.9 Hz, 1H), 5.87 (brd, J=4.5 Hz, 1H), 3.89-3.67 (m, 2H), 3.50-3.27 (m, 2H), 3.06 (s, 3H), 3.00 (d, J=4.9 Hz, 3H), 2.44-2.26 (m, 1H), 1.97 (s, 3H), 1.80-1.73 (m, 2H), 1.15-0.97 (m, 3H), 0.67-0.54 (m, 1H).

Step b: To a degassed mixture of Compound (59) (4 mg, 0.0071 mmol), isobutylamine (2.1 uL, 0.021 mmol), 2-(di-tert-butylphosphino)biphenyl (0.4 mg, 0.001 mmol) and sodium tert-butoxide (1.37 mg, 0.014 mmol) in 1,4-dioxane (0.7 mL) was added Pd$_2$(dba)$_3$ (0.7 mg, 0.0007 mmol) and this was heated at 80° C. for 45 min. After cooling to RT, the mixture was diluted with MeOH (1 mL) and filtered. The filtrate was concentrated and the residue was purified by preparative HPLC (50-100% ACN in 5 mM aqueous ammonium acetate) to afford Compound (60) as a white solid (2.3 mg, 58%). ESI-MS m/z calculated for [M+H]$^+$: 555.3; found: 555.0; $^1$H NMR (400 MHz, CDCl$_3$) δ 7.72 (s, 1H), 7.65 (s, 1H), 7.40-7.28 (m, 2H), 6.75-6.62 (m, 2H), 5.96 (t, J=6.0 Hz, 1H), 5.61 (brd, J=4.5 Hz, 1H), 4.29-3.95 (m, 1H), 3.90-3.65 (m, 2H), 3.53-3.24 (m, 2H), 3.05 (s, 3H), 3.00 (d, J=6.8 Hz, 2H), 2.89 (d, J=4.9 Hz, 3H), 2.42-2.27 (m, 1H), 2.05-1.84 (m, 4H), 1.76 (p, J=6.6 Hz, 2H), 1.13-0.91 (m, 9H), 0.75-0.55 (m, 1H).

6-{[3-(β-Alanylamino)propyl](methylsulfonyl)amino}-2-(4-bromophenyl)-5-cyclopropyl-N-methyl-2H-indazole-3-carboxamide (61)

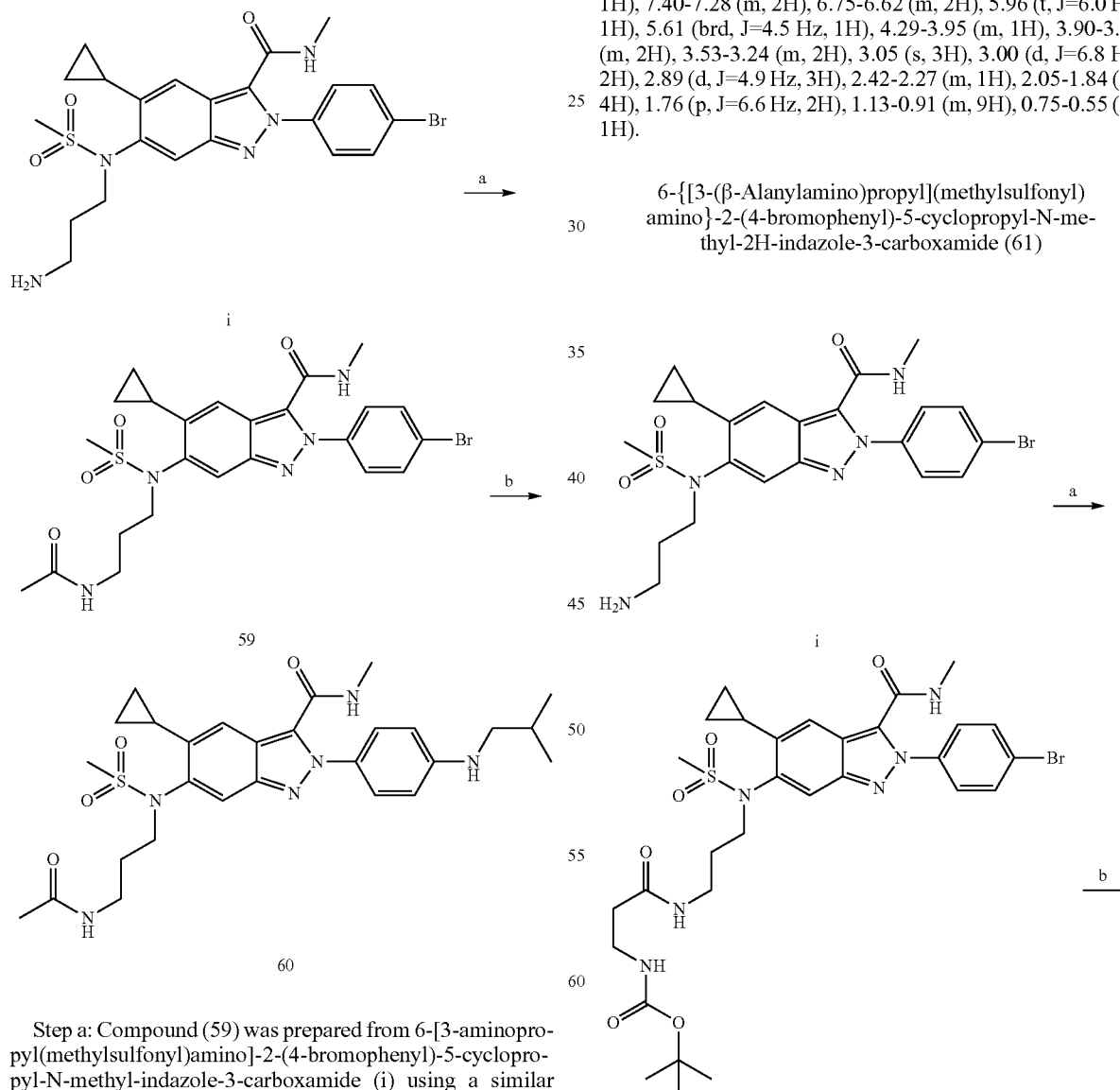

Step a: Compound (59) was prepared from 6-[3-aminopropyl(methylsulfonyl)amino]-2-(4-bromophenyl)-5-cyclopropyl-N-methyl-indazole-3-carboxamide (i) using a similar procedure to the synthesis of Compound (8) (step c), using acetic acid instead of tetrazole acetic acid, to afford the desired product as a white solid (5 mg, 23%). ESI-MS m/z

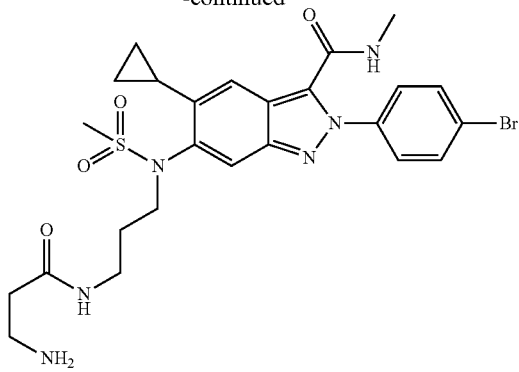

61

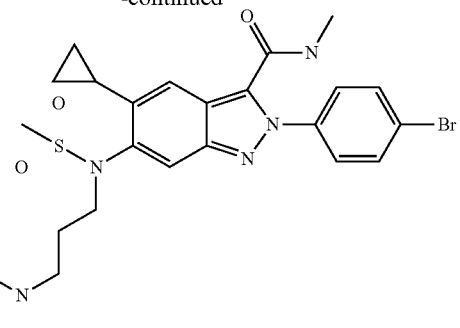

62

Step a: tert-Butyl {3-[(3-{[2-(4-bromophenyl)-5-cyclopropyl-3-(methylcarbamoyl)-2H-indazol-6-yl](methylsulfonyl)amino}propyl)amino]-3-oxopropyl}carbamate (ii) was prepared in a similar manner the synthesis of Compound (8) (step c) using N-tert-butyloxycarbonyl-beta-alanine instead of tetrazole acetic acid.

Step b: A mixture of compound (ii) (20 mg, 0.029 mmol) and trifluoroacetic acid (50 uL) in DCM (0.5 mL) was stirred at 40° C. for 1 h. After cooling to RT, solid potassium carbonate (50 mg) was added and the mixture was stirred vigorously for 10 min. Water (0.5 mL) was then added and the organic phase was separated. The aqueous phase was extracted with DCM (1 mL) and the combined organics were dried (MgSO$_4$) then concentrated in vacuo. The residue was purified by flash column chromatography eluting with MeOH/DCM (0-20%) to afford Compound (61) as a white solid (5.4 mg, 32%). ESI-MS m/z calculated for [M+H]$^+$: 591.1/593.1; found: 591.1/593.1; $^1$H NMR (400 MHz, CDCl$_3$) δ 7.74 (s, 1H), 7.69-7.60 (m, 2H), 7.50-7.42 (m, 2H), 7.35 (s, 1H), 7.24 (t, J=4.3 Hz, 1H), 5.95 (brd, J=4.6 Hz, 1H), 3.92-3.68 (m, 2H), 3.46-3.22 (m, 2H), 3.06 (s, 3H), 3.02-2.90 (m, 5H), 2.38 (tt, J=8.4, 5.4 Hz, 1H), 2.31-2.16 (m, 2H), 1.92-1.68 (m, 2H), 1.12-0.96 (m, 3H), 0.67-0.54 (m, 1H).

2-(4-Bromophenyl)-6-[{3-[(cyclobutylcarbonyl)amino]propyl}(methylsulfonyl)amino]-5-cyclopropyl-N-methyl-2H-indazole-3-carboxamide (62)

Step a: To a solution of 6-[3-aminopropyl(methylsulfonyl)amino]-2-(4-bromophenyl)-5-cyclopropyl-N-methyl-indazole-3-carboxamide (i) (5 mg, 0.01 mmol) in DCM (0.5 mL) at 0° C. was added pyridine (50 µL) followed by cyclobutanecarbonyl chloride (3 µL, 0.026 mmol). The mixture was then stirred at RT for 16 h. More pyridine (20 µL) and cyclobutylcarbonyl chloride (10 µL) were added and the mixture was left to stir for another 5 h. The solvent was then evaporated under reduced pressure. The residue was taken up in EtOAc (2 mL), washed with saturated aqueous sodium bicarbonate solution (1 mL), dried (MgSO$_4$) and concentrated in vacuo. The crude material was purified by preparative LCMS (5-40-70-100% ACN in 0.1% aqueous formic acid) to afford Compound (62) as a white solid (2.5 mg, 43%). ESI-MS m/z calculated for [M+H]$^+$: 602.1/604.1; found: 601.9/603.9; $^1$H NMR (400 MHz, CDCl$_3$) δ 7.74 (s, 1H), 7.71-7.60 (m, 2H), 7.50-7.41 (m, 2H), 7.36 (s, 1H), 5.82 (t, J=6.0 Hz, 2H), 3.92-3.65 (m, 2H), 3.55-3.26 (m, 2H), 3.04 (d, J=11.1 Hz, 3H), 3.02-2.90 (m, 4H), 2.44-2.30 (m, 1H), 2.30-2.07 (m, 4H), 2.03-1.81 (m, 2H), 1.77 (p, J=6.6 Hz, 2H), 1.17-0.94 (m, 3H), 0.72-0.52 (m, 1H).

(1R,2S)-2-[(3-{[2-(4-Bromophenyl)-5-cyclopropyl-3-(methylcarbamoyl)-2H-indazol-6-yl](methylsulfonyl)amino}propyl)carbamoyl]cyclopentanecarboxylic acid (63)

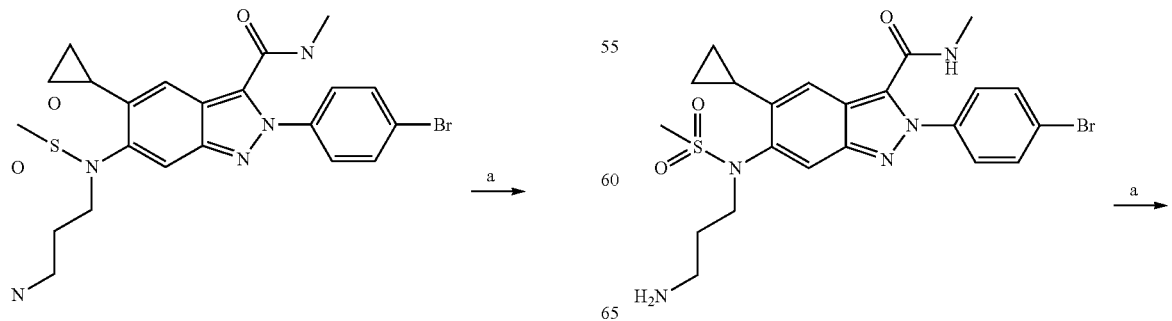

87
-continued

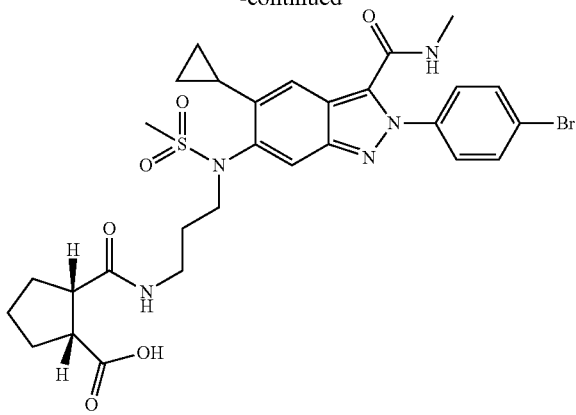

63

Step a: A mixture of Compound (7) (6.4 mg, 0.012 mmol) and cis-1,2-cyclopentanedicarboxylic acid (1.9 mg, 0.014 mmol) in pyridine (0.2 mL) was stirred at RT over the weekend. The solvent was removed under pressure. The crude material was purified by preparative LCMS (5-100% ACN in 0.1% aqueous formic acid) to afford Compound (63) as a white solid (0.7 mg, 8%). ESI-MS m/z calculated for [M+H]$^+$: 660.2/662.2; found: 660.0/662.0; $^1$H NMR (400 MHz, CDCl$_3$) δ 7.93 (s, 0.5H), 7.87 (s, 0.5H), 7.71 (d, J=8.7 Hz, 2H), 7.51 (dd, J=8.8, 2.2 Hz, 2H), 7.40 (d, J=3.7 Hz, 1H), 6.02-5.92 (m, 1H), 5.87 (d, J=4.1 Hz, 1H), 4.05-3.68 (m, 2H), 3.68-3.40 (m, 1H), 3.35-2.95 (m, 3H), 3.21 (s, 3H), 3.05 (d, J=4.9 Hz, 3H), 2.55-2.37 (m, 1H), 2.28-2.11 (m, 1H), 2.10-1.89 (m, 7H), 1.20-0.90 (m, 3H), 0.72-0.47 (m, 1H).

2-(4-Bromophenyl)-5-cyclopropyl-N-methyl-6-{[3-({[4-methylmorpholin-3-yl]carbonyl}amino)propyl](methylsulfonyl)amino}-2H-indazole-3-carboxamide (64)

88
-continued

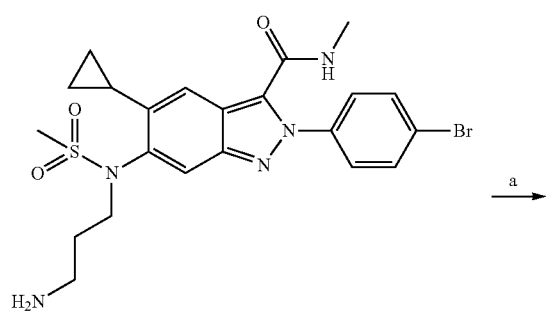

64

Step a: The intermediate compound was prepared following a similar procedure outlined in the synthesis of Compound (61), Step a and Step b using morpholine-3,4-dicarboxylic acid 4-tert-butylester instead of N-tert-butyloxycarbonyl-beta-alanine.

Step b: Compound (64) was prepared in a similar manner to Compound (65) see below (step a) to afford a white solid (5.9 mg, 58%). ESI-MS m/z calculated for [M+H]$^+$: 647.2/649.2; found: 647.1/649.0; $^1$H NMR (400 MHz, CDCl$_3$) δ 7.81 (s, 1H), 7.71 (d, J=8.8 Hz, 2H), 7.52 (d, J=8.7 Hz, 2H), 7.41 (s, 1H), 6.95 (brd, J=6.3 Hz, 1H), 5.84 (brs, 1H), 3.98 (brd, J=11.5 Hz, 1H), 3.93-3.72 (m, 3H), 3.67-3.18 (m, 4H), 3.10 (s, 3H), 3.05 (d, J=4.9 Hz, 3H), 2.90-2.71 (m, 2H), 2.52-2.34 (m, 2H), 2.28 (d, J=4.5 Hz, 3H), 2.02-1.79 (m, 2H), 1.21-1.09 (m, 2H), 1.09-0.99 (m, 1H), 0.77-0.57 (m, 1H).

Route (b): 2-(4-Bromophenyl)-5-cyclopropyl-6-{[3-(dimethylamino)propyl](methylsulfonyl)amino}-N-methyl-2H-indazole-3-carboxamide (65)

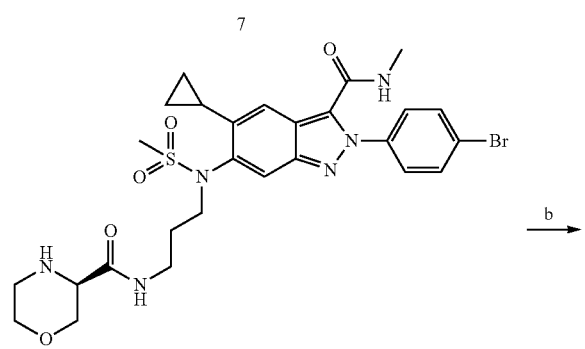

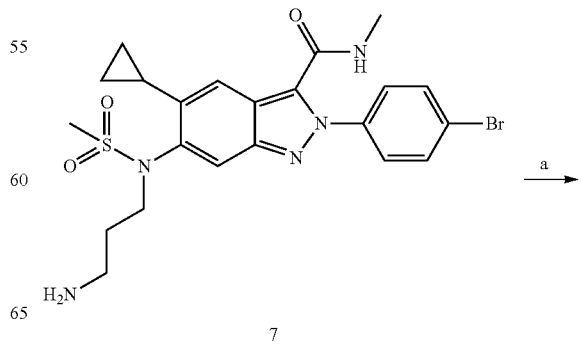

-continued

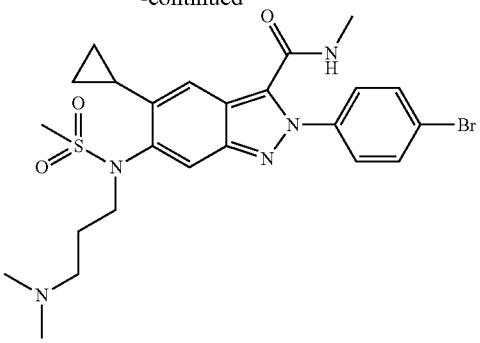

65

Step a: To a solution of Compound (7) (20 mg, 0.038 mmol) in MeOH (0.2 mL) at was added excess formaldehyde solution (10 μl, 37% aq solution) followed by sodium cyanoborohydride (4 mg, 0.058 mmol) and the mixture was stirred at RT for 30 min. The mixture was concentrated under reduced pressure. The residue was redissolved in DCM (10 mL), washed with saturated aqueous sodium bicarbonate (5 mL), brine (5 mL), dried (MgSO$_4$), and concentrated in vacuo. The crude material was purified by preparative LCMS (5-15-35-100% ACN in 0.1% aqueous formic acid) to afford Compound (65) as a white solid (2.12 mg, 10%). ESI-MS m/z calculated for [M+H]$^+$: 548.1/550.1; found: 548.1/550.1; $^1$H NMR (400 MHz, CDCl$_3$) δ 7.79 (s, 1H), 7.70 (d, J=8.7 Hz, 2H), 7.52 (d, J=8.7 Hz, 2H), 7.40 (s, 1H), 6.03 (brd, J=3.9 Hz, 1H), 4.00-3.77 (m, 2H), 3.11 (s, 3H), 3.05 (d, J=4.9 Hz, 3H), 2.66 (t, J=7.3 Hz, 2H), 2.42 (s, 6H), 2.06-1.81 (m, 3H), 1.21-1.05 (m, 2H), 1.07-0.93 (m, 1H), 0.79-0.56 (m, 1H).

Route (a): Methyl 4-[(3-{[2-(4-bromophenyl)-5-cyclopropyl-3-(methylcarbamoyl)-2H-indazol-6-yl](methylsulfonyl)amino}propyl)amino]-4-oxobutanoate (66); and N-(3-{[2-(4-bromophenyl)-5-cyclopropyl-3-(methylcarbamoyl)-2H-indazol-6-yl](methylsulfonyl)amino}propyl)-N-(propan-2-yl)butanediamide (67); and Route (c): 4-[(3-{[2-(4-bromophenyl)-5-cyclopropyl-3-(methylcarbamoyl)-2H-indazol-6-yl](methylsulfonyl)amino}propyl)amino]-4-oxobutanoic acid (68); and 2-(4-bromophenyl)-5-cyclopropyl-6-{[3-(2,5-dioxopyrrolidin-1-yl)propyl](methylsulfonyl)amino}-N-methyl-2H-indazole-3-carboxamide (69)

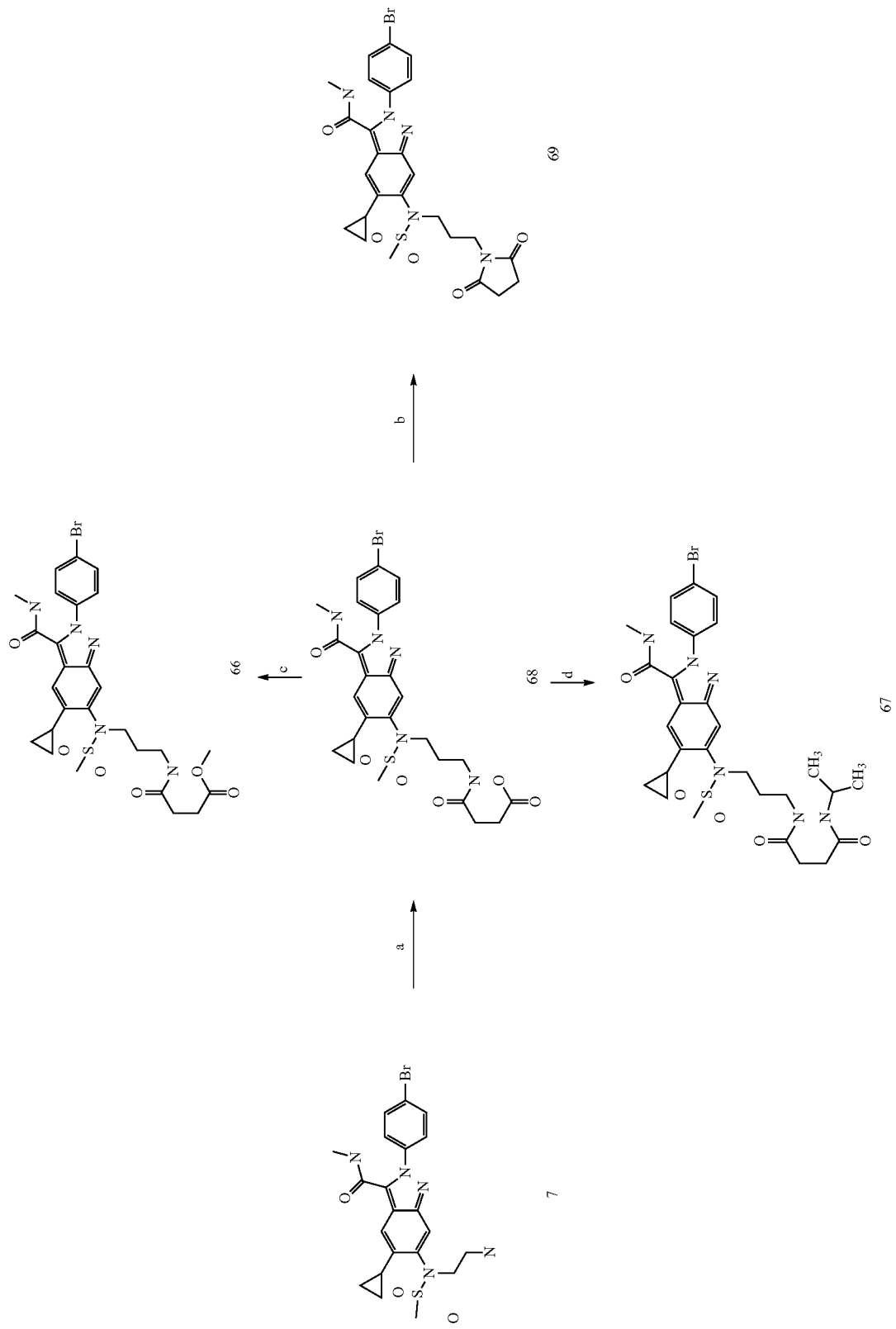

Step a: To a mixture of Compound (7) (95 mg, 0.18 mmol) and succinic acid (32 mg, 0.27 mmol) in DMF (3 mL) at 0° C. was added HATU (83 mg, 0.22 mmol) and DIPEA (48 μL, 0.27 mmol). The mixture was stirred at RT for 1.5 h. The solvent was removed under pressure, the residue was redissolved in EtOAc (5 mL) and washed with saturated aqueous sodium bicarbonate (3 mL). The aqueous phase was neutralized with hydrochloric acid, then extracted with EtOAc (2×5 mL). The combined organics were dried (MgSO$_4$) and the solvent was removed in vacuo. The residue was purified by reverse phase flash column chromatography (5-100%) eluting with ACN/0.1% aqueous formic acid to afford Compound (68) as a white solid (40 mg, 34%). ESI-MS m/z calculated for [M+H]$^+$: 620.1/622.1; found: 619.9/621.9; $^1$H NMR (400 MHz, CDCl$_3$) δ 7.77 (s, 1H), 7.66 (d, J=8.8 Hz, 2H), 7.45 (d, J=8.7 Hz, 2H), 7.34 (s, 1H), 6.28 (brs, 1H), 5.98 (brs, 1H), 3.90-3.66 (m, 2H), 3.49-3.30 (m, 2H), 3.06 (s, 3H), 2.99 (d, J=4.9 Hz, 3H), 2.69-2.57 (m, 2H), 2.48-2.40 (m, 2H), 2.40-2.33 (m, 1H), 1.81-1.75 (m, 2H), 1.14-0.92 (m, 3H), 0.63-0.52 (m, 1H).

Step b: To a stirred solution of Compound (68) (45 mg, 0.073 mmol) in ACN (5 mL) and MeOH (50 μL) were added potassium carbonate (104 mg, 0.75 mmol) and methyl iodide (0.45 mL, 7.2 mmol). The reaction mixture was then stirred at RT. The reaction mixture was filtered and the residue washed with EtOAc (2 mL) and ACN (2 mL). The volatiles were then removed in vacuo and the residue was purified by preparative HPLC (40-60-100% ACN in 0.1% aqueous formic acid) to afford Compound (69) as a white solid (5.1 mg, 11%). ESI-MS m/z calculated for [M+H]$^+$: 602.1/604.1; found: 601.9/603.9; $^1$H NMR (400 MHz, CDCl$_3$) δ 7.78 (s, 1H), 7.71 (d, J=8.7 Hz, 2H), 7.51 (d, J=8.7 Hz, 2H), 7.41 (s, 1H), 5.90-5.81 (brm, 1H), 3.88-3.72 (m, 2H), 3.60 (t, J=7.1 Hz, 2H), 3.11 (s, 3H), 3.05 (d, J=4.9 Hz, 3H), 2.73 (s, 4H), 2.47-2.37 (m, 1H), 2.07-1.85 (m, 2H), 1.20-1.10 (m, 2H), 1.08-0.98 (m, 1H), 0.70-0.61 (m, 1H).

Step c: A mixture of Compound (68), iodomethane (0.08 mL, 1.3 mmol) and potassium carbonate (15 mg, 0.11 mmol) in ACN (0.5 mL) was stirred at RT for 16 h. The mixture was then filtered and the solvent was removed under pressure. The residue was purified by preparative LCMS (5-40-70-100% ACN in 0.1% aqueous formic acid) to afford Compound (66) (5.5 mg, 67%) as a white solid. ESI-MS m/z calculated for [M+H]$^+$: 634.1/636.1; found: 633.9/635.9; $^1$H NMR (400 MHz, CDCl$_3$) δ 7.74 (s, 1H), 7.70-7.62 (m, 2H), 7.50-7.44 (m, 2H), 7.36 (s, 1H), 6.06 (t, J=6.0 Hz, 1H), 5.85 (brd, J=4.7 Hz, 1H), 3.94-3.71 (m, 2H), 3.68 (s, 3H), 3.52-3.25 (m, 2H), 3.07 (s, 3H), 3.00 (d, J=4.9 Hz, 3H), 2.66 (dd, J=9.9, 4.1 Hz, 2H), 2.46 (dd, J=8.3, 5.2 Hz, 2H), 2.42-2.28 (m, 1H), 1.77 (p, J=6.6 Hz, 2H), 1.16-0.94 (m, 3H), 0.68-0.54 (m, 1H).

Step d: To a mixture of Compound (68) (5 mg, 0.008 mmol) and isopropylamine (5 μL, 0.012 mmol) in DMF (0.5 mL) at 0° C. was added HATU (3.7 mg, 0.01 mmol) and DIPEA (2.1 μL, 0.012 mmol). The mixture was stirred at RT for 16 h and the solvent was then removed in vacuo. The residue was purified by reverse phase flash column chromatography eluting with ACN in 0.1% aqueous formic acid (5-100%) to afford Compound (67) (5.0 mg, 94%). ESI-MS m/z calculated for [M+H]$^+$: 661.2/663.2; found: 661.0/663.0; $^1$H NMR (400 MHz, CDCl$_3$) δ 7.73 (s, 1H), 7.68-7.61 (m, 2H), 7.50-7.42 (m, 2H), 7.34 (s, 1H), 6.43 (t, J=6.0 Hz, 1H), 6.08 (brd, J=4.8 Hz, 1H), 5.79 (brd, J=7.4 Hz, 1H), 4.12-3.87 (m, 1H), 3.87-3.65 (m, 2H), 3.45-3.19 (m, 2H), 3.07 (s, 3H), 3.00 (d, J=4.9 Hz, 3H), 2.51-2.26 (m, 5H), 1.78-1.75 (m, 2H), 1.17-0.88 (m, 9H), 0.68-0.51 (m, 1H).

Route (d): 2-(4-Bromophenyl)-5-cyclopropyl-N-methyl-6-{(methylsulfonyl)[3-(2-oxoimidazolidin-1-yl)propyl]amino}-2H-indazole-3-carboxamide (70)

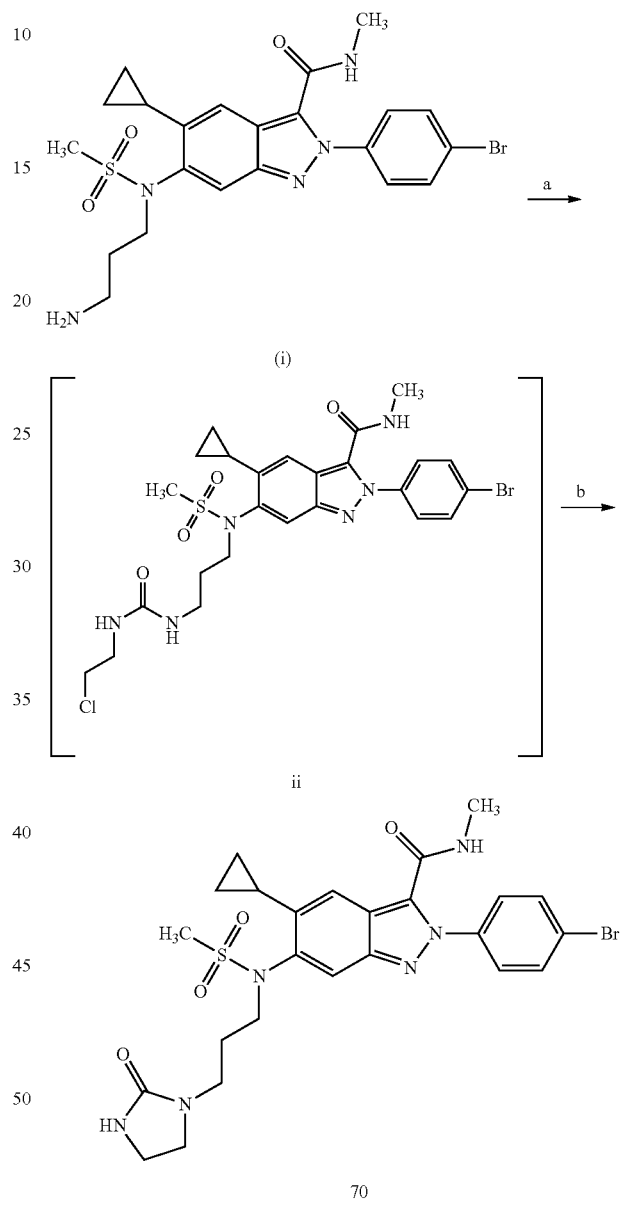

Step a: To a solution of 6-[(3-aminopropyl)(methylsulfonyl)amino]-2-(4-bromophenyl)-5-cyclopropyl-N-methyl-2H-indazole-3-carboxamide (i), similarly prepared to Compound (7), (13 mg, 0.025 mmol) in DCM (0.3 mL) was added 2-chloroethyl isocyanate (10 μL, 0.12 mmol) and the mixture was stirred at RT. After 2.5 h the mixture was concentrated to dryness to give crude 2-(4-bromophenyl)-6-[(3-{[(2-chloroethyl)carbamoyl]amino}propyl)(methylsulfonyl)amino]-5-cyclopropyl-N-methyl-2H-indazole-3-carboxamide (ii) which was used directly in the next step without purification.

Step b: To a suspension of crude compound (ii) in ethanol (0.3 mL) was added 3M aqueous sodium hydroxide (0.2 mL, 0.60 mmol) and this was stirred at 40° C. for 1 h and then at RT for 3 days. The mixture was neutralised by addition of 6M hydrochloric acid, the ethanol was removed under reduced pressure and the resulting aqueous suspension was extracted with DCM (1 mL). The organic layer was dried (MgSO₄) and concentrated to dryness. The residue was purified by preparative LCMS (5-30-50-100% ACN in 0.1% aqueous formic acid) to give Compound (70) as a white solid (1.5 mg, 10%). ESI-MS m/z calculated for [M+H]⁺: 589.1/591.1; found: 589.1/591.1; ¹H NMR (400 MHz, CDCl₃) δ 8.37 (brs, 1H), 7.76 (d, J=6.4 Hz, 1H), 7.71-7.59 (m, 2H), 7.51-7.41 (m, 2H), 7.35 (d, J=4.4 Hz, 1H), 6.20 (brd, J=4.7 Hz, 1H), 4.77-4.53 (m, 2H), 3.92-3.65 (m, 4H), 3.54-3.27 (m, 2H), 3.07 (s, 3H), 3.01 (d, J=4.9 Hz, 3H), 2.39-2.32 (m, 1H), 1.93-1.86 (m, 2H), 1.12-0.94 (m, 3H), 0.70-0.56 (m, 1H).

Method E Examples 2-(4-bromophenyl)-5-cyclopropyl-6-[(2-{[(4-fluorobenzyl)sulfonyl]amino}ethyl)methylsulfonyl)amino]-N-methyl-2H-indazole-3-carboxamide (9)

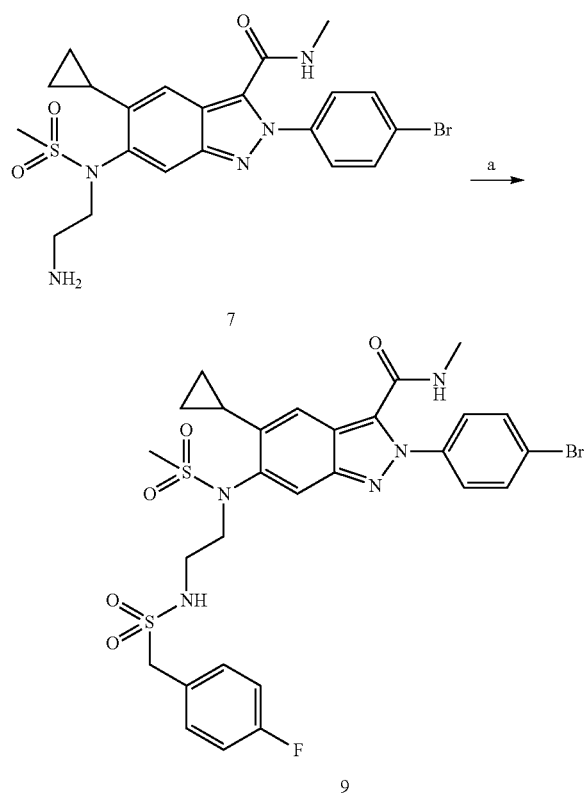

Step a: To a solution of Compound (7) (34 mg, 67 μmol) prepared according to Method D in DMF (3 mL) at 0° C. was added DIPEA (18 ΞL, 100 μmol) followed by 4-(fluorophenyl)methanesulfonyl chloride (17 mg, 81 μmol) and the mixture was left stirring for 16 h at RT (monitored by LCMS). The solvent was removed in vacuo to give the crude mixture which was purified by flash column chromatography eluting with EtOAc/hexane (5-100%) to give partially purified product (34 mg, 75%). A portion of this compound (10 mg) was purified further by preparative HPLC to give Compound (9) (3.34 mg). ESI-MS m/z calculated for [M+H]⁺: 678.09/680.08; found: 677.96/679.96. ¹H NMR (400 MHz, CDCl₃) δ 7.74 (s, 1H), 7.67 (brd, J=8.8 Hz, 2H), 7.47 (brd, J=8.8 Hz, 2H), 7.40-7.31 (m, 3H), 7.09-6.98 (m, 2H), 5.82 (d, J=4.7 Hz, 1H), 4.70 (t, J=6.1 Hz, 1H), 4.23 (s, 2H), 3.92-3.68 (m, 2H), 3.15 (ddd, J=14.9, 12.0, 6.1 Hz, 2H), 3.09 (s, 3H), 2.99 (d, J=4.9 Hz, 3H), 2.35-2.19 (m, 1H), 1.14-0.85 (m, 3H), 0.59-0.43 (m, 1H).

Method F Examples 2-(4-fluorophenyl)-6-[2-hydroxyethyl(methylsulfonyl)amino]-5-methoxy-N-methyl-indazole-3-carboxamide (12)

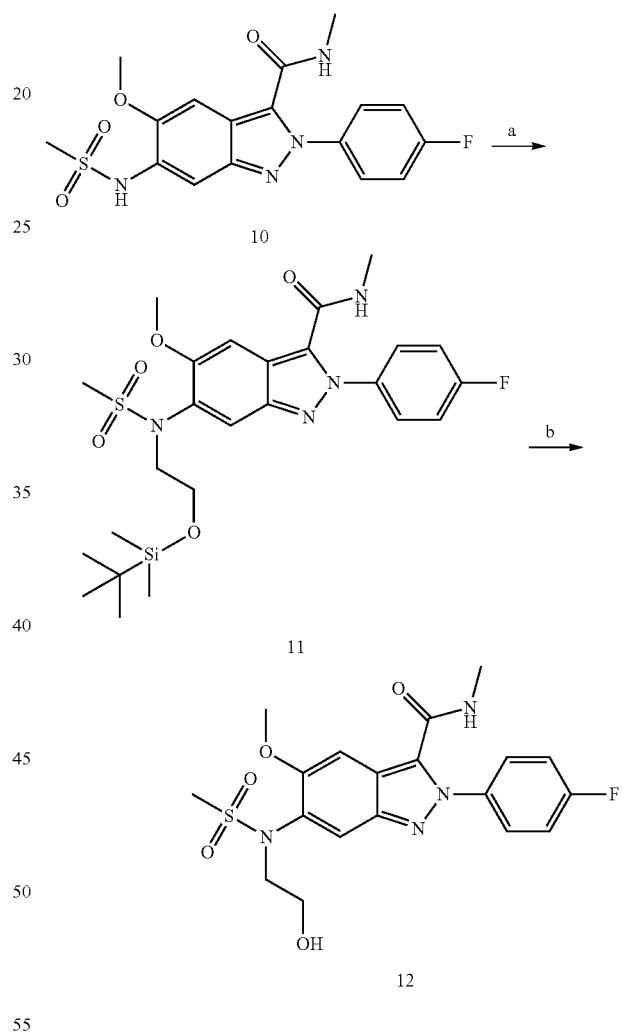

Step a: To a stirred solution of 2-(4-fluorophenyl)-5-methoxy-N-methyl-6-[(methylsulfonyl)amino]-2H-indazole-3-carboxamide (10) (250 mg, 0.64 mmol) in DMF (15 mL) was added potassium carbonate (173 mg, 1.26 mmol) and 2-(bromoethoxy)(tert-butyl)dimethylsilane (228 mg, 0.95 mmol) and the reaction mixture was heated at 80° C. for 5 h (monitored by TLC and LCMS). Water was then added to the reaction mixture and the product was extracted into DCM. The organic phase was dried (MgSO₄) and concentrated in vacuo. The crude mixture was purified by flash column chromatography using EtOAc/hexane (5-20%) to give 6-[(2-{[tert-butyl(dimethyl)silyl]oxy}ethyl)(methylsulfonyl)

amino]-2-(4-fluorophenyl)-5-methoxy-N-methyl-2H-indazole-3-carboxamide (11) (250 mg, 75%). ESI-MS m/z calculated for [M+H]⁺: 551.22; found 551.30.

NB: 2-(4-Fluorophenyl)-5-methoxy-N-methyl-6-[(methylsulfonyl)amino]-2H-indazole-3-carboxamide (10) was prepared following procedure described in Method A Steps d-i using 5-methoxy-2,4-dinitrobenzaldehyde in place of 5-cyclopropyl-2,4-dinitrobenzaldehyde.

Step b: To a stirred solution of Compound (11) (250 mg, 0.45 mmol) in MeOH (20 mL) was added ammonium fluoride (166 mg, 4.5 mmol) and water (5 mL). The reaction mixture was heated to 60° C. for 5 h (monitored by TLC and LCMS). MeOH was removed in vacuo and the residue was diluted with water. The resulting precipitate was filtered, washed with ethanol and dried in vacuo at 40° C. to give Compound (12) (65 mg, 33%). ESI-MS m/z calculated for [M+Na]⁺: 459.11; found: 459.11; $^1$H NMR (400 MHz, d$_6$-DMSO) δ 8.65 (s, 1H), 7.77 (s, 1H), 7.65-7.52 (m, 2H), 7.46-7.32 (m, 2H), 7.15 (s, 1H), 4.80-4.70 (m, 1H), 3.92 (s, 3H), 3.78-3.39 (m, 4H), 3.08 (s, 3H), 2.88-2.77 (m, 3H).

Method G Examples

2-[(2-{[5-cyclopropyl-2-(4-fluorophenyl)-3-(methylcarbamoyl)-2H-indazol-6-yl](methylsulfonyl)amino}ethoxy)carbonyl]benzoic acid (15)

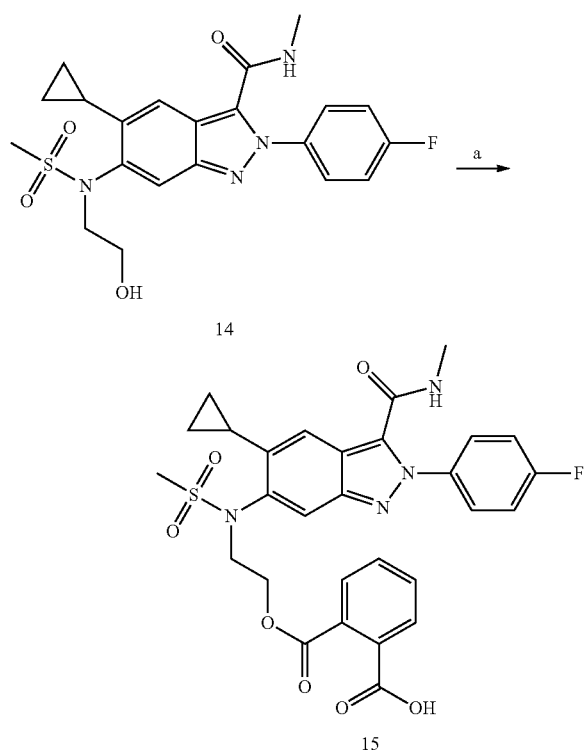

Step a: To a solution of 5-cyclopropyl-2-(4-fluorophenyl)-6-[(2-hydroxyethyl)(methylsulfonyl)amino]-N-methyl-2H-indazole-3-carboxamide (14) (5.00 mg, 0.0112 mmol) in pyridine (0.200 mL) at RT was added phthalic anhydride (8.29 mg, 0.560 mmol). The reaction mixture was heated under microwave irradiation at 100° C. for 15 min. A further portion of phthalic anhydride (8.29 mg, 0.560 mmol) was added and the reaction mixture reheated at 100° C. for 30 min and 110° C. for 30 min. A further portion of phthalic anhydride (16.6 mg, 1.12 mmol) was added and the reaction mixture was heated at 120° C. for 15 min. The reaction mixture was concentrated in vacuo, the residue redissolved in MeOH (1 mL) and purified by preparative LCMS (40-80% ACN in 0.1% aqueous formic acid). 2-[(2-{[5-cyclopropyl-2-(4-fluorophenyl)-3-(methylcarbamoyl)-2H-indazol-6-yl](methylsulfonyl)amino}ethoxy)carbonyl]benzoic acid (15) was isolated as a white solid (4.29 mg, 64%). ESI-MS m/z calculated for [M+H]⁺: 595.16; found: 594.98; $^1$H NMR (400 MHz, d$_4$-MeOH) δ 7.85 (s, 1H), 7.75 (brd, J=7.4 Hz, 2H), 7.63-7.58 (m, 2H), 7.53 (ddd, J=19.3, 15.5, 6.6 Hz, 1H), 7.48-7.42 (m, 2H), 7.34 (brs, 1H), 7.33-7.26 (m, 1H), 4.51-4.37 (m, 2H), 4.32-4.23 (m, 1H), 4.11-4.02 (m, 1H), 3.10 (s, 3H), 2.92 (s, 3H), 2.39-2.30 (m, 1H), 1.06-0.94 (m, 3H), 0.66-0.59 (m, 1H).

NB: 5-Cyclopropyl-2-(4-fluorophenyl)-6-[(2-hydroxyethyl)(methylsulfonyl)amino]-N-methyl-2H-indazole-3-carboxamide (14) was prepared following the procedure described in Method F using 5-cyclopropyl-2-(4-fluorophenyl)-N-methyl-6-[(methylsulfonyl)amino]-2H-indazole-3-carboxamide (13) in place of 2-(4-fluorophenyl)-5-methoxy-N-methyl-6-[(methylsulfonyl)amino]-2H-indazole-3-carboxamide (10). 5-cyclopropyl-2-(4-fluorophenyl)-N-methyl-6-[(methylsulfonyl)amino]-2H-indazole-3-carboxamide (13) in turn was prepared according to Method A using 4-fluoroaniline in place of 4-bromoaniline in Step d. Alternatively, esterification may be carried out as for Compound (116) with a suitable carboxylic acid using a coupling agent (e.g. DCC), 4-DMAP in DMF.

Method H Examples 2-({3-[2-(4-Fluorophenyl)-3-(methylcarbamoyl)-2H-indazol-6-yl]phenyl}carbamoyl)benzoic acid (17)

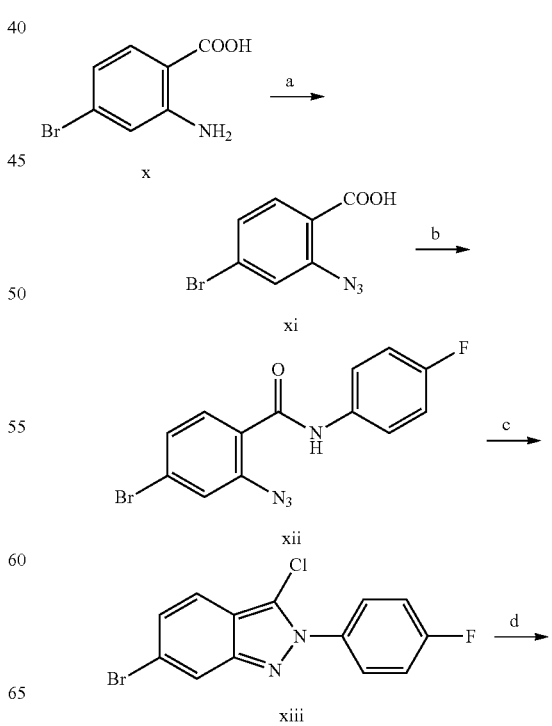

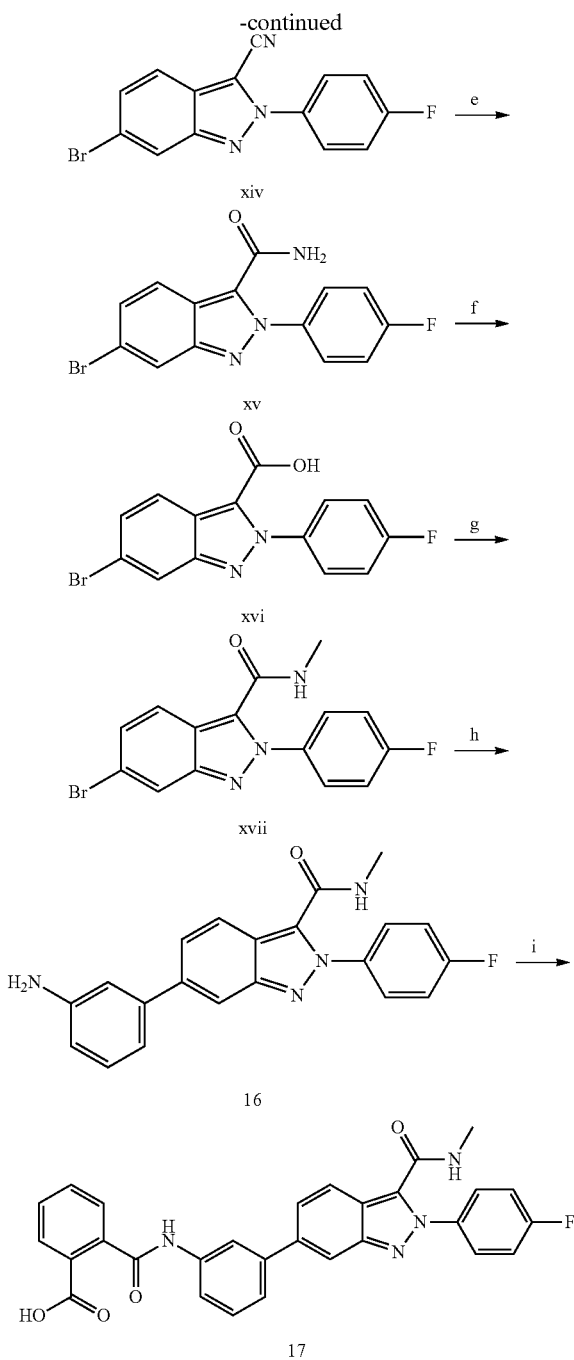

Step a: To a stirred suspension of 2-amino-4-bromobenzoic acid (x) (10 g, 46.3 mmol) in water (20 mL) was added conc. hydrochloric acid (88 mL) at 5 PC and the reaction mixture was heated at 80° C. for 30 min. The reaction mixture was cooled to 0 PC and a solution of sodium nitrite (3.83 mg, 55.55 mmol) in water (10 mL) was added dropwise. After 1 h at 0 PC a solution of sodium azide (2.95 mg, 45.37 mmol) and sodium acetate (55.9 g, 681.64 mmol) in water (58 mL) was prepared and the above mixture was added to this dropwise. The resulting reaction mixture was stirred at RT for 3 h. The observed solid product was filtered and washed with water (3×50 mL) and dried (Na$_2$SO$_4$) to give 2-azido-4-bromobenzoic acid (xi) as an off-white solid (10.12 g, 90%).

Step b: To a stirred solution of compound (xi) (15 g, 61.98 mmol) in DMF (150 mL) was added HATU (28.28 g, 74.34 mmol) at 0° C. The reaction mixture was stirred for 15 min and DIPEA (16.01 mL, 92.26 mmol) was added followed by 4-fluoroaniline (7.57 g, 68.68 mmol) at the same temperature. The reaction mixture was allowed to warm to RT and stirring was continued for 16 h. The reaction was then poured into cold water (500 mL) and stirred for 15 min. The solid was filtered and washed with water (3×100 mL) and dried (Na$_2$SO$_4$) to give 2-azido-4-bromo-N-(4-fluorophenyl)-benzamide (xii) (19 g, 91%) as an off-white solid.

Step c: A mixture of compound (xii) (6.44 g, 19.20 mmol) and POCl$_3$ (50 mL) was heated at 95° C. for 6 h. The volatiles were removed under reduced pressure and the residue was basified by the addition of an ice-cold saturated solution of sodium carbonate. The solid obtained was filtered and dried (Na$_2$SO$_4$) to give the crude product which was purified by column chromatography on 100-200 mesh silica gel eluting with EtOAc/hexane (3-5%) to give 6-bromo-3-chloro-2-(4-fluorophenyl)-2H-indazole (xiii) (4 g, 64%) as a white solid. ESI-MS m/z calculated for [M+H]$^+$: 326.95; found: 326.95.

Step d: To a stirred solution of compound (xiii) (4.49 g, 12.86 mmol) in DMF (50 mL) was added sodium cyanide (1.34 g, 27.73 mmol) at RT and the reaction mixture was then heated at 130° C. for 2 h. The reaction mixture was then diluted with saturated FeCl$_3$ solution and extracted with EtOAc (3×75 mL). The combined organic layers were washed with water, dried (Na$_2$SO$_4$) and concentrated to give the crude product which was purified by column chromatography on 100-200 mesh silica gel eluting with EtOAc/hexane (2-4%) to give 6-bromo-2-(4-fluorophenyl)-2H-indazole-3-carbonitrile (xiv) (2.2 g, 50%) as white solid. ESI-MS m/z calculated for [M+H]$^+$: 317.99; found: 317.90.

Step e: To a stirred suspension of compound (xiv) (50 mg, 0.16 mmol) in ethanol:water (1:1, 6 mL) was added sodium hydroxide (63 mg, 0.16 mmol) and the reaction mixture was heated at 70° C. for 2 h. The reaction mixture was cooled to RT and the volatiles were removed under reduced pressure. The residue was acidified to pH 2 upon addition of 2N hydrochloric acid. The resulting precipitate was filtered, washed with water (2×20 mL) and dried (Na$_2$SO$_4$) to give 6-bromo-2-(4-fluorophenyl)-2H-indazole-3-carboxamide (xv) (50 mg, 94%) as white solid. ESI-MS m/z calculated for [M+H]$^+$: 334.00; found: 334.00.

Step f: A stirred suspension of compound (xv) in conc. sulfuric acid (5 mL) and water (5 mL) were heated to 90° C. After 2 h the reaction mixture was diluted with water, neutralized with sodium bicarbonate and extracted with EtOAc (3×15 mL). The organic layer was dried (Na$_2$SO$_4$) and concentrated to give 6-bromo-2-(4-fluorophenyl)-2H-indazole-3-carboxylic acid (xvi) (70 mg, 35%) as a white solid. ESI-MS m/z calculated for [M+H]$^+$: 336.98; found: 336.80.

Step g: To a stirred solution of compound (xvi) (50 mg, 0.15 mmol) in DMF (5 mL) were added HATU (85 mg, 0.22 mmol) DIPEA (0.1 mL, 0.45 mmol) and methyl amine solution (0.26 mL, 0.15 mmol) at 0° C. and the reaction mixture was stirred at RT. After 12 h the reaction mixture was diluted with water and the precipitated solid was filtered to give 6-bromo-2-(4-fluorophenyl)-N-methyl-2H-indazole-3-carboxamide (xvii) (30 mg, 58%) as a white solid. ESI-MS m/z calculated for [M+H]$^+$: 348.01; found: 347.90.

Step h: A suspension of compound (xvii) (10 mg, 0.03 mmol), boronic acid (5.9 mg, 0.04 mmol), cesium carbonate (14 mg, 0.04 mmol) and tetrakis(triphenylphosphine)palladium (2 mg, 0.001 mmol) in ethanol (2 mL) were degassed and stirred under an atmosphere of nitrogen then heated to 8° C. After 3 h the reaction mixture was concentrated and the residue was partitioned between EtOAc (25 mL) and water (15 mL). The organic layer was separated and the aqueous layer was extracted with EtOAc (3×15 mL). The combined organics were washed with brine (15 mL), dried (MgSO₄) and concentrated to give 6-(3-aminophenyl)-2-(4-fluorophenyl)-N-methyl-2H-indazole-3-carboxamide (16) (12 mg) as a pale brown oil. The crude material was used directly. ESI-MS m/z calculated for [M+H]⁺: 361.13; found: 361.14.

Step i: To a solution of Compound (16) (10 mg, 0.03 mmol) in ACN (3 mL) was added phthalic anhydride (8.2 mg, 0.06 mmol) and the reaction mixture was heated to 70° C. and stirred for 15 h. The reaction mixture was then cooled to RT and the resulting precipitate was collected by filtration. The residue was washed with cold ACN (5 mL) to afford Compound (17) as an off-white amorphous solid (7.83 mg, 55%). ESI-MS m/z calculated for [M+H]⁺: 509.15; found: 509.08. ¹H NMR (400 MHz, d₆-DMSO) δ 13.07 (brs, 1H), 10.47 (s, 1H), 8.77-8.71 (m, 1H), 7.99-7.87 (m, 3H), 7.77-7.38 (m, 12H), 2.85 (d, J=4.5 Hz, 3H).

Method I Examples

Route (a): 5-Ethenyl-6-[ethyl(methylsulfonyl)amino]-2-(4-fluorophenyl)-N-methyl-2H-indazole-3-carboxamide (71); and 5-ethyl-6-[ethyl(methylsulfonyl)amino]-2-(4-fluorophenyl)-N-methyl-2H-indazole-3-carboxamide (72)

Step a: To a mixture of 5-bromo-6-[ethyl(methylsulfonyl)amino]-2-(4-fluorophenyl)-N-methyl-2H-indazole-3-carboxamide (i) (21 mg, 0.044 mmol), vinyl boronic acid, pinacol ester (15 μL, 0.087 mmol) and PdCl₂(dppf).CH₂Cl₂ (2.2 mg, 0.0027 mmol) in 1,4-dioxane (900 μL) was added a solution of cesium carbonate (45.2 mg, 0.14 mmol) in water (300 μL). The reaction was heated under microwave irradiation at 80° C. for 20 min. Acetone (4 mL) was added, the mixture was filtered and the filtrate concentrated to dryness. The residue was purified by reverse phase flash column chromatography eluting with ACN/water (0-100%) to give Compound (71) as a white solid (7 mg, 39%). ESI-MS m/z calculated for [M+H]⁺: 417.1; found: 417.1; ¹H NMR (400 MHz, Acetone) δ 8.17 (d, J=0.6 Hz, 1H), 7.93-7.86 (m, 2H), 7.80-7.71 (m, 2H), 7.42-7.33 (m, 2H), 7.26 (ddd, J=17.5, 11.0, 0.5 Hz, 1H), 5.85 (dd, J=17.6, 1.4 Hz, 1H), 5.35 (dd, J=11.0, 1.4 Hz, 1H), 3.85-3.76 (m, 2H), 3.16 (s, 3H), 3.00 (d, J=4.7 Hz, 3H), 1.15 (t, J=7.2 Hz, 3H).

Step b: To a solution of Compound (71) (6 mg, 0.013 mmol) in MeOH (500 μL) was added 10% palladium on carbon (3 mg) and the mixture was stirred at RT under an atmosphere of hydrogen. After 1 h, the mixture was filtered and concentrated to dryness to give Compound (72) as a white solid (5 mg, 92%). ESI-MS m/z calculated for [M+H]⁺: 419.1; found: 419.2; ¹H NMR (400 MHz, Acetone) δ 7.87 (s, 1H), 7.84-7.77 (m, 2H), 7.77-7.70 (m, 2H), 7.40-7.32 (m, 2H), 3.86-3.78 (m, 2H), 3.14 (s, 3H), 2.99 (d, J=4.7 Hz, 3H), 2.97-2.87 (m, 2H), 1.34 (t, J=7.5 Hz, 3H), 1.18 (t, J=7.2 Hz, 3H).

Route (b): 5-(Cyclopent-1-en-1-yl)-6-[ethyl(methylsulfonyl)amino]-2-(4-fluorophenyl)-N-methyl-2H-indazole-3-carboxamide (73); and 5-cyclopentyl-6-[ethyl(methylsulfonyl)amino]-2-(4-fluorophenyl)-N-methyl-2H-indazole-3-carboxamide (74)

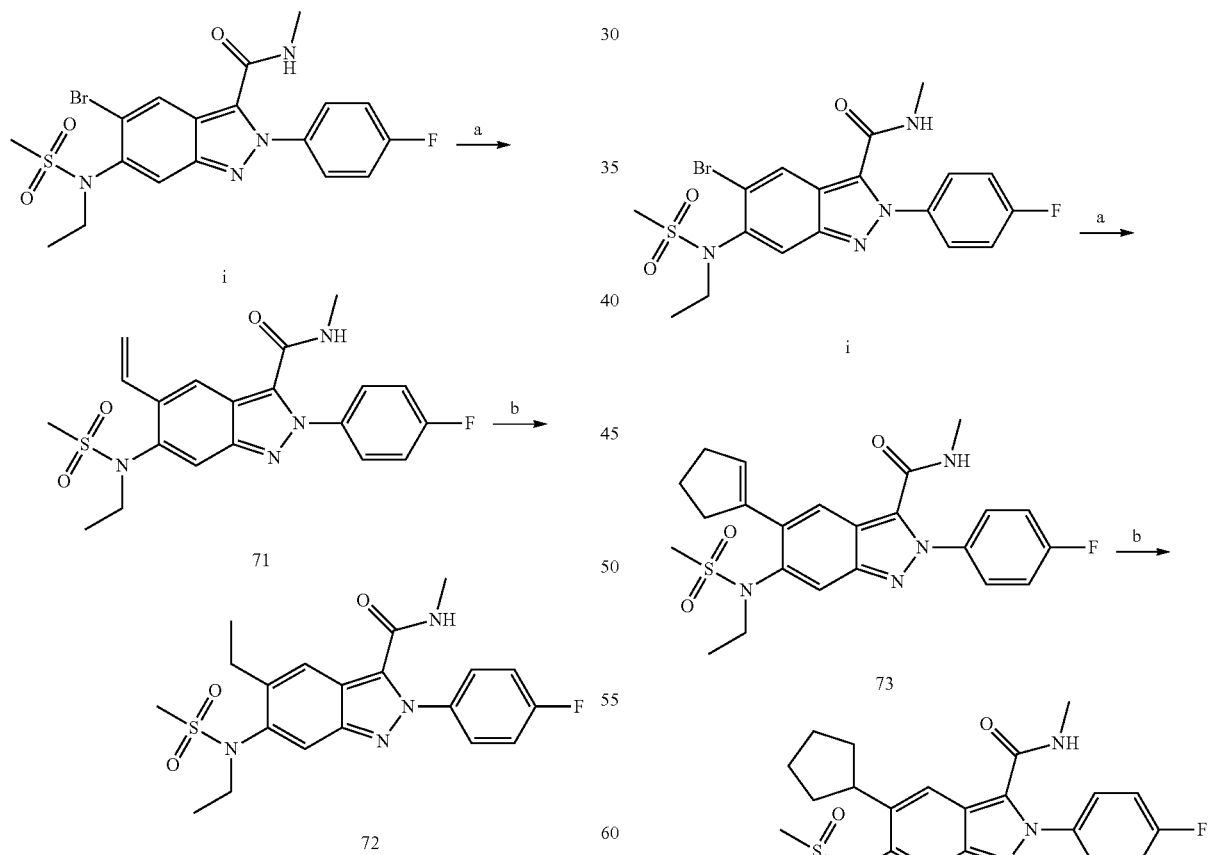

Step a: To a mixture of 5-bromo-6-[ethyl(methylsulfonyl)amino]-2-(4-fluorophenyl)-N-methyl-2H-indazole-3-carboxamide (i) (20 mg, 0.043 mmol), 1-cyclopentenylboronic acid pinacol ester (30 μL) and PdCl$_2$(dppf).CH$_2$Cl$_2$ (4 mg, 0.0049 mmol) in 1,4-dioxane (900 μL) was added a solution of cesium carbonate (44 mg, 0.14 mmol) in water (300 μL). The reaction was heated under microwave irradiation at 100° C. for 20 min. Acetone (3 mL) was added, the mixture was filtered and the filtrate concentrated to dryness. The residue was purified by flash column chromatography eluting with MeOH/DCM (0-10%) to give Compound (73) as a white solid (8 mg, 42%). ESI-MS m/z calculated for [M+H]$^+$: 457.2; found: 457.1; $^1$H NMR (400 MHz, CDCl$_3$) δ 7.78 (s, 1H), 7.73 (s, 1H), 7.61-7.54 (m, 2H), 7.26-7.18 (m, 2H), 6.25-6.19 (m, 1H), 6.06-5.96 (m, 1H), 3.93-3.47 (m, 2H), 3.06 (s, 3H), 3.02-2.98 (m, 3H), 2.95-2.69 (m, 2H), 2.60-2.51 (m, 2H), 2.08-1.95 (m, 2H), 1.19 (t, J=7.2 Hz, 3H).

NMR (400 MHz, CDCl$_3$) δ 7.81 (s, 1H), 7.62 (d, J=0.5 Hz, 1H), 7.54-7.47 (m, 2H), 7.19-7.12 (m, 2H), 5.82-5.70 (m, 1H), 3.77-3.61 (m, 2H), 3.56-3.45 (m, 1H), 2.98-2.91 (m, 6H), 2.29-2.17 (m, 1H), 2.07-1.96 (m, 1H), 1.89-1.76 (m, 2H), 1.75-1.62 (m, 2H), 1.62-1.55 (m, 1H), 1.55-1.45 (m, 1H), 1.12 (t, J=7.1 Hz, 3H).

Route (c): 6-[Ethyl(methylsulfonyl)amino]-2-(4-fluorophenyl)-5-(3-hydroxyprop-1-yn-1-yl)-N-methyl-2H-indazole-3-carboxamide (75); 6-[ethyl(methylsulfonyl)amino]-2-(4-fluorophenyl)-5[(1Z)-3-hydroxyprop-1-en-1-yl]-N-methyl-2H-indazole-3-carboxamide (76); and 6-[Ethyl(methylsulfonyl)amino]-5-ethynyl-2-(4-fluorophenyl)-N-methyl-2H-indazole-3-carboxamide (77)

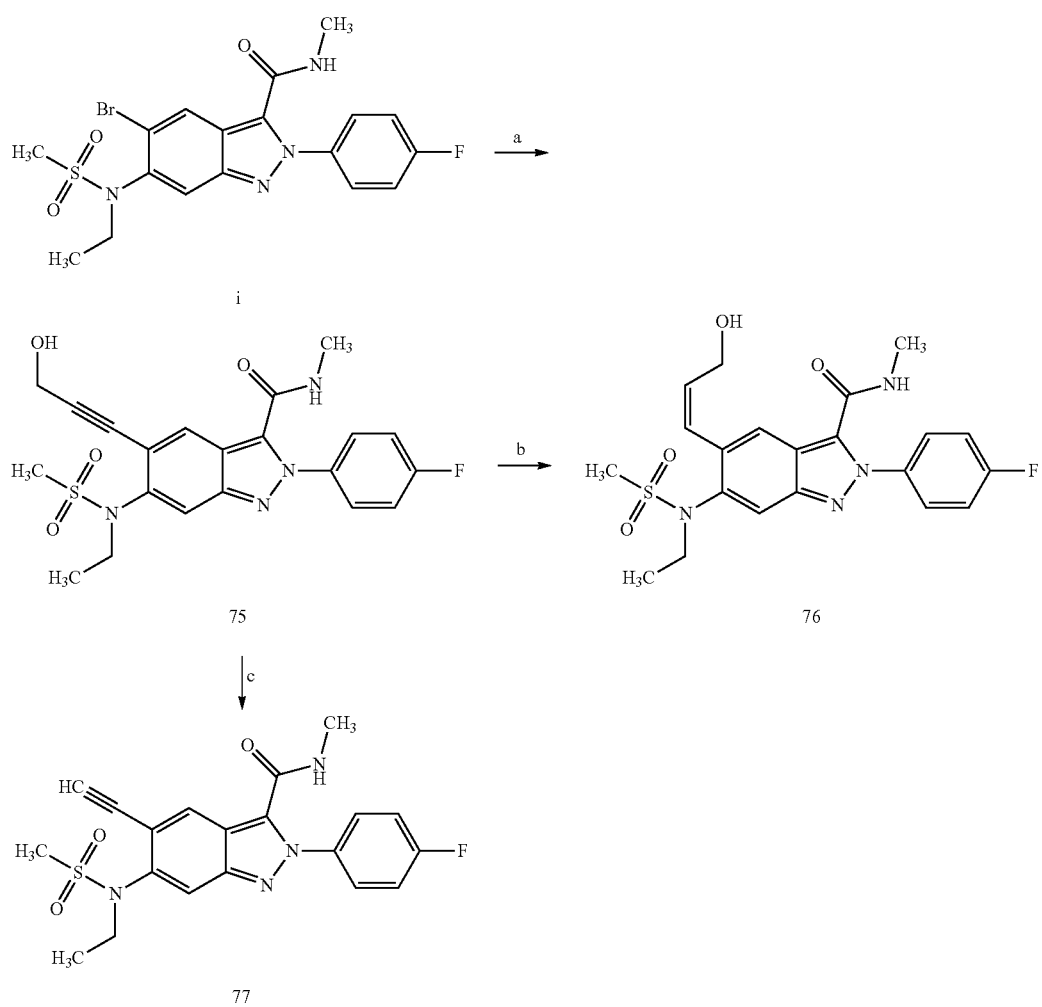

Step b: To a solution of Compound (73) (5 mg, 0.011 mmol) in MeOH (500 μL) was added 10% palladium on carbon (3 mg) and the mixture was stirred at RT under an atmosphere of hydrogen. After 2.5 h, the mixture was filtered and concentrated to dryness to give 5-cyclopentyl-6-[ethyl(methylsulfonyl)amino]-2-(4-fluorophenyl)-N-methyl-2H-indazole-3-carboxamide (74) as a white solid (4 mg, 81%). ESI-MS m/z calculated for [M+H]$^+$: 459.2; found: 459.1; $^1$H Step a: To a degassed solution of 5-bromo-6-[ethyl(methylsulfonyl)amino]-2-(4-fluorophenyl)-N-methyl-2H-indazole-3-carboxamide (i) (19 mg, 0.040 mmol) in ACN (800 μL) were added PdCl$_2$(MeCN)$_2$ (1.2 mg, 0.0046 mmol), 2'-dicyclohexylphosphino-2,6-di-isopropyl-4-sulfonato-1,1'-biphenyl hydrate sodium salt (9 mg, 0.017 mmol) and cesium carbonate (70 mg, 0.21 mmol) and the mixture was stirred at RT for 15 min. Deoxygenated water (400 μL) and propargyl alcohol (15 µL, 0.26 mmol) were added and the reaction was heated at 100° C. After 2.5 h, the reaction was cooled to RT and concentrated to dryness. The residue was purified by reverse phase flash column chromatography eluting with ACN/water (0-100%) to give Compound (75) as a white solid (5 mg, 28%). ESI-MS m/z calculated for [M+H]$^+$: 445.1; found: 445.0; $^1$H NMR (400 MHz, Acetone) δ 8.07 (s, 1H), 7.84 (brs, 1H), 7.80 (d, J=0.6 Hz, 1H), 7.79-7.72 (m, 2H), 7.42-7.32 (m, 2H), 4.53 (brs, 2H), 4.44 (brs, 1H), 3.87 (q, J=7.1 Hz, 2H), 3.14 (s, 3H), 3.03-2.97 (m, 3H), 1.20 (t, J=7.1 Hz, 3H).

Step b: To a solution of Compound (75) (5 mg, 0.011 mmol) in EtOAc (500 µL) was added quinoline (1 µL, 0.0085 mmol), followed by Lindlar's catalyst (1 mg) and the mixture was stirred at RT under an atmosphere of hydrogen. After 17 h, more quinoline (2 µL, 0.017 mmol) and Lindlar's catalyst (2 mg) were added. After a further 23 h, more Lindlar's catalyst (3 mg) was added. After a further 23 h, the reaction mixture was filtered and concentrated to dryness. The residue was purified by preparative LCMS (5-30-45-100% ACN in 0.1% aqueous formic acid) to give Compound (76) as a white solid (1 mg, 27%). ESI-MS m/z calculated for [M+H]$^+$: 447.1; found: 447.1; $^1$H NMR (400 MHz, Acetone) δ 8.16 (s, 1H), 7.90 (d, J=0.5 Hz, 1H), 7.85-7.72 (m, 4H), 7.42-7.32 (m, 2H), 6.87 (ddd, J=11.7, 2.5, 1.5 Hz, 1H), 6.04 (dt, J=11.8, 6.5 Hz, 1H), 4.38-4.28 (m, 2H), 3.86-3.67 (m, 2H), 3.16 (s, 3H), 3.01-2.96 (m, 3H), 1.15 (t, J=7.2 Hz, 3H).

Step c: To a mixture of Compound (75) (7 mg, 0.016 mmol) in diethyl ether (1 mL) were added manganese dioxide (23 mg, 0.27 mmol) and powdered potassium hydroxide (9 mg, 0.16 mmol). The reaction was stirred at RT for 20 h and then concentrated to dryness. The residue was purified by flash column chromatography eluting with MeOH/DCM (0-10%) to give Compound (77) as a white solid (2 mg, 31%). ESI-MS m/z calculated for [M+H]$^+$: 415.1; found: 415.1; $^1$H NMR (400 MHz, Acetone) δ 8.16 (s, 1H), 7.91-7.81 (m, 2H), 7.79-7.71 (m, 2H), 7.41-7.32 (m, 2H), 3.91 (s, 1H), 3.86 (q, J=7.1 Hz, 2H), 3.12 (s, 3H), 3.01-2.96 (m, 3H), 1.20 (t, J=7.1 Hz, 3H).

Route (d): 5-(Difluoromethoxy)-6-[ethyl(methylsulfonyl)amino]-2-(4-fluorophenyl)-N-methyl-2H-indazole-3-carboxamide (78)

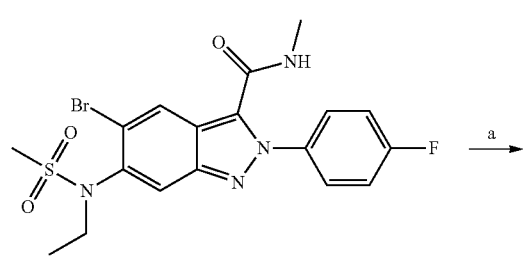

i

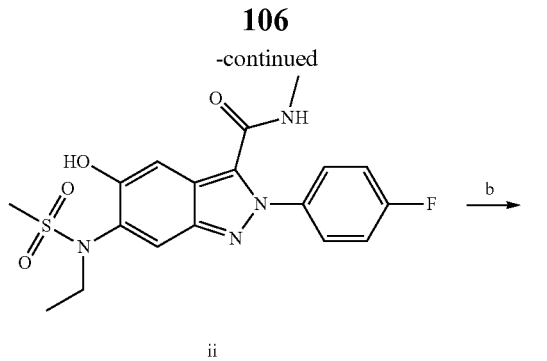

ii

78

Step a: To a degassed mixture of 5-bromo-6-[ethyl(methylsulfonyl)amino]-2-(4-fluorophenyl)-N-methyl-2H-indazole-3-carboxamide (i) (31 mg, 0.066 mmol) and potassium hydroxide (19 mg, 0.34 mmol) in 1,4-dioxane (0.5 mL) and water (0.5 mL) were added t-butyl-XPhos (2.4 mg, 0.0057 mmol) and Pd$_2$(dba)$_3$ (2.7 mg, 0.0029 mmol) and the resultant mixture was heated at 100° C. After 5 h, more tert-butyl-XPhos (5.2 mg, 0.012 mmol) and Pd$_2$(dba)$_3$ (5.6 mg, 0.0061) were added and heating was continued at 100° C. After 18 h, the reaction was cooled to RT and concentrated to dryness. The residue was purified by reverse phase flash column chromatography eluting with ACN/water (0-100%) to give 6-[ethyl(methylsulfonyl)amino]-2-(4-fluorophenyl)-5-hydroxy-N-methyl-2H-indazole-3-carboxamide (ii) as a white solid (5 mg, 20%).

Step b: To a solution of compound (ii) (4 mg, 0.0098 mmol) and potassium carbonate (27 mg, 0.20 mmol) in DMF (450 µL) and water (50 µL) was added sodium chlorodifluoroacetate (28 mg, 0.18 mmol) and the mixture was heated at 100° C. After 20 h, the reaction was cooled to RT and concentrated to dryness. The residue was purified by preparative LCMS (5-40-60-100% ACN in 0.1% aqueous formic acid) to give Compound (78) as a white solid (1 mg, 22%). ESI-MS m/z calculated for [M+H]$^+$: 457.1; found: 457.1; $^1$H NMR (400 MHz, Acetone) δ 7.94 (s, 1H), 7.79-7.72 (m, 3H), 7.70 (s, 1H), 7.42-7.34 (m, 2H), 7.11 (t, J=74.0 Hz, 1H), 3.84-3.75 (m, 2H), 3.14 (s, 3H), 2.95 (d, J=4.7 Hz, 3H), 1.20 (t, J=7.2 Hz, 3H).

Method J Examples

5-Cyclopropyl-6-[(3-hydroxypropyl)(methylsulfonyl)amino]-N-methyl-2-{4-[(propan-2-yloxy)methyl]phenyl}-2H-indazole-3-carboxamide (79)

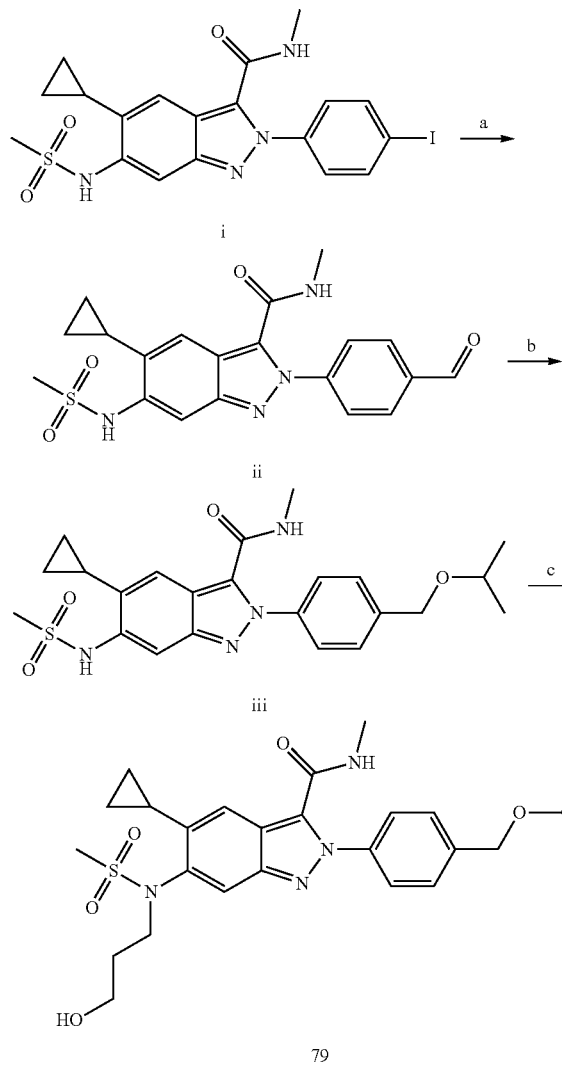

Step a: To a degassed solution of 5-cyclopropyl-2-(4-iodophenyl)-N-methyl-6-[(methylsulfonyl)amino]-2H-indazole-3-carboxamide (i) (201 mg, 0.39 mmol) in DMF (5 mL) were added triethylamine (110 µL, 0.78 mmol), triethylsilane (190 µL, 1.2 mmol), Pd(OAc)$_2$ (9 mg, 0.040 mmol) and 1,3-bis(diphenylphosphino)propane (17 mg, 0.041 mmol). The reaction was heated under a pressure of carbon monoxide (100 psi) at 75° C. for 17 h. The reaction mixture was concentrated to dryness and purified by reverse phase flash column chromatography eluting with ACN/water (0-100%) to give 5-cyclopropyl-2-(4-formylphenyl)-N-methyl-6-[(methylsulfonyl)amino]-2H-indazole-3-carboxamide (ii) as an off-white solid (54 mg, 33%).

Step b: To a mixture of compound (ii) (4 mg, 0.0097 mmol) in nitromethane (250 µL) were added trifluoroacetic acid (12 µL, 0.16 mmol), 2-propanol (12 µL, 0.16 mmol) and triethylsilane (9 µL, 0.056 mmol) and the reaction was heated at 50° C. After 4 h, the mixture was cooled to RT and concentrated to dryness. The residue was purified by reverse phase flash column chromatography eluting with ACN/water (0-100%) to give 5-cyclopropyl-N-methyl-6-[(methylsulfonyl)amino]-2-{4-[(propan-2-yloxy)methyl]phenyl}-2H-indazole-3-carboxamide (iii) as a white solid (2 mg, 35%).

Step c: To a solution of compound (iii) (8 mg, 0.018 mmol) in DMF (500 µL) were added potassium carbonate (8 mg, 0.058 mmol) and 3-bromopropanol (5 µL, 0.057 mmol) and the reaction was heated at 80° C. for 1 h. The residue was purified by preparative LCMS (5-40-60-100% ACN in 0.1% aqueous formic acid) to give Compound (79) as a white solid (2 mg, 22%). ESI-MS rniz calculated for [M+H]$^+$: 515.2; found: 515.1; $^1$H NMR (400 MHz, Acetone) δ 7.88 (d, J=0.5 Hz, 1H), 7.73 (brs, 1H), 7.67-7.60 (m, 2H), 7.58-7.49 (m, 2H), 7.42 (d, J=0.5 Hz, 1H), 4.64 (s, 2H), 4.00-3.86 (m, 2H), 3.84-3.71 (m, 1H), 3.72-3.63 (m, 2H), 3.62-3.55 (m, 1H), 3.19 (s, 3H), 3.02-2.93 (m, 3H), 2.55-2.41 (m, 1H), 1.97-1.70 (m, 2H), 1.24 (d, J=6.1 Hz, 6H), 1.13-0.96 (m, 3H), 0.66-0.52 (m, 1H).

Method K Examples

Route (a): racemic trans-6-(4-acetyl-1-benzylpyrrolidin-3-yl)-2-(4-bromophenyl)-5-cyclopropyl-N-methyl-2H-indazole-3-carboxamide (80)

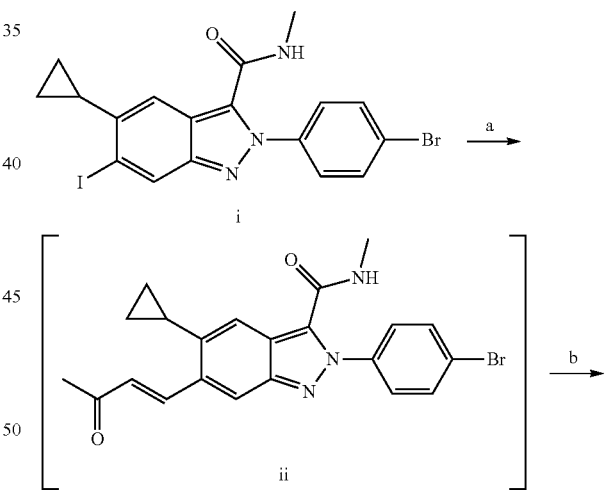

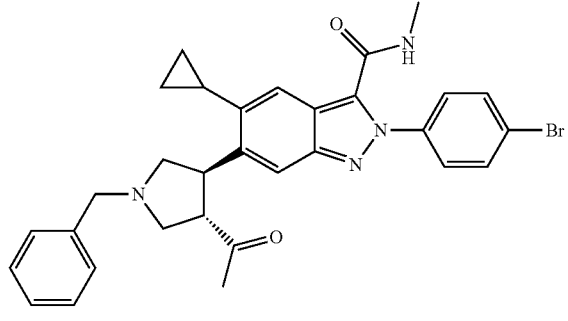

Step a: To a suspension of 2-(4-bromophenyl)-5-cyclopropyl-6-iodo-N-methyl-indazole-3-carboxamide (i) (11 mg, 0.02 mmol) in DMF (1 mL) was added potassium carbonate (8 mg, 0.05 mmol), palladium(II) acetate (1 mg, 0.001 mmol) and but-3-en-2-one (4 μL, 0.05 mmol). The reaction mixture was heated under microwave irradiation at 120° C. for 20 min. The reaction mixture was then diluted with EtOAc (10 mL), washed with water (2×7 mL), dried (MgSO₄) and concentrated to dryness to give crude 2-(4-bromophenyl)-5-cyclopropyl-N-methyl-6-[(1E)-3-oxobut-1-en-1-yl]-2H-indazole-3-carboxamide (ii), which was used directly in the next step without purification.

Step b: To a stirred suspension of crude compound (ii) in DCM (500 μL) at 0 PC was added trifluoroacetic acid (50 μL) followed by N-(methoxymethyl)-1-phenyl-N-(trimethylsilylmethyl)methanamine (10 μL, 0.04 mmol). The reaction mixture was then left to warm to RT and stirred for 1 day whereupon a further portion of N-(methoxymethyl)-1-phenyl-N-(trimethylsilylmethyl)methanamine (30 μL, 0.12 mmol) and trifluoroacetic acid (80 μL) were added. The resultant solution was stirred at RT for 16 h, then quenched with aqueous saturated ammonium chloride (1 mL) and concentrated to dryness. The residue was partitioned between water (10 mL) and EtOAc (10 mL), the organic layer was separated, washed with water (10 mL), brine (10 mL), then dried (MgSO₄) and concentrated to dryness. The crude material was purified by preparative HPLC (5-100% ACN in 0.1% aqueous formic acid) to give Compound (80) as a white solid (1.0 mg, 8% over 2 steps). ESI-MS m/z calculated for [M+H]⁺: 571.2/573.2; found: 571.2/573.2; ¹H NMR (400 MHz, CDCl₃) δ 7.97 (s, 1H), 7.66 (d, J=8.5 Hz, 2H), 7.51-7.46 (m, 3H), 7.44-7.29 (m, 5H), 5.92-5.82 (brm, 1H), 4.51-4.42 (m, 1H), 3.78-3.66 (m, 2H), 3.47-3.39 (m, 1H), 3.25-3.09 (m, 2H), 3.04 (d, J=4.9 Hz, 3H), 2.85-2.77 (m, 2H), 2.11 (s, 3H), 2.08-1.99 (m, 1H), 1.05-0.97 (m, 2H), 0.76-0.62 (m, 2H).

Route (b): 2-(4-Bromophenyl)-5-cyclopropyl-6-[(2E)-4-hydroxybut-2-en-2-yl]-N-methyl-2H-indazole-3-carboxamide (81); and 2-(4-bromophenyl)-5-cyclopropyl-6-[(2E)-4-hydroxybut-2-en-2-yl]-N-methyl-2H-indazole-3-carboxamide (82)

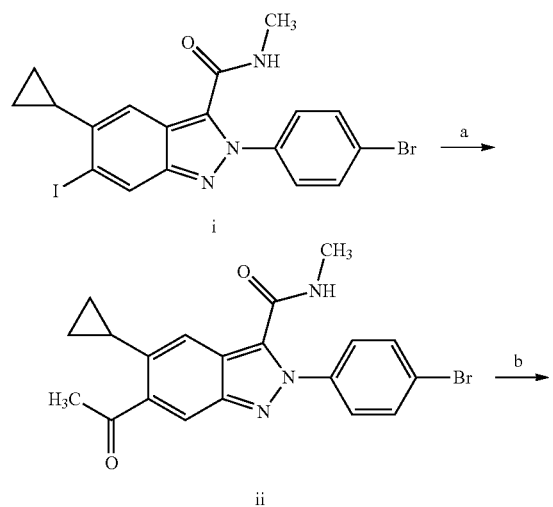

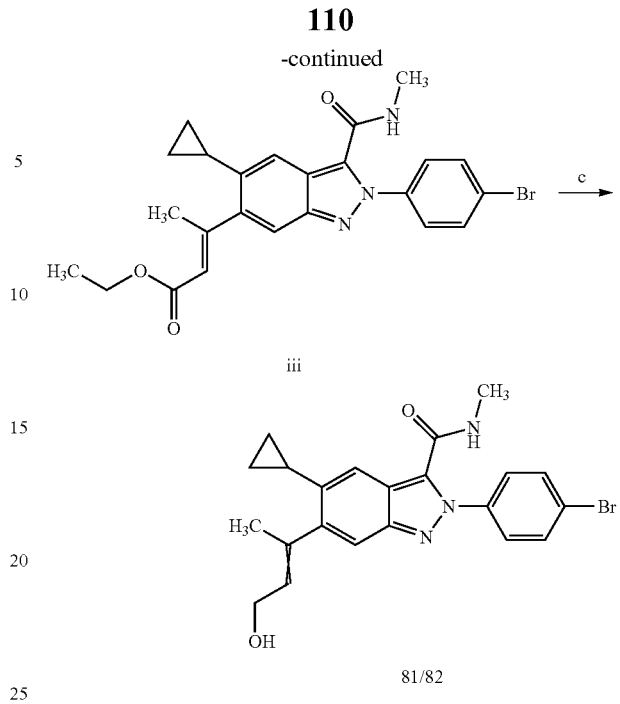

81/82

Step a: To a suspension of 2-(4-bromophenyl)-5-cyclopropyl-6-iodo-N-methyl-indazole-3-carboxamide (i) (82 mg, 0.17 mmol), Pd₂(dba)₃ (3.2 mg, 0.021 mmol) and lithium chloride (34 mg, 0.81 mmol) in DMF (3 mL) at RT were added acetic anhydride (76 μL, 0.81 mmol) and DIPEA (56 μL, 0.32 mmol). The reaction mixture was sonicated for 30 s and then heated by microwave irradiation at 150° C. for 1 h. The reaction mixture was then diluted with EtOAc (10 mL) and washed with water (2×10 mL). The organics were dried (MgSO₄) and loaded onto silica gel for purification, which was performed by flash column chromatography eluting with EtOAc/cyclohexane (0-100%) to give 6-acetyl-2-(4-bromophenyl)-5-cyclopropyl-N-methyl-2H-indazole-3-carboxamide (ii) as a pale yellow solid (8 mg, 12%).

Step b: To a stirred suspension of sodium hydride (60% dispersion in mineral oil, 4 mg, 0.1 mmol) in THF (200 μL) at RT under argon was added cautiously triethylphosphonoacetate (16 μL, 0.076 mmol). After the effervescence had subsided, the reaction mixture was stirred for 5 min at RT whereupon compound (ii) (8 mg, 0.02 mmol) in THF (400 μL) was added dropwise. The resultant orange reaction mixture was then first stirred for 16 h at RT, followed by 16 h at 45° C. The reaction mixture was then cooled to RT, quenched by the dropwise addition of water (1 mL) and then concentrated to dryness. The residue was partitioned between EtOAc (10 mL) and water (10 mL), the organic layer was separated, washed with water (10 mL) and brine (10 mL), then dried (MgSO₄) and concentrated. The residue was purified by flash column chromatography eluting with EtOAc/cyclohexane (0-100%) to give ethyl (2Z)-3-[2-(4-bromophenyl)-5-cyclopropyl-3-(methylcarbamoyl)-2H-indazol-6-yl]but-2-enoate (iii) as a white solid (6 mg, 59%).

Step c: A solution of compound (iii) (6 mg, 0.01 mmol) in THF (200 μL) was cooled to −78° C., whereupon diisobutylaluminium hydride (1.0 M in THF, 34 μL, 0.034 mmol) was added dropwise. After 30 mins, the reaction mixture was removed from the cold bath and stirred at RT for 16 h. A further portion of diisobutylaluminium hydride was added (60 μL, 0.06 mmol) at RT and stirring continued. After 1 h, the reaction mixture was quenched by the dropwise addition of water (10 mL) and this was extracted with EtOAc (2×10 mL).

The combined organics were dried (MgSO₄) and loaded onto silica gel for purification, which was performed by preparative HPLC (5-100% ACN in 0.1% aqueous formic acid) to give Compound (81) and Compound (82) (1:1 mixture of isomers) as a white solid (1 mg, 19%). ESI-MS m/z calculated for [M+H]⁺: 440.1/442.1; found: 440.1/442.1; ¹H NMR (400 MHz, CDCl₃) δ 7.72-7.65 (m, 4H), 7.55-7.49 (m, 5H), 7.47 (s, 1H), 7.38 (s, 2H), 5.94-5.80 (m, 3H), 5.79-5.72 (m, 1H), 4.44 (d, J=6.3 Hz, 2H), 3.97 (d, J=6.9 Hz, 2H), 3.06 (d, J=5.2 Hz, 6H), 2.20-2.14 (m, 6H), 2.10-1.98 (m, 2H), 1.40 (brs, 1H), 1.22 (brs, 1H), 1.07-0.97 (m, 4H), 0.86-0.76 (m, 4H).

Routes (c) and (d): 5-Cyclopropyl-6-(3,5-dimethyl-1,2-oxazol-4-yl)-2-(4-fluorophenyl)-N-methyl-2H-indazole-3-carboxamide (83); and 5-Cyclopropyl-6-(1-ethyl-1H-imidazol-2-yl)-2-(4-fluorophenyl)-N-methyl-2H-indazole-3-carboxamide (84)

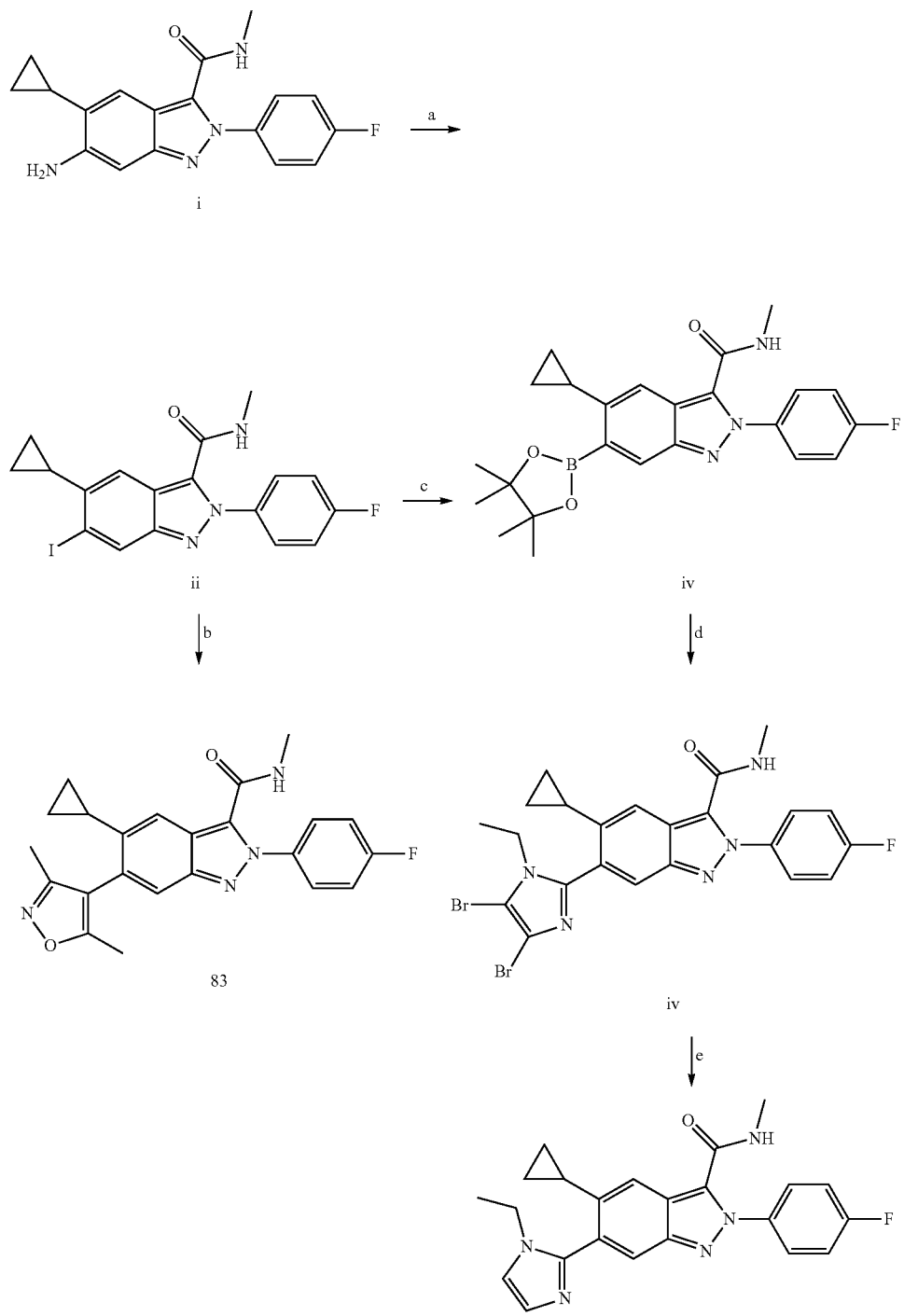

Step a: To a stirred suspension of 6-amino-5-cyclopropyl-2-(4-fluorophenyl)-N-methyl-2H-indazole-3-carboxamide (i) (0.50 g, 1.54 mmol) in 6 N Hydrochloric acid (25 mL) at −10° C. was added dropwise a solution of sodium nitrite (0.16 g, 2.31 mmol) in water (1 mL) so as to maintain the internal temperature above −5° C. The reaction mixture was stirred for 30 min whereupon a suspension of potassium iodide (1.50 g, 9.06 mmol) in EtOAc:water (1:1 v/v, 50 mL) cooled to 0° C. was added over 30 min. After 1 h, the reaction mixture was diluted with EtOAc (20 mL) and the organic layer was separated and washed with saturated sodium thiosulphate (2×10 mL), brine (10 mL) and dried (MgSO$_4$). The volatiles were removed in vacuo and the residue was then purified by column chromatography eluting with EtOAc/hexane (20-40%) to give 5-cyclopropyl-2-(4-fluorophenyl)-6-iodo-N-methyl-2H-indazole-3-carboxamide (ii) as a pale yellow solid (0.16 g, 23%). ESI-MS m/z calculated for [M+H]$^+$: 436.0; found: 436.0; $^1$H NMR (400 MHz, DMSO) δ 8.66 (brs, 1H), 8.38 (s, 1H), 7.65-7.54 (m, 2H), 7.49-7.31 (m, 3H), 2.87-2.2.73 (m, 3H), 2.10-1.95 (m, 1H), 1.09-0.95 (m, 2H), 0.79-0.67 (m, 2H).

Step b: To a degassed mixture of compound (ii) (10 mg, 0.023 mmol), 3,5-dimethylisoxazole-4-boronic acid (5 mg, 0.034 mmol) and 1M aqueous sodium carbonate (0.1 mL, 0.10 mmol) in 1,4-dioxane (0.4 mL) was added Pd(PPh$_3$)$_4$ (3 mg, 0.002 mmol) and the reaction was stirred at 100° C. After 16 h, the mixture was cooled to RT, diluted with EtOAc (1 mL), washed with saturated sodium bicarbonate (1 mL) and dried (MgSO$_4$) and concentrated to dryness. The residue was purified by flash column chromatography eluting with EtOAc/cyclohexane (15-30%) to give Compound (83) as a white solid (2.2 mg, 24%). ESI-MS m/z calculated for [M+H]$^+$: 405.2; found: 405.2; $^1$H NMR (400 MHz, CDCl$_3$) δ 7.62-7.53 (m, 3H), 7.47 (s, 1H), 7.24-7.17 (m, 2H), 5.75 (brd, J=3.5 Hz, 1H), 3.00 (d, J=4.9 Hz, 3H), 2.30 (s, 3H), 2.16 (s, 3H), 1.68 (tt, J=8.8, 5.6 Hz, 1H), 0.88 (ddd, J=5.3, 2.7, 2.0 Hz, 2H), 0.77-0.62 (m, 2H).

Step c: To a degassed solution of compound (ii) (25 mg, 0.057 mmol) in DMSO (1 mL) were added bis(pinacolato) diboron (18 mg, 0.071 mmol), Pd(dppf)$_2$Cl$_2$.CH$_2$Cl$_2$ (2 mg, 0.0024 mmol) and potassium acetate (17 mg, 0.17 mmol) and the resultant mixture was heated at 100° C. for 16 h. The mixture was diluted with EtOAc (15 mL), this was separated and the aqueous layer was extracted with EtOAc (15 mL). The combined organic portions were dried (Na$_2$SO$_4$) and concentrated to dryness. The residue was purified by column chromatography eluting with EtOAc/hexane (5-50%) to give 5-cyclopropyl-2-(4-fluorophenyl)-N-methyl-6-(4,4,5,5-tetramethyl-1,3,2-dioxaborolan-2-yl)-2H-indazole-3-carboxamide (iv) as a tan solid (12 mg, 48%).

Step d: To a degassed mixture of compound (iv) (10 mg, 0.023 mmol), 2,4,5-tribromo-1-ethyl-1H-imidazole (11 mg, 0.034 mmol) and 1M aqueous sodium carbonate (0.1 mL, 0.10 mmol) in 1,4-dioxane (0.4 mL) was added Pd(PPh$_3$)$_4$ (3 mg, 0.002 mmol)) and the reaction was stirred at 100° C. After 16 h, the mixture was cooled to RT, diluted with EtOAc (1 mL), washed with saturated sodium bicarbonate (1 mL) and dried (MgSO$_4$) and concentrated to dryness. The residue was purified by flash column chromatography eluting with EtOAc/heptane (5-50%) to give 5-cyclopropyl-6-(4,5-dibromo-1-ethyl-1H-imidazol-2-yl)-2-(4-fluorophenyl)-N-methyl-2H-indazole-3-carboxamide (v) as a white solid (12 mg, 93%).

Step e: To a solution of compound (v) (5 mg, 0.0089 mmol) in MeOH (0.3 mL) and EtOAc (0.3 mL) was added palladium on carbon (10 mg) and the resultant mixture was stirred at RT under an atmosphere of hydrogen for 16 h. The reaction mixture was filtered and concentrated to dryness. The residue was purified by preparative LCMS (5-20-30-100% ACN in 0.1% aqueous formic acid) to give Compound (84) as a white solid (1.3 mg, 36%). ESI-MS m/z calculated for [M+H]$^+$: 404.2; found: 404.2; $^1$H NMR (400 MHz, CDCl$_3$) δ 7.71 (s, 1H), 7.64-7.52 (m, 2H), 7.47 (s, 1H), 7.25-7.15 (m, 3H), 7.10 (d, J=1.1 Hz, 1H), 6.39 (brd, J=4.5 Hz, 1H), 3.86 (q, J=7.3 Hz, 2H), 3.00 (d, J=4.8 Hz, 3H), 1.77 (ddd, J=13.7, 8.4, 5.4 Hz, 1H), 1.33 (t, J=7.3 Hz, 3H), 0.80 (dd, J=7.7, 0.6 Hz, 2H), 0.67 (q, J=5.6 Hz, 2H).

Route (e), (f) and (g): racemic ethyl 5-[5-cyclopropyl-3-(methylcarbamoyl)-2-(4-methylphenyl)-2H-indazol-6-yl]-5-(methylsulfonyl)pentanoate (85); and racemic 5-cyclopropyl-N-methyl-2-(4-methylphenyl)-6-[1-(methylsulfonyl)propyl]-2H-indazole-3-carboxamide (86)

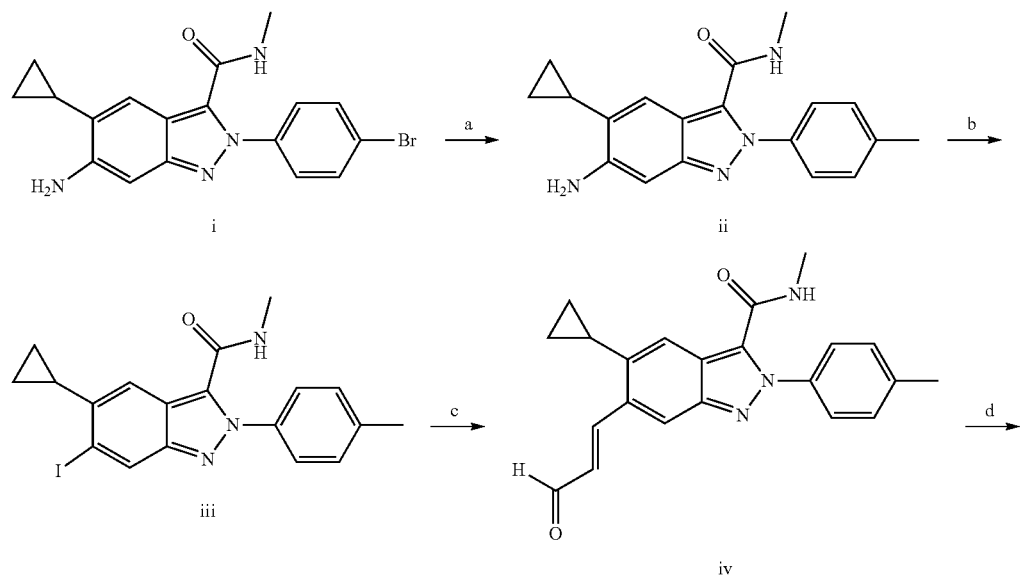

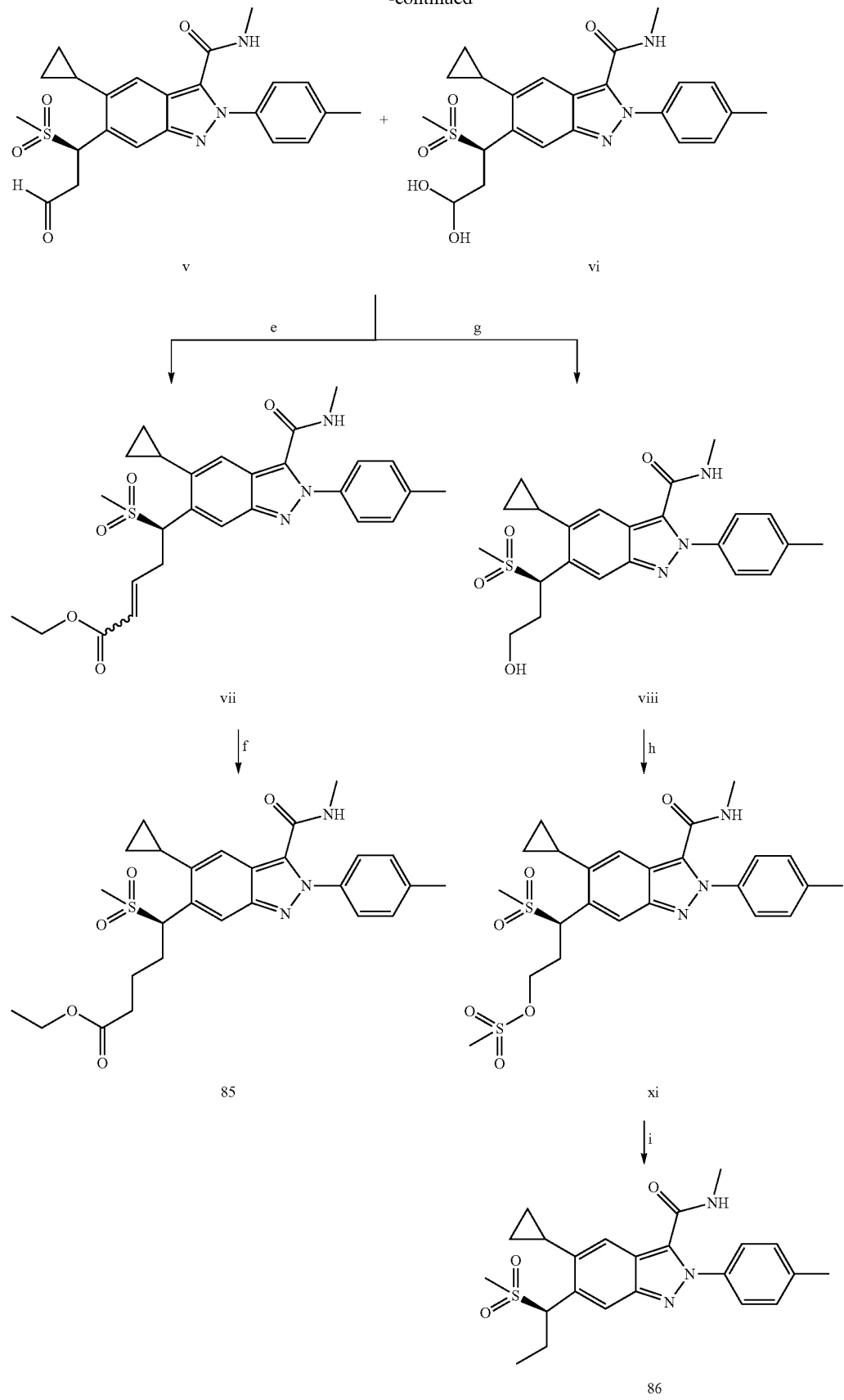

Step a: To a suspension of 6-amino-2-(4-bromophenyl)-5-cyclopropyl-N-methyl-2H-indazole-3-carboxamide (i) (250 mg, 0.65 mmol), a solution of cesium carbonate (425 mg, 1.3 mmol) in water (1 mL) and PdCl$_2$(dppf).CH$_2$Cl$_2$ (15 mg, 0.018 mmol) in 1,4-dioxane (4 mL) was added a 2 M solution of trimethylboroxine in tetrahydrofuran (250 μL, 0.5 mmol). The reaction mixture was sonicated for 2 min and then heated under microwave irradiation at 110° C. for 15 min. The reaction mixture was concentrated in vacuo to give a brown solid. The solid was suspended in water (60 mL) and sonicated for 5 min to give a fine suspension. The suspension was then heated with stirring at 70° C. for 2 h, then cooled to RT, filtered and dried (MgSO$_4$) to give 6-amino-5-cyclopropyl-N-methyl-2-(4-methylphenyl)-2H-indazole-3-carboxamide (ii) as a brown solid (396 mg, 95%), which was used without further purification.

Step b: 5-Cyclopropyl-6-iodo-N-methyl-2-(4-methylphenyl)-2H-indazole-3-carboxamide (iii) was prepared following the procedure described in Method BP5, Step a, starting from compound (ii) (38 mg, 0.124 mmol) to afford a tan solid (17 mg, 33%).

Step c: 5-Cyclopropyl-N-methyl-2-(4-methylphenyl)-6-[(1E)-3-oxoprop-1-en-1-yl]-2H-indazole-3-carboxamide (iv) was prepared following the procedure described in Method BP8, Step a, using acrolein instead of but-3-en-2-one and with benzyl(triethyl)ammonium chloride (1.5 equiv.) added to yield a white solid (47 mg, 71%).

Step d: To a solution of compound (iv) (47 mg, 0.131 mmol) in 1,4-dioxane (24 mL) and 1 M hydrochloric acid (22 mL) was added a 2.7 M aqueous solution of sodium methanesulfinate (2.4 mL, 6.5 mmol) and the reaction was stirred at RT for 2 d. The reaction mixture was diluted with water (100 mL) and extracted with EtOAc (3×50 mL). The combined organic layers were washed with saturated aqueous sodium bicarbonate (50 mL) and brine (20 mL), then dried (MgSO$_4$) and concentrated to dryness to obtain an approximately 1:1 mixture of racemic 5-cyclopropyl-N-methyl-2-(4-methylphenyl)-6-[1-(methylsulfonyl)-3-oxopropyl]-2H-indazole-3-carboxamide (v) and racemic 5-cyclopropyl-6-[3,3-dihydroxy-1-(methylsulfonyl)propyl]-N-methyl-2-(4-methylphenyl)-2H-indazole-3-carboxamide (vi) as an off-white solid (60 mg), which was used without further purification.

Step e: To a solution of an approximately 1:1 mixture of racemic 5-cyclopropyl-N-methyl-2-(4-methylphenyl)-6-[1-(methylsulfonyl)-3-oxopropyl]-2H-indazole-3-carboxamide (v) and compound (vi) (16 mg, 0.036 mmol) in DCM (10 mL) under argon was added ethyl (triphenyl-λ$^5$-phosphanylidene)acetate (20 mg, 0.057 mmol), and the reaction was stirred at RT under argon for 1 h. The reaction mixture was evaporated to dryness and purified by flash column chromatography eluting with EtOAc/heptane (50-100%) to give racemic ethyl 5-[5-cyclopropyl-3-(methylcarbamoyl)-2-(4-methylphenyl)-2H-indazol-6-yl]-5-(methylsulfonyl)pent-2-enoate (vii) as a mixture of E and Z isomers (≈4:1) as an oil (18 mg, 99%).

Step f: To a solution of compound (vii) (mixture of E and Z isomers, ≈4:1) (16 mg, 0.027 mmol) in ethanol (10 mL) and EtOAc (1 mL) under argon was added 10% palladium on carbon (5 mg), and the mixture was stirred under a hydrogen atmosphere at RT for 20 h. The reaction mixture was filtered, evaporated to dryness and then purified by flash column chromatography eluting with EtOAc/heptane (50-100%) to give Compound (85) as a white solid (12 mg, 87%). ESI-MS m/z calculated for [M+H]$^+$: 512.2; found: 512.1. $^1$H NMR (400 MHz, CDCl$_3$) δ 8.02 (s, 1H), 7.81 (s, 1H), 7.46 (d, J=8.3 Hz, 2H), 7.34 (d, J=8.1 Hz, 2H), 5.74-5.66 (m, 1H), 5.09 (dd, J=11.3, 3.8 Hz, 1H), 4.09 (q, J=7.1 Hz, 2H), 2.93 (d, J=4.9 Hz, 3H), 2.72 (s, 3H), 2.59-2.49 (m, 1H), 2.46 (s, 3H), 2.38-2.28 (m, 2H), 2.28-2.18 (m, 1H), 2.13-2.04 (m, 1H), 1.75-1.64 (m, 1H), 1.64-1.51 (m, 1H), 1.22 (t, J=7.1 Hz, 3H), 1.10-1.04 (m, 2H), 1.03-0.94 (m, 1H), 0.60-0.52 (m, 1H).

Step g: To a solution of an approximately 1:1 mixture of compound (v) and compound (vi) (14.2 mg, 0.032 mmol) in 1,4-dioxane (5 mL) and water (5 mL) was added sodium borohydride (28 mg, 0.74 mmol) and the reaction was stirred at RT for 1 h. The reaction mixture was acidified with 2 N aqueous sulfuric acid, then diluted with water (15 mL) and extracted with EtOAc (2×30 mL). The combined organic extracts were washed with brine (7 mL), dried (MgSO$_4$) and evaporated to dryness. The residue was purified by flash column chromatography eluting with EtOAc/heptane (50-100%) to give racemic 5-cyclopropyl-6-[3-hydroxy-1-(methylsulfonyl)propyl]-N-methyl-2-(4-methylphenyl)-2H-indazole-3-carboxamide (viii) as a white solid (11 mg, 79%).

Step h: To a solution of compound (viii) (9 mg, 0.02 mmol) in DCM (4 mL) at 0° C. were added DIPEA (30 μL, 0.17 mmol) and methanesulfonyl chloride (6 μL, 0.078 mmol). The reaction was stirred at 0° C. for 1 h, at which time it was diluted with DCM (12 mL) and saturated aqueous sodium bicarbonate (4 mL). The aqueous layer was separated and extracted with DCM (12 mL). The combined organic layers were washed with water (5 mL), dried (MgSO$_4$) and evaporated to dryness. The residue was purified by flash column chromatography eluting with EtOAc/heptane (50-100%) to afford racemic 3-[5-cyclopropyl-3-(methylcarbamoyl)-2-(4-methylphenyl)-2H-indazol-6-yl]-3-(methylsulfonyl)propyl methanesulfonate (ix) as a white solid (8 mg, 69%).

Step i: To a solution of compound (ix) (6 mg, 0.012 mmol) in tetrahydrofuran (0.5 mL) under argon was added a 1 M solution of lithium triethylborohydride in tetrahydrofuran (75 μL, 0.075 mmol) and the reaction was stirred at RT for 20 min. Saturated aqueous ammonium chloride (2 mL) and water (2 mL) were added to the reaction mixture, followed by extraction with EtOAc (2×10 mL). The combined organic layers were washed with brine (5 mL), dried (MgSO$_4$) and evaporated to dryness. The residue was purified by flash column chromatography eluting with EtOAc/heptane (50-100%) to give Compound (86) as a white solid (4 mg, 87%). ESI-MS m/z calculated for [M+H]$^+$: 426.2; found: 426.1. $^1$H NMR (400 MHz, CDCl$_3$) δ 8.03 (s, 1H), 7.84 (s, 1H), 7.50-7.44 (m, 2H), 7.34 (d, J=8.0 Hz, 2H), 5.70-5.59 (m, 1H), 5.02 (dd, J=11.4, 3.8 Hz, 1H), 2.94 (d, J=4.9 Hz, 3H), 2.72 (s, 3H), 2.65-2.53 (m, 1H), 2.46 (s, 3H), 2.32-2.16 (m, 1H), 2.14-2.05 (m, 1H), 1.10-1.04 (m, 2H), 1.03-0.93 (m, 1H), 0.97 (t, J=7.4 Hz, 3H), 0.58-0.51 (m, 1H).

Method L Examples

5-Cyclopropyl-6-(ethylsulfamoyl)-2-(4-fluorophenyl)-N-methyl-2H-indazole-3-carboxamide (87)

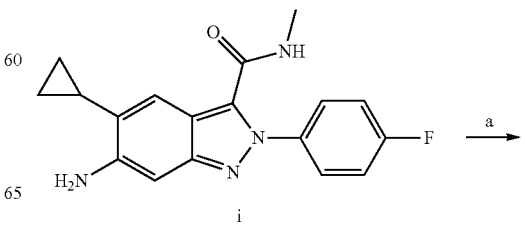

i

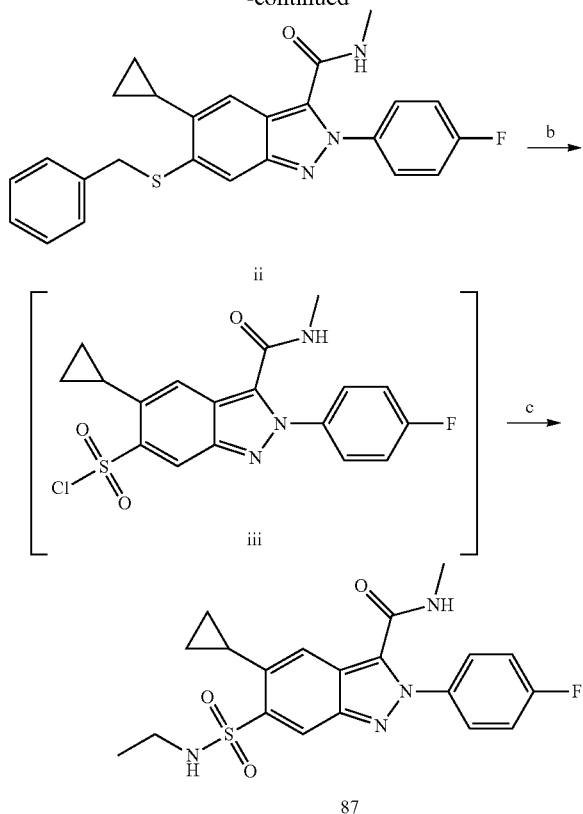

Step a: To a degassed suspension of 6-amino-5-cyclopropyl-2-(4-fluorophenyl)-N-methyl-2H-indazole-3-carboxamide (i) (125 mg, 0.29 mmol) and DIPEA (100 μL, 0.57 mmol) in 1,4-dioxane (12.5 mL) were added Pd$_2$(dba)$_3$ (3.9 mg, 0.04 mmol), xantphos (4.9 mg, 0.09 mmol) and benzyl mercaptan (36 mg, 0.29 mmol) and the mixture was then heated at reflux. After 3 h, the reaction mixture was cooled to RT, filtered and the filtrate was concentrated to dryness. The residue was purified by flash column chromatography eluting with EtOAc/hexane (10-40%) to give 6-(benzylsulfanyl)-5-cyclopropyl-2-(4-fluorophenyl)-N-methyl-2H-indazole-3-carboxamide (ii) as a brown solid (54 mg, 43%).

Step b: To a stirred solution of compound (ii) in DCM (6 mL) was added iodosobenzene (67 mg, 0.31 mmol) and concentrated hydrochloric acid (1.2 mL). The reaction mixture was stirred at RT for 30 min and then diluted with DCM (3 mL). The organics were washed with saturated aqueous sodium bicarbonate (8 mL) and the aqueous layer was then back-extracted into DCM (3×4 mL). The combined organics were dried (Na$_2$SO$_4$) and concentrated to dryness to give crude 5-cyclopropyl-2-(4-fluorophenyl)-3-(methylcarbamoyl)-2H-indazole-6-sulfonyl chloride (iii), which was used directly in the next step without purification.

Step c: To a solution of crude compound (iii) in DCM (6 mL) were added triethylamine (230 μL, 1.67 mmol) and ethylamine (2.0 M in THF, 1.5 mL, 3.0 mmol) and the reaction was stirred at RT for 2 h. The mixture was concentrated to dryness and the residue was purified by column chromatography eluting with EtOAc/hexane (20-45%) to give Compound (87) as an off-white solid (12 mg, 29% over 2 steps). ESI-MS m/z calculated for [M+H]$^+$: 417.1; found: 417.1; $^1$H NMR (400 MHz, CDCl$_3$) δ 8.70 (brs, 1H), 8.30 (s, 1H), 7.75-7.59 (m, 3H), 7.50-7.35 (m, 3H), 2.97-2.86 (m, 2H), 2.82 (s, 3H), 2.66-2.56 (m, 1H), 1.14-0.97 (m, 5H), 0.93-0.79 (m, 2H).

Method M Examples

Routes (a), (b), (c) and (d): Ethyl 4-{[2-(4-bromophenyl)-5-cyclopropyl-3-(methylcarbamoyl)-2H-indazol-6-yl](methylsulfonyl)amino}butanoate (88); 4-{[2-(4-bromophenyl)-5-cyclopropyl-3-(methylcarbamoyl)-2H-indazol-6-yl](methylsulfonyl)amino}butanoic acid (89); N-[2-(4-bromophenyl)-5-cyclopropyl-3-(methylcarbamoyl)-2H-indazol-6-yl]-N-(methylsulfonyl)-beta-alanine (90); 2-(4-bromophenyl)-5-cyclopropyl-N-methyl-6-((methylsulfonyl)[3-oxo-3-(propan-2-ylamino)propyl]amino)-2H-indazole-3-carboxamide (91); butan-2-yl 4-{[2-(4-bromophenyl)-5-cyclopropyl-3-(methylcarbamoyl)-2H-indazol-6-yl](methylsulfonyl)amino}butanoate (92); phenyl 4-{[2-(4-bromophenyl)-5-cyclopropyl-3-(methylcarbamoyl)-2H-indazol-6-yl](methylsulfonyl)amino}butanoate (93); [(2,2-dimethylpropanoyl)oxy]methyl 4-{[2-(4-bromophenyl)-5-cyclopropyl-3-(methylcarbamoyl)-2H-indazol-6-yl](methylsulfonyl)amino}butanoate (94)

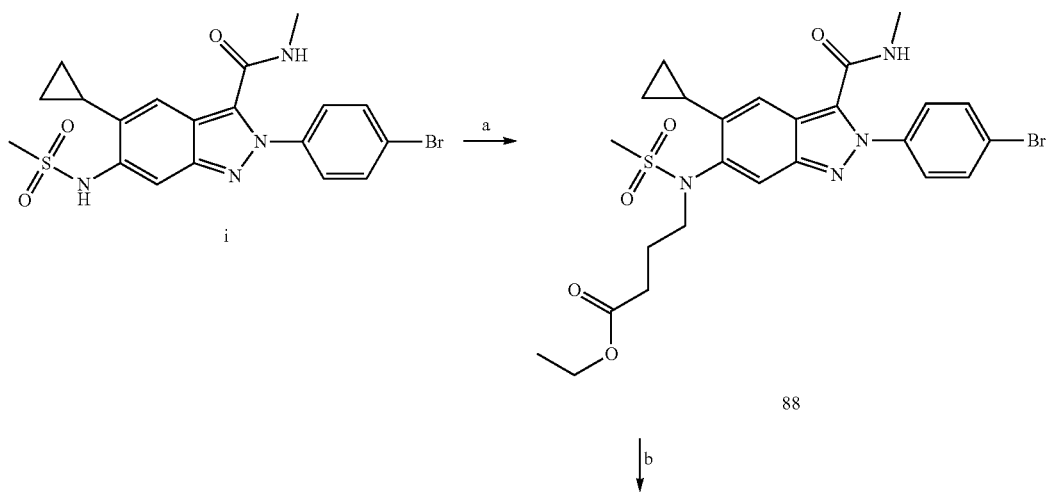

-continued

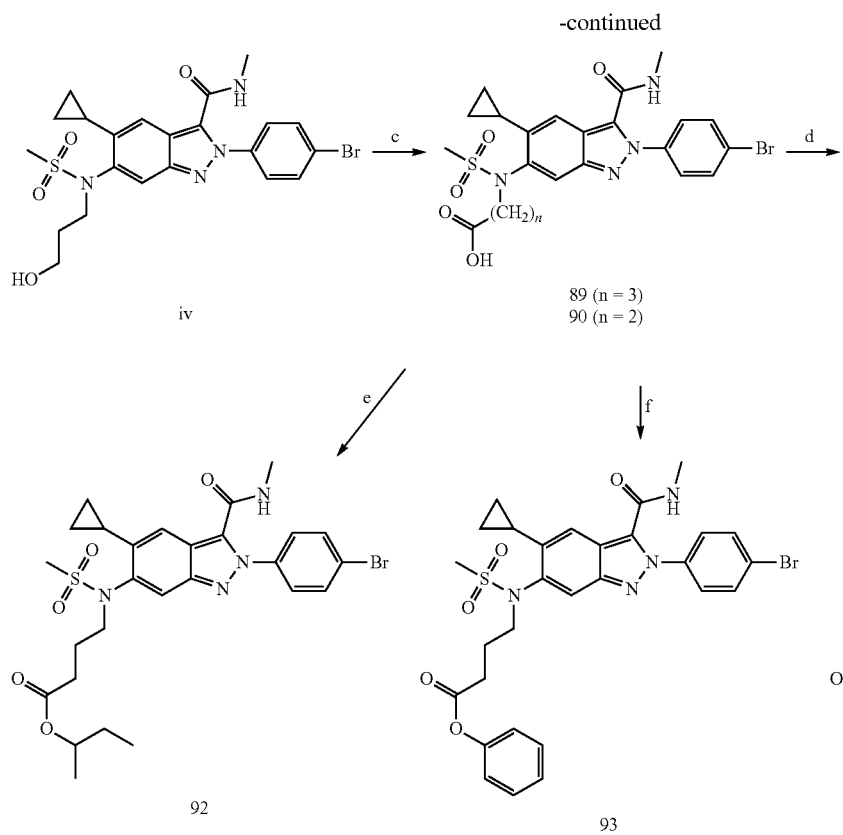

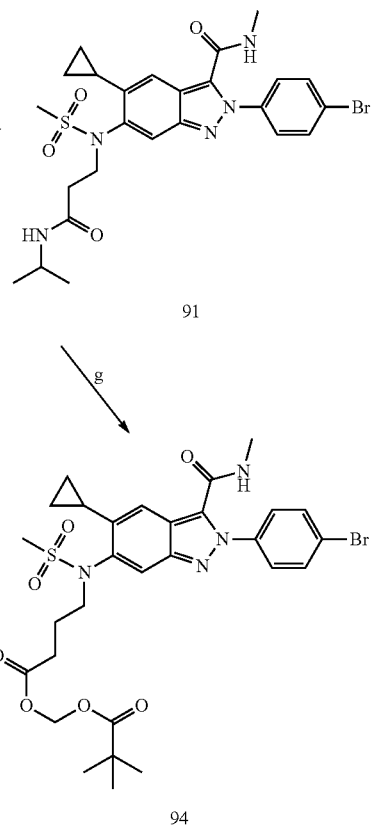

Step a: To a solution of 2-(4-bromophenyl)-5-cyclopropyl-N-methyl-6-[(methylsulfonyl)amino]-2H-indazole-3-carboxamide (i) (25 mg, 0.054 mmol) in ACN at 80° C. was added potassium carbonate (45 mg, 0.32 mmol) followed by ethyl 4-bromobutyrate (25 μL, 0.17 mmol). The mixture was heated at 80° C. for 3 h and the solvent was then removed under reduced pressure. The residue was suspended in EtOAc, washed with water, dried (MgSO$_4$) and concentrated to dryness. The crude material was purified by flash chromatography eluting with EtOAc/hexane (10-100%) to give Compound (88) as a white solid (18 mg, 58%). ESI-MS m/z calculated for [M+H]$^+$: 577.1/579.1; found: 577.0/579.0; $^1$H NMR (400 MHz, CDCl$_3$) δ 7.73 (s, 1H), 7.70-7.57 (m, 2H), 7.51-7.41 (m, 2H), 7.37 (s, 1H), 5.81 (d, J=4.2 Hz, 1H), 4.11 (q, J=7.1 Hz, 2H), 3.79 (t, J=7.5 Hz, 2H), 3.06 (s, 3H), 3.01 (d, J=4.9 Hz, 3H), 2.48-2.32 (m, 3H), 2.02-1.81 (m, 2H), 1.22 (t, J=7.1 Hz, 3H), 1.14-0.91 (m, 3H), 0.66-0.52 (m, 1H).

Step b: To a solution of Compound (88) (16 mg, 0.028 mmol) in 1,4-dioxane (0.2 mL) was added lithium hydroxide (10 mg, 0.42 mmol) followed by 2-propanol (0.2 mL) and water (0.1 mL). The mixture was stirred at 60° C. for 1.5 h, cooled to RT, neutralised by addition of 1M Hydrochloric acid and concentrated to dryness. The residue was purified by reverse phase flash chromatography eluting with ACN/0.1% aqueous formic acid (5-100%) to give Compound (89) as a white solid (1.8 mg, 12%). ESI-MS m/z calculated for [M+H]$^+$: 549.1/551.1; found: 549.4/551.4; $^1$H NMR (400 MHz, CDCl$_3$) δ 7.73 (s, 1H), 7.65 (d, J=8.6 Hz, 2H), 7.46 (d, J=8.6 Hz, 2H), 7.36 (s, 1H), 5.90 (d, J=4.1 Hz, 1H), 3.80 (t, J=7.3 Hz, 2H), 3.05 (s, 3H), 3.00 (d, J=4.9 Hz, 3H), 2.52-2.25 (m, 3H), 1.98-1.87 (m, 2H), 1.13-0.93 (m, 3H), 0.64-0.51 (m, 1H).

Step c: Periodic acid (20 mg, 0.088 mmol) was suspended in ACN (2 mL) and sonicated at RT until a solution had formed. A solution of 2-(4-bromophenyl)-5-cyclopropyl-6-[(3-hydroxypropyl)(methylsulfonyl)amino]-N-methyl-2H-indazole-3-carboxamide (iv) (20 mg, 0.0096 mmol) in ACN (0.8 mL) was then added at 0° C. followed by a freshly prepared solution of pyridinium chlorochromate in ACN (4 mg/mL, 0.04 mL) and the mixture was stirred at RT for 3 h. EtOAc (5 mL) was added, followed by 50% saturated aqueous sodium chloride (2 mL). The organic phase was separated, washed with saturated aqueous sodium bicarbonate (2 mL), dried (MgSO$_4$) and concentrated to dryness. The residue was purified by preparative LCMS (5-40-100% ACN in 0.1% aqueous formic acid) to give Compound (90) as a white solid (5.4 mg, 26%). ESI-MS m/z calculated for [M+H]$^+$: 535.0/537.0; found: 535.1/537.1; $^1$H NMR (400 MHz, CDCl$_3$) δ 7.75 (s, 1H), 7.69-7.61 (m, 2H), 7.48-7.40 (m, 2H), 7.38 (s, 1H), 5.85 (brd, J=4.3 Hz, 1H), 4.08 (dtd, J=20.7, 14.0, 6.7 Hz, 2H), 3.11 (s, 3H), 2.99 (d, J=4.9 Hz, 3H), 2.78-2.56 (m, 2H), 2.37-2.29 (m, 1H), 1.12-0.95 (m, 3H), 0.67-0.51 (m, 1H).

Step d: To a mixture of Compound (90) (6 mg, 0.011 mmol) and isopropylamine (0.01 mL, 0.12 mmol) in DMF (0.5 mL) at 0° C. were added HATU (5 mg, 0.013 mmol) and DIPEA (0.03 mL, 0.017 mmol). The mixture was then stirred at RT for 2 h, at which time the reaction mixture was concentrated to dryness. The residue was purified by preparative LCMS (5-30-100% ACN in 0.1% aqueous formic acid) to give Compound (91) as a white solid (4.5 mg, 77%). ESI-MS m/z calculated for [M+H]$^+$: 576.1/578.1; found: 575.9/577.9; $^1$H NMR (400 MHz, CDCl$_3$) δ 7.71 (s, 1H), 7.69-7.55 (m, 2H), 7.49-7.38 (m, 2H), 7.35 (s, 1H), 5.90 (brd, J=4.3 Hz, 1H), 5.51 (brd, J=6.4 Hz, 1H), 4.23-3.85 (m, 3H), 3.11 (s, 3H), 3.00 (d, J=4.7 Hz, 3H), 2.58-2.21 (m, 3H), 1.19-0.88 (m, 9H), 0.72-0.50 (m, 1H).

Step e: To a solution of Compound (89) (10 mg, 0.018 mmol) in isobutanol (1 mL) was added dropwise sulfuric acid (100 µL) at RT and the reaction mixture was heated at reflux for 4 h. The solvent was evaporated under reduced pressure and the residue was dissolved in EtOAc (10 mL). The organic layer was washed with water (5 mL), 5% aqueous sodium bicarbonate (5 mL), water (5 mL) and brine (3 mL). The organic layer was dried (MgSO$_4$) and concentrated to dryness. The residue was purified by flash column chromatography eluting with EtOAc/cyclohexane (0-50%) to give Compound (92) as a white solid (2.3 mg, 21%). ESI-MS m/z calculated for [M+H]$^+$: 605.1/607.1; found: 604.9/606.9; $^1$H NMR (400 MHz, CDCl$_3$) δ 7.75-7.72 (m, 1H), 7.69-7.63 (m, 2H), 7.50-7.43 (m, 2H), 7.37 (s, 1H), 5.80 (d, J=4.3 Hz, 1H), 4.89-4.73 (m, 1H), 3.79 (t, J=7.5 Hz, 2H), 3.06 (s, 3H), 3.01 (d, J=4.9 Hz, 3H), 2.49-2.32 (m, 3H), 2.00-1.84 (m, 2H), 1.53-1.41 (m, 2H), 1.17 (d, J=6.3 Hz, 3H), 1.13-1.06 (m, 2H), 1.05-0.95 (m, 1H), 0.88-0.81 (m, 3H), 0.59 (dd, J=9.4, 4.0 Hz, 1H).

Step f: To a solution of Compound (89) (10 mg, 0.018 mmol) in DMF (600 µL) under argon was added phenol (4 mg, 0.043 mmol), followed by DIPEA (16 µL, 0.092 mmol) and HATU (14 mg, 0.037 mmol). The reaction was stirred at RT for 4 h, at which time the mixture was added to water (20 mL) and the resultant precipitate was collected by filtration and dried to give Compound (93) as a light brown solid (5 mg, 45%). ESI-MS m/z calculated for [M+H]$^+$: 625.1/627.1; found: 624.9/626.9; $^1$H NMR (400 MHz, CDCl$_3$) δ 7.77 (s, 1H), 7.69-7.63 (m, 2H), 7.51-7.44 (m, 2H), 7.40-7.32 (m, 3H), 7.25-7.17 (m, 1H), 7.07-7.01 (m, 2H), 5.79 (s, 1H), 3.95-3.82 (m, 2H), 3.08 (s, 3H), 3.01 (d, J=4.9 Hz, 3H), 2.70 (t, J=7.2 Hz, 2H), 2.50-2.37 (m, 1H), 2.12-1.96 (m, 2H), 1.15-1.09 (m, 2H), 1.02 (d, J=5.2 Hz, 1H), 0.62 (dd, J=8.3, 4.9 Hz, 1H).

Step g: To a solution of Compound (89) (11 mg, 0.019 mmol) in DMF (2 mL) were added chloromethyl pivalate (5 µL, 0.035 mmol) and sodium iodide (5.5 mg, 0.037 mmol), followed by DIPEA (4 µL, 0.023 mmol). After stirring at RT for 16 h, more chloromethyl pivalate (5 µL, 0.035 mmol), sodium iodide (5 mg, 0.033 mmol) and DIPEA (4 µL, 0.023 mmol) were added and the reaction mixture was stirred at RT for a further 7 days. The mixture was diluted with water (3 mL) and extracted with EtOAc (3×5 mL). The combined organics were washed with 2.5% aqueous sodium bicarbonate (5 mL), dried (Na$_2$SO$_4$) and concentrated to dryness. The residue was purified by flash column chromatography eluting with EtOAc/cyclohexane (0-50%) to give Compound (94) as an off-white solid (7.6 mg, 58%). ESI-MS m/z calculated for [M+H]$^+$: 663.1/665.1; found: 663.0/665.0; $^1$H NMR (400 MHz, CDCl$_3$) δ 7.76 (s, 1H), 7.73-7.67 (m, 2H), 7.55-7.48 (m, 2H), 7.40 (s, 1H), 5.90 (d, J=4.6 Hz, 1H), 5.80-5.70 (m, 2H), 3.92-3.75 (m, 2H), 3.10 (s, 3H), 3.04 (t, J=6.5 Hz, 3H), 2.56-2.39 (m, 3H), 2.04-1.90 (m, 2H), 1.26-1.19 (m, 9H), 1.18-0.99 (m, 3H), 0.68-0.55 (m, 1H).

Method N Examples 2-(4-Bromophenyl)-5-cyclopropyl-6-{[2-(2,2-dimethyl-1,3-dioxan-5-0-ethyl](methylsulfonyl)amino}-N-methyl-2H-indazole-3-carboxamide (95); 2-(4-bromophenyl)-5-cyclopropyl-6-{[4-hydroxy-3-(hydroxymethyl)butyl](methylsulfonyl)amino}-N-methyl-2H-indazole-3-carboxamide (96); and 2-(4-bromophenyl)-5-cyclopropyl-N-methyl-6-{(methylsulfonyl)[2-(2-oxo-1,3-dioxan-5-yl)-ethyl]amino}-2H-indazole-3-carboxamide (97)

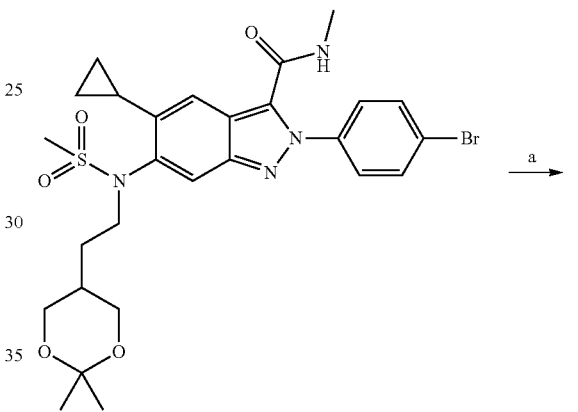

95

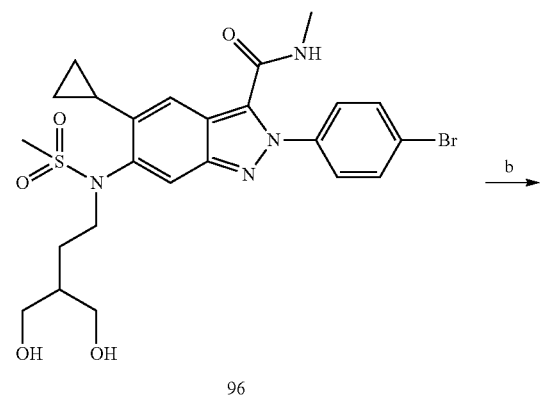

96

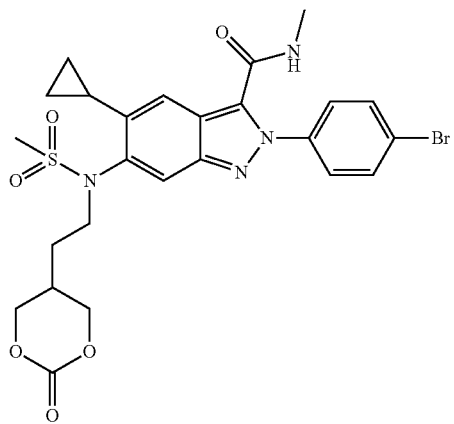

97

Step a: To a solution of Compound (95), [M+H]⁺: 604.9/606.9/¹H NMR (400 MHz, MeOD) δ 7.85 (s, 1H), 7.74-7.68 (m, 2H), 7.55-7.49 (m, 2H), 7.34 (s, 1H), 3.94-3.84 (m, 2H), 3.84-3.73 (m, 2H), 3.63-3.51 (m, 2H), 3.12 (s, 3H), 2.94 (s, 3H), 2.46-2.36 (m, 1H), 1.94-1.81 (m, 1H), 1.62-1.51 (m, 2H), 1.35 (s, 3H), 1.34 (s, 3H) 1.14-0.96 (m, 3H), 0.72-0.62 (m, 1H), (15 mg, 0.025 mmol) in tetrahydrofuran (1 mL) were added MeOH (2 mL), water (1 mL) and trifluoroacetic acid (0.1 mL). The reaction was stirred at RT for 15 min, at which time the reaction mixture was partitioned between dilute sodium bicarbonate (1 mL) and DCM (2 mL). The layers were separated and the aqueous portion was extracted with DCM (2 mL). The combined organics were washed with brine (1 mL), dried (MgSO₄) and concentrated to dryness. The crude material was purified by flash column chromatography eluting with MeOH/DCM (0-10%) to afford Compound (96) as a white solid (6 mg, 43%). ESI-MS m/z calculated for [M+H]⁺: 565.1/567.1; found: 564.9/566.9; ¹H NMR (400 MHz, CDCl₃) δ 7.74-7.72 (m, 1H), 7.69-7.64 (m, 2H), 7.49-7.45 (m, 2H), 7.35 (s, 1H), 5.98-5.89 (m, 1H), 3.90-3.71 (m, 4H), 3.66 (ddd, J=16.8, 10.6, 6.3 Hz, 2H), 3.06 (s, 3H), 3.00 (d, J=4.9 Hz, 3H), 2.38 (tt, J=8.4, 5.5 Hz, 1H), 2.18 (s, 2H), 1.87-1.77 (m, 1H), 1.75-1.62 (m, 2H), 1.14-1.30 (m, 2H), 1.01-0.93 (m, 1H), 0.66-0.58 (m, 1H).

Step b: To a solution of Compound (96) (3 mg, 0.0053 mmol) in DCM (1 mL) at 0° C. was added carbonyldiimidazole (1 mg, 0.0058 mmol) and the mixture was stirred at RT for 24 h. The reaction was quenched with water (1 mL) and extracted with DCM (2×2 mL). The combined organics were dried (MgSO₄) and concentrated to dryness. The crude material was purified by reverse phase flash column chromatography eluting with ACN/water (0-100%) to afford Compound (97) as a white solid (1 mg, 32%). ESI-MS m/z calculated for [M+H]⁺: 591.1/593.1; found: 590.9/592.9; ¹H NMR (400 MHz, Acetone) δ 7.91 (s, 1H), 7.85-7.77 (m, 1H), 7.77-7.71 (m, 2H), 7.65-7.59 (m, 2H), 7.40 (s, 1H), 4.58-4.45 (m, 2H), 4.28-4.18 (m, 2H), 3.96 (t, J=7.6 Hz, 2H), 3.17 (s, 3H), 2.95 (d, J=3.9 Hz, 3H), 2.56-2.41 (m, 2H), 1.85-1.67 (m, 2H), 1.12-0.94 (m, 3H), 0.63-54 (m, 1H).

Method O Examples

Routes (a), (b) and (c): 2-(4-bromophenyl)-5-cyclopropyl-N-methyl-6-[(methylsulfonyl)prop-2-en-1-yl)amino]-2H-indazole-3-carboxamide (98); 2-(4-bromophenyl)-5-cyclopropyl-N-methyl-6-[3-methylsulfanylpropyl(methylsulfonyl)amino]-2H-indazole-3-carboxamide (99); 2-(4-bromophenyl)-5-cyclopropyl-N-methyl-6-[methylsulfonyl(3-methylsulfonylpropyl)amino]-2H-indazole-3-carboxamide (100); 2-(4-bromophenyl)-5-cyclopropyl-N-methyl-6-[3-methylsulfinylpropyl(methyl sulfonyl)amino]-2H-indazole-3-carboxamide (101)

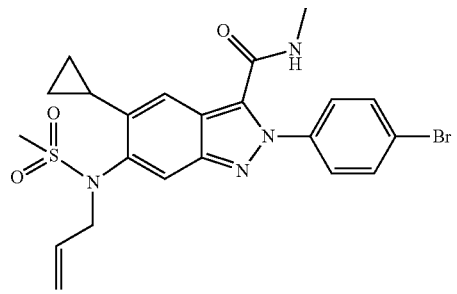

96

↑b

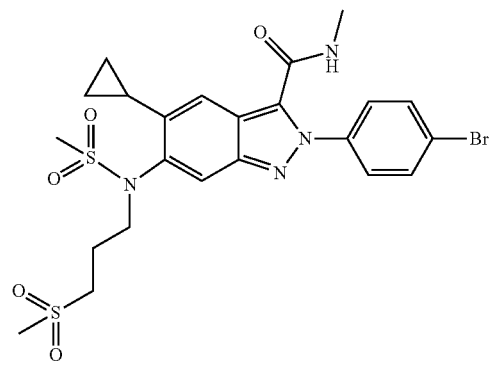

100

↓d

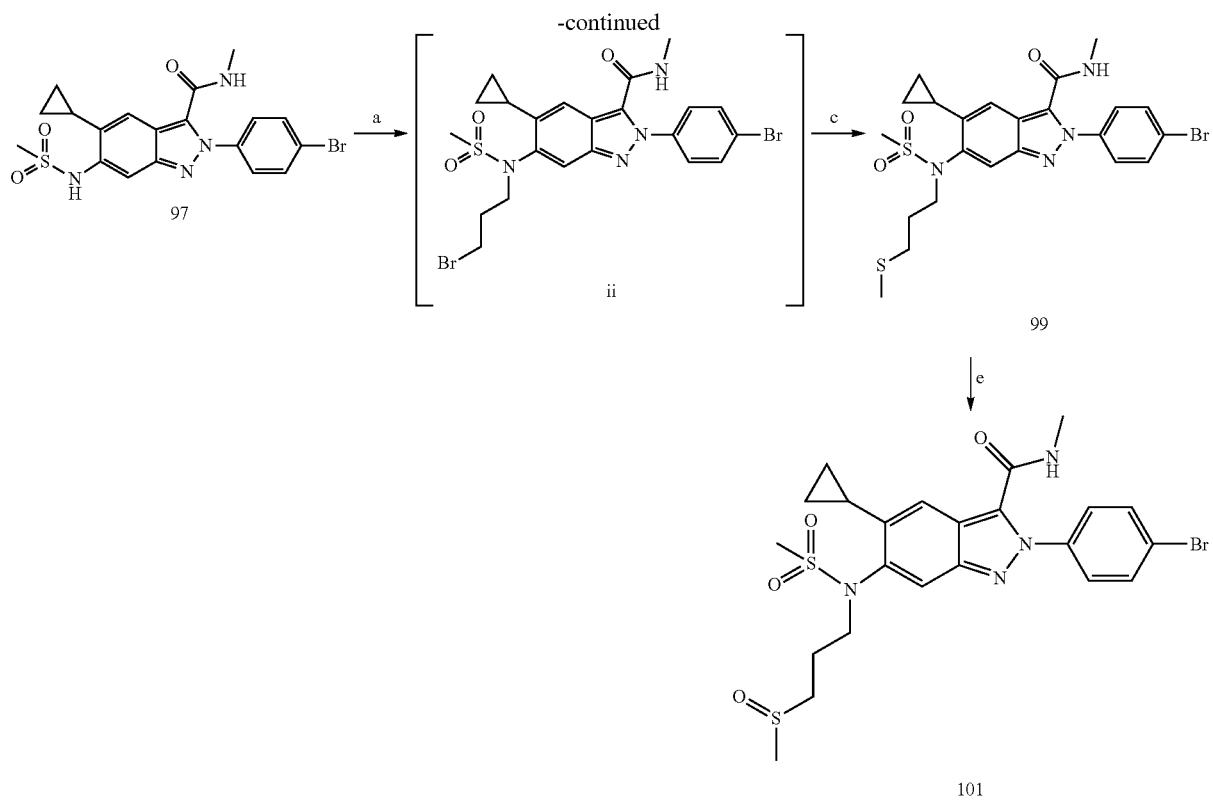

Step a: To 2-(4-bromophenyl)-5-cyclopropyl-6-(methanesulfonamido)-N-methyl-indazole-3-carboxamide (i) (20 mg, 0.043 mmol) in ACN (1 mL) was added potassium carbonate (36 mg, 0.26 mmol) followed by 1,3-dibromopropane (13 µL, 0.13 mmol) and the mixture was heated at 80° C. for 1.5 h. The mixture was cooled to RT and the solvent was removed under reduced pressure. The residue was redissolved in EtOAc (2 mL), washed with water (1 mL), dried (MgSO$_4$) and concentrated in vacuo to afford 2-(4-bromophenyl)-6-[3-bromopropyl(methylsulfonyl)amino]-5-cyclopropyl-N-methyl-indazole-3-carboxamide (ii) as an off-white solid (20 mg, 79%) which was used in the subsequent step without further purification.

Step b: To a solution of 2-(benzyloxy)ethanol (24 µL, 0.17 mmol) in THF (0.5 mL) was added sodium hydride (6.8 mg, 0.17 mmol) and the mixture was stirred at 60° C. for 30 min. The mixture was cooled to RT, then added to a solution of compound (ii) (20 mg, 0.034 mmol) in THF (0.2 mL) and stirred at 60° C. for 1 h. The mixture was quenched with saturated aqueous ammonium chloride (0.5 mL), extracted with EtOAc (2×2 mL), dried (MgSO$_4$) and concentrated to dryness. The crude material was purified by preparative LCMS (5-50-100% ACN in 0.1% aqueous formic acid) to afford Compound (98) as a white solid (2.5 mg, 15%). ESI-MS m/z calculated for [M+H]$^+$: 503.1/505.1; found: 503.0/505.0; $^1$H NMR (400 MHz, CDCl$_3$) δ 7.69 (d, J=0.5 Hz, 1H), 7.68-7.62 (m, 2H), 7.50-7.42 (m, 2H), 7.39 (s, 1H), 6.17-5.88 (m, 1H), 5.82 (brd, J=4.0 Hz, 1H), 5.21 (d, J=0.8 Hz, 1H), 5.18 (dd, J=5.6, 1.2 Hz, 1H), 4.45 (dd, J=14.6, 7.4 Hz, 1H), 4.19 (dd, J=14.8, 5.7 Hz, 1H), 3.09 (s, 3H), 3.01 (d, J=4.9 Hz, 3H), 2.38 (tt, J=8.7, 5.7 Hz, 1H), 1.14-0.93 (m, 3H), 0.64-0.49 (m, 1H).

Step c: Compound (ii) (12 mg, 0.021 mmol) and sodium thiomethoxide (7.4 mg, 0.11 mmol) in MeOH (0.2 mL) was stirred at RT for 16 h. The mixture was concentrated in vacuo and the residue was purified by preparative LCMS (5-70-90-100% ACN in 0.1% aqueous formic acid) followed by flash column chromatography eluting with EtOAc/cyclohexane (5-100%) to afford Compound (99) as a white solid (3.5 mg, 30%). ESI-MS m/z calculated for [M+H]$^+$: 551.1/553.1; found: 550.9/552.9; $^1$H NMR (400 MHz, CDCl$_3$) δ 7.73 (s, 1H), 7.69-7.62 (m, 2H), 7.50-7.43 (m, 2H), 7.36 (s, 1H), 5.83 (brd, J=4.6 Hz, 1H), 3.99-3.72 (m, 2H), 3.06 (s, 3H), 3.00 (d, J=4.9 Hz, 3H), 2.63-2.47 (m, 2H), 2.47-2.32 (m, 1H), 2.04 (s, 3H), 2.01-1.72 (m, 2H), 1.12-0.96 (m, 3H), 0.67-0.52 (m, 1H).

Step d: To a solution of crude compound (ii) (24 mg, 0.043 mmol) in MeOH (0.2 mL) were added water (0.6 mL) and oxone (32 mg, 0.052 mmol). After the mixture was stirred at RT for 1 h, a further quantity of oxone (32 mg, 0.052 mmol) was added and stirring was continued at RT for 3 h. The solvent was removed under reduced pressure and the residue was partitioned between DCM (1 mL) and 1M sodium hydroxide (1 mL). The organic phase was collected, dried (MgSO$_4$) and concentrated to dryness. The crude material was purified by preparative LCMS (5-50-100% ACN in 0.1% aqueous formic acid) to afford Compound (100) as a white solid (3.73 mg, 15%). ESI-MS m/z calculated for [M+H]$^+$: 583.1/585.1; found: 582.9/584.9. $^1$H NMR (400 MHz, CDCl$_3$) δ 7.76 (s, 1H), 7.71-7.61 (m, 2H), 7.51-7.43 (m, 2H), 7.38 (s, 1H), 5.81 (brd, J=4.5 Hz, 1H), 3.99-3.84 (m, 2H), 3.21-3.10 (m, 2H), 3.06 (s, 3H), 3.00 (d, J=4.9 Hz, 3H), 2.91 (s, 3H), 2.36 (tt, J=8.3, 5.3 Hz, 1H), 2.25-2.09 (m, 2H), 1.16-0.96 (m, 3H), 0.72-0.53 (m, 1H).

Step e: To a solution of Compound (99) (5 mg, 0.0091 mmol) in MeOH (0.2 mL) at 0° C. was added dropwise a freshly prepared solution of aqueous sodium periodate (0.2 M, 45 µL). The mixture was then stirred at RT for 2 h before being filtered, and concentrated in vacuo. The residue was purified by preparative LCMS (5-20-100% ACN in 0.1% aqueous formic acid) to afford Compound (101) as a white solid (4.9 mg, 96%). ESI-MS m/z calculated for [M+H]$^+$: 567.1/568.1; found: 566.8/568.8; $^1$H NMR (400 MHz, CDCl$_3$) δ 7.74 (s, 1H), 7.70-7.61 (m, 2H), 7.52-7.42 (m, 2H), 7.36 (s, 1H), 5.94 (brs, 1H), 4.05-3.76 (m, 2H), 3.06 (s, 3H), 2.99 (d, J=4.9 Hz, 3H), 2.91-2.68 (m, 2H), 2.57 (d, J=1.0 Hz, 3H), 2.42-2.25 (m, 1H), 2.16-2.03 (m, 2H), 1.06 (ddt, J=13.9, 8.8, 5.5 Hz, 3H), 0.63 (dt, J=9.6, 4.6 Hz, 1H).

Route (d): 2-(4-Bromophenyl)-5-cyclopropyl-N-methyl-6-[methylsulfonyl(3-sulfamoylpropyl)amino]-2H-indazole-3-carboxamide (102)

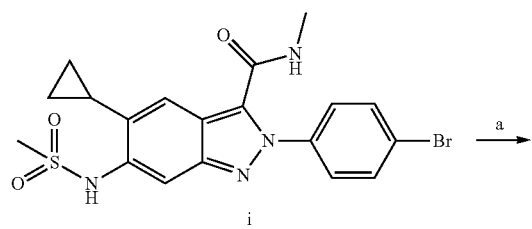

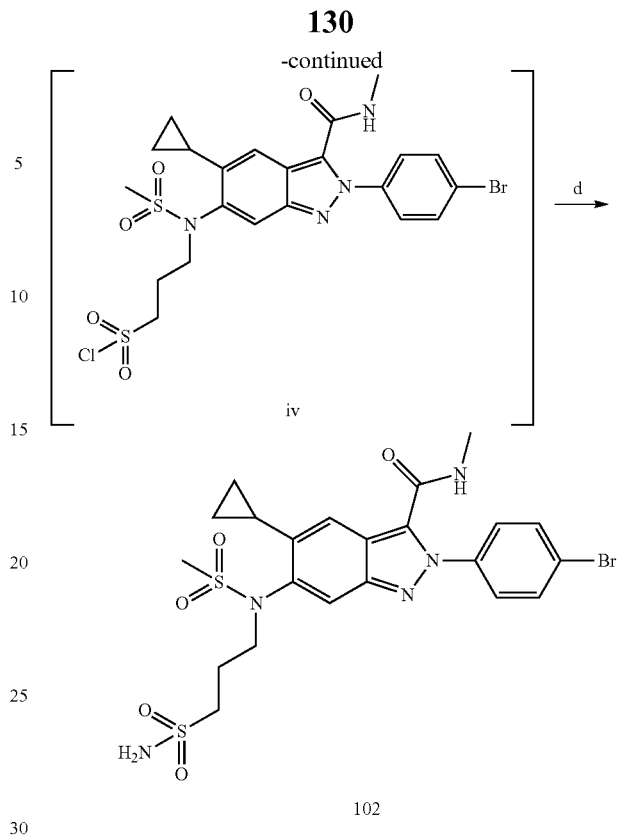

Step a: To a solution of 2-(4-bromophenyl)-5-cyclopropyl-6-(methanesulfonamido)-N-methyl-indazole-3-carboxamide (i) (20 mg, 0.043 mmol) in ACN (1 mL) was added potassium carbonate (36 mg, 0.26 mmol) followed by 1,3-dibromopropane (13 μL, 0.13 mmol) and the mixture was heated at 80° C. for 1.5 h. The reaction was cooled to RT and the solvent was removed under reduced pressure. The residue was redissolved in EtOAc (2 mL), washed with water (1 mL), dried (MgSO$_4$) and concentrated in vacuo to afford 2-(4-bromophenyl)-6-[3-bromopropyl(methylsulfonyl)amino]-5-cyclopropyl-N-methyl-indazole-3-carboxamide (ii) which was used directly in the subsequent step without further purification.

Step b: To a solution of crude compound (ii) (12.5 mg, 0.022 mmol) in ethanol (0.25 mL) was added a solution of sodium sulfite (11 mg, 0.11 mmol) in water (0.25 mL). The mixture was heated to 100° C. and stirred for 16 h. The suspension was filtered to remove the solids and the filtrate was concentrated under reduced pressure to give the crude material, 3-[[2-(4-bromophenyl)-5-cyclopropyl-3-(methylcarbamoyl)indazol-6-yl]-methylsulfonyl-amino]propane-1-sulfonic acid (iii) (20 mg, 77%) which was taken on without further purification.

Step c: A mixture of compound (iii) (10 mg crude, 0.02 mmol) and POCl$_3$ (0.5 mL) was stirred at 130° C. for 3 h. The mixture was concentrated under pressure to give 3-[[2-(4-bromophenyl)-5-cyclopropyl-3-(methylcarbamoyl)indazol-6-yl]methylsulfonyl-amino]propane-1-sulfonyl chloride (iv) which was used directly without purification.

Step d: To a suspension of compound (iv) (10 mg, 0.02 mmol) in ACN (0.5 mL) at 0° C. was added dropwise a 25% aqueous ammonia solution (0.1 mL). After addition was complete, the mixture was diluted with DCM (1 mL) and the organic phase was separated. The aqueous phase was extracted with DCM (1 mL) and the combined organic extracts were dried (MgSO$_4$) then concentrated in vacuo. The residue was purified by preparative LCMS (5-40-100% ACN in 0.1% aqueous formic acid) to afford Compound (102) (0.8 mg, 5%). ESI-MS m/z calculated for [M+H]$^+$: 584.1/586.1; found: 583.9/585.9; $^1$H NMR (400 MHz, CDCl$_3$) δ 7.76 (s, 1H), 7.70-7.64 (m, 2H), 7.50-7.43 (m, 2H), 7.38 (s, 1H), 5.83 (brd, J=4.8 Hz, 1H), 4.66 (s, 2H), 3.92 (t, J=7.1 Hz, 2H), 3.25 (t, J=7.4 Hz, 2H), 3.06 (s, 3H), 3.00 (d, J=4.9 Hz, 3H), 2.42-2.26 (m, 1H), 2.26-2.07 (m, 2H), 1.16-0.95 (m, 3H), 0.70-0.50 (m, 1H).

Method P Examples

Routes (a) and (b): 2-(4-Bromophenyl)-5-cyclopropyl-6-(1,1-dioxido-1,2,5-thiadiazolidin-2-yl)-N-methyl-2H-indazole-3-carboxamide (103); 2-(4-bromophenyl)-5-cyclopropyl-N-methyl-6-(5-methyl-1,1-dioxido-1,2,5-thiadiazolidin-2-yl)-2H-indazole-3-carboxamide (104); and 5-cyclopropyl-N-methyl-2-{4-[(2-methylpropyl)amino]phenyl}-6-(2-oxopyrrolidin-1-yl)-2H-indazole-3-carboxamide (105)

and the filtrate was purified by preparative HPLC (5-40-70-100% ACN in 0.1% aqueous formic acid) followed by reverse phase flash column chromatography eluting with acetonitrile/0.1% aqueous formic acid (5-100%) to afford Compound (103) as a white solid (1.6 mg, 4% over two steps). ESI-MS m/z calculated for [M+H]$^+$: 490.4/492.4; found: 490.1/492.1; $^1$H NMR (400 MHz, CDCl$_3$) δ 8.00 (s, 1H), 7.70-7.61 (m, 2H), 7.51-7.43 (m, 3H), 5.82 (brs, 1H), 4.49 (t, J=7.5 Hz, 1H), 4.02 (t, J=6.4 Hz, 2H), 3.75 (dd, J=13.8, 6.5 Hz, 2H), 3.01 (d, J=4.9 Hz, 3H), 2.45-2.29 (m, 1H), 1.09-0.99 (m, 2H), 0.81-0.71 (m, 2H).

Step b: To a suspension of Compound (103) (3 mg, 0.0062 mmol) in ethanol (0.5 mL) was added iodomethane (25 µL, 0.40 mmol) followed by a solution of sodium hydroxide (1M, 0.1 mL). The mixture was stirred at RT for 30 min. The mixture was then neutralised with 1M hydrochloric acid and the resulting solution was concentrated under reduced pressure. The residue was then purified by preparative LCMS (5-100% ACN in 0.1% aqueous formic acid) to afford Compound (104) as a white solid (1.1 mg, 36%). ESI-MS m/z calculated for [M+H]$^+$: 504.4/506.4; found: 504.0/506.0; $^1$H

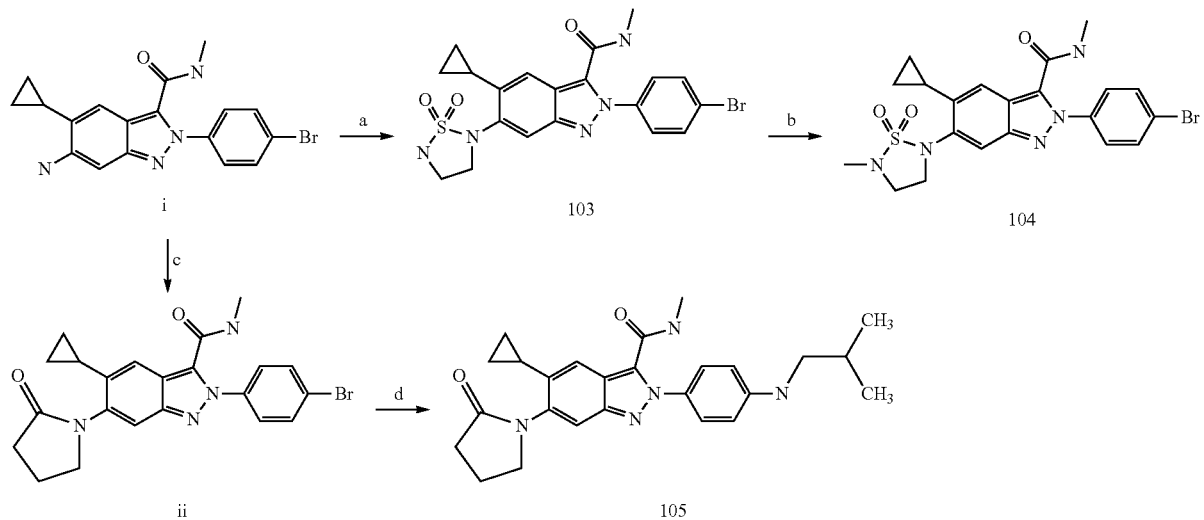

Step a: N-(2-chloroethyl)sulfamoyl chloride (1 mmol, 178 mg) was prepared freshly according to the following procedure: A mixture of 2-chloroethyl amine hydrochloride and sulfuryl chloride (097 mL, 12 mmol) in ACN (16 mL) was heated to 80° C. and stirred for 16 h. The mixture was then concentrated to give N-(2-chloroethyl)-sulfamoyl chloride as a pale yellow oil. This material was used directly without purification.

To a suspension of 6-amino-2-(4-bromophenyl)-5-cyclopropyl-N-methyl-indazole-3-carboxamide (i) (30 mg, 0.078 mmol) in DCM (0.8 mL) at 0° C. was added triethylamine (22 µL, 0.16 mmol) followed by a freshly prepared N-(2-chloroethyl)sulfamoyl chloride (28 mg, 0.16 mmol). The mixture was stirred at RT for 30 min at which time complete conversion to the acyclic sulfonamide intermediate occurred. The mixture was partitioned between DCM (25 mL) and saturated aqueous sodium bicarbonate solution (10 mL). The organic extract was collected and dried (MgSO$_4$) and concentrated in vacuo. The residue was dissolved in DMSO (2 mL) and potassium carbonate (10.8 mg, 0.78 mmol) was added. The mixture was stirred at RT for 4 days. The mixture was filtered NMR (400 MHz, CDCl$_3$) δ 7.99 (s, 1H), 7.70-7.62 (m, 2H), 7.51-7.39 (m, 3H), 5.85 (bd, J=4.6 Hz, 1H), 3.91 (t, J=6.5 Hz, 2H), 3.53 (t, J=6.5 Hz, 2H), 3.01 (d, J=4.9 Hz, 3H), 2.87 (s, 3H), 2.40 (tt, J=7.9, 5.3 Hz, 1H), 1.10-0.96 (m, 2H), 0.83-0.69 (m, 2H).

Step c: To a suspension of compound (i) (22 mg, 0.057 mmol) in DCM (0.5 mL) at RT was added 4-DMAP (10 mg, 0.086 mmol) followed by 4-bromobutyryl chloride (7.3 µL, 0.063 mmol). The mixture was left to stir for 16 h. The solvent was removed in vacuo. The residue (bromide intermediate), was dissolved in DMF (0.5 mL) and sodium hydride (6.9 mg, 0.17 mmol) was added. The mixture was left to stir at RT for 15 min. The solvent was removed in vacuo and the residue was dissolved in EtOAc (10 mL) and washed with saturated aqueous ammonium chloride (5 mL), brine (5 mL), dried (MgSO$_4$) and concentrated to dryness. The residue was purified by flash column chromatography eluting with EtOAc/hexane (5-100%) to afford 2-(4-bromophenyl)-5-cyclopropyl-N-methyl-6-(2-oxopyrrolidin-1-yl)indazole-3-carboxamide (ii) as a white solid (11 mg, 43%).

Step d: To a solution of compound (ii) (11 mg, 0.024 mmol) in 1,4-dioxane (0.6 mL) were added isobutylamine (7.2 µL, 0.073 mmol), sodium tert-butoxide (4.7 mg, 0.049 mmol) and (2-biphenyl)di-tert-butylphosphine (1 mg, 0.005 mmol). The resulting mixture was deoxygenated by bubbling through nitrogen for ~20 min. Pd$_2$(dba)$_3$ (2 mg, 0.002 mmol) was then added and the vial was sealed and heated at 80° C. for 16 h. The mixture was cooled to RT, EtOAc (10 mL) was added and filtered through celite. The filtrate was concentrated under reduced pressure. The residue was purified by preparative LCMS (5-50-70-100% ACN in 0.5% formic acid) to afford Compound (105) as a white solid (2.62 mg, 24%). ESI-MS m/z calculated for [M+H]$^+$: 446.3; found: 446.3; $^1$H NMR (400 MHz, CDCl$_3$) δ 7.81 (s, 1H), 7.57 (s, 1H), 7.30 (bd, J=8.8 Hz, 2H), 6.65 (d, J=8.8 Hz, 2H), 5.67 (d, J=4.1 Hz, 1H), 4.07 (s, 1H), 3.86 (t, J=7.0 Hz, 2H), 2.99 (d, J=6.8 Hz, 2H), 2.90 (d, J=4.9 Hz, 3H), 2.63 (t, J=8.1 Hz, 2H), 2.35-2.19 (m, 2H), 2.05-1.84 (m, 2H), 1.01 (d, J=6.7 Hz, 6H), 0.91 (dd, J=8.4, 1.6 Hz, 2H), 0.74 (q, J=5.2 Hz, 2H).

Method Q Examples

Routes (a) and (b): 2-(4-Bromophenyl)-5-cyclopropyl-6-[2-hydroxypropyl(methylsulfonyl)amino]-N-methyl-2H-indazole-3-carboxamide (106); 2-(4-bromophenyl)-5-cyclopropyl-N-methyl-6-[methylsulfonyl(piperidin-4-yl)-amino]-2H-indazole-3-carboxamide (107); and 2-(4-bromophenyl)-5-cyclopropyl-N-methyl-6-[methylsulfonyl-(1-methylsulfonyl(piperidin-4-yl))amino]-2H-indazole-3-carboxamide (108)

mixture was concentrated under reduced pressure and the residue was purified by preparative LCMS (5-40-80-100% ACN in 0.1° A) aqueous formic acid) to afford Compound (106) as a white solid (1 mg, 19%). ESI-MS m/z calculated for [M+H]$^+$: 521.1/523.1; found: 521.1/523.1. $^1$H NMR (400 MHz, CDCl$_3$) δ 7.85 (s, 0.6H), 7.79 (s, 0.4H), 7.70-7.59 (m, 2H), 7.51-7.43 (m, 2H), 7.39 (m, 1H), 5.81 (brd, J=4.2 Hz, 1H), 4.08-3.87 (m, 2H), 3.78-3.41 (m, 1H), 3.23 (s, 1.8H), 3.11 (s, 1.2H), 3.01 (d, J=4.9 Hz, 3H), 2.60-2.31 (m, 1H), 1.19 (d, J=6.0 Hz, 3H), 1.16-0.89 (m, 3H), 0.68-0.45 (m, 1H).

Step c: tert-Butyl 4-[[2-(4-bromophenyl)-5-cyclopropyl-3-(methylcarbamoyl)indazol-6-yl]-methylsulfonyl-amino]piperidine-1-carboxylate (iii) was prepared from compound (i) according to Method C, Step a using N-Boc-4-bromopiperidine instead of 3-bromo-1-propanol. A catalytic amount of sodium iodide (0.5 equiv.) was also used and the mixture was heated at 110° C. for 24 h.

Step d: To a solution of compound (iii) (69 mg, 0.11 mmol) in DCM (1 mL) was added trifluoroacetic acid (0.1 mL, 1.3 mmol) and the mixture was stirred at RT for 16 h. More trifluoroacetic acid (50 μL, 0.65 mmol) was added and the mixture was heated at 40° C. for 16 h. The mixture was cooled to RT, washed with saturated aqueous sodium bicarbonate solution (1 mL), dried (MgSO$_4$) and the solvent was removed in vacuo. The residue was purified by reverse phase flash column chromatography eluting with ACN/0.1% aqueous formic acid (5-100%) to afford Compound (107) as a white solid (26 mg, 45%). ESI-MS m/z calculated for [M+H]$^+$: 546.1/548.1; found: 545.9/547.9. $^1$H NMR (400 MHz,

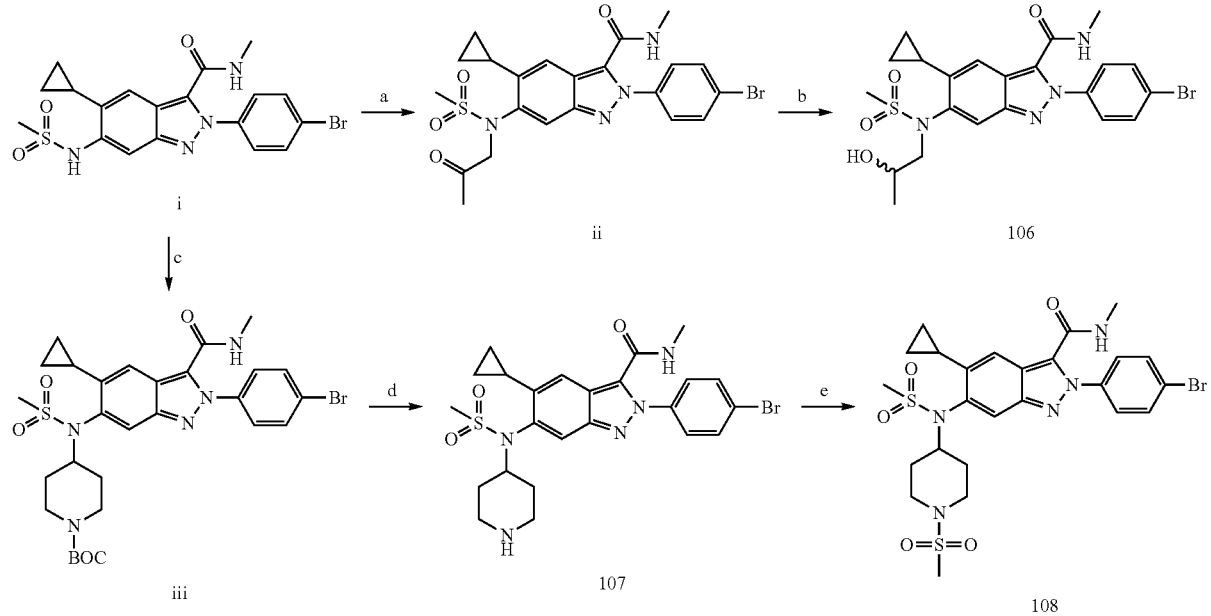

Step a: 6-[Acetonyl(methylsulfonyl)amino]-2-(4-bromophenyl)-5-cyclopropyl-N-methyl-indazole-3-carboxamide (ii) was prepared from 2-(4-bromophenyl)-5-cyclopropyl-6-(methanesulfonamido)-N-methyl-indazole-3-carboxamide (i) according to the procedure in Method C, Step a using chloroacetone instead of 3-bromo-1-propanol.

Step b: To a solution of compound (ii) (7 mg, 0.013 mmol) in a mixture of tetrahydrofuran (0.2 mL) and MeOH (0.1 mL) was added sodium borohydride (5 mg, 0.13 mmol) at 0° C. The mixture was warmed to RT and stirred for 16 h. The CDCl$_3$) δ 7.73-7.62 (m, 3H), 7.48 (d, J=8.7 Hz, 2H), 7.26 (2, 1H), 6.09 (brd, J=1.9 Hz, 1H), 4.32 (tt, J=12.2, 4.0 Hz, 1H), 3.35-3.19 (m, 2H), 3.06 (s, 3H), 2.99 (d, J=4.9 Hz, 3H), 2.82 (dd, J=22.7, 10.6 Hz, 2H), 2.43-2.31 (m, 1H), 2.22-2.19 (m, 2H), 2.10-1.95 (m, 1H), 1.63-1.54 (m, 1H), 1.20-1.12 (m, 1H), 1.12-1.02 (m, 1H), 1.02-0.91 (m, 1H), 0.76-0.64 (m, 1H).

Step e: To a solution of Compound (107) (4 mg, 0.0079 mmol) in DCM at 0° C. was added DIPEA (4.1 μL, 0.024 mmol) followed by methanesulfonyl chloride (30 μL, 0.039 mmol) and the mixture was stirred at RT for 2 h. The solvent was removed in vacuo and the residue was purified by preparative LCMS (5-30-100% ACN/0.1% aqueous formic acid) to afford Compound (108) as a white solid (1 mg, 25%). ESI-MS m/z calculated for [M+H]⁺: 624.1/626.1; found: 624.0/626.0. ¹H NMR (400 MHz, CDCl₃) δ 7.75-7.61 (m, 3H), 7.51-7.44 (m, 2H), 7.29 (s, 1H), 5.73 (brd, J=4.9 Hz, 1H), 4.38-4.26 (m, 1H), 3.94-3.74 (m, 2H), 3.08 (s, 3H), 3.01 (d, J=4.9 Hz, 3H), 2.86-2.70 (m, 5H), 2.46-2.34 (m, 1H), 2.23 (dd, J=11.5, 7.1 Hz, 2H), 2.00-1.89 (m, 1H), 1.65-1.60 (m, 1H), 1.21-1.06 (m, 2H), 1.03-0.95 (m, 1H), 0.78-0.66 (m, 1H).

Method R Examples 5-cyclopropyl-6-[ethyl(methylsulfonyl)amino]-2-[6-(isobutylamino)-3-pyridyl]-N-methyl-2H-indazole-3-carboxamide (110)

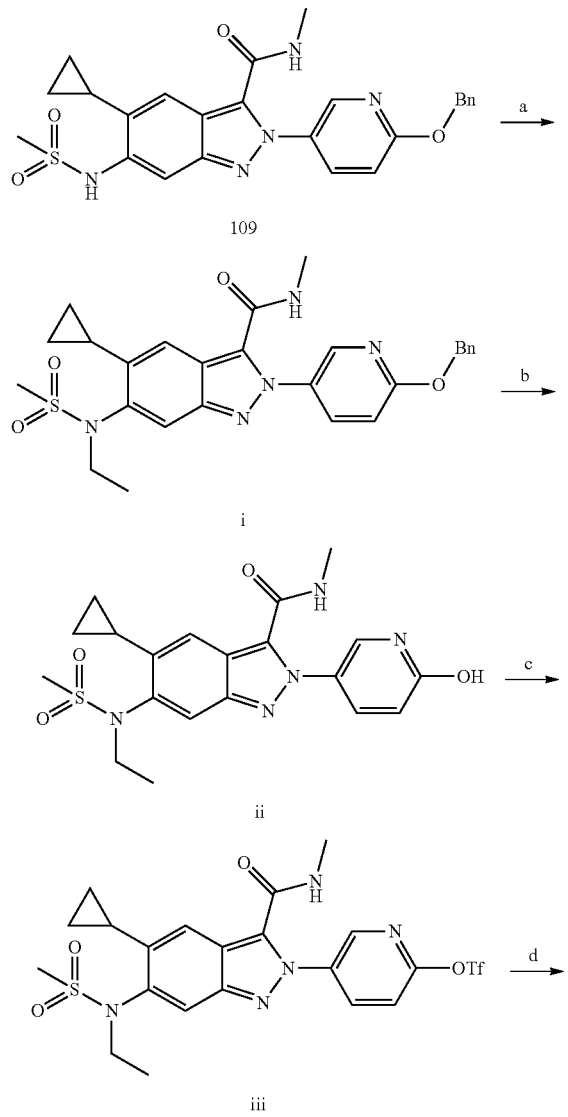

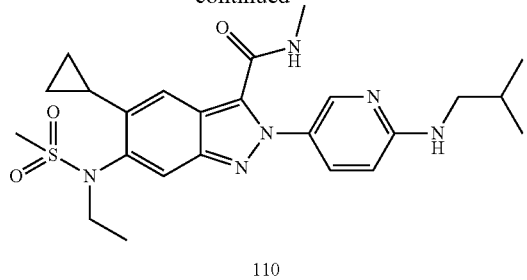

Step a: 2-(6-benzyloxy-3-pyridyl)-5-cyclopropyl-6-(methanesulfonamido)-N-methyl-indazole-3-carboxamide (109) ESI-MS m/z calculated for [M+H]⁺: 492.1 was prepared according to procedure outlined in Method A using 6-benzyloxypyridin-3-amine instead of 4-bromoaniline. To a solution of compound (109) (120 mg, 0.24 mmol) in acetonitrile (10 mL) was added potassium carbonate (100 mg, 0.72 mmol) followed by bromoethane (0.09 mL, 1.2 mmol). The mixture was heated to 80° C. and stirred for 1.5 h. The mixture was cooled to RT and the solvent was removed under reduced pressure. The residue was diluted with ethyl acetate (10 mL), washed with water (2 mL), brine (2 mL), dried (MgSO₄) and concentrated in vacuo to afford 2-(6-benzyloxy-3-pyridyl)-5-cyclopropyl-6-[ethyl(methylsulfonyl)amino]-N-methyl-indazole-3-carboxamide (i) (100 mg, 80%). This material was used without purification.

Note: 8 mg of crude compound (i) was purified by preparative LCMS (5-40-100% acetonitrile in 0.1% aqueous formic acid). ESI-MS m/z calculated for [M+H]⁺: 520.2; found: 520.1; ¹H NMR (400 MHz, CDCl₃) δ 8.38 (d, J=2.3 Hz, 1H), 7.83 (dd, J=8.8, 2.7 Hz, 1H), 7.72 (d, J=0.4 Hz, 1H), 7.48 (dd, J=7.8, 1.0 Hz, 2H), 7.43-7.32 (m, 4H), 6.94 (dd, J=8.8, 0.6 Hz, 1H), 5.92 (brd, J=4.3 Hz, 1H), 5.45 (s, 2H), 3.82 (qd, J=7.1, 4.0 Hz, 2H), 3.07 (s, 3H), 3.03 (d, J=4.9 Hz, 3H), 2.44 (tt, J=8.5, 5.4 Hz, 1H), 1.24 (t, J=7.2 Hz, 3H), 1.13-1.04 (m, 2H), 1.03-0.93 (m, 1H), 0.64-0.52 (m, 1H).

Step b: To the solution of compound (i) (80 mg, 0.15 mmol) in dichloromethane (3.5 mL) at −40° C. was added dropwise, 1M boron trichloride solution (0.31 mL, 0.31 mmol) and the mixture was then warmed to RT and stirred for 1 h. Additional boron trichloride solution (0.3 mL) was added at 0° C. and the mixture was again stirred at RT for 2.5 h. The mixture was diluted with dichloromethane (10 mL), washed with saturated aqueous sodium bicarbonate solution (4 mL), brine (4 mL), dried (MgSO₄) and concentrated in vacuo. The residue was purified by reverse phase flash column chromatography eluting with acetonitrile/0.1% aqueous formic acid (5-100%) to addord 5-cyclopropyl-6-[ethyl(methylsulfonyl)amino]-2-(6-hydroxy-3-pyridyl)-N-methyl-indazole-3-carboxamide (ii) (12 mg, 17% over 4 steps). ESI-MS m/z calculated for [M+H]⁺: 430.2; found: 430.1.

Step c: To a suspension of compound (ii) (4.85 mg, 0.011 mmol) in dichloromethane (0.3 mL) at 0° C. was added triethylamine (10 μL, 0.068 mmol) followed by triflic anhydride (5 μL, 0.03 mmol). After 10 min, more triethylamine (8 μL) and triflic anhydride (2 μL) were added. Saturated aqueous sodium bicarbonate solution (1 mL) and the mixture was extracted with dichloromethane. The organic extract was dried (MgSO₄) and concentrated in vacuo to afford 5-cyclopropyl-6-[ethyl(methylsulfonyl)amino]-2-(6-hydroxy-3-pyridyl)-N-methyl-indazole-3-carboxamide (iii) was used directly without purification. ESI-MS m/z calculated for [M+H]⁺: 562.1; found: 562.0.

Step d: To a solution of compound (iii) (4.7 mg, 0.0084 mmol) and isobutylamine (0.1 mL) in 1,4-dioxane (0.3 mL) was heated to 40° C. and stirred for 45 min. More isobutylamine (100 µL) was added and the mixture was heated at 70° C. for 1.5 h. The mixture was cooled to RT and concentrated under reduced pressure. The residue was purified by preparative LCMS (5-30-50-100% acetonitrile in 0.1% aqueous formic acid) to give Compound (110) as a white solid. ESI-MS m/z calculated for [M+H]$^+$: 485.2; found: 485.2; $^1$H NMR (400 MHz, CDCl$_3$) δ 8.11 (d, J=1.9 Hz, 1H), 7.86 (dd, J=9.3, 2.1 Hz, 1H), 7.68 (s, 1H), 7.32 (s, 1H), 6.82 (brs, 1H), 6.69 (d, J=9.3 Hz, 1H), 6.17 (brs, 1H), 3.88-3.71 (m, 2H), 3.24-3.13 (m, 2H), 3.08 (s, 3H), 3.03 (d, J=4.9 Hz, 3H), 2.39 (ddd, J=13.9, 8.4, 5.5 Hz, 1H), 2.04-1.89 (m, 1H), 1.23 (t, J=7.1 Hz, 3H), 1.11-0.97 (m, 9H), 0.66-0.45 (m, 1H).

The following compounds were similarly prepared by reference to the general methods and/or examples previously described.

TABLE 1

Compounds and their general method(s) of synthesis

| No. | Structure | Observed LCMS m/z [M + H]$^+$/$^1$H NMR | Method |
|---|---|---|---|
| 18 | 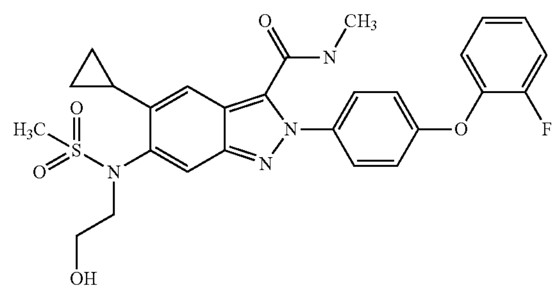 [SMILES: CNC(=O)c1c2cc(C3CC3)c(N(CCO)S(C)(=O)=O)cc2nn1-c1ccc(Oc2ccccc2F)cc1] | [M + H]$^+$ 539/(400 MHz, CDCl$_3$) δ 7.79 (d, J = 0.4 Hz, 1H), 7.53 (d, J = 9.0 Hz, 2H), 7.50 (s, 1H), 7.24-7.14 (m, 4H), 7.10 (d, J = 8.8 Hz, 2H), 5.72 (d, J = 4.5 Hz, 1H), 4.17-4.00 (m, 1H), 3.82-3.63 (m, 3H), 3.18 (s, 3H), 2.96 (d, J = 4.9 Hz, 3H), 2.50-2.31 (m, 1H), 1.13-1.01 (m, 3H), 0.63-0.49 (m, 1H). | B$^{(1)}$ |
| 19 | 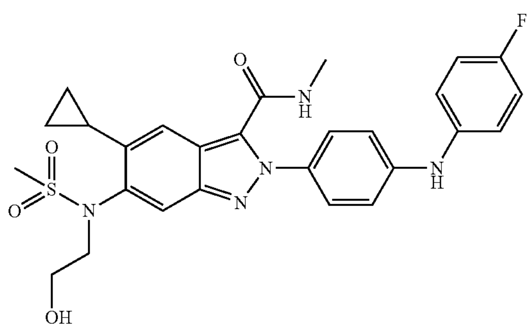 [SMILES: CNC(=O)c1c2cc(C3CC3)c(N(CCO)S(C)(=O)=O)cc2nn1-c1ccc(Nc2ccc(F)cc2)cc1] | [M + H]$^+$ 538/(400 MHz, CDCl$_3$) δ 7.77 (s, 1H), 7.55 (s, 1H), 7.38 (bd, J = 8.8 Hz, 2H), 7.19-7.10 (m, 2H), 7.08-7.01 (m, 2H), 6.99 (bd, J = 8.9 Hz, 2H), 5.92 (s, 1H), 5.78 (bd, J = 4.6 Hz, 1H), 4.10 (dd, J = 8.8, 6.1 Hz, 1H), 3.83-3.60 (m, 3H), 3.18 (s, 3H), 2.94 (d, J = 4.9 Hz, 3H), 2.47-2.27 (m, 1H), 1.14-0.93 (m, 3H), 0.64-0.47 (m, 1H). | C$^{(2)}$ |
| 20 | 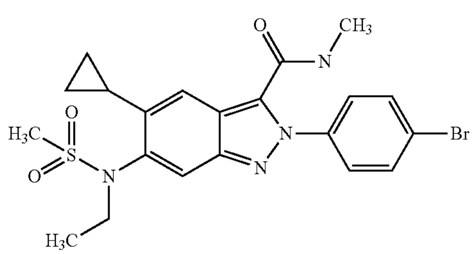 [SMILES: CCN(c1cc2nn(-c3ccc(Br)cc3)c(C(=O)NC)c2cc1C1CC1)S(C)(=O)=O] | [M + H]$^+$ 491/493/(400 MHz, CDCl$_3$) δ 7.72 (s, 1H), 7.66 (bd, J = 8.8 Hz, 2H), 7.47 (bd, J = 8.8 Hz, 2H), 7.38 (s, 1H), 5.81 (s, 1H), 3.92-3.68 (m, 2H), 3.07 (s, 3H), 3.02 (d, J = 4.9 Hz, 3H), 2.52-2.32 (m, 1H), 1.24 (t, J = 7.2 Hz, 3H), 1.13-0.91 (m, 3H), 0.63-0.48 (m, 1H). | C$^{(3)}$ |
| 21 | 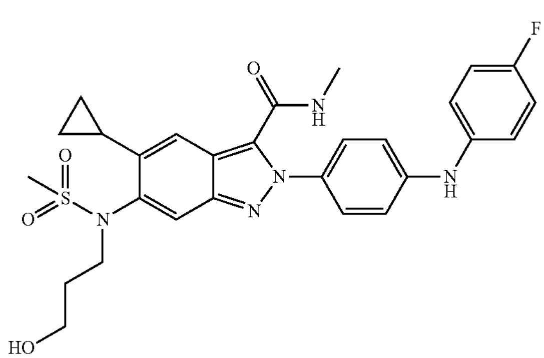 [SMILES: CNC(=O)c1c2cc(C3CC3)c(N(CCCO)S(C)(=O)=O)cc2nn1-c1ccc(Nc2ccc(F)cc2)cc1] | [M + H]$^+$ 552/(400 MHz, CDCl$_3$) δ 7.73 (s, 1H), 7.52 (s, 1H), 7.38 (d, J = 8.8 Hz, 2H), 7.20-6.94 (m, 6H), 5.89 (s, 1H), 5.82-5.65 (m, 1H), 4.07-3.60 (m, 4H), 3.07 (s, 3H), 2.94 (d, J = 4.9 Hz, 3H), 2.49-2.22 (m, 1H), 1.89-1.73 (m, 2H), 1.16-0.92 (m, 3H), 0.72-0.53 (m, 1H). | C$^{(4)}$ |

TABLE 1-continued

Compounds and their general method(s) of synthesis

| No. | Structure | Observed LCMS m/z [M + H]+/1H NMR | Method |
|---|---|---|---|
| 22 | 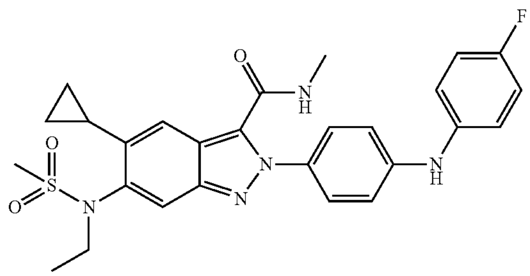 [SMILES: CCN(c1cc2nn(-c3ccc(Nc4ccc(F)cc4)cc3)c(C(=O)NC)c2cc1C1CC1)S(C)(=O)=O] | [M + H]+ 522/(400 MHz, CDCl3) δ 7.69 (d, J = 0.4 Hz, 1H), 7.53 (bs, 1H), 7.38 (d, J = 8.8 Hz, 2H), 7.19-7.09 (m, 2H), 7.09-7.01 (m, 2H), 6.99 (d, J = 8.9 Hz, 2H), 5.91 (s, 1H), 5.81-5.68 (m, 1H), 3.93-3.63 (m, 2H), 3.06 (s, 3H), 2.94 (d, J = 4.9 Hz, 3H), 2.47-2.30 (m, 1H), 1.23 (t, J = 7.1 Hz, 3H), 1.09-0.91 (m, 3H), 0.66-0.50 (m, 1H). | C(5) |
| 23 | 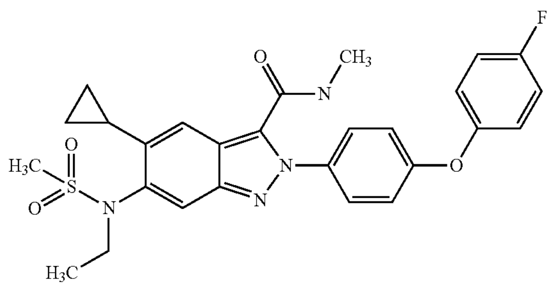 [SMILES: CCN(c1cc2nn(-c3ccc(Oc4ccc(F)cc4)cc3)c(C(=O)NC)c2cc1C1CC1)S(C)(=O)=O] | [M + H]+ 523/(400 MHz, CDCl3) δ 7.71 (s, 1H), 7.52 (d, J = 8.9 Hz, 2H), 7.44 (s, 1H), 7.12-7.02 (m, 6H), 5.90-5.62 (m, 1H), 4.01-3.66 (m, 2H), 3.06 (s, 3H), 2.99 (d, J = 4.9 Hz, 3H), 2.50-2.25 (m, 1H), 1.24 (t, J = 7.2 Hz, 3H), 1.10-0.92 (m, 3H), 0.65-0.51 (m, 1H). | C(6) |
| 24 | 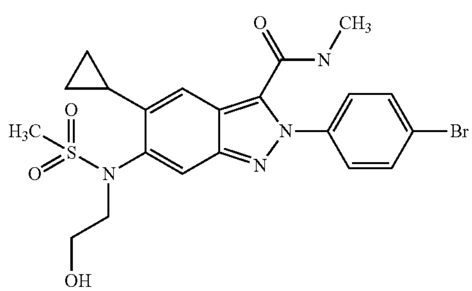 [SMILES: CNC(=O)c1c2cc(C3CC3)c(N(CCO)S(C)(=O)=O)cc2nn1-c1ccc(Br)cc1] | [M + H]+ 507/509/(400 MHz, CDCl3) δ 7.80 (s, 1H), 7.66 (bd, J = 8.8 Hz, 2H), 7.47 (bd, J = 8.8 Hz, 2H), 7.39 (s, 1H), 5.85 (d, J = 4.2 Hz, 1H), 4.22-3.97 (m, 1H), 3.83-3.62 (m, 3H), 3.19 (s, 3H), 3.01 (d, J = 4.9 Hz, 3H), 2.49-2.32 (m, 1H), 1.19-0.91 (m, 3H), 0.65-0.42 (m, 1H). | C(2) |
| 25 | 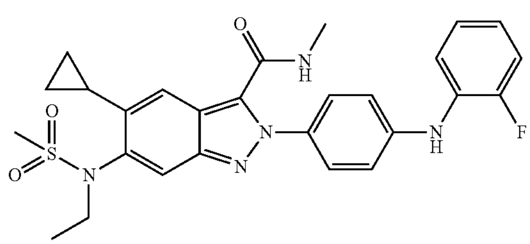 | [M + H]+ 522/(400 MHz, CDCl3) δ 7.72 (s, 1H), 7.54 (s, 1H), 7.47 (d, J = 8.8 Hz, 2H), 7.41 (dt, J = 8.2, 1.5 Hz, 1H), 7.22-7.06 (m, 4H), 7.02-6.91 (m, 1H), 5.99 (s, 1H), 5.70 (d, J = 4.7 Hz, 1H), 3.93-3.70 (m, 2H), 3.06 (s, 3H), 2.97 (d, J = 4.9 Hz, 3H), 2.51-2.25 (m, 1H), 1.24 (t, J = 7.1 Hz, 3H), 1.12-0.92 (m, 3H), 0.69-0.51 (m, 1H). | C(3) |
| 26 | 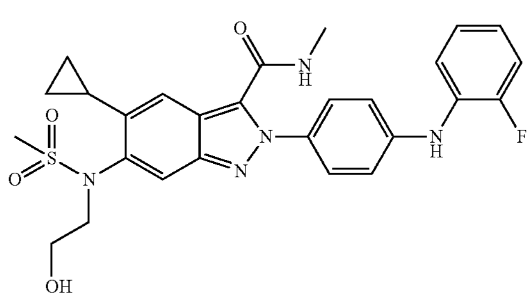 [SMILES: CNC(=O)c1c2cc(C3CC3)c(N(CCO)S(C)(=O)=O)cc2nn1-c1ccc(Nc2ccccc2F)cc1] | [M + H]+ 538/(400 MHz, CDCl3) δ 7.80 (s, 1H), 7.57 (s, 1H), 7.47 (d, J = 8.8 Hz, 2H), 7.41 (dt, J = 8.2, 1.5 Hz, 1H), 7.21-7.04 (m, 4H), 7.04-6.90 (m, 1H), 5.99 (s, 1H), 5.69 (d, J = 4.2 Hz, 1H), 4.21-4.00 (m, 1H), 3.86-3.68 (m, 3H), 3.19 (s, 3H), 2.96 (d, J = 4.9 Hz, 3H), 2.52-2.27 (m, 1H), 1.94 (bs, 1H), 1.13-0.94 (m, 3H), 0.67-0.44 (m, 1H). | C(2) |

TABLE 1-continued

Compounds and their general method(s) of synthesis

| No. | Structure | Observed LCMS m/z [M + H]+/1H NMR | Method |
|---|---|---|---|
| 27 | 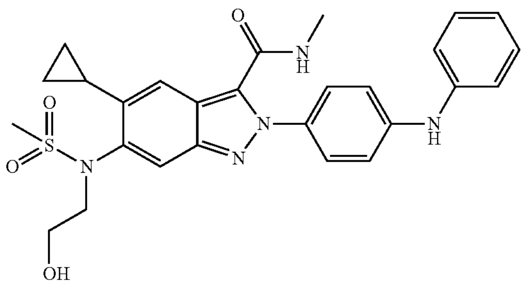 | [M + H]+ 520/(400 MHz, CDCl3) δ 7.79 (s, 1H), 7.58 (s, 1H), 7.41 (bd, J = 8.8 Hz, 2H), 7.38-7.29 (m, 2H), 7.17 (dd, J = 8.6, 1.1 Hz, 2H), 7.12 (bd, J = 8.9 Hz, 2H), 7.09-7.01 (m, 1H), 5.99 (s, 1H), 5.72 (d, J = 4.5 Hz, 1H), 4.24-3.95 (m, 1H), 3.86-3.61 (m, 3H), 3.18 (s, 3H), 2.95 (d, J = 4.9 Hz, 3H), 2.47-2.30 (m, 1H), 1.17-0.91 (m, 3H), 0.74-0.39 (m, 1H). | C(7) |
| 28 | 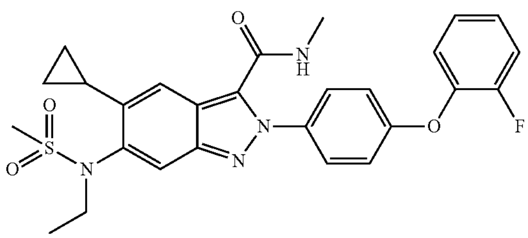 [SMILES: CCN(c1cc2nn(-c3ccc(Oc4ccccc4F)cc3)c(C(=O)NC)c2cc1C1CC1)S(C)(=O)=O] | [M + H]+ 523/(400 MHz, CDCl3) δ 7.71 (s, 1H), 7.53 (bd, J = 9.0 Hz, 2H), 7.48 (s, 1H), 7.24-7.14 (m, 4H), 7.10 (bd, J = 8.9 Hz, 2H), 5.68 (bd, J = 3.4 Hz, 1H), 3.92-3.63 (m, 2H), 3.06 (s, 3H), 2.97 (d, J = 4.9 Hz, 3H), 2.52-2.25 (m, 1H), 1.24 (t, J = 7.2 Hz, 3H), 1.13-0.90 (m, 3H), 0.65-0.50 (m, 1H). | C(5) |
| 29 | 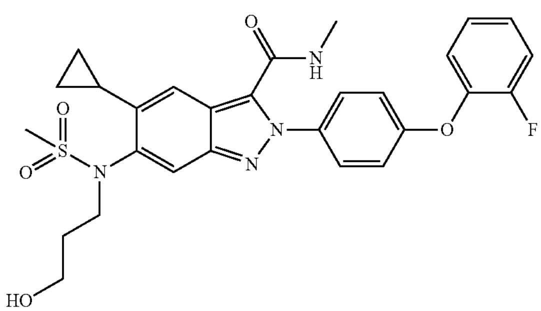 [SMILES: CNC(=O)c1c2cc(C3CC3)c(N(CCCO)S(C)(=O)=O)cc2nn1-c1ccc(Oc2ccccc2F)cc1] | [M + H]+ 553/(400 MHz, CDCl3) δ 7.75 (s, 1H), 7.53 (d, J = 9.0 Hz, 2H), 7.48 (s, 1H), 7.24-7.14 (m, 4H), 7.10 (d, J = 8.9 Hz, 2H), 5.66 (bd, J = 4.8 Hz, 1H), 4.09-3.59 (m, 4H), 3.07 (s, 3H), 2.96 (d, J = 4.9 Hz, 3H), 2.52-2.24 (m, 1H), 1.95-1.72 (m, 3H), 1.19-0.85 (m, 3H), 0.72-0.52 (m, 1H). | C(8) |
| 30 | 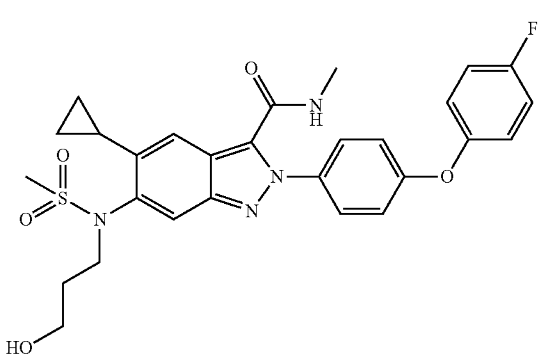 [SMILES: CNC(=O)c1c2cc(C3CC3)c(N(CCCO)S(C)(=O)=O)cc2nn1-c1ccc(Oc2ccc(F)cc2)cc1] | [M + H]+ 553/(400 MHz, CDCl3) δ 7.75 (s, 1H), 7.52 (d, J = 8.8 Hz, 2H), 7.44 (s, 1H), 7.18-7.02 (m, 6H), 5.72 (bd, J = 4.4 Hz, 1H), 4.04-3.64 (m, 4H), 3.07 (s, 3H), 2.99 (d, J = 4.9 Hz, 3H), 2.55-2.21 (m, 1H), 1.97-1.62 (m, 3H), 1.12-0.96 (m, 3H), 0.72-0.54 (m, 1H). | C(8) |

TABLE 1-continued

Compounds and their general method(s) of synthesis

| No. | Structure | Observed LCMS m/z [M + H]+/1H NMR | Method |
|---|---|---|---|
| 31 | 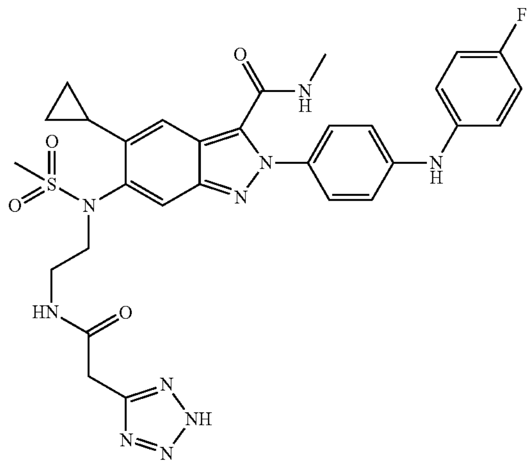 [SMILES: CNC(=O)c1c2cc(C3CC3)c(N(CCNC(=O)Cc3nn[nH]n3)S(C)(=O)=O)cc2nn1-c1ccc(Nc2ccc(F)cc2)cc1] | [M + H]+ 647/(400 MHz, $d_4$-methanol) δ 9.42 (s, 1H), 8.96 (d, J = 8.8 Hz, 2H), 8.91 (s, 1H), 8.75 (dd, J = 8.9, 4.7 Hz, 2H), 8.69-8.53 (m, 4H), 5.69-5.31 (m, 4H), 5.01 (t, J = 5.2 Hz, 2H), 4.70 (s, 3H), 4.49 (s, 3H), 3.98-3.73 (m, 1H), 2.70-2.44 (m, 3H), 2.31-2.13 (m, 1H). | D[(9)] |
| 32 | 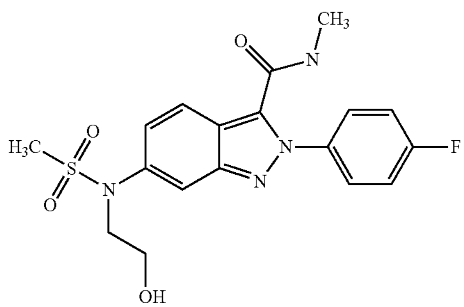 [SMILES: CNC(=O)c1c2ccc(N(CCO)S(C)(=O)=O)cc2nn1-c1ccc(F)cc1] | [M + H]+: 407.12/(400 MHz, $d_6$-DMSO) δ 8.74 (br s, 1H), 7.91-7.77 (m, 2H), 7.70-7.59 (m, 2H), 7.48-7.36 (m, 2H), 7.25 (d, J = 9.1 Hz, 1H), 4.89-4.80 (m, 1H), 3.83-3.70 (m, 2H), 3.50-3.38 (m, 2H), 3.08 (s, 3H), 2.87-2.77 (m, 3H). | F[(10)] |
| 33 | 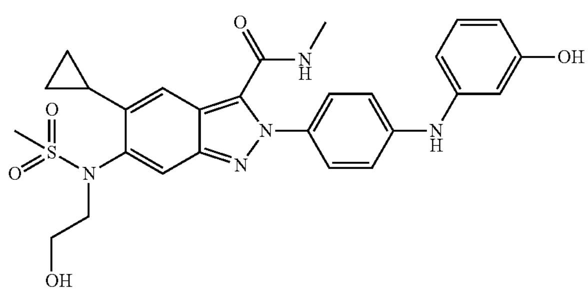 [SMILES: CNC(=O)c1c2cc(C3CC3)c(N(CCO)S(C)(=O)=O)cc2nn1-c1ccc(Nc2cccc(O)c2)cc1] | [M + H]+: 536.15/(400 MHz, $d_6$-DMSO) δ 9.31 (s, 1H), 8.59 (q, J = 4.5 Hz, 1H), 8.38 (s, 1H), 7.88 (s, 1H), 7.40 (bd, J = 8.9 Hz, 2H), 7.27 (s, 1H), 7.14 (bd, J = 8.9 Hz, 2H), 7.06 (t, J = 8.0 Hz, 1H), 6.70-6.47 (m, 2H), 6.33 (ddd, J = 8.0, 2.1, 0.9 Hz, 1H), 4.93 (t, J = 5.2 Hz, 1H), 3.99-3.73 (m, 1H), 3.65-3.40 (m, 3H), 3.21 (s, 3H), 2.82 (d, J = 4.6 Hz, 3H), 2.32-2.19 (m, 1H), 1.09-0.78 (m, 3H), 0.60-0.40 (m, 1H). | C[(11)] |
| 34 | 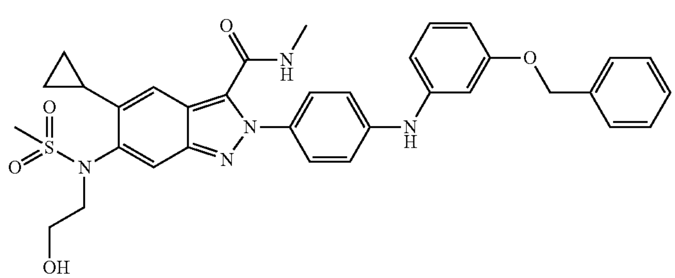 [SMILES: CNC(=O)c1c2cc(C3CC3)c(N(CCO)S(C)(=O)=O)cc2nn1-c1ccc(Nc2cccc(OCc3ccccc3)c2)cc1] | [M + H]+: 626.19/(400 MHz, CDCl3) δ 7.80 (s, 1H), 7.59 (s, 1H), 7.47-7.28 (m, 7H), 7.27-7.22 (m, 1H), 7.11 (bd, J = 8.8 Hz, 2H), 6.80 (t, J = 2.2 Hz, 1H), 6.74 (dd, J = 7.9, 1.4 Hz, 1H), 6.68 (dd, J = 8.3, 1.8 Hz, 1H), 5.97 (s, 1H), 5.68 (s, 1H), 5.08 (s, 2H), 4.24-3.98 (m, 1H), 3.85-3.58 (m, 3H), 3.19 (s, 3H), 2.95 (d, J = 4.9 Hz, 3H), 2.55-2.23 (m, 1H), 1.95 (bs, 1H), 1.15-0.91 (m, 3H), 0.64-0.47 (m, 1H). | C[(12)] |

TABLE 1-continued

Compounds and their general method(s) of synthesis

| No. | Structure | Observed LCMS m/z [M + H]+/1H NMR | Method |
|---|---|---|---|
| 35 | 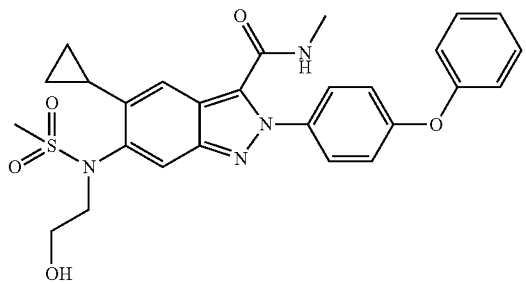 [SMILES: CNC(=O)c1c2cc(C3CC3)c(N(CCO)S(C)(=O)=O)cc2nn1-c1ccc(Oc2ccccc2)cc1] | [M + H]+: 521.14/(400 MHz, CDCl3) δ 7.80 (s, 1H), 7.53 (bd, J = 8.9 Hz, 2H), 7.50 (s, 1H), 7.46-7.30 (m, 2H), 7.23-7.16 (m, 1H), 7.15-7.06 (m, 4H), 5.74 (bd, J = 4.0 Hz, 1H), 4.24-3.95 (m, 1H), 3.90-3.61 (m, 3H), 3.19 (s, 3H), 2.98 (d, J = 4.9 Hz, 3H), 2.61-2.21 (m, 1H), 1.94 (t, J = 5.2 Hz, 1H), 1.15-0.83 (m, 3H), 0.68-0.45 (m, 1H). | C(13) |
| 36 | 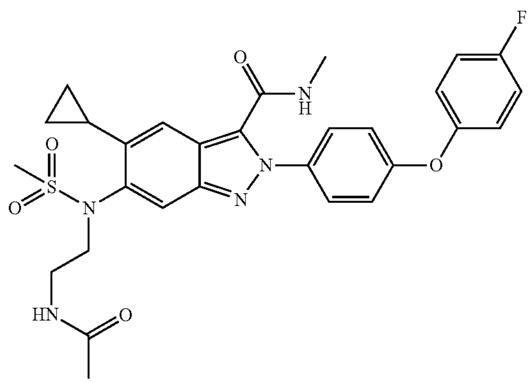 [SMILES: CNC(=O)c1c2cc(C3CC3)c(N(CCNC(C)=O)S(C)(=O)=O)cc2nn1-c1ccc(Oc2ccc(F)cc2)cc1] | [M + H]+: 579.96/(400 MHz, CDCl3) δ 7.76 (s, 1H), 7.52 (bd, J = 8.9 Hz, 2H), 7.46 (s, 1H), 7.14-7.02 (m, 6H), 6.09 (bs, 1H), 5.73 (bs, 1H), 4.02-3.68 (m, 2H), 3.60-3.31 (m, 2H), 3.07 (s, 3H), 2.98 (d, J = 4.9 Hz, 3H), 2.42-2.24 (m, 1H), 1.97 (s, 3H), 1.18-0.92 (m, 3H), 0.72-0.56 (m, 1H). | C(14) |
| 37 | 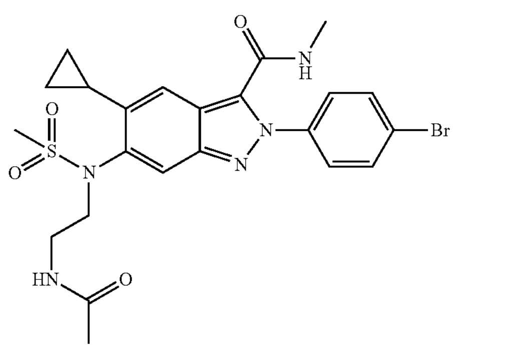 [SMILES: CNC(=O)c1c2cc(C3CC3)c(N(CCNC(C)=O)S(C)(=O)=O)cc2nn1-c1ccc(Br)cc1] | [M + H]+: 547.84/549.84/(400 MHz, CDCl3) δ 7.77 (s, 1H), 7.67 (bd, J = 8.8 Hz, 2H), 7.47 (bd, J = 8.8 Hz, 2H), 7.39 (s, 1H), 6.07 (bs, 1H), 5.77 (d, J = 4.3 Hz, 1H), 4.08-3.69 (m, 2H), 3.57-3.28 (m, 2H), 3.07 (s, 3H), 3.00 (d, J = 4.9 Hz, 3H), 2.44-2.25 (m, 1H), 1.97 (s, 3H), 1.16-0.90 (m, 3H), 0.72-0.53 (m, 1H). | D(15) |
| 38 | 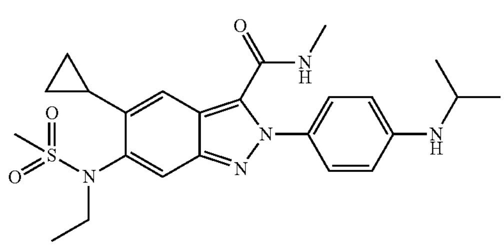 [SMILES: CCN(c1cc2nn(-c3ccc(NC(C)C)cc3)c(C(=O)NC)c2cc1C1CC1)S(C)(=O)=O] | [M + H]+: 470.12/(400 MHz, CDCl3) δ 7.69 (s, 1H), 7.66 (s, 1H), 7.33 (bd, J = 8.8 Hz, 2H), 6.66 (bd, J = 8.9 Hz, 2H), 5.62 (s, 1H), 3.90-3.75 (m, 2H), 3.75-3.60 (m, 1H), 3.05 (s, 3H), 2.90 (d, J = 4.9 Hz, 3H), 2.47-2.29 (m, 1H), 1.27 (d, J = 6.3 Hz, 6H), 1.23 (t, J = 7.1 Hz, 3H), 1.10-0.92 (m, 3H), 0.70-0.54 (m, 1H). | C(16) |
| 39 | 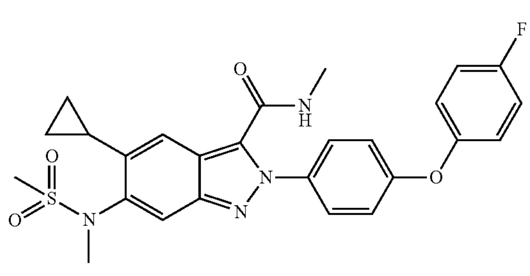 [SMILES: CNC(=O)c1c2cc(C3CC3)c(N(C)S(C)(=O)=O)cc2nn1-c1ccc(Oc2ccc(F)cc2)cc1] | [M + H]+: 509.10/(400 MHz, CDCl3) δ 7.72 (s, 1H), 7.55-7.42 (m, 3H), 7.14-7.00 (m, 6H), 5.82 (bd, J = 4.3 Hz, 1H), 3.37 (s, 3H), 3.08 (s, 3H), 2.99 (d, J = 4.9 Hz, 3H), 2.38 (tt, J = 8.6, 5.8 Hz, 1H), 1.21-0.74 (m, 3H), 0.74-0.25 (m, 1H). | B(17) |

TABLE 1-continued

Compounds and their general method(s) of synthesis

| No. | Structure | Observed LCMS m/z [M + H]+/1H NMR | Method |
|---|---|---|---|
| 40 | 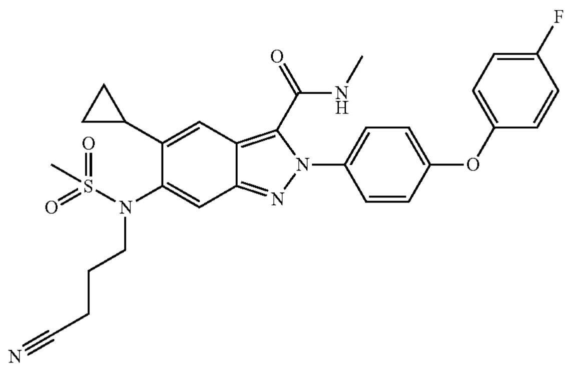 [SMILES: CNC(=O)c1c2cc(C3CC3)c(N(CCCC#N)S(C)(=O)=O)cc2nn1-c1ccc(Oc2ccc(F)cc2)cc1] | [M + H]+: 562.11/(400 MHz, CDCl3) δ 7.74 (s, 1H), 7.52 (bd, J = 9.0 Hz, 2H), 7.46 (s, 1H), 7.16-7.02 (m, 6H), 5.79 (bd, J = 4.7 Hz, 1H), 3.97-3.64 (m, 2H), 3.05 (s, 3H), 2.98 (d, J = 4.9 Hz, 3H), 2.62-2.43 (m, 2H), 2.43-2.29 (m, 1H), 2.05-1.97 (m, 2H), 1.26 (t, J = 7.1 Hz, 1H), 1.15-0.97 (m, 3H), 0.71-0.51 (m, 1H). | B(18) |
| 111 | 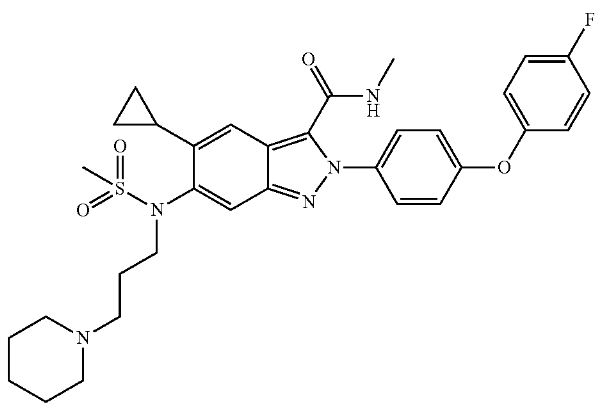 [SMILES: CNC(=O)c1c2cc(C3CC3)c(N(CCCN3CCCCC3)S(C)(=O)=O)cc2nn1-c1ccc(Oc2ccc(F)cc2)cc1] | [M + H]+: 620.2/(400 MHz, CDCl3) δ 7.73 (s, 1H), 7.53 (brd, J = 8.9 Hz, 2H), 7.43 (s, 1H), 7.12-7.01 (m, 6H), 5.83 (d, J = 5.0 Hz, 1H), 3.81 (t, J = 7.4 Hz, 2H), 3.07 (s, 3H), 2.99 (d, J = 4.9 Hz, 3H), 2.56-2.42 (m, 5H), 2.41-2.28 (m, 1H), 1.98-1.84 (m, 3H), 1.70-1.60 (m, 4H), 1.52-1.37 (m, 2H), 1.11-0.94 (m, 3H), 0.73-0.58 (m, 1H). | B |
| 112 | 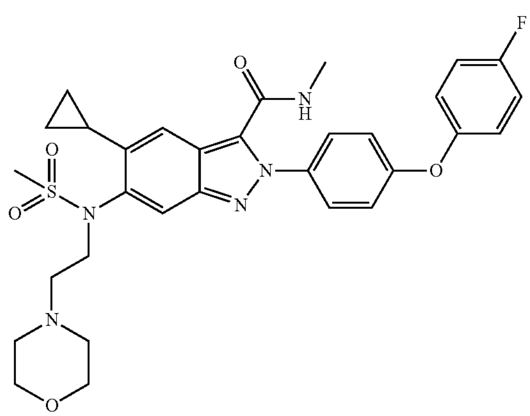 [SMILES: CNC(=O)c1c2cc(C3CC3)c(N(CCN3CCOCC3)S(C)(=O)=O)cc2nn1-c1ccc(Oc2ccc(F)cc2)cc1] | [M + H]+: 608.2/(400 MHz, CDCl3) δ 7.74 (s, 1H), 7.56-7.48 (m, 2H), 7.47 (s, 1H), 7.11-7.02 (m, 6H), 5.81-5.65 (m, 1H), 4.24 (ddd, J = 14.4, 9.1, 5.0 Hz, 1H), 3.82-3.61 (m, 4H), 3.60-3.50 (m, 1H), 3.27 (s, 3H), 3.00 (d, J = 4.9 Hz, 3H), 2.74-2.51 (m, 3H), 2.49-2.34 (m, 4H), 1.16-0.90 (m, 3H), 0.63-0.51 (m, 1H). | B |
| 113 | 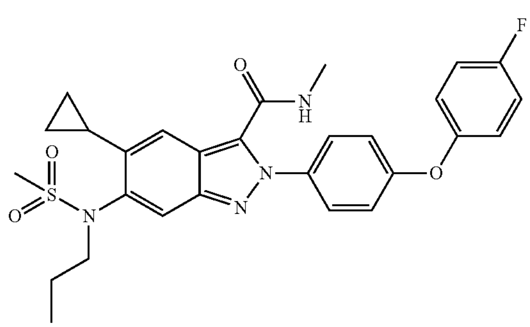 [SMILES: CCCN(c1cc2nn(-c3ccc(Oc4ccc(F)cc4)cc3)c(C(=O)NC)c2cc1C1CC1)S(C)(=O)=O] | [M + H]+: 537.1/(400 MHz, CDCl3) δ 7.72 (s, 1H), 7.52 (brd, J = 8.9 Hz, 2H), 7.43 (s, 1H), 7.12-7.04 (m, 6H), 5.75 (d, J = 5.5 Hz, 1H), 3.80-3.57 (m, 2H), 3.06 (s, 3H), 2.99 (d, J = 4.9 Hz, 3H), 2.49-2.33 (m, 1H), 1.75-1.57 (m, 2H), 1.14-0.96 (m, 3H), 0.93 (t, J = 7.4 Hz, 3H), 0.61 (dd, J = 9.3, 4.2 Hz, 1H). | B |

TABLE 1-continued

Compounds and their general method(s) of synthesis

| No. | Structure | Observed LCMS m/z [M + H]+/1H NMR | Method |
|---|---|---|---|
| 114 | 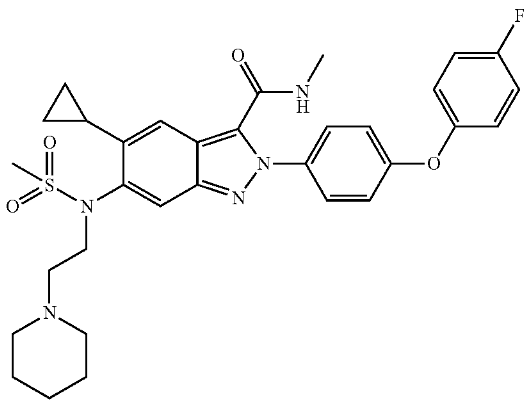 [SMILES: CNC(=O)c1c2cc(C3CC3)c(N(CCN3CCCCC3)S(C)(=O)=O)cc2nn1-c1ccc(Oc2ccc(F)cc2)cc1] | [M + H]+: 606.2/(400 MHz, CDCl3) δ 7.74 (s, 1H), 7.53 (brd, J = 8.9 Hz, 2H), 7.45 (s, 1H), 7.14-7.01 (m, 6H), 5.77 (s, 1H), 4.26 (ddd, J = 14.6, 9.0, 5.5 Hz, 1H), 3.67-3.41 (m, 1H), 3.29 (s, 3H), 2.99 (d, J = 4.9 Hz, 3H), 2.70-2.48 (m, 3H), 2.48-2.22 (m, 4H), 1.62-1.37 (m, 6H), 1.09-0.97 (m, 3H), 0.63-0.46 (m, 1H). | B |
| 115 | 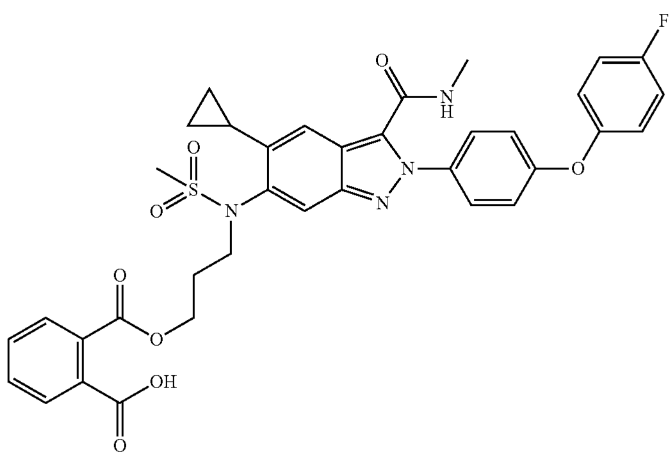 [SMILES: CNC(=O)c1c2cc(C3CC3)c(N(CCCOC(=O)c3ccccc3C(=O)O)S(C)(=O)=O)cc2nn1-c1ccc(Oc2ccc(F)cc2)cc1] | [M + H]+: 701.0/(400 MHz, CDCl3) δ 7.88-7.60 (m, 3H), 7.60-7.43 (m, 4H), 7.41 (s, 1H), 7.15-6.97 (m, 6H), 5.91 (d, J = 4.8 Hz, 1H), 4.49-4.22 (m, 2H), 4.03-3.75 (m, 2H), 3.13 (s, 3H), 2.98 (d, J = 4.9 Hz, 3H), 2.50-2.29 (m, 1H), 2.10-2.01 (m, 2H), 1.11-0.89 (m, 3H), 0.64-0.44 (m, 1H). | B then G |
| 116 | 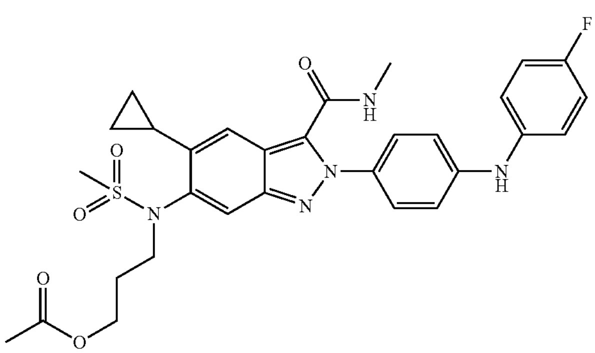 [SMILES: CNC(=O)c1c2cc(C3CC3)c(N(CCCOC(C)=O)S(C)(=O)=O)cc2nn1-c1ccc(Nc2ccc(F)cc2)cc1] | [M + H]+: 594.1/(400 MHz, CDCl3) δ 7.71 (s, 1H), 7.53 (s, 1H), 7.38 (brd, J = 8.8 Hz, 2H), 7.21-7.10 (m, 2H), 7.10-6.86 (m, 4H), 5.91 (s, 1H), 5.74 (d, J = 4.7 Hz, 1H), 4.12 (ddd, J = 6.2, 5.0, 1.5 Hz, 2H), 3.96-3.67 (m, 2H), 3.06 (s, 3H), 2.94 (d, J = 4.9 Hz, 3H), 2.47-2.27 (m, 1H), 2.02 (s, 3H), 1.98-1.85 (m, 2H), 1.13-0.95 (m, 3H), 0.66-0.52 (m, 1H). | G |
| 117 | 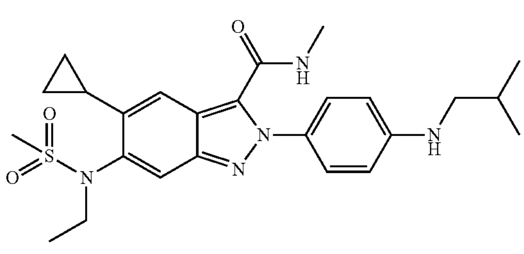 [SMILES: CCN(c1cc2nn(-c3ccc(NCC(C)C)cc3)c(C(=O)NC)c2cc1C1CC1)S(C)(=O)=O] | [M + H]+: 484.2/(400 MHz, CDCl3) δ 7.69 (s, 1H), 7.65 (s, 1H), 7.32 (brd, J = 8.8 Hz, 2H), 6.67 (brd, J = 8.9 Hz, 2H), 5.63 (d, J = 4.4 Hz, 1H), 4.10 (brs, 1H), 3.94-3.62 (m, 2H), 3.05 (s, 3H), 3.00 (d, J = 6.8 Hz, 2H), 2.89 (d, J = 4.9 Hz, 3H), 2.47-2.28 (m, 1H), 1.99-1.86 (m, 1H), 1.22 (t, J = 7.1 Hz, 3H), 1.10-0.87 (m, 9H), 0.70-0.52 (m, 1H). | C |

TABLE 1-continued

Compounds and their general method(s) of synthesis

| No. | Structure | Observed LCMS m/z [M + H]+/1H NMR | Method |
|---|---|---|---|
| 118 | 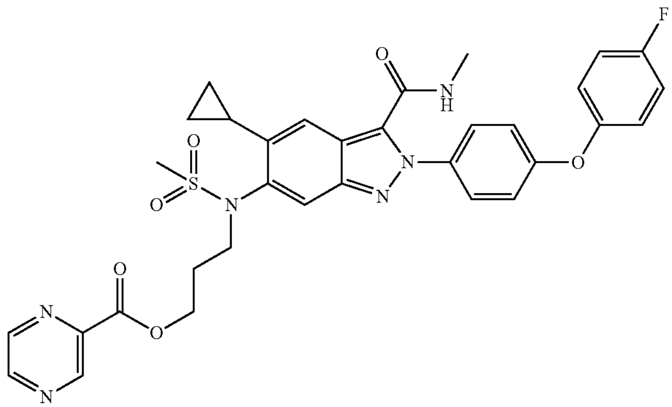 [SMILES: CNC(=O)c1c2cc(C3CC3)c(N(CCCOC(=O)c3cnccn3)S(C)(=O)=O)cc2nn1-c1ccc(Oc2ccc(F)cc2)cc1] | [M + H]+: 659.0/(400 MHz, CDCl3) δ 9.19 (d, J = 1.4 Hz, 1H), 8.81-8.62 (m, 2H), 7.77 (brs, 1H), 7.52 (brd, J = 9.0 Hz, 2H), 7.43 (s, 1H), 7.18-6.95 (m, 6H), 5.83 (d, J = 4.9 Hz, 1H), 4.66-4.39 (m, 2H), 4.04-3.80 (m, 2H), 3.07 (s, 3H), 2.99 (d, J = 4.9 Hz, 3H), 2.41 (tt, J = 8.4, 5.4 Hz, 1H), 2.27-2.10 (m, 2H), 1.16-0.92 (m, 3H), 0.67-0.54 (m, 1H). | B then G |
| 119 | 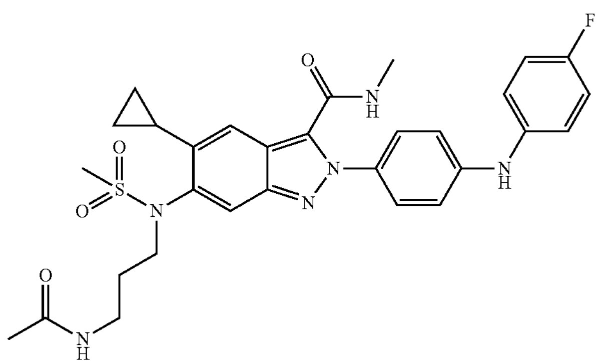 [SMILES: CNC(=O)c1c2cc(C3CC3)c(N(CCCNC(C)=O)S(C)(=O)=O)cc2nn1-c1ccc(Nc2ccc(F)cc2)cc1] | [M + H]+: 593.0/(400 MHz, CDCl3) δ 7.72 (s, 1H), 7.53 (s, 1H), 7.39 (d, J = 8.8 Hz, 2H), 7.20-7.10 (m, 2H), 7.10-6.94 (m, 4H), 6.02-5.80 (m, 2H), 5.73 (d, J = 4.8 Hz, 1H), 3.98-3.63 (m, 2H), 3.54-3.28 (m, 2H), 3.05 (s, 3H), 2.94 (d, J = 4.9 Hz, 3H), 2.44-2.22 (m, 1H), 1.97 (s, 3H), 1.77 (p, J = 6.7 Hz, 2H), 1.15-0.94 (m, 3H), 0.73-0.51 (m, 1H). | D |
| 120 | 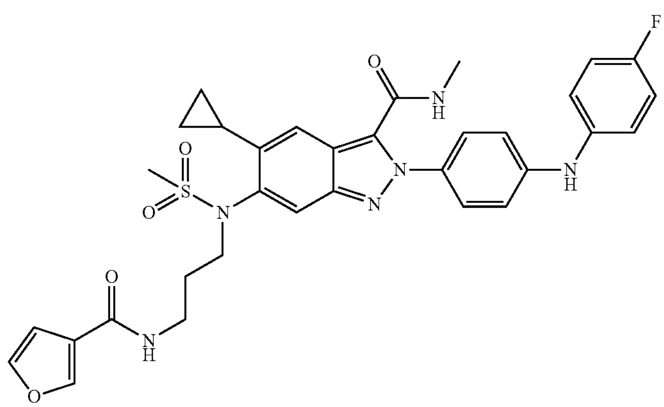 [SMILES: CNC(=O)c1c2cc(C3CC3)c(N(CCCNC(=O)c3ccoc3)S(C)(=O)=O)cc2nn1-c1ccc(Nc2ccc(F)cc2)cc1] | [M + H]+: 645.1/(400 MHz, CDCl3) δ 7.95 (dd, J = 1.5, 0.9 Hz, 1H), 7.75 (s, 1H), 7.53 (s, 1H), 7.44-7.41 (m, 1H), 7.39 (brd, J = 8.8 Hz, 2H), 7.18-7.10 (m, 2H), 7.10-6.95 (m, 4H), 6.71-6.54 (m, 2H), 5.91 (s, 1H), 5.74 (d, J = 4.9 Hz, 1H), 4.04-3.71 (m, 2H), 3.71-3.49 (m, 2H), 3.06 (s, 3H), 2.94 (d, J = 4.9 Hz, 3H), 2.47-2.22 (m, 1H), 1.82 (p, J = 6.2 Hz, 2H), 1.16-0.92 (m, 3H), 0.76-0.52 (m, 1H). | D |
| 121 | 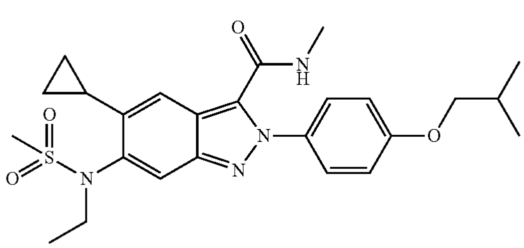 [SMILES: CCN(c1cc2nn(-c3ccc(OCC(C)C)cc3)c(C(=O)NC)c2cc1C1CC1)S(C)(=O)=O] | [M + H]+: 485.2/(400 MHz, CDCl3) δ 7.71 (d, J = 0.5 Hz, 1H), 7.55 (brs, 1H), 7.48 (d, J = 9.0 Hz, 2H), 7.03 (d, J = 9.0 Hz, 2H), 5.60 (brs, 1 3.90-3.66 (m, 4H), 3.06 (s, 3H), 2.93 (d, J = 4.9 Hz, 3H), 2.52-2.29 (m, 1H), 2.13 (dt, J = 13.3, 6.7 Hz, 1H), 1.23 (t, J = 7.1 Hz, 3H), 1.09-0.92 (m, 9H), 0.66-0.46 (m, 1H). | C |

TABLE 1-continued

Compounds and their general method(s) of synthesis

| No. | Structure | Observed LCMS m/z [M + H]⁺/¹H NMR | Method |
|---|---|---|---|
| 122 | 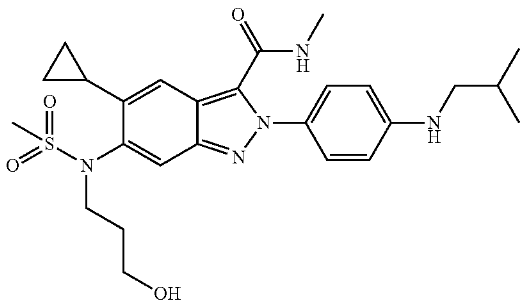 [SMILES: CNC(=O)c1c2cc(C3CC3)c(N(CCCO)S(C)(=O)=O)cc2nn1-c1ccc(NCC(C)C)cc1] | [M + H]+: 514.2/(400 MHz, CDCl₃) δ 7.77 (s, 1H), 7.70 (s, 1H), 7.37 (brd, J = 8.8 Hz, 2H), 6.72 (brd, J = 8.8 Hz, 2H), 5.63 (s, 1H), 4.00-3.75 (m, 4H), 3.11 (s, 3H), 3.05 (d, J = 6.8 Hz, 2H), 2.94 (d, J = 4.9 Hz, 3H), 2.48-2.31 (m, 1H), 2.04-1.90 (m, 2H), 1.90-1.77 (m, 2H), 1.19-0.96 (m, 9H), 0.76-0.61 (m, 1H). | C then F |
| 123 | 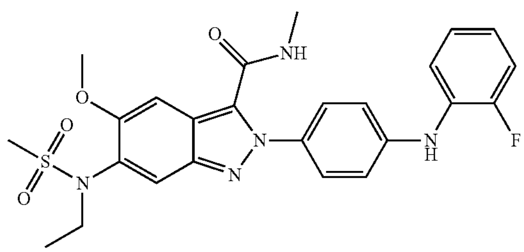 [SMILES: CCN(c1cc2nn(-c3ccc(Nc4ccccc4F)cc3)c(C(=O)NC)c2cc1OC)S(C)(=O)=O] | [M + H]+: 512.2/(400 MHz, Acetone) δ 7.70 (s, 1H), 7.57-7.48 (m, 4H), 7.41 (s, 1H), 7.33 (s, 1H), 7.27-7.16 (m, 4H), 7.10-7.01 (m, 1H), 4.01 (s, 3H), 3.80-3.65 (m, 2H), 3.02 (s, 3H), 2.95 (d, J = 4.7 Hz, 3H), 1.16 (t, J = 7.2 Hz, 3H). | C |
| 124 | 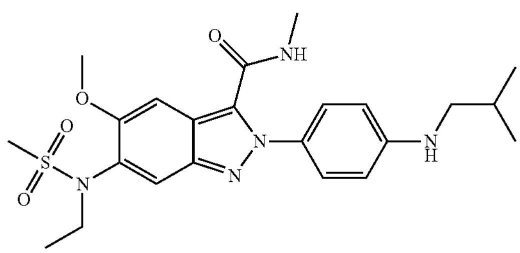 [SMILES: CCN(c1cc2nn(-c3ccc(NCC(C)C)cc3)c(C(=O)NC)c2cc1OC)S(C)(=O)=O] | [M + H]+: 474.2/(400 MHz, Acetone) δ 7.67 (s, 1H), 7.40-7.35 (m, 2H), 7.34 (s, 1H), 7.16 (brs, 1H), 6.82-6.73 (m, 2H), 5.51-5.42 (m, 1H), 4.00 (s, 3H), 3.81-3.65 (m, 2H), 3.07-2.99 (m, 5H), 2.91 (d, J = 4.8 Hz, 3H), 1.98 (dd, J = 13.4, 6.7 Hz, 1H), 1.15 (t, J = 7.2 Hz, 3H), 1.04 (d, J = 6.7 Hz, 6H). | C |
| 125 | 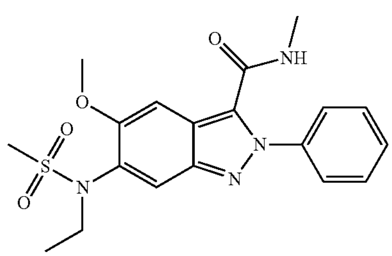 [SMILES: CCN(c1cc2nn(-c3ccccc3)c(C(=O)NC)c2cc1OC)S(C)(=O)=O] | [M + H]+: 403.1/(400 MHz, Acetone) δ 7.67 (s, 1H), 7.64-7.61 (m, 2H), 7.55-7.45 (m, 4H), 7.26 (s, 1H), 3.96 (s, 3H), 3.73-3.64 (m, 2H), 2.98 (s, 3H), 2.90 (d, J = 4.8 Hz, 3H), 1.11 (t, J = 7.2 Hz, 3H). | C |
| 126 | 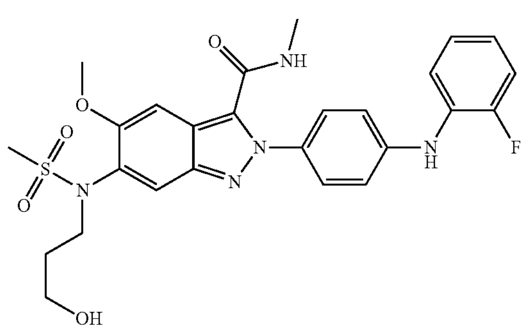 [SMILES: CNC(=O)c1c2cc(OC)c(N(CCCO)S(C)(=O)=O)cc2nn1-c1ccc(Nc2ccccc2F)cc1] | [M + H]+: 542.2/(400 MHz, Acetone) δ 7.71 (s, 1H), 7.57-7.48 (m, 3H), 7.42 (s, 1H), 7.32 (s, 1H), 7.27-7.16 (m, 4H), 7.09-7.01 (m, 1H), 4.01 (s, 3H), 3.87-3.76 (m, 2H), 3.71-3.64 (m, 2H), 3.51 (t, J = 5.4 Hz, 1H), 3.34 (d, J = 6.5 Hz, 1H), 3.05 (s, 3H), 2.95 (d, J = 4.7 Hz, 3H), 1.78-1.68 (m, 2H). | C then F |

TABLE 1-continued

Compounds and their general method(s) of synthesis

| No. | Structure | Observed LCMS m/z [M + H]+/1H NMR | Method |
|---|---|---|---|
| 127 | 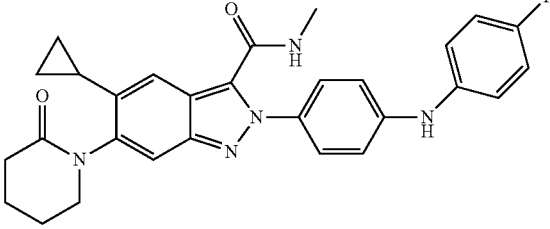 | [M + H]+: 498.3/(400 MHz, CDCl3) δ 7.66 (s, 1H), 7.51 (s, 1H), 7.23 (d, J = 8.8 Hz, 2H), 7.16-7.07 (m, 2H), 7.06-6.96 (m, 2H), 6.88 (brd, J = 8.8 Hz, 2H), 6.21 (brs, 1H), 5.93 (brs, 1H), 3.89-3.43 (m, 2H), 2.92 (d, J = 4.9 Hz, 3H), 2.71-2.48 (m, 2H), 2.11-1.94 (m, 4H), 1.94-1.82 (m, 1H), 1.07-0.76 (m, 3H), 0.59-0.40 (m, 1H). | P |
| 128 | 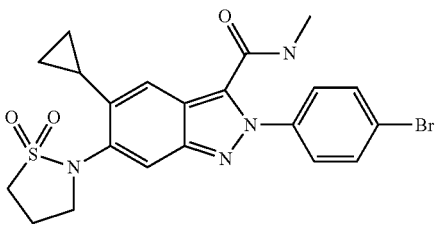 [SMILES: CNC(=O)c1c2cc(C3CC3)c(N3CCCS3(=O)=O)cc2nn1-c1ccc(Br)cc1] | [M + H]+: 489.1/491.1/(400 MHz, CDCl3) δ 7.94 (s, 1H), 7.64 (brd, J = 8.7 Hz, 2H), 7.47 (s, 1H), 7.44 (d, J = 5.1 Hz, 2H), 5.88 (s, 1H), 3.83 (t, J = 6.8 Hz, 2H), 3.38 (t, J = 7.6 Hz, 2H), 3.00 (d, J = 4.9 Hz, 3H), 2.66-2.46 (m, 2H), 2.40-2.22 (m, 1H), 1.08-0.92 (m, 2H), 0.85-0.66 (m, 2H). | P |
| 129 | 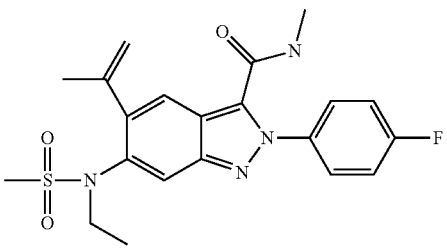 [SMILES: C=C(C)c1cc2c(C(=O)NC)n(-c3ccc(F)cc3)nc2cc1N(CC)S(C)(=O)=O] | [M + H]+: 431.2/(400 MHz, Acetone) δ 7.85-7.79 (m, 2H), 7.78 (s, 1H), 7.77-7.71 (m, 2H), 7.40-7.32 (m, 2H), 5.29-5.25 (m, 1H), 5.14-5.10 (m, 1H), 3.94-3.63 (m, 2H), 3.24 (s, 3H), 2.98 (d, J = 4.0 Hz, 3H), 2.23 (s, 3H), 1.21 (t, J = 7.2 Hz, 3H). | I |
| 130 | 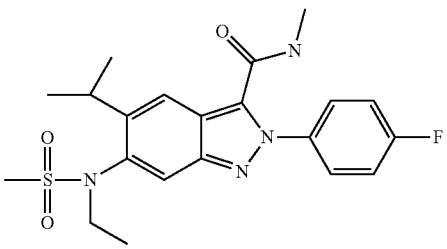 [SMILES: CCN(c1cc2nn(-c3ccc(F)cc3)c(C(=O)NC)c2cc1C(C)C)S(C)(=O)=O] | [M + H]+: 433.2/(400 MHz, Acetone) δ 7.92 (s, 1H), 7.86 (d, J = 0.6 Hz, 1H), 7.83-7.76 (m, 1H), 7.77-7.70 (m, 2H), 7.40-7.32 (m, 2H), 3.87-3.78 (m, 2H), 3.67-3.57 (m, 1H), 3.14 (s, 3H), 3.01-2.95 (m, 3H), 1.35 (d, J = 6.9 Hz, 3H), 1.29 (d, J = 6.9 Hz, 3H), 1.19 (t, J = 7.2 Hz, 3H). | I |
| 131 | 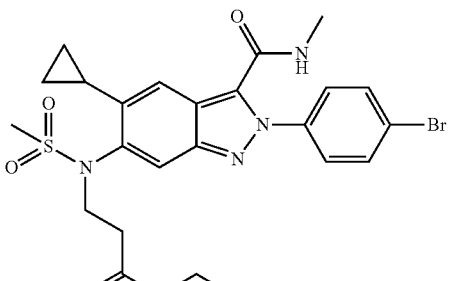 | [M + H]+: 563.0/565.0/(400 MHz, CDCl3) δ 7.71 (brs, 1H), 7.68-7.63 (m, 2H), 7.49-7.43 (m, 2H), 7.38 (s, 1H), 5.80 (brd, J = 4.3 Hz, 1H), 4.16-4.00 (m, 4H), 3.12 (s, 3H), 3.01 (d, J = 4.9 Hz, 3H), 2.74-2.52 (m, 2H), 2.34 (tt, J = 8.4, 5.5 Hz, 1H), 1.21 (t, J = 7.1 Hz, 3H), 1.13-0.93 (m, 3H), 0.67-0.56 (m, 1H). | M |
| 132 | 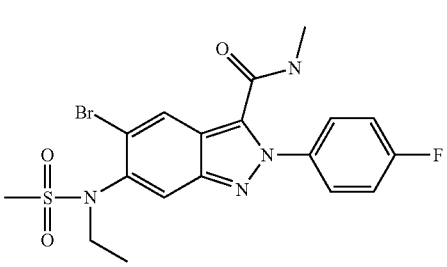 [SMILES: CCN(c1cc2nn(-c3ccc(F)cc3)c(C(=O)NC)c2cc1Br)S(C)(=O)=O] | [M + H]+: 469.1/471.1/NMR (400 MHz, Acetone) δ 8.28 (s, 1H), 8.00 (s, 1H), 7.88 (brs, 1H), 7.79-7.72 (m, 2H), 7.41-7.34 (m, 2H), 3.97-3.86 (m, 1H), 3.80-3.68 (m, 1H), 3.19 (s, 3H), 2.99 (d, J = 3.9 Hz, 3H), 1.23 (t, J = 7.2 Hz, 3H). | A |

TABLE 1-continued

Compounds and their general method(s) of synthesis

| No. | Structure | Observed LCMS m/z [M + H]+/1H NMR | Method |
|---|---|---|---|
| 133 | 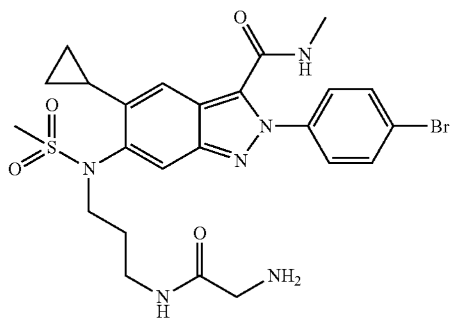 [SMILES: CNC(=O)c1c2cc(C3CC3)c(N(CCCNC(=O)CN)S(C)(=O)=O)cc2nn1-c1ccc(Br)cc1] | [M + H]+: 577.0/579.0/(400 MHz, CDCl3) δ 7.75 (s, 1H), 7.69-7.62 (m, 2H), 7.51-7.43 (m, 3H), 7.36 (s, 1H), 5.86 (brd, J = 4.5 Hz, 1H), 3.87-3.71 (m, 2H), 3.50-3.35 (m, 2H), 3.33 (s, 2H), 3.06 (s, 3H), 3.00 (d, J = 4.9 Hz, 3H), 2.47-2.31 (m, 1H), 1.89-1.74 (m, 2H), 1.14-0.97 (m, 3H), 0.66-0.54 (m, 1H). | D |
| 134 | 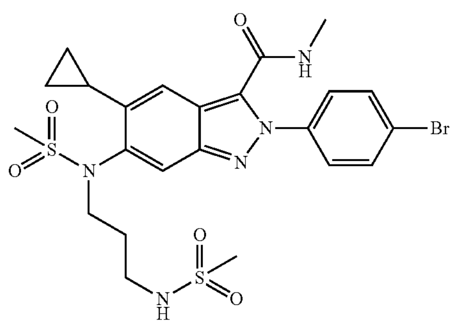 [SMILES: CNC(=O)c1c2cc(C3CC3)c(N(CCCNS(C)(=O)=O)S(C)(=O)=O)cc2nn1-c1ccc(Br)cc1] | [M + H]+: 598.0/600.0/(400 MHz, CDCl3) δ 7.75 (s, 1H), 7.71-7.59 (m, 2H), 7.51-7.41 (m, 2H), 7.36 (s, 1H), 5.84 (brd, J = 4.7 Hz, 1H), 4.83 (t, J = 6.5 Hz, 1H), 3.99-3.71 (m, 2H), 3.44-3.25 (m, 2H), 3.06 (s, 3H), 3.00 (d, J = 4.9 Hz, 3H), 2.96 (s, 3H), 2.35 (tt, J = 8.3, 5.4 Hz, 1H), 1.91-1.72 (m, 2H), 1.15-0.96 (m, 3H), 0.69-0.54 (m, 1H). | D |
| 135 | 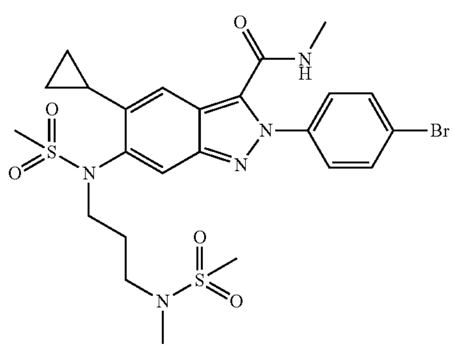 [SMILES: CNC(=O)c1c2cc(C3CC3)c(N(CCCN(C)S(C)(=O)=O)S(C)(=O)=O)cc2nn1-c1ccc(Br)cc1] | [M + H]+: 612.0/614.0/(400 MHz, CDCl3) δ 7.76 (s, 1H), 7.69-7.63 (m, 2H), 7.51-7.44 (m, 2H), 7.37 (s, 1H), 5.80 (brd, J = 4.0 Hz, 1H), 3.92-3.64 (m, 2H), 3.27-3.09 (m, 2H), 3.06 (s, 3H), 3.01 (d, J = 4.9 Hz, 3H), 2.80 (s, 3H), 2.77 (s, 3H), 2.42-2.29 (m, 1H), 1.99-1.84 (m, 2H), 1.14-0.95 (m, 3H), 0.69-0.59 (m, 1H). | D |
| 136 | 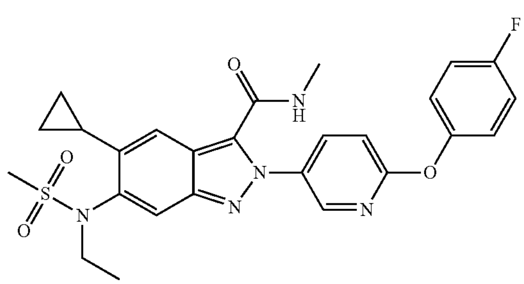 [SMILES: CCN(c1cc2nn(-c3ccc(Oc4ccc(F)cc4)nc3)c(C(=O)NC)c2cc1C1CC1)S(C)(=O)=O] | [M + H]+: 524.1/(400 MHz, CDCl3) δ 8.33 (dd, J = 2.8, 0.48 Hz, 1H), 7.96 (dd, J = 8.8, 2.8 Hz, 1H), 7.73 (brs, 1H), 7.10-7.20 (m, 4H), 7.06 (dd, J = 8.8, 0.48 Hz, 1H), 6.00-6.09 (m, 1H), 3.79-3.86 (m, 2H), 3.07 (s, 3H), 3.05 (d, J = 4.9 Hz, 3H), 2.40-2.48 (m, 1H), 1.25 (t, J = 7.1 Hz, 3H), 1.07-1.12 (m, 2H), 0.94-1.01 (m, 1H), 0.54-0.61 (m, 1H). | A |
| 137 | 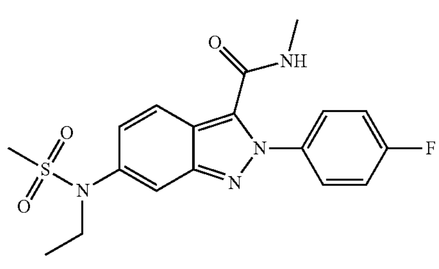 [SMILES: CCN(c1ccc2c(C(=O)NC)n(-c3ccc(F)cc3)nc2c1)S(C)(=O)=O] | [M + H]+: 391.1/(400 MHz, Acetone) δ 7.92 (dd, J = 9.0, 0.8 Hz, 1H), 7.84-7.71 (m, 4H), 7.41-7.33 (m, 2H), 7.28 (dd, J = 9.0, 1.8 Hz, 1H), 3.88 (q, J = 7.1 Hz, 2H), 3.03 (s, 3H), 2.99 (d, J = 4.8 Hz, 3H), 1.17 (t, J = 7.1 Hz, 3H). | I |

TABLE 1-continued

Compounds and their general method(s) of synthesis

| No. | Structure | Observed LCMS m/z [M + H]+/1H NMR | Method |
|---|---|---|---|
| 138 | 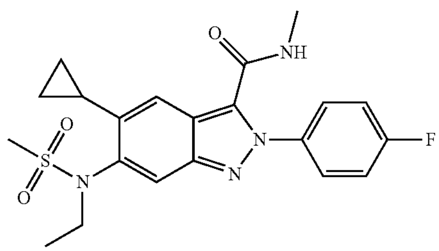 [SMILES: CCN(c1cc2nn(-c3ccc(F)cc3)c(C(=O)NC)c2cc1C1CC1)S(C)(=O)=O] | [M + H]+: 431.1/(400 MHz, Acetone) δ 7.87 (s, 1H), 7.81-7.67 (m, 3H), 7.44 (s, 1H), 7.39-7.30 (m, 2H), 3.91-3.82 (m, 2H), 3.17 (s, 3H), 2.97 (d, J = 4.7 Hz, 3H), 2.50-2.41 (m, 1H), 1.23 (t, J = 7.2 Hz, 3H), 1.10-0.96 (m, 3H), 0.63-0.52 (m, 1H). | I |
| 139 | 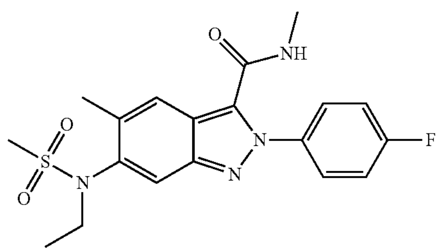 [SMILES: CCN(c1cc2nn(-c3ccc(F)cc3)c(C(=O)NC)c2cc1C)S(C)(=O)=O] | [M + H]+: 405.1/(400 MHz, Acetone) δ 7.88 (s, 1H), 7.81-7.69 (m, 4H), 7.40-7.31 (m, 2H), 3.89-3.76 (m, 2H), 3.14 (s, 3H), 2.99 (d, J = 4.7 Hz, 3H), 2.50 (d, J = 0.7 Hz, 3H), 1.18 (t, J = 7.1 Hz, 3H). | I |
| 140 | 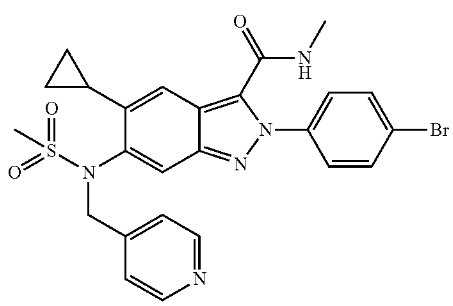 [SMILES: CNC(=O)c1c2cc(C3CC3)c(N(Cc3ccncc3)S(C)(=O)=O)cc2nn1-c1ccc(Br)cc1] | [M + H]+: 554.0/556.0/(400 MHz, CDCl3) δ 8.55 (d, J = 5.6 Hz, 2H), 7.71-7.58 (m, 3H), 7.51-7.42 (m, 2H), 7.33 (s, 1H), 7.25-7.23 (m, 2H), 5.76 (d, J = 3.8 Hz, 1H), 4.88 (dd, J = 58.9, 14.4 Hz, 2H), 3.05 (s, 3H), 2.99 (d, J = 4.9 Hz, 3H), 2.34-2.10 (m, 1H), 1.10-0.84 (m, 3H), 0.48-0.30 (m, 1H). | C |
| 141 | 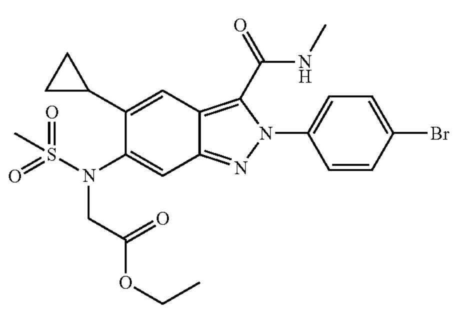 [SMILES: CCOC(=O)CN(c1cc2nn(-c3ccc(Br)cc3)c(C(=O)NC)c2cc1C1CC1)S(C)(=O)=O] | [M + H]+: 549.0/551.0/(400 MHz, CDCl3) δ 8.12 (s, 1H), 7.72-7.59 (m, 2H), 7.50-7.41 (m, 3H), 5.85 (brd, J = 4.3 Hz, 1H), 4.98 (brd, J = 17.7 Hz, 1H), 4.34-4.14 (m, 2H), 4.06 (brd, J = 17.5 Hz, 1H), 3.35 (s, 3H), 3.01 (d, J = 4.9 Hz, 3H), 2.47-2.27 (m, 1H), 1.28 (t, J = 7.2 Hz, 3H), 1.13-0.97 (m, 3H), 0.57-0.39 (m, 1H). | M |
| 142 | 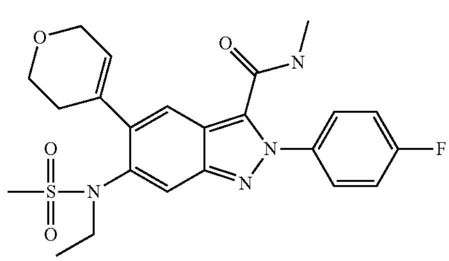 [SMILES: CCN(c1cc2nn(-c3ccc(F)cc3)c(C(=O)NC)c2cc1C1=CCOCC1)S(C)(=O)=O] | [M + H]+: 473.1/(400 MHz, Acetone) δ 7.85-7.78 (m, 2H), 7.78-7.71 (m, 3H), 7.40-7.32 (m, 2H), 5.95-5.90 (m, 1H), 4.27 (q, J = 2.7 Hz, 2H), 3.95-3.62 (m, 4H), 3.24 (s, 3H), 3.00-2.95 (m, 3H), 2.76-2.30 (m, 2H), 1.20 (t, J = 7.2 Hz, 3H). | I |

TABLE 1-continued

Compounds and their general method(s) of synthesis

| No. | Structure | Observed LCMS m/z [M + H]+/1H NMR | Method |
|---|---|---|---|
| 143 | 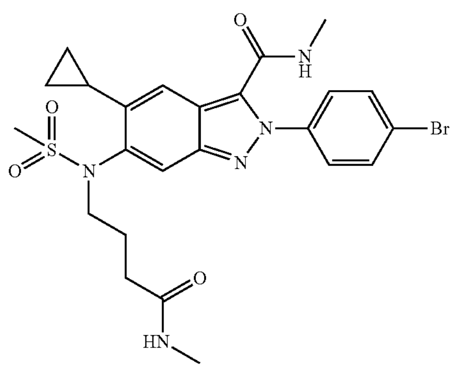 [SMILES: CNC(=O)CCCN(c1cc2nn(-c3ccc(Br)cc3)c(C(=O)NC)c2cc1C1CC1)S(C)(=O)=O] | [M + H]+: 561.8/563.8/(400 MHz, CDCl3) δ 7.76 (s, 1H), 7.73-7.64 (m, 2H), 7.53-7.46 (m, 2H), 7.38 (s, 1H), 6.01 (brd, J = 4.7 Hz, 1H), 5.73 (brd, J = 3.7 Hz, 1H), 3.80 (t, J = 7.0 Hz, 2H), 3.09 (s, 3H), 3.03 (d, J = 4.9 Hz, 3H), 2.81 (d, J = 4.8 Hz, 3H), 2.41 (tt, J = 8.4, 5.4 Hz, 1H), 2.36-2.22 (m, 2H), 1.94 (p, J = 7.0 Hz, 2H), 1.18-0.93 (m, 3H), 0.71-0.55 (m, 1H). | M |
| 144 | 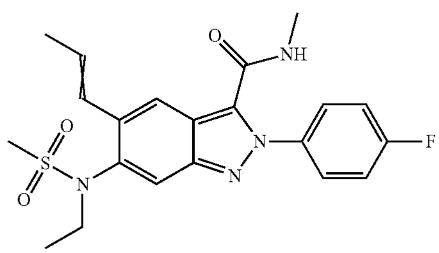 [SMILES: CC=Cc1cc2c(C(=O)NC)n(-c3ccc(F)cc3)nc2cc1N(CC)S(C)(=O)=O] | cis: [M + H]+: 431.1/(400 MHz, Acetone) δ 7.89 (d, J = 0.6 Hz, 1H), 7.82 (s, 1H), 7.80-7.71 (m, 3H), 7.41-7.32 (m, 2H), 6.82-6.75 (m, 1H), 6.01-5.89 (m, 1H), 3.87-3.70 (m, 2H), 3.14 (s, 3H), 2.98 (d, J = 4.8 Hz, 3H), 1.87 (dd, J = 7.0, 1.9 Hz, 3H), 1.13 (t, 3H). trans: 1H NMR (400 MHz, Acetone) δ 8.05 (s, 1H), 7.85 (d, J = 0.6 Hz, 1H), 7.80-7.70 (m, 3H), 7.41-7.32 (m, 2H), 6.92 (ddd, J = 15.7, 1.8, 0.6 Hz, 1H), 6.32 (dq, J = 15.7, 6.6 Hz, 1H), 3.87-3.68 (m, 2H), 3.15 (s, 3H), 3.00 (d, J = 4.8 Hz, 3H), 1.94 (dd, J = 6.7, 1.8 Hz, 3H), 1.15 (t, J = 7.1 Hz, 3H). | I |
| 145 | 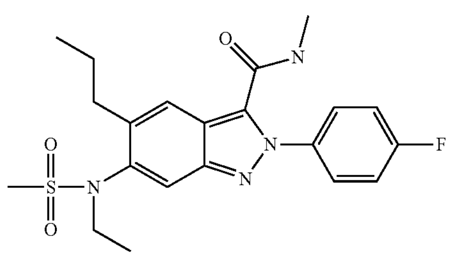 [SMILES: CCCc1cc2c(C(=O)NC)n(-c3ccc(F)cc3)nc2cc1N(CC)S(C)(=O)=O] | [M + H]+: 433.1/(400 MHz, Acetone) δ 7.87 (s, 1H), 7.82 (s, 1H), 7.80-7.70 (m, 3H), 7.39-7.32 (m, 2H), 3.82 (q, J = 7.2 Hz, 2H), 3.14 (s, 3H), 2.98 (d, J = 3.9 Hz, 3H), 2.92-2.84 (m, 2H), 1.89-1.69 (m, 2H), 1.19 (t, J = 7.2 Hz, 3H), 1.07 (t, J = 7.3 Hz, 3H). | I |
| 146 | 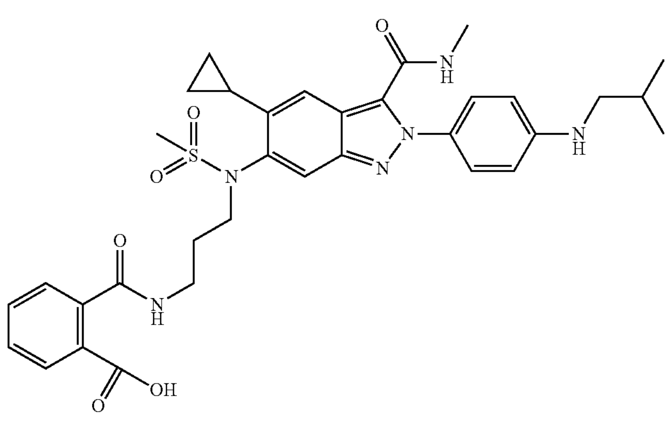 [SMILES: CNC(=O)c1c2cc(C3CC3)c(N(CCCNC(=O)c3ccccc3C(=O)O)S(C)(=O)=O)cc2nn1-c1ccc(NCC(C)C)cc1] | [M + H]+: 661.1/(400 MHz, CDCl3) δ 7.95 (d, J = 7.4 Hz, 1H), 7.75 (s, 1H), 7.54 (s, 1H), 7.52-7.38 (m, 3H), 7.32-7.26 (m, 2H), 6.92 (brs, 1H), 6.65 (d, J = 8.8 Hz, 2H), 5.91 (brd, J = 4.0 Hz, 1H), 3.83 (t, J = 6.8 Hz, 2H), 3.63-3.42 (m, 2H), 3.01 (s, 3H), 2.99 (d, J = 6.8 Hz, 2H), 2.87 (d, J = 4.8 Hz, 3H), 2.36-2.28 (m, 1H), 1.93 (dq, J = 20.1, 6.8 Hz, 1H), 1.86-1.77 (m, 2H), 1.07-0.94 (m, 9H), 0.64-0.53 (m, 1H). | D |

TABLE 1-continued

Compounds and their general method(s) of synthesis

| No. | Structure | Observed LCMS m/z [M + H]+/1H NMR | Method |
|---|---|---|---|
| 147 | 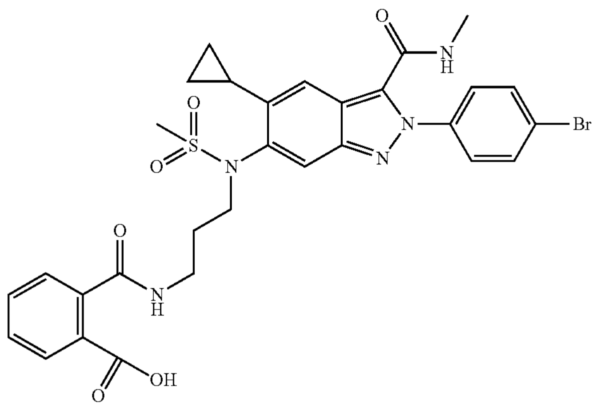 [SMILES: CNC(=O)c1c2cc(C3CC3)c(N(CCCNC(=O)c3ccccc3C(=O)O)S(C)(=O)=O)cc2nn1-c1ccc(Br)cc1] | [M + H]+: 667.9/669.9/(400 MHz, CDCl₃) δ 7.99 (d, J = 7.7 Hz, 1H), 7.82 (s, 1H), 7.66 (d, J = 8.7 Hz, 2H), 7.57-7.40 (m, 5H), 7.32 (d, J = 7.2 Hz, 1H), 6.75 (s, 1H), 6.11 (s, 1H), 3.87 (t, J = 6.6 Hz, 2H), 3.57 (d, J = 6.2 Hz, 2H), 3.05 (s, 3H), 2.99 (d, J = 4.9 Hz, 3H), 2.36 (s, 1H), 1.88-1.80 (m, 2H), 1.11-0.93 (m, 3H), 0.63-0.54 (m, 1H). | D |
| 148 | 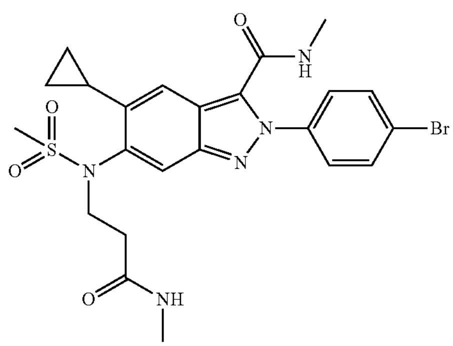 [SMILES: CNC(=O)CCN(c1cc2nn(-c3ccc(Br)cc3)c(C(=O)NC)c2cc1C1CC1)S(C)(=O)=O] | [M + H]+: 547.9/549.9/(400 MHz, CDCl₃) δ 7.74-7.69 (m, 1H), 7.69-7.61 (m, 2H), 7.50-7.42 (m, 2H), 7.36 (s, 1H), 5.87 (brd, J = 4.7 Hz, 1H), 5.63 (brd, J = 4.3 Hz, 1H), 4.07 (dtd, J = 20.8, 14.0, 6.7 Hz, 2H), 3.10 (s, 3H), 3.00 (d, J = 4.9 Hz, 3H), 2.77 (d, J = 4.8 Hz, 3H), 2.57-2.36 (m, 2H), 2.30 (tt, J = 8.4, 5.4 Hz, 1H), 1.14-0.81 (m, 3H), 0.73-0.52 (m, 1H). | M |
| 149 | 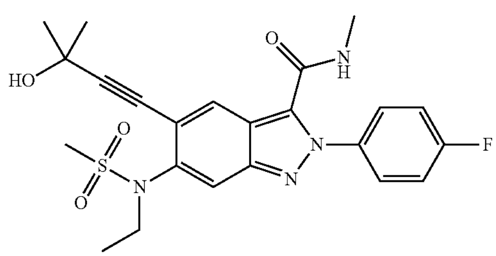 [SMILES: CCN(c1cc2nn(-c3ccc(F)cc3)c(C(=O)NC)c2cc1C#CC(C)(C)O)S(C)(=O)=O] | [M + H]+: 495.1/(400 MHz, Acetone) δ 8.02 (s, 1H), 7.85 (brs, 1H), 7.81 (d, J = 0.7 Hz, 1H), 7.80-7.72 (m, 2H), 7.42-7.33 (m, 2H), 4.53 (s, 1H), 3.89 (q, J = 7.1 Hz, 2H), 3.15 (s, 3H), 3.02-2.96 (m, 3H), 1.62 (s, 6H), 1.21 (t, J = 7.1 Hz, 3H). | I |
| 150 | 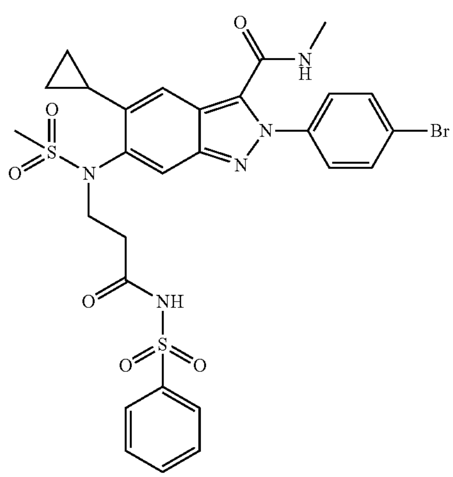 [SMILES: CNC(=O)c1c2cc(C3CC3)c(N(CCC(=O)NS(=O)(=O)c3ccccc3)S(C)(=O)=O)cc2nn1-c1ccc(Br)cc1] | [M + H]+: 674.0/676.0/(400 MHz, CDCl₃) δ 8.98 (brs, 1H), 8.06-7.95 (m, 2H), 7.70-7.60 (m, 3H), 7.59 (s, 1H), 7.57-7.49 (m, 2H), 7.48-7.40 (m, 2H), 7.30 (s, 1H), 6.01 (brd, J = 4.7 Hz, 1H), 3.98 (dd, J = 10.9, 6.6 Hz, 2H), 3.01 (s, 3H), 2.99 (d, J = 4.9 Hz, 3H), 2.60-2.41 (m, 2H), 2.22-2.09 (m, 1H), 1.06-0.83 (m, 3H), 0.57 (dd, J = 12.5, 6.9 Hz, 1H). | M |

TABLE 1-continued

Compounds and their general method(s) of synthesis

| No. | Structure | Observed LCMS m/z [M + H]⁺/¹H NMR | Method |
|---|---|---|---|
| 151 | 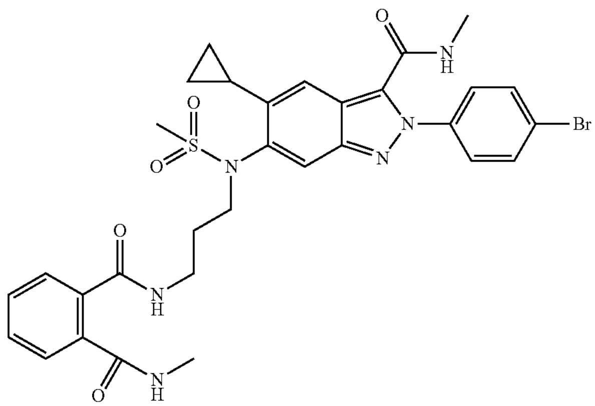 [SMILES: CNC(=O)c1ccccc1C(=O)NCCCN(c1cc2nn(-c3ccc(Br)cc3)c(C(=O)NC)c2cc1C1CC1)S(C)(=O)=O] | [M + H]+: 681.0/683.0/(400 MHz, CDCl₃) δ 7.76 (s, 1H), 7.69-7.61 (m, 2H), 7.59-7.50 (m, 2H), 7.50-7.39 (m, 4H), 7.35 (s, 1H), 6.96 (t, J = 6.0 Hz, 1H), 6.61 (brd, J = 4.4 Hz, 1H), 6.01 (brd, J = 4.9 Hz, 1H), 4.02-3.70 (m, 2H), 3.63-3.39 (m, 2H), 3.08 (s, 3H), 3.01 (d, J = 4.9 Hz, 3H), 2.92 (d, J = 4.9 Hz, 3H), 2.49-2.29 (m, 1H), 1.92-1.81 (m, 2H), 1.15-0.92 (m, 3H), 0.71-0.46 (m, 1H). | D |
| 152 | 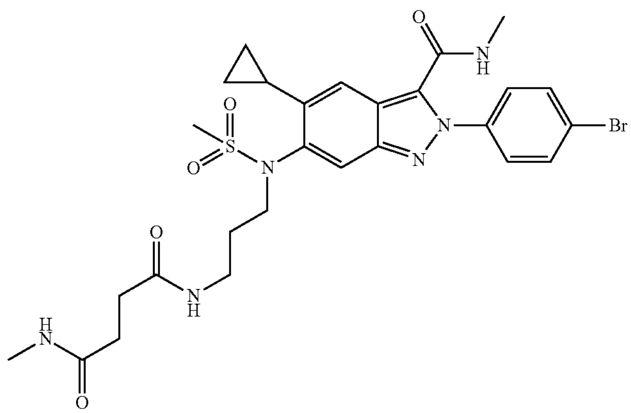 [SMILES: CNC(=O)CCC(=O)NCCCN(c1cc2nn(-c3ccc(Br)cc3)c(C(=O)NC)c2cc1C1CC1)S(C)(=O)=O] | [M + H]+: 633.0/635.0/(400 MHz, CDCl₃) δ 7.72 (s, 1H), 7.69-7.60 (m, 2H), 7.50-7.41 (m, 2H), 7.33 (s, 1H), 6.45 (t, J = 5.9 Hz, 1H), 6.20 (d, J = 4.8 Hz, 1H), 6.11 (d, J = 4.1 Hz, 1H), 3.76 (dd, J = 13.5, 6.9 Hz, 2H), 3.46-3.14 (m, 2H), 3.06 (s, 3H), 2.99 (d, J = 4.9 Hz, 3H), 2.74 (d, J = 4.8 Hz, 3H), 2.49-2.24 (m, 5H), 1.79-1.66 (m, 2H), 1.18-0.87 (m, 3H), 0.59 (td, J = 5.4, 2.1 Hz, 1H). | D |
| 153 | 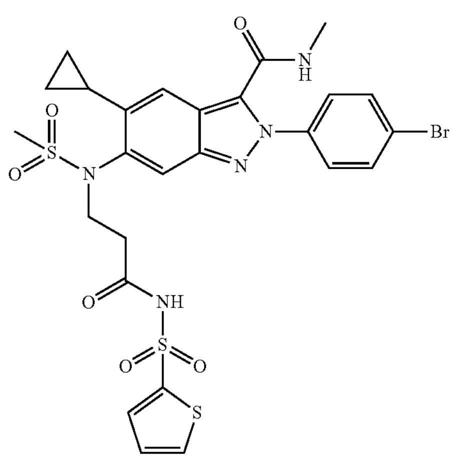 [SMILES: CNC(=O)c1c2cc(C3CC3)c(N(CCC(=O)NS(=O)(=O)c3cccs3)S(C)(=O)=O)cc2nn1-c1ccc(Br)cc1] | [M + H]+: 679.9/691.9/(400 MHz, CDCl₃) δ 7.82 (dd, J = 3.8, 1.3 Hz, 1H), 7.69-7.62 (m, 3H), 7.60 (s, 1H), 7.43 (d, J = 8.7 Hz, 2H), 7.27 (s, 1H), 7.08 (dd, J = 4.9, 3.9 Hz, 1H), 6.11 (brd, J = 4.6 Hz, 1H), 3.99 (t, J = 6.7 Hz, 2H), 3.05 (s, 3H), 2.98 (d, J = 4.9 Hz, 3H), 2.63-2.37 (m, 2H), 2.28-2.08 (m, 1H), 1.06-0.79 (m, 3H), 0.70-0.47 (m, 1H). | M |

TABLE 1-continued

Compounds and their general method(s) of synthesis

| No. | Structure | Observed LCMS m/z [M + H]+/1H NMR | Method |
|---|---|---|---|
| 154 | 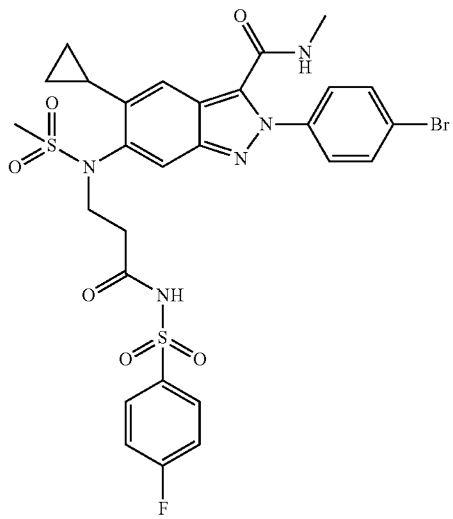 [SMILES: CNC(=O)c1c2cc(C3CC3)c(N(CCC(=O)NS(=O)(=O)c3ccc(F)cc3)S(C)(=O)=O)cc2nn1-c1ccc(Br)cc1] | [M + H]+: 692.0/694.0/(400 MHz, CDCl$_3$) δ 8.11-7.93 (m, 2H), 7.70-7.60 (m, 2H), 7.57 (s, 1H), 7.46-7.34 (m, 2H), 7.26 (s, 1H), 7.23-7.08 (m, 2H), 6.17 (d, J = 4.9 Hz, 1H), 4.09-3.77 (m, 2H), 3.03 (s, 3H), 2.97 (d, J = 4.9 Hz, 3H), 2.60-2.34 (m, 2H), 2.20-2.05 (m, 1H), 1.06-0.78 (m, 3H), 0.69-0.46 (m, 1H). | M |
| 155 | 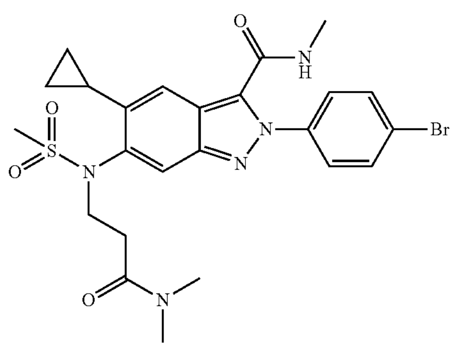 [SMILES: CNC(=O)c1c2cc(C3CC3)c(N(CCC(=O)N(C)C)S(C)(=O)=O)cc2nn1-c1ccc(Br)cc1] | [M + H]+: 561.9/563.9/(400 MHz, CDCl$_3$) δ 7.73 (s, 1H), 7.69-7.61 (m, 2H), 7.50-7.41 (m, 2H), 7.36 (s, 1H), 5.85 (brd, J = 4.6 Hz, 1H), 4.22-3.85 (m, 2H), 3.13 (s, 3H), 3.00 (d, J = 4.9 Hz, 3H), 2.91 (d, J = 3.7 Hz, 6H), 2.76-2.49 (m, 2H), 2.36 (tt, J = 8.4, 5.4 Hz, 1H), 1.17-0.86 (m, 3H), 0.70-0.53 (m, 1H). | M |
| 156 | 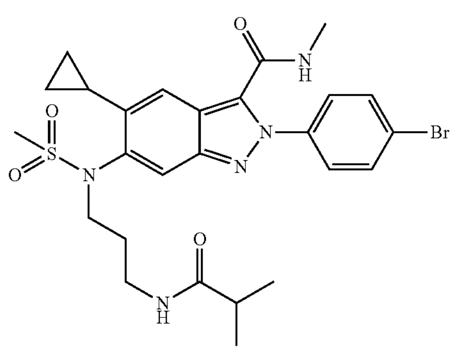 [SMILES: CNC(=O)c1c2cc(C3CC3)c(N(CCCNC(=O)C(C)C)S(C)(=O)=O)cc2nn1-c1ccc(Br)cc1] | [M + H]+: 590.0/592.0/(400 MHz, CDCl$_3$) δ 7.75 (s, 1H), 7.70-7.59 (m, 2H), 7.51-7.41 (m, 2H), 7.36 (s, 1H), 5.94 (t, J = 5.8 Hz, 1H), 5.85 (brd, J = 4.5 Hz, 1H), 3.88-3.67 (m, 2H), 3.50-3.30 (m, 2H), 3.06 (s, 3H), 3.00 (d, J = 4.9 Hz, 3H), 2.45-2.27 (m, 2H), 1.77 (p, J = 6.5 Hz, 2H), 1.15 (d, J = 6.9 Hz, 6H), 1.12-0.95 (m, 3H), 0.67-0.55 (m, 1H). | D |
| 157 | 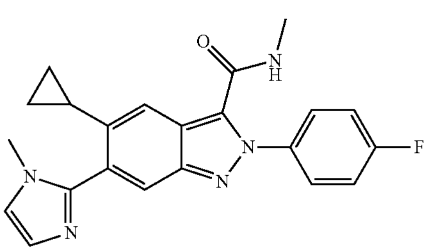 [SMILES: CNC(=O)c1c2cc(C3CC3)c(-c3nccn3C)cc2nn1-c1ccc(F)cc1] | [M + H]+: 390.2/(400 MHz, DMSO) δ 8.65 (q, J = 4.3 Hz, 1H), 7.70 (d, J = 0.5 Hz, 1H), 7.68-7.59 (m, 2H), 7.45-7.35 (m, 3H), 7.29 (d, J = 1.1 Hz, 1H), 7.02 (d, J = 1.2 Hz, 1H), 3.51 (s, 3H), 2.83 (d, J = 4.6 Hz, 3H), 1.82-1.71 (m, 1H), 0.82-0.73 (m, 2H), 0.73-0.65 (m, 2H). | K |

TABLE 1-continued

Compounds and their general method(s) of synthesis

| No. | Structure | Observed LCMS m/z [M + H]+/1H NMR | Method |
|---|---|---|---|
| 158 | 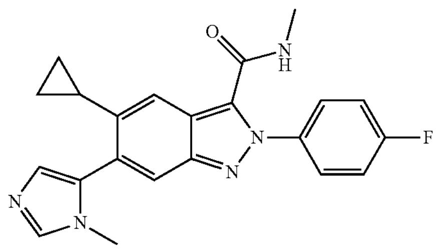 [SMILES: CNC(=O)c1c2cc(C3CC3)c(-c3cncn3C)cc2nn1-c1ccc(F)cc1] | [M + H]+: 390.2/(400 MHz, DMSO) δ 8.71-8.58 (m, 1H), 8.51 (s, 1H), 7.75 (s, 1H), 7.70-7.56 (m, 3H), 7.49-7.31 (m, 3H), 6.99 (s, 1H), 3.49 (s, 2H), 2.83 (d, J = 4.4 Hz, 3H), 1.70-1.59 (m, 1H), 0.93-0.81 (m, 2H), 0.81-0.71 (m, 2H). | K |
| 159 | 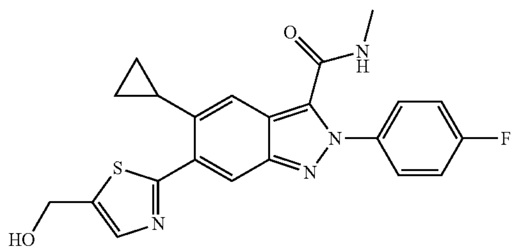 [SMILES: CNC(=O)c1c2cc(C3CC3)c(-c3ncc(CO)s3)cc2nn1-c1ccc(F)cc1] | [M + H]+: 423.2/(400 MHz, DMSO) δ 8.76-8.63 (m, 1H), 8.04 (s, 1H), 7.82 (s, 1H), 7.69-7.59 (m, 2H), 7.54 (s, 1H), 7.46-7.35 (m, 2H), 5.65 (br s, 1H), 4.77 (s, 2H), 2.84 (d, J = 4.5 Hz, 3H), 2.45-2.35 (m, 1H), 0.99-0.85 (m, 2H), 0.84-0.71 (m, 2H). | K |
| 160 | 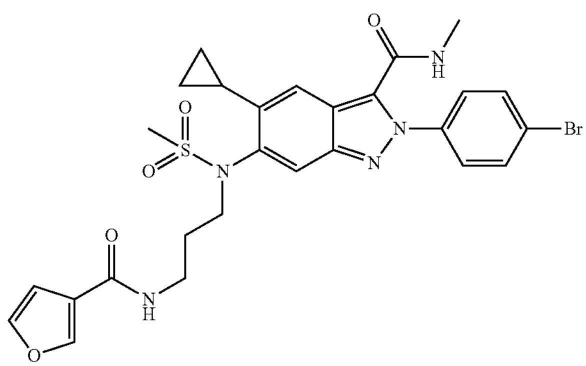 [SMILES: CNC(=O)c1c2cc(C3CC3)c(N(CCCNC(=O)c3ccoc3)S(C)(=O)=O)cc2nn1-c1ccc(Br)cc1] | [M + H]+: 613.9/615.9/(400 MHz, CDCl3) δ 7.95 (dd, J = 1.5, 0.9 Hz, 1H), 7.78 (s, 1H), 7.71-7.60 (m, 2H), 7.51-7.45 (m, 2H), 7.43 (t, J = 1.7 Hz, 1H), 7.37 (s, 1H), 6.66 (dd, J = 1.9, 0.9 Hz, 1H), 6.60 (t, J = 6.1 Hz, 1H), 5.79 (brd, J = 4.4 Hz, 1H), 4.02-3.73 (m, 2H), 3.73-3.47 (m, 2H), 3.07 (s, 3H), 3.01 (d, J = 4.9 Hz, 3H), 2.40 (tt, J = 8.4, 4.3 Hz, 1H), 1.83 (p, J = 6.5 Hz, 2H), 1.18-0.92 (m, 3H), 0.72-0.53 (m, 1H). | D |
| 161 | 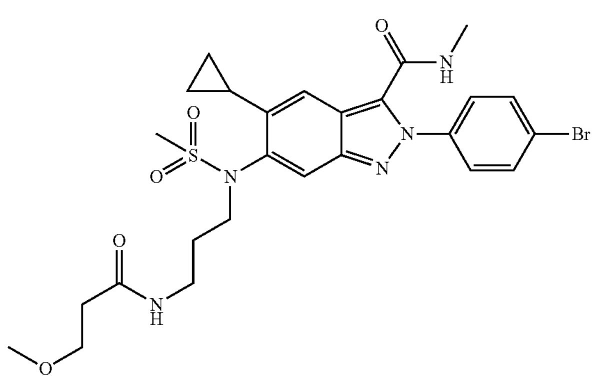 [SMILES: CNC(=O)c1c2cc(C3CC3)c(N(CCCNC(=O)CCOC)S(C)(=O)=O)cc2nn1-c1ccc(Br)cc1] | [M + H]+: 606.0/608.0/(400 MHz, CDCl3) δ 7.74 (s, 1H), 7.71-7.61 (m, 2H), 7.51-7.41 (m, 2H), 7.36 (s, 1H), 6.48 (t, J = 5.7 Hz, 1H), 5.82 (brd, J = 4.6 Hz, 1H), 3.91-3.67 (m, 2H), 3.62 (t, J = 5.8 Hz, 2H), 3.52-3.26 (m, 5H), 3.06 (s, 3H), 3.00 (d, J = 4.9 Hz, 3H), 2.51-2.31 (m, 3H), 1.79 (p, J = 7.4 Hz, 2H), 1.16-0.95 (m, 3H), 0.67-0.53 (m, 1H). | D |

TABLE 1-continued

Compounds and their general method(s) of synthesis

| No. | Structure | Observed LCMS m/z [M + H]+/$^1$H NMR | Method |
|---|---|---|---|
| 162 | 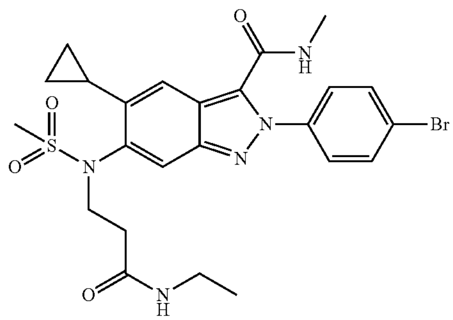 | [M + H]+: 561.9/563.9/(400 MHz, CDCl$_3$) δ 7.72 (s, 1H), 7.69-7.62 (m, 2H), 7.50-7.40 (m, 2H), 7.36 (s, 1H), 5.87 (brd, J = 4.6 Hz, 1H), 5.60 (t, J = 4.7 Hz, 1H), 4.26-3.84 (m, 2H), 3.34-3.16 (m, 2H), 3.11 (s, 3H), 3.00 (d, J = 4.9 Hz, 3H), 2.58-2.35 (m, 2H), 2.31 (tt, J = 8.5, 5.5 Hz, 1H), 1.15-0.87 (m, 6H), 0.73-0.46 (m, 1H). | M |
| 163 | 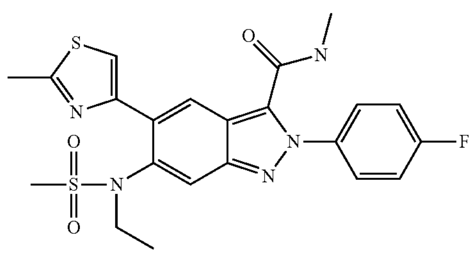 [SMILES: CCN(c1cc2nn(-c3ccc(F)cc3)c(C(=O)NC)c2cc1-c1csc(C)n1)S(C)(=O)=O] | [M + H]+: 488.0/(400 MHz, Acetone) δ 8.42 (s, 1H), 7.93 (d, J = 0.6 Hz, 1H), 7.92-7.87 (m, 1H), 7.85 (s, 1H), 7.80-7.74 (m, 2H), 7.41-7.33 (m, 2H), 3.85-3.54 (m, 2H), 3.11 (s, 3H), 3.01-2.96 (m, 3H), 2.78 (s, 3H), 1.12 (t, J = 7.2 Hz, 3H). | I |
| 164 | 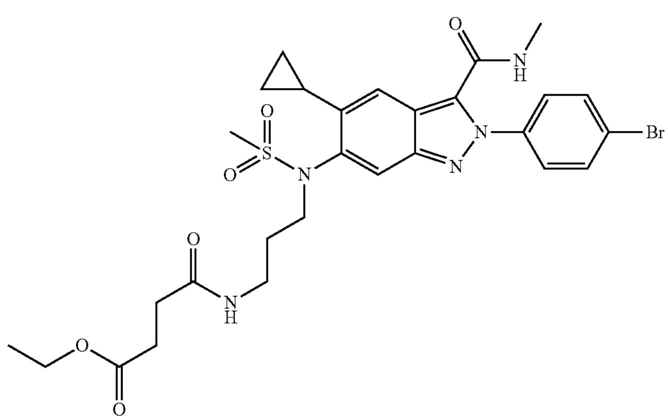 [SMILES: CCOC(=O)CCC(=O)NCCCN(c1cc2nn(-c3ccc(Br)cc3)c(C(=O)NC)c2cc1C1CC1)S(C)(=O)=O] | [M + H]+: 648.0/650.0/(400 MHz, CDCl$_3$) δ 7.75 (s, 1H), 7.70-7.62 (m, 2H), 7.50-7.42 (m, 2H), 7.36 (s, 1H), 6.07 (t, J = 6.0 Hz, 1H), 5.85 (brd, J = 4.8 Hz, 1H), 4.13 (q, J = 7.1 Hz, 2H), 3.93-3.66 (m, 2H), 3.58-3.22 (m, 2H), 3.07 (s, 3H), 3.00 (d, J = 4.9 Hz, 3H), 2.65 (dd, J = 9.9, 4.2 Hz, 2H), 2.45 (t, J = 6.8 Hz, 2H), 2.42-2.29 (m, 1H), 1.77 (p, J = 6.6 Hz, 2H), 1.25 (t, J = 7.1 Hz, 3H), 1.14-0.92 (m, 3H), 0.70-0.49 (m, 1H). | D |
| 165 | 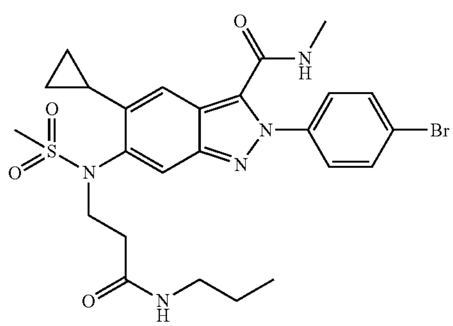 [SMILES: CCCNC(=O)CCN(c1cc2nn(-c3ccc(Br)cc3)c(C(=O)NC)c2cc1C1CC1)S(C)(=O)=O] | [M + H]+: 575.9/577.9/(400 MHz, CDCl$_3$) δ 7.73 (s, 1H), 7.70-7.59 (m, 2H), 7.49-7.40 (m, 2H), 7.36 (s, 1H), 5.82 (brd, J = 4.2 Hz, 1H), 5.61 (t, J = 5.2 Hz, 1H), 4.23-3.93 (m, 2H), 3.23-3.14 (m, 2H), 3.11 (s, 3H), 3.00 (d, J = 4.9 Hz, 3H), 2.61-2.37 (m, 2H), 2.37-2.20 (m, 1H), 1.49 (dq, J = 14.6, 7.4 Hz, 2H), 1.10-0.93 (m, 3H), 0.90 (t, J = 7.4 Hz, 3H), 0.69-0.54 (m, 1H). | M |

TABLE 1-continued

Compounds and their general method(s) of synthesis

| No. | Structure | Observed LCMS m/z [M + H]+/1H NMR | Method |
|---|---|---|---|
| 166 | 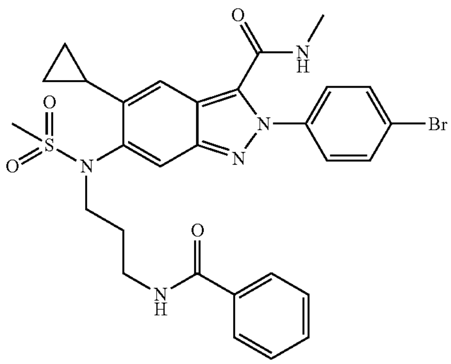 [SMILES: CNC(=O)c1c2cc(C3CC3)c(N(CCCNC(=O)c3ccccc3)S(C)(=O)=O)cc2nn1-c1ccc(Br)cc1] | [M + H]+: 623.9/625.9/(400 MHz, CDCl3) δ 7.85-7.76 (m, 3H), 7.71-7.61 (m, 2H), 7.54-7.41 (m, 5H), 7.37 (s, 1H), 6.85 (t, J = 6.2 Hz, 1H), 5.80 (brd, J = 4.4 Hz, 1H), 4.05-3.76 (m, 2H), 3.76-3.50 (m, 2H), 3.07 (s, 3H), 3.01 (d, J = 4.9 Hz, 3H), 2.51-2.30 (m, 1H), 1.88 (p, J = 6.3 Hz, 2H), 1.20-0.92 (m, 3H), 0.80-0.49 (m, 1H). | D |
| 167 | 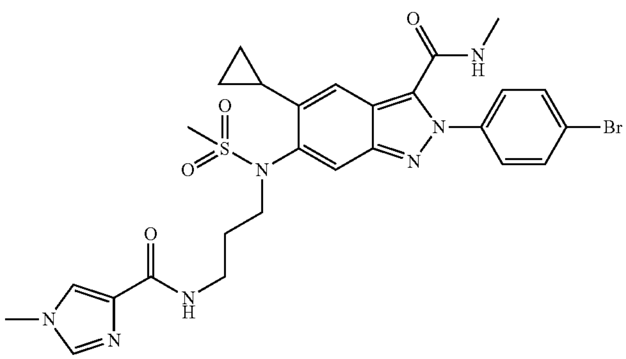 [SMILES: CNC(=O)c1c2cc(C3CC3)c(N(CCCNC(=O)c3cn(C)cn3)S(C)(=O)=O)cc2nn1-c1ccc(Br)cc1] | [M + H]+: 628.0/630.0/(400 MHz, CDCl3) δ 7.74 (s, 1H), 7.69-7.58 (m, 2H), 7.52-7.40 (m, 3H), 7.38-7.30 (m, 2H), 7.26 (m, 1H), 5.88 (brd, J = 4.8 Hz, 1H), 3.97-3.76 (m, 2H), 3.71 (s, 3H), 3.58-3.38 (m, 2H), 3.07 (s, 3H), 3.01 (d, J = 4.9 Hz, 3H), 2.52-2.29 (m, 1H), 1.96-1.84 (m, 2H), 1.16-0.84 (m, 3H), 0.68-0.55 (m, 1H). | D |
| 168 | 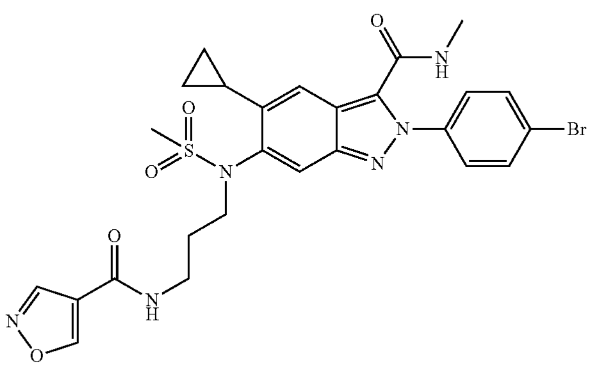 [SMILES: CNC(=O)c1c2cc(C3CC3)c(N(CCCNC(=O)c3cnoc3)S(C)(=O)=O)cc2nn1-c1ccc(Br)cc1] | [M + H]+: 614.9/616.9/(400 MHz, CDCl3) δ 8.90 (s, 1H), 8.59 (s, 1H), 7.79 (s, 1H), 7.71-7.59 (m, 2H), 7.50-7.42 (m, 2H), 7.38 (s, 1H), 6.92 (t, J = 6.3 Hz, 1H), 5.74 (brd, J = 5.0 Hz, 1H), 4.00-3.77 (m, 2H), 3.77-3.54 (m, 2H), 3.08 (s, 3H), 3.01 (d, J = 4.9 Hz, 3H), 2.47-2.25 (m, 1H), 1.89-1.74 (m, 2H), 1.20-0.90 (m, 3H), 0.76-0.50 (m, 1H). | D |
| 169 | 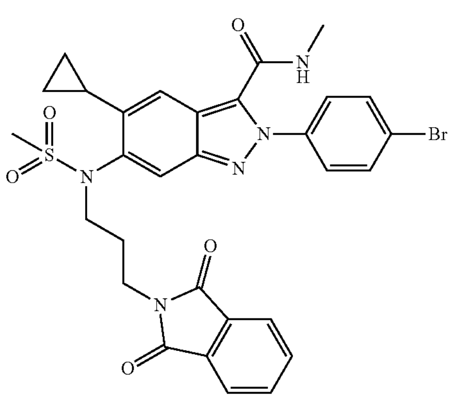 [SMILES: CNC(=O)c1c2cc(C3CC3)c(N(CCCN3C(=O)c4ccccc4C3=O)S(C)(=O)=O)cc2nn1-c1ccc(Br)cc1] | [M + H]+: 649.9/651.9/(400 MHz, CDCl3) δ 7.86 (dd, J = 5.6 and 2.7 Hz, 2H), 7.77 (s, 1H), 7.75 (dd, J = 5.4 and 3.1 Hz, 2H), 7.69 (d, J = 8.6 Hz, 2H), 7.50 (d, J = 8.6 Hz, 2H), 7.38 (s, 1H), 5.95-5.84 (brm, 1H), 3.91-3.83 (m, 2H), 3.82-3.75 (m, 2H), 3.13 (s, 3H), 3.04 (d, J = 4.9 Hz, 3H), 2.48-2.39 (m, 1H), 2.19-1.95 (m, 2H), 1.19-1.11 (m, 2H), 1.05-0.97 (m, 1H), 0.68-0.58 (m, 1H). | D |

TABLE 1-continued

Compounds and their general method(s) of synthesis

| No. | Structure | Observed LCMS m/z [M + H]+/1H NMR | Method |
|---|---|---|---|
| 170 | 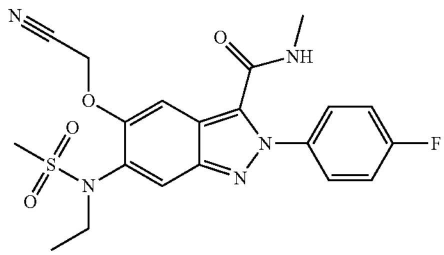 [SMILES: CCN(c1cc2nn(-c3ccc(F)cc3)c(C(=O)NC)c2cc1OCC#N)S(C)(=O)=O] | [M + H]+: 446.0/(400 MHz, Acetone) δ 7.82 (s, 1H), 7.78-7.70 (m, 2H), 7.67-7.58 (m, 1H), 7.56 (s, 1H), 7.41-7.32 (m, 2H), 5.34 (s, 2H), 3.84-3.71 (m, 2H), 3.09 (s, 3H), 2.96-2.91 (m, 3H), 1.18 (t, J = 7.2 Hz, 3H). | I |
| 171 | 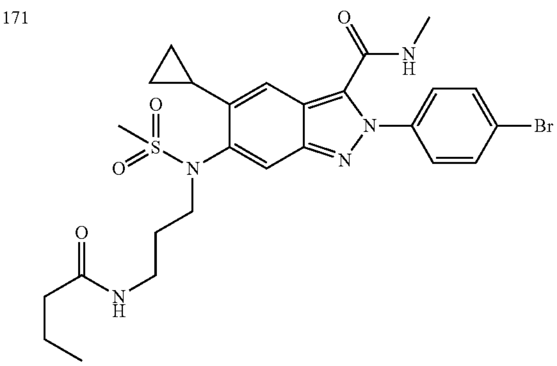 | [M + H]+: 589.9/591.9/(400 MHz, CDCl3) δ 7.75 (s, 1H), 7.71-7.55 (m, 2H), 7.50-7.40 (m, 2H), 7.37 (s, 1H), 5.89 (t, J = 6.0 Hz, 1H), 5.79 (brd, J = 4.9 Hz, 1H), 3.94-3.64 (m, 2H), 3.57-3.28 (m, 2H), 3.06 (s, 3H), 3.01 (d, J = 4.9 Hz, 3H), 2.47-2.29 (m, 1H), 2.21-2.08 (m, 2H), 1.85-1.71 (m, 2H), 1.71-1.62 (m, 2H), 1.16-0.97 (m, 3H), 0.95 (t, J = 7.4 Hz, 3H), 0.67-0.53 (m, 1H). | D |
| 172 | 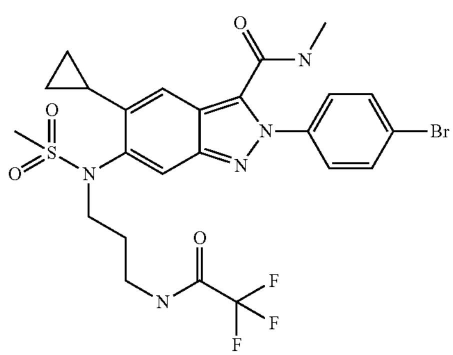 [SMILES: CNC(=O)c1c2cc(C3CC3)c(N(CCCNC(=O)C(F)(F)F)S(C)(=O)=O)cc2nn1-c1ccc(Br)cc1] | [M + H]+: 616.0/618.0/(400 MHz, CDCl3) δ 7.77 (s, 1H), 7.71-7.59 (m, 2H), 7.51-7.41 (m, 2H), 7.39 (s, 1H), 7.16 (t, J = 5.7 Hz, 1H), 5.77 (brd, J = 4.5 Hz, 1H), 3.95-3.71 (m, 2H), 3.62 (q, J = 6.3 Hz, 2H), 3.07 (s, 3H), 3.00 (d, J = 4.9 Hz, 3H), 2.44-2.25 (m, 1H), 1.89-1.78 (m, 2H), 1.17-0.96 (m, 3H), 0.71-0.54 (m, 1H). | D |
| 173 | 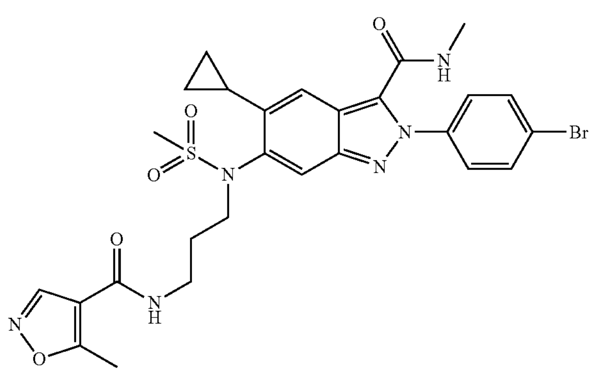 [SMILES: CNC(=O)c1c2cc(C3CC3)c(N(CCCNC(=O)c3cnoc3C)S(C)(=O)=O)cc2nn1-c1ccc(Br)cc1] | [M + H]+: 628.9/630.9/(400 MHz, CDCl3) δ 8.40 (d, J = 0.5 Hz, 1H), 7.78 (s, 1H), 7.72-7.60 (m, 2H), 7.51-7.41 (m, 2H), 7.37 (s, 1H), 6.71 (t, J = 6.2 Hz, 1H), 5.81 (brd, J = 4.7 Hz, 1H), 4.02-3.75 (m, 2H), 3.75-3.54 (m, 2H), 3.07 (s, 3H), 3.00 (d, J = 4.9 Hz, 3H), 2.72 (d, J = 0.5 Hz, 3H), 2.43-2.27 (m, 1H), 1.95-1.70 (m, 2H), 1.22-0.90 (m, 3H), 0.75-0.49 (m, 1H). | D |

TABLE 1-continued

Compounds and their general method(s) of synthesis

| No. | Structure | Observed LCMS m/z [M + H]+/1H NMR | Method |
|---|---|---|---|
| 174 | 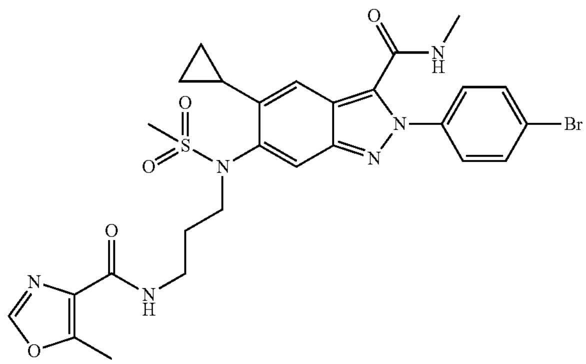 [SMILES: CNC(=O)c1c2cc(C3CC3)c(N(CCCNC(=O)c3ncoc3C)S(C)(=O)=O)cc2nn1-c1ccc(Br)cc1] | [M + H]+: 629.9/631.9/(400 MHz, CDCl$_3$) δ 7.75 (s, 1H), 7.69-7.61 (m, 3H), 7.51-7.42 (m, 2H), 7.36 (s, 1H), 7.21 (t, J = 6.3 Hz, 1H), 5.81 (brd, J = 4.6 Hz, 1H), 3.99-3.69 (m, 2H), 3.64-3.43 (m, 2H), 3.07 (s, 3H), 3.01 (d, J = 4.9 Hz, 3H), 2.64 (s, 3H), 2.46-2.32 (m, 1H), 1.96-1.76 (m, 2H), 1.18-0.89 (m, 3H), 0.73-0.54 (m, 1H). | D |
| 175 | 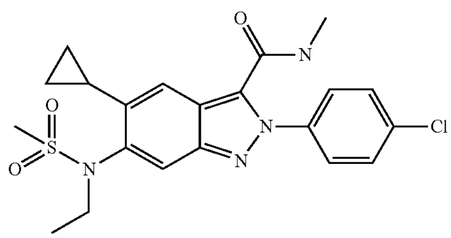 [SMILES: CCN(c1cc2nn(-c3ccc(Cl)cc3)c(C(=O)NC)c2cc1C1CC1)S(C)(=O)=O] | [M + H]+: 447.1/(400 MHz, CD$_3$CN) δ 7.82 (d, J = 0.5 Hz, 1H), 7.69-7.49 (m, 4H), 7.41 (s, 1H), 7.02 (brs, 1H), 3.81 (q, J = 7.2 Hz, 2H), 3.12 (s, 3H), 2.93 (d, J = 4.8 Hz, 3H), 2.49-2.32 (m, 1H), 1.21 (t, J = 7.2 Hz, 3H), 1.13-0.94 (m, 3H), 0.77-0.54 (m, 1H). | C |
| 176 | 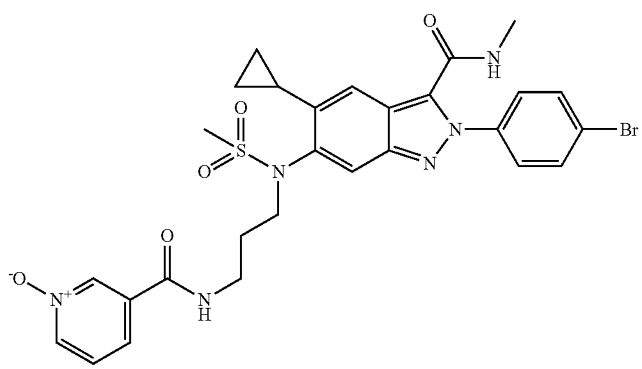 | [M + H]+: 641.05/643.03/(400 MHz, CDCl$_3$) δ 8.44 (s, 1H), 8.29 (d, J = 6.2 Hz, 1H), 7.86 (s, 1H), 7.78-7.64 (m, 3H), 7.52 (d, J = 8.7 Hz, 2H), 7.46-7.34 (m, 2H), 6.98 (br s, 1H), 6.30 (s, 1H), 4.02-3.81 (m, 2H), 3.83-3.59 (m, 2H), 3.12 (s, 3H), 3.06 (d, J = 4.9 Hz, 3H), 2.47-2.26 (m, 1H), 2.04-1.82 (m, 2H), 1.24-0.97 (m, 3H), 0.80-0.61 (m, 1H). | D |
| 177 | 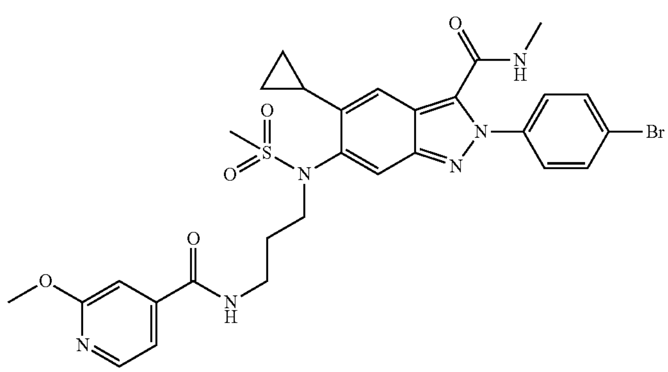 [SMILES: CNC(=O)c1c2cc(C3CC3)c(N(CCCNC(=O)c3ccnc(OC)c3)S(C)(=O)=O)cc2nn1-c1ccc(Br)cc1] | [M + H]+: 654.94/656.94/(400 MHz, CDCl$_3$) δ 8.31 (d, J = 5.3 Hz, 1H), 7.84 (s, 1H), 7.76-7.67 (m, 2H), 7.52 (d, J = 8.8 Hz, 2H), 7.43 (s, 1H), 7.26 (dd, J = 5.3, 1.5 Hz, 1H), 7.16 (s, 1H), 7.02 (br t, J = 5.4 Hz, 1H), 5.79 (br d, J = 5.5 Hz, 1H), 4.02 (s, 3H), 3.98-3.83 (m, 2H), 3.80-3.67 (m, 2H), 3.12 (s, 3H), 3.05 (d, J = 4.9 Hz, 3H), 2.53-2.33 (m, 1H), 2.01-1.82 (m, 2H), 1.24-1.02 (m, 3H), 0.77-0.60 (m, 1H). | D |

TABLE 1-continued

Compounds and their general method(s) of synthesis

| No. | Structure | Observed LCMS m/z [M + H]+/1H NMR | Method |
|---|---|---|---|
| 178 | 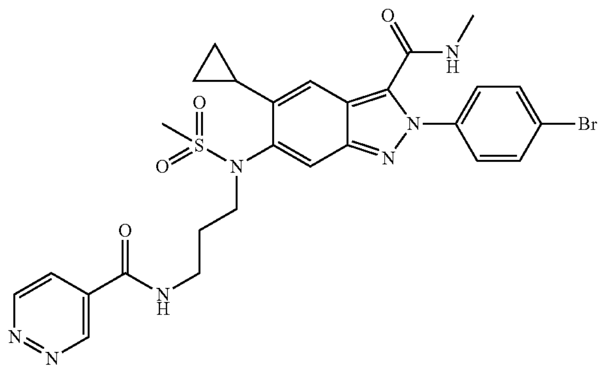 [SMILES: CNC(=O)c1c2cc(C3CC3)c(N(CCCNC(=O)c3ccnnc3)S(C)(=O)=O)cc2nn1-c1ccc(Br)cc1] | [M + H]+: 625.98/627.98/(400 MHz, CDCl₃) δ 9.54 (dd, J = 2.2, 1.2 Hz, 1H), 9.42 (dd, J = 5.3, 1.2 Hz, 1H), 7.89 (dd, J = 5.3, 2.4 Hz, 1H), 7.85 (s, 1H), 7.72 (d, J = 8.8 Hz, 2H), 7.53 (d, J = 8.8 Hz, 2H), 7.44 (s, 1H), 5.90 (br s, 2H), 4.06-3.90 (m, 2H), 3.83 (dt, J = 11.8, 6.0 Hz, 2H), 3.13 (s, 3H), 3.06 (d, J = 4.9 Hz, 3H), 2.49-2.31 (m, 1H), 2.01-1.85 (m, 2H), 1.24-1.01 (m, 3H), 0.80-0.60 (m, 1H). | D |
| 179 | 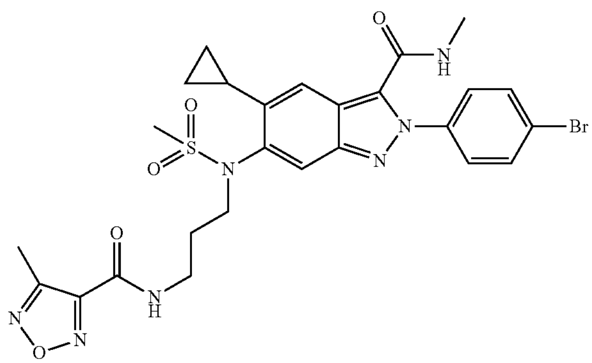 [SMILES: CNC(=O)c1c2cc(C3CC3)c(N(CCCNC(=O)c3nonc3C)S(C)(=O)=O)cc2nn1-c1ccc(Br)cc1] | [M + H]+: 629.9/631.9/(400 MHz, CDCl₃) δ 7.77 (s, 1H), 7.71-7.62 (m, 2H), 7.51-7.42 (m, 2H), 7.38 (s, 1H), 7.28-7.26 (m, 1H), 5.78 (brd, J = 4.5 Hz, 1 3.96-3.74 (m, 2H), 3.70-3.52 (m, 2H), 3.07 (s, 3H), 3.01 (d, J = 4.9 Hz, 3H), 2.60 (s, 3H), 2.47-2.30 (m, 1H), 1.97-1.80 (m, 2H), 1.17-0.89 (m, 3H), 0.74-0.49 (m, 1H). | D |
| 180 | 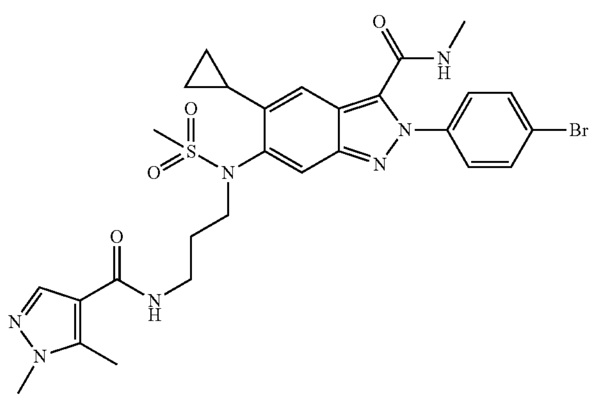 [SMILES: CNC(=O)c1c2cc(C3CC3)c(N(CCCNC(=O)c3cnn(C)c3C)S(C)(=O)=O)cc2nn1-c1ccc(Br)cc1] | [M + H]+: 641.9/643.9/(400 MHz, CDCl₃) δ 7.77 (s, 1H), 7.70-7.62 (m, 2H), 7.59 (s, 1H), 7.51-7.41 (m, 2H), 7.36 (s, 1H), 6.34 (t, J = 6.1 Hz, 1H), 5.84 (brd, J = 4.6 Hz, 1H), 3.98-3.80 (m, 2H), 3.79 (s, 3H), 3.69-3.36 (m, 2H), 3.07 (s, 3H), 3.01 (d, J = 4.9 Hz, 3H), 2.55 (s, 3H), 2.40 (tt, J = 8.3, 5.5 Hz, 1H), 1.92-1.75 (m, 2H), 1.18-0.95 (m, 3H), 0.71-0.46 (m, 1H). | D |
| 181 | 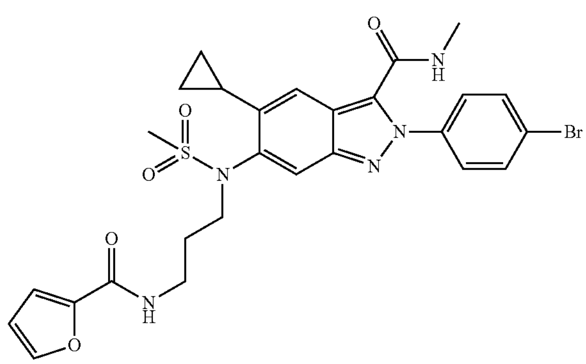 [SMILES: CNC(=O)c1c2cc(C3CC3)c(N(CCCNC(=O)c3ccco3)S(C)(=O)=O)cc2nn1-c1ccc(Br)cc1] | [M + H]+: 613.9/615.9/(400 MHz, CDCl₃) δ 7.76 (s, 1H), 7.71-7.59 (m, 2H), 7.50-7.41 (m, 3H), 7.36 (s, 1H), 7.08 (dd, J = 3.5, 0.8 Hz, 1H), 6.77 (t, J = 6.2 Hz, 1H), 6.49 (dd, J = 3.5, 1.8 Hz, 1H), 5.84 (brd, J = 4.7 Hz, 1H), 3.99-3.70 (m, 2H), 3.70-3.46 (m, 2H), 3.07 (s, 3H), 3.00 (d, J = 4.9 Hz, 3H), 2.49-2.30 (m, 1H), 1.88 (p, J = 6.8 Hz, 2H), 1.15-0.93 (m, 3H), 0.69-0.49 (m, 1H). | D |

TABLE 1-continued

Compounds and their general method(s) of synthesis

| No. | Structure | Observed LCMS m/z [M + H]+/¹H NMR | Method |
|---|---|---|---|
| 182 | AND Enantiomer | [M + H]+: 645.0/647.0/(400 MHz, CDCl₃) δ 7.77 (2 x s, 1H), 7.70-7.60 (m, 2H), 7.51-7.41 (m, 2H), 7.36 (2 x s, 1H), 6.36 (brd, J = 4.8 Hz, 0.5H), 6.20 (t, J = 6.1 Hz, 0.5H), 6.10 (t, J = 6.1 Hz, 0.5H), 6.04 (brd, J = 4.9 Hz, 0.5H), 3.90-3.69 (m, 2H), 3.68-3.25 (m, 4H), 3.06 (s, 3H), 3.04-2.92 (m, 4H), 2.83 (2 x s, 3H), 2.53 (d, J = 8.9 Hz, 1H), 2.42-2.25 (m, 2H), 1.83-1.77 (m, 2H), 1.15-0.93 (m, 3H), 0.72-0.52 (m, 1H). | D |
| 183 | 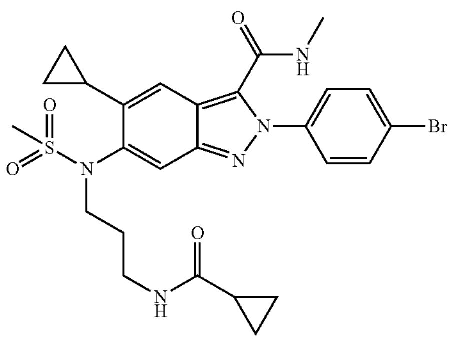 [SMILES: CNC(=O)c1c2cc(C3CC3)c(N(CCCNC(=O)C3CC3)S(C)(=O)=O)cc2nn1-c1ccc(Br)cc1] | [M + H]+: 587.9/589.9/(400 MHz, CDCl₃) δ 7.79 (s, 1H), 7.71 (d, J = 8.7 Hz, 2H), 7.51 (d, J = 8.7 Hz, 2H), 7.41 (s, 1H), 6.11 (brt, J = 5.9 Hz, 1H), 5.91-5.83 (brm, 1H), 3.97-3.76 (m, 2H), 3.58-3.35 (m, 2H), 3.11 (s, 3H), 3.05 (d, J = 4.8 Hz, 3H), 2.49-2.38 (m, 1H), 1.89-1.75 (m, 2H), 1.44-1.33 (m, 1H), 1.20-1.02 (m, 3H), 1.02-0.95 (m, 2H), 0.82-0.73 (m, 2H), 0.70-0.60 (m, 1H). | D |
| 184 | 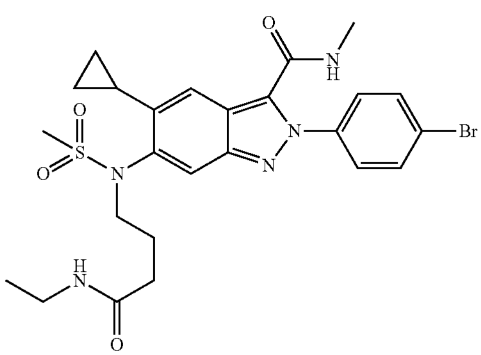 [SMILES: CCNC(=O)CCCN(c1cc2nn(-c3ccc(Br)cc3)c(C(=O)NC)c2cc1C1CC1)S(C)(=O)=O] | [M + H]+: 575.9/577.9/(400 MHz, CDCl₃) δ 7.73 (s, 1H), 7.69-7.64 (m, 2H), 7.50-7.44 (m, 2H), 7.35 (s, 1H), 5.98-5.86 (m, 1H), 5.70-5.58 (m, 1H), 3.78 (t, J = 7.0 Hz, 2H), 3.27 (qd, J = 7.3, 5.7 Hz, 2H), 3.06 (s, 3H), 3.00 (d, J = 4.9 Hz, 3H), 2.44-2.35 (m, 1H), 2.35-2.20 (m, 2H), 1.97-1.86 (m, 2H), 1.12 (t, J = 7.3 Hz, 3H), 1.10-1.05 (m, 2H), 0.93-0.81 (m, 1H), 0.65-0.58 (m, 1H). | M |
| 185 | 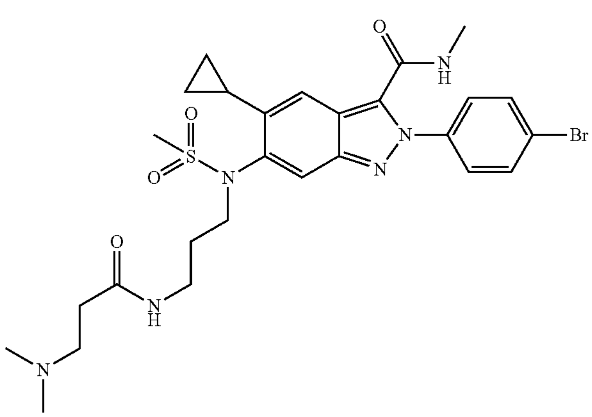 [SMILES: CNC(=O)c1c2cc(C3CC3)c(N(CCCNC(=O)CCN(C)C)S(C)(=O)=O)cc2nn1-c1ccc(Br)cc1] | [M + H]+: 619.1/621.1/(400 MHz, CDCl₃) δ 8.43 (t, J = 5.5 Hz, 1H), 7.73 (s, 1H), 7.69-7.59 (m, 2H), 7.50-7.40 (m, 2H), 7.36 (s, 1H), 5.87 (brd, J = 4.7 Hz, 1H), 3.77 (dd, J = 10.9, 4.7 Hz, 2H), 3.41-3.16 (m, 2H), 3.05 (s, 3H), 3.00 (d, J = 4.9 Hz, 3H), 2.56-2.45 (m, 2H), 2.40 (tt, J = 8.4, 5.5 Hz, 1H), 2.32 (t, J = 6.1 Hz, 2H), 2.23 (s, 6H), 1.87-1.68 (m, 2H), 1.15-0.91 (m, 3H), 0.68-0.46 (m, 1H). | D |

TABLE 1-continued

Compounds and their general method(s) of synthesis

| No. | Structure | Observed LCMS m/z [M + H]+/1H NMR | Method |
|---|---|---|---|
| 186 | 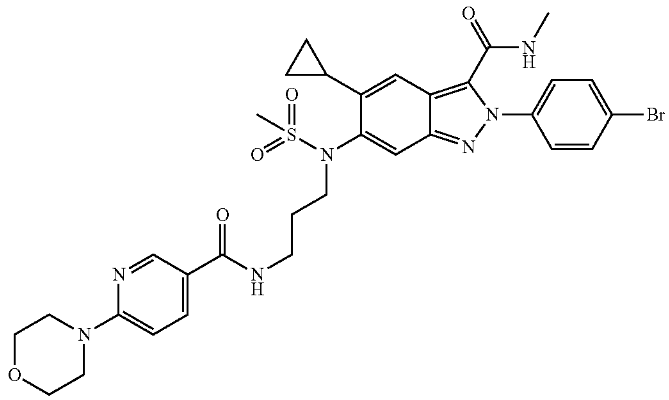 [SMILES: CNC(=O)c1c2cc(C3CC3)c(N(CCCNC(=O)c3ccc(N4CCOCC4)nc3)S(C)(=O)=O)cc2nn1-c1ccc(Br)cc1] | [M + H]+: 710.07/712.07/(400 MHz, CDCl₃) δ 8.66 (d, J = 2.1 Hz, 1H), 7.98 (dd, J = 9.0, 2.5 Hz, 1H), 7.83 (s, 1H), 7.71 (d, J = 8.8 Hz, 2H), 7.52 (d, J = 8.8 Hz, 2H), 7.42 (s, 1H), 6.75 (br t, J = 6.5 Hz, 1H), 6.66 (d, J = 8.8 Hz, 1H), 5.82 (br d, J = 5.1 Hz, 1H), 4.09-3.81 (m, 6H), 3.80-3.58 (m, 6H), 3.11 (s, 3H), 3.05 (d, J = 4.9 Hz, 3H), 2.55-2.36 (m, 1H), 1.99-1.82 (m, 2H), 1.21-0.98 (m, 3H), 0.74-0.60 (m, 1H). | D |
| 187 | 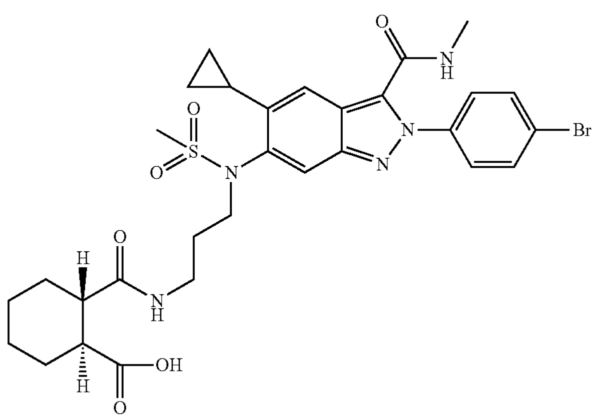 [SMILES: CNC(=O)c1c2cc(C3CC3)c(N(CCCNC(=O)[C@H]3CCCC[C@@H]3C(=O)O)S(C)(=O)=O)cc2nn1-c1ccc(Br)cc1] | [M + H]+: 674.0/676.0/(400 MHz, CDCl₃) δ 7.91 (s, 0.5H), 7.74 (s, 0.5H), 7.69 (dd, J = 8.7, 1.5 Hz, 2H), 7.48 (d, J = 8.6 Hz, 2H), 7.35 (d, J = 10.4 Hz, 1H), 6.23-6.08 (m, 1.5H), 6.06-5.95 (m, 0.5H), 3.95-3.51 (m, 3H), 3.13 (s, 1H), 3.07 (s, 2H), 3.03 (d, J = 4.9 Hz, 3H), 2.77-2.58 (m, 1H), 2.52-2.25 (m, 3H), 2.18-2.06 (m, 1H), 1.95-1.20 (m, 9H), 1.17-0.93 (m, 3H), 0.67-0.46 (m, 1H). | D |
| 188 | 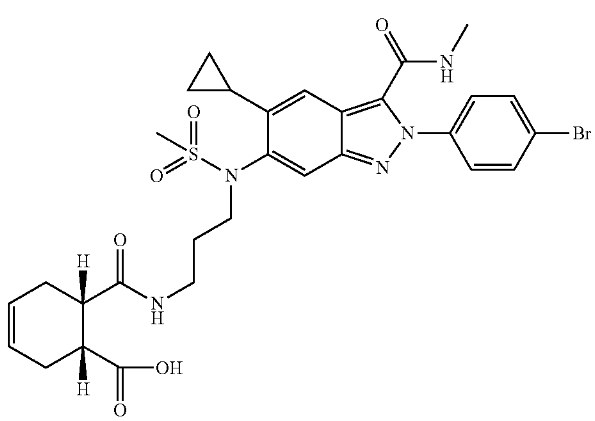 [SMILES: CNC(=O)c1c2cc(C3CC3)c(N(CCCNC(=O)[C@H]3CC=CC[C@H]3C(=O)O)S(C)(=O)=O)cc2nn1-c1ccc(Br)cc1] | [M + H]+: 672.0/674.0/(400 MHz, CDCl₃) δ 7.82 (s, 1H), 7.71 (d, J = 8.4 Hz, 2H), 7.51 (dd, J = 8.7, 3.2 Hz, 2H), 7.40 (s, 1H), 6.73-6.51 (m, 1H), 6.10-5.95 (m, 1H), 5.87-5.65 (m, 2H), 3.96-3.69 (m, 2H), 3.64-3.41 (m, 2H), 3.11 (d, J = 1.7 Hz, 3H), 3.04 (d, J = 4.8 Hz, 3H), 2.99-2.86 (m, 1H), 2.73-2.58 (m, 1H), 2.55-2.24 (m, 4H), 1.92-1.75 (m, 3H), 1.21-0.99 (m, 3H), 0.76-0.55 (m, 1H). | D |

TABLE 1-continued

Compounds and their general method(s) of synthesis

| No. | Structure | Observed LCMS m/z [M + H]+/1H NMR | Method |
|---|---|---|---|
| 189 | 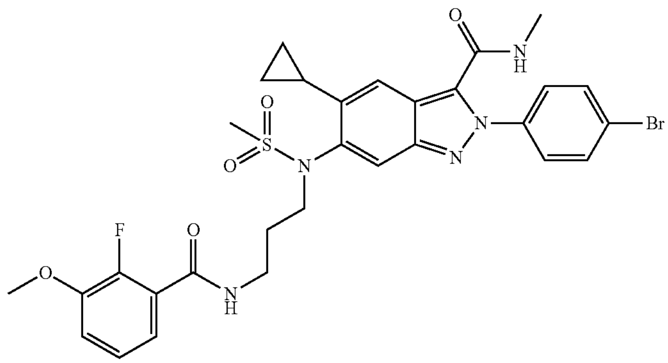 [SMILES: CNC(=O)c1c2cc(C3CC3)c(N(CCCNC(=O)c3cccc(OC)c3F)S(C)(=O)=O)cc2nn1-c1ccc(Br)cc1] | [M + H]+: 671.99/673.99/(400 MHz, CDCl$_3$) δ 7.76 (s, 1H), 7.66 (d, J = 8.7 Hz, 2H), 7.58-7.49 (m, 1H), 7.47 (d, J = 8.7 Hz, 2H), 7.36 (s, 1H), 7.20-7.03 (m, 2H), 7.02-6.91 (m, 1H), 5.88 (brd, J = 4.8 Hz, 1H), 3.97-3.77 (m, 5H), 3.65-3.46 (m, 2H), 3.07 (s, 3H), 3.01 (d, J = 4.9 Hz, 3H), 2.48-2.32 (m, 1H), 1.91 (p, J = 6.7 Hz, 2H), 1.13-1.05 (m, 2H), 1.04-0.96 (m, 1H), 0.69-0.50 (m, 1H). | D |
| 190 | 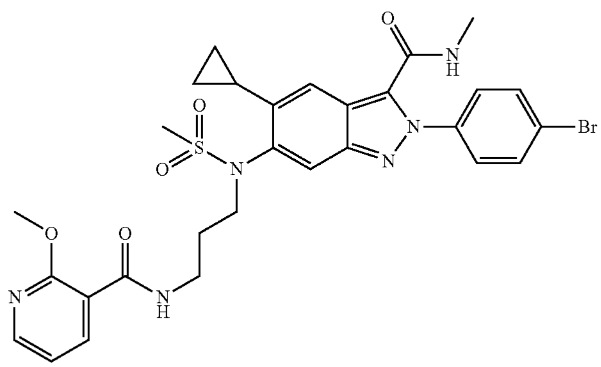 [SMILES: CNC(=O)c1c2cc(C3CC3)c(N(CCCNC(=O)c3cccnc3OC)S(C)(=O)=O)cc2nn1-c1ccc(Br)cc1] | [M + H]+: 654.99/656.99/(400 MHz, CDCl$_3$) δ 8.52 (dd, J = 7.5, 2.0 Hz, 1H), 8.36-8.24 (m, 2H), 7.82 (s, 1H), 7.71 (d, J = 8.8 Hz, 2H), 7.51 (d, J = 8.8 Hz, 2H), 7.41 (s, 1H), 7.08 (dd, J = 7.5, 4.9 Hz, 1H), 5.89 (br d, J = 5.0 Hz, 1H), 4.15 (s, 3H), 4.03-3.83 (m, 2H), 3.72-3.50 (m, 2H), 3.12 (s, 3H), 3.05 (d, J = 4.9 Hz, 3H), 2.57-2.41 (m, 1H), 1.95 (p, J = 6.5 Hz, 2H), 1.19-1.10 (m, 2H), 1.10-1.00 (m, 1H), 0.73-0.59 (m, 1H). | D |
| 191 | 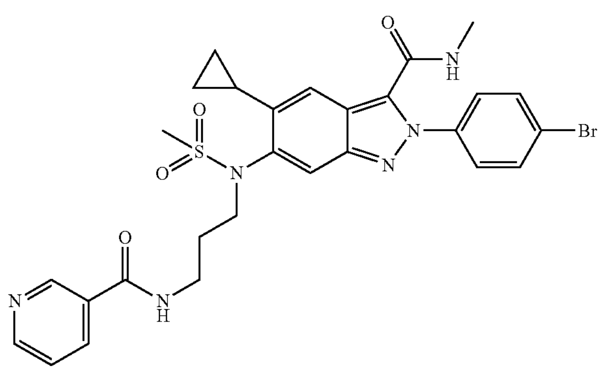 [SMILES: CNC(=O)c1c2cc(C3CC3)c(N(CCCNC(=O)c3cccnc3)S(C)(=O)=O)cc2nn1-c1ccc(Br)cc1] | [M + H]+: 625.06/627.05/(400 MHz, CDCl$_3$) δ 8.95 (d, J = 1.7 Hz, 1H), 8.76 (dd, J = 4.8, 1.6 Hz, 1H), 8.26-8.12 (m, 1H), 7.85 (s, 1H), 7.71 (d, J = 8.8 Hz, 2H), 7.52 (d, J = 8.8 Hz, 2H), 7.48-7.38 (m, 2H), 6.95 (br t, J = 5.8 Hz, 1H), 6.06 (br d, J = 4.4 Hz, 1H), 4.01-3.85 (m, 2H), 3.86-3.64 (m, 2H), 3.12 (s, 3H), 3.06 (d, J = 4.9 Hz, 3H), 2.54-2.30 (m, 1H), 2.01-1.86 (m, 2H), 1.22-1.00 (m, 3H), 0.67 (dd, J = 9.7, 4.1 Hz, 1H). | D |
| 192 | 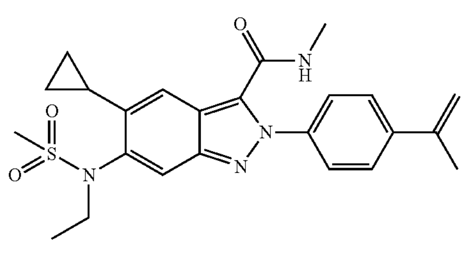 [SMILES: C=C(C)c1ccc(-n2nc3cc(N(CC)S(C)(=O)=O)c(C4CC4)cc3c2C(=O)NC)cc1] | [M + H]+: 453.2/(400 MHz, CD$_3$CN) δ 7.82 (d, J = 2.8 Hz, 1H), 7.75-7.45 (m, 4H), 7.41 (s, 1H), 7.01 (brs, 1H), 5.55 (d, J = 0.7 Hz, 1H), 5.30-5.16 (m, 1H), 3.92-3.65 (m, 2H), 3.12 (s, 3H), 3.03-2.81 (m, 3H), 2.49-2.33 (m, 3H), 2.31-2.19 (m, 3H), 1.28-1.13 (m, 3H), 1.13-0.94 (m, 3H), 0.73-0.54 (m, 1H). | C |

TABLE 1-continued

Compounds and their general method(s) of synthesis

| No. | Structure | Observed LCMS m/z [M + H]+/1H NMR | Method |
|---|---|---|---|
| 193 | 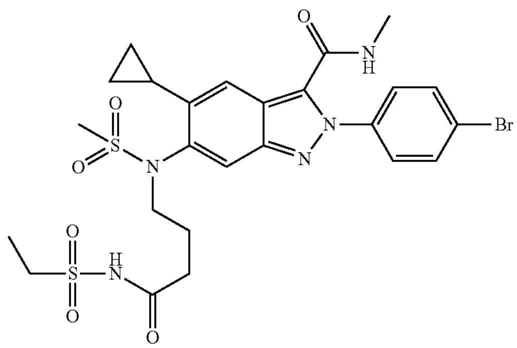 [SMILES: CCS(=O)(=O)NC(=O)CCCN(c1cc2nn(-c3ccc(Br)cc3)c(C(=O)NC)c2cc1C1CC1)S(C)(=O)=O] | [M + H]+: 640.0/642.0/(400 MHz, CDCl₃) δ 7.74 (s, 1H), 7.69-7.63 (m, 2H), 7.49-7.43 (m, 2H), 7.33 (s, 1H), 6.13-6.04 (m, 1H), 3.80 (t, J = 6.5 Hz, 2H), 3.40 (q, J = 7.4 Hz, 2H), 3.05 (s, 3H), 2.99 (d, J = 4.9 Hz, 3H), 2.57-2.40 (m, 2H), 2.37-2.45 (m, 1H), 1.95-1.85 (m, 2H), 1.35 (t, J = 7.4 Hz, 3H), 1.11-1.04 (m, 2H), 1.04-0.98 (m, 1H), 0.65-0.58 (m, 1H). | M |
| 194 | 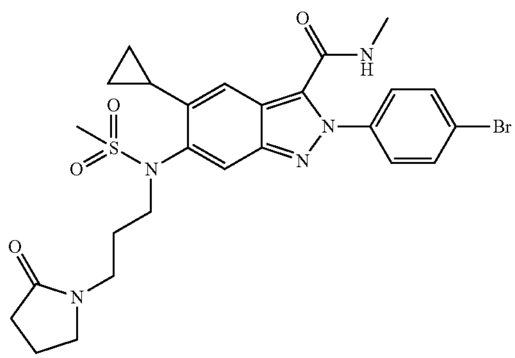 [SMILES: CNC(=O)c1c2cc(C3CC3)c(N(CCCN3CCCC3=O)S(C)(=O)=O)cc2nn1-c1ccc(Br)cc1] | [M + H]+: 587.9/589.9/(400 MHz, CDCl₃) δ 7.75 (s, 1H), 7.71-7.59 (m, 2H), 7.52-7.42 (m, 2H), 7.36 (s, 1H), 5.84 (brd, J = 4.7 Hz, 1H), 3.73 (t, J = 7.8 Hz, 2H), 3.43-3.17 (m, 4H), 3.06 (s, 3H), 3.00 (d, J = 4.9 Hz, 3H), 2.45-2.26 (m, 3H), 2.08-1.95 (m, 2H), 1.95-1.75 (m, 2H), 1.16-0.91 (m, 3H), 0.70-0.49 (m, 1H). | C |
| 195 | AND Enantiomer | [M + H]+: 532.0/534.0/(400 MHz, CDCl₃) δ 7.77 (s, 0.5H), 7.72 (s, 0.5H), 7.67 (d, J = 8.7 Hz, 2H), 7.51-7.42 (m, 2H), 7.35 (s, 0.5H), 7.33 (s, 0.5H), 6.10 (brd, J = 4.9 Hz, 0.5H), 5.91 (brd, J = 6.6 Hz, 0.5H), 4.85-4.70 (m, 1H), 3.54-3.41 (m, 1H), 3.30-2.93 (m, 9H), 2.32-2.25 (m, 2H), 1.91-1.83 (m, 1H), 1.21-0.93 (m, 3H), 0.76-0.57 (m, 1H). | C |
| 196 | 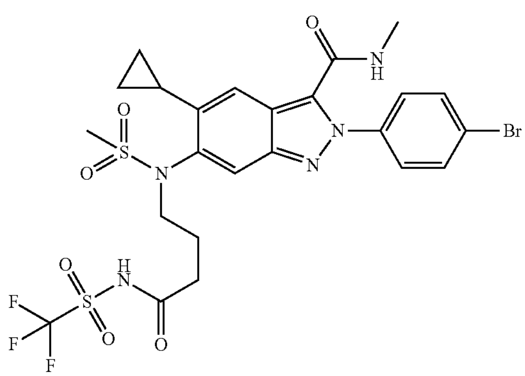 [SMILES: CNC(=O)c1c2cc(C3CC3)c(N(CCCC(=O)NS(=O)(=O)C(F)(F)F)S(C)(=O)=O)cc2nn1-c1ccc(Br)cc1] | [M + H]+: 679.9/681.9/(400 MHz, MeOD) δ 7.83 (d, J = 0.5 Hz, 1H), 7.74-7.69 (m, 2H), 7.56-7.50 (m, 2H), 7.36 (s, 1H), 3.79 (t, J = 7.7 Hz, 2H), 3.19-3.09 (s, 3H), 2.94 (s, 3H), 2.44-2.35 (m, 1H), 2.34-2.23 (m, 2H), 1.95-1.79 (m, 2H), 1.16-0.94 (m, 2H), 0.94-0.84 (m, 1H), 0.72-0.62 (m, 1H). | M |

TABLE 1-continued

Compounds and their general method(s) of synthesis

| No. | Structure | Observed LCMS m/z [M + H]+/1H NMR | Method |
|---|---|---|---|
| 197 | 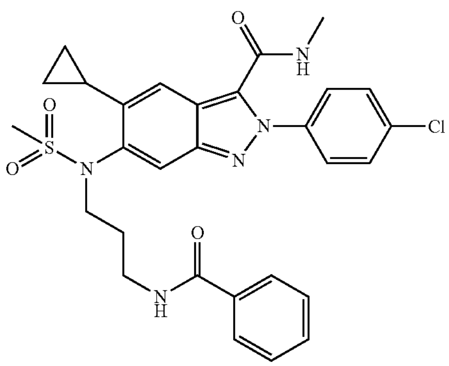 [SMILES: CNC(=O)c1c2cc(C3CC3)c(N(CCCNC(=O)c3ccccc3)S(C)(=O)=O)cc2nn1-c1ccc(Cl)cc1] | [M + H]+: 580.0/(400 MHz, CDCl₃) δ 7.87-7.72 (m, 3H), 7.59-7.40 (m, 7H), 7.38 (s, 1H), 6.85 (t, J = 6.0 Hz, 1H), 5.77 (brd, J = 4.2 Hz, 1H), 4.00-3.78 (m, 2H), 3.78-3.56 (m, 2H), 3.08 (s, 3H), 3.01 (d, J = 4.9 Hz, 3H), 2.54-2.35 (m, 1H), 1.97-1.78 (m, 2H), 1.15-0.95 (m, 3H), 0.71-0.54 (m, 1H). | D then C |
| 198 | 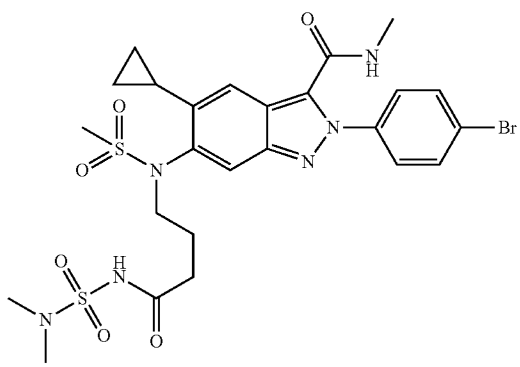 [SMILES: CNC(=O)c1c2cc(C3CC3)c(N(CCCC(=O)NS(=O)(=O)N(C)C)S(C)(=O)=O)cc2nn1-c1ccc(Br)cc1] | [M + H]+: 654.9/656.9/(400 MHz, CDCl₃) δ 8.04 (brs, 1H), 7.77 (s, 1H), 7.73-7.62 (m, 2H), 7.51-45 (m, 2H), 7.37 (s, 1H), 5.89 (brs, 1H), 3.83 (t, J = 6.4 Hz, 2H), 3.06 (s, 3H), 3.01 (d, J = 4.9 Hz, 3H), 2.94 (s, 6H), 2.58-2.42 (m, 2H), 2.41-2.31 (m, 1H), 1.99-1.88 (m, 2H), 1.17-1.07 (m, 2H), 1.07-1.00 (m, 1H), 0.71-0.60 (m, 1H). | M |
| 199 | 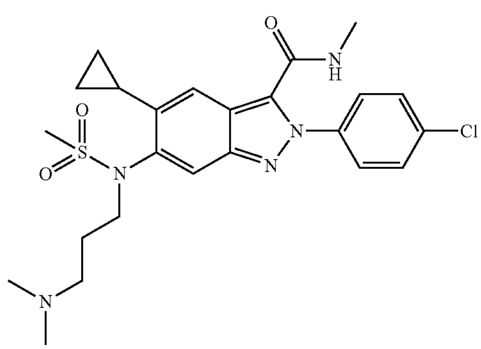 [SMILES: CNC(=O)c1c2cc(C3CC3)c(N(CCCN(C)C)S(C)(=O)=O)cc2nn1-c1ccc(Cl)cc1] | [M + H]+: 504.12/(400 MHz, CDCl₃) δ 7.79 (s, 1H), 7.65-7.51 (m, 3H), 7.41 (s, 1H), 5.89 (br d, J = 5.0 Hz, 1H), 3.99-3.74 (m, 2H), 3.11 (s, 3H), 3.05 (d, J = 4.9 Hz, 3H), 2.52 (t, J = 7.2 Hz, 2H), 2.48-2.40 (m, 1H), 2.32 (s, 6H), 2.02-1.82 (m, 2H), 1.18-1.07 (m, 2H), 1.07-0.93 (m, 1H), 0.79-0.59 (m, 1H). | D then C |
| 200 | 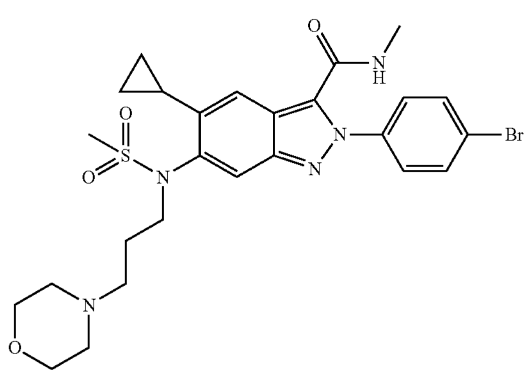 [SMILES: CNC(=O)c1c2cc(C3CC3)c(N(CCCN3CCOCC3)S(C)(=O)=O)cc2nn1-c1ccc(Br)cc1] | [M + H]+: 590.1/592.1/(400 MHz, CDCl₃) δ 7.73 (s, 1H), 7.69-7.63 (m, 2H), 7.47 (d, J = 8.8 Hz, 2H), 7.36 (s, 1H), 5.85 (brd, J = 5.4 Hz, 1H), 3.92-3.74 (m, 2H), 3.74-3.60 (m, 4H), 3.06 (s, 3H), 3.01 (d, J = 4.9 Hz, 3H), 2.53-2.35 (m, 7H), 1.95-1.68 (m, 2H), 1.17-0.92 (m, 3H), 0.72-0.50 (m, 1H). | C |

TABLE 1-continued

Compounds and their general method(s) of synthesis

| No. | Structure | Observed LCMS m/z [M + H]+/1H NMR | Method |
|---|---|---|---|
| 201 | 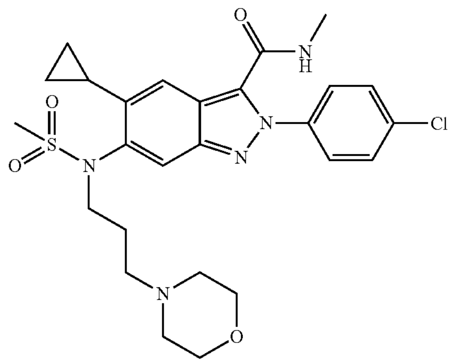 [SMILES: CNC(=O)c1c2cc(C3CC3)c(N(CCCN3CCOCC3)S(C)(=O)=O)cc2nn1-c1ccc(Cl)cc1] | [M + H]+: 546.2/(400 MHz, CDCl₃) δ 7.73 (s, 1H), 7.57-7.47 (m, 4H), 7.37 (s, 1H), 5.81 (brd, J = 4.5 Hz, 1H), 3.87-3.71 (m, 2H), 3.71-3.60 (m, 4H), 3.06 (s, 3H), 3.01 (d, J = 4.9 Hz, 3H), 2.49-2.28 (m, 7H), 1.91-1.78 (m, 2H), 1.14-0.91 (m, 3H), 0.71-0.55 (m, 1H). | C |
| 202 | 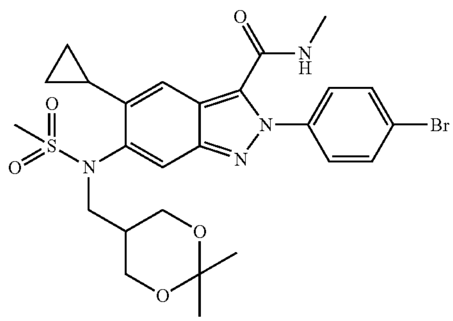 [SMILES: CNC(=O)c1c2cc(C3CC3)c(N(CC3COC(C)(C)OC3)S(C)(=O)=O)cc2nn1-c1ccc(Br)cc1] | [M + H]+: 590.9/592.9/(400 MHz, MeOD) δ 7.90 (d, J = 6.9 Hz, 1H), 7.76-7.68 (m, 2H), 7.56-7.48 (m, 2H), 7.34 (s, 1H), 4.12-3.99 (m, 2H), 3.95 (dd, J = 11.9, 3.9 Hz, 1H), 3.89-3.76 (m, 2H), 3.72-3.63 (m, 1H), 3.14 (s, 3H), 2.94 (s, 3H), 2.49-2.36 (m, 1H), 1.83-1.74 (m, 1H), 1.37 (s, 3H), 1.36 (s, 3H), 1.16-1.02 (m, 3H), 0.68-0.60 (m, 1H). | C |
| 203 | 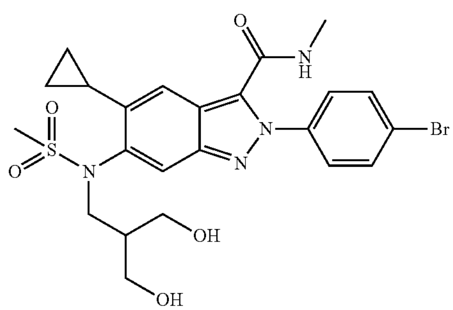 [SMILES: CNC(=O)c1c2cc(C3CC3)c(N(CC(CO)CO)S(C)(=O)=O)cc2nn1-c1ccc(Br)cc1] | [M + H]+: 550.9/552.9/(400 MHz, CDCl₃) δ 7.78 (s, 1H), 7.71-7.65 (m, 2H), 7.50-7.44 (m, 2H), 7.36 (s, 1H), 5.89-5.79 (m, 1H), 4.12-4.02 (m, 2H), 3.94-3.80 (m, 4H), 3.10 (s, 3H), 3.00 (d, J = 4.9 Hz, 3H), 2.46-2.36 (m, 1H), 1.91-1.76 (m, 1H), 1.18-0.99 (m, 3H), 0.65-0.53 (m, 1H). | N |
| 204 | 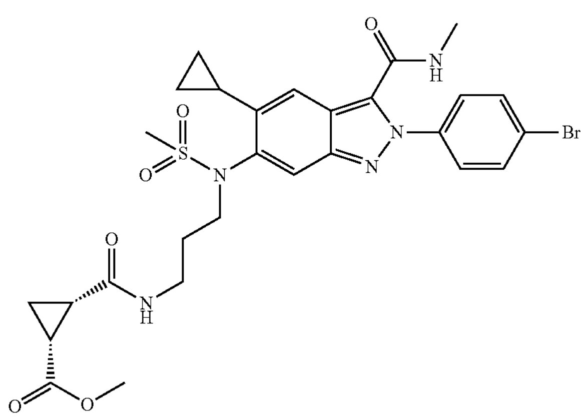 [SMILES: CNC(=O)c1c2cc(C3CC3)c(N(CCCNC(=O)[C@H]3C[C@H]3C(=O)OC)S(C)(=O)=O)cc2nn1-c1ccc(Br)cc1] | [M + H]+: 645.95/647.93/(400 MHz, CDCl₃) δ 7.80 (d, J = 3.9 Hz, 1H), 7.70 (d, J = 8.7 Hz, 2H), 7.51 (d, J = 8.7 Hz, 2H), 7.40 (s, 1H), 6.57-6.38 (m, 1H), 5.96-5.80 (m, 1H), 4.05-3.75 (m, 2H), 3.73 (s, 3H), 3.64-3.27 (m, 3H), 3.12 (s, 3H), 3.05 (d, J = 4.8 Hz, 3H), 2.56-2.29 (m, 1H), 2.12-1.94 (m, 2H), 1.90-1.69 (m, 2H), 1.38-1.21 (m, 1H), 1.23-0.92 (m, 3H), 0.71-0.54 (m, 1H). | D |

TABLE 1-continued

Compounds and their general method(s) of synthesis

| No. | Structure | Observed LCMS m/z [M + H]+/1H NMR | Method |
|---|---|---|---|
| 205 | 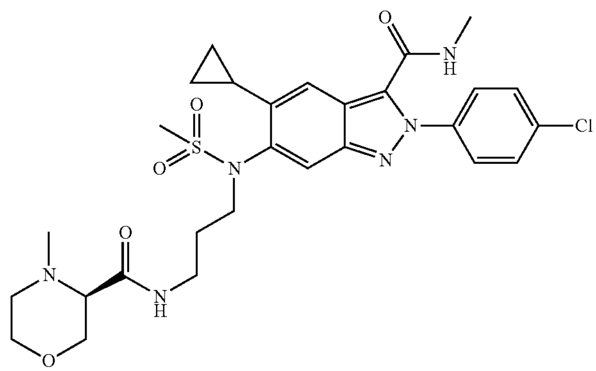 [SMILES: CNC(=O)c1c2cc(C3CC3)c(N(CCCNC(=O)[C@H]3COCCN3C)S(C)(=O)=O)cc2nn1-c1ccc(Cl)cc1] | [M + H]+: 603.12/(400 MHz, CDCl$_3$) δ 7.81 (s, 1H), 7.64-7.49 (m, 4H), 7.42 (d, J = 1.6 Hz, 1H), 6.94 (br d, J = 4.9 Hz, 1H), 5.83 (br s, 1H), 4.04-3.92 (m, 1H), 3.92-3.74 (m, 3H), 3.66-3.20 (m, 4H), 3.10 (s, 3H), 3.05 (d, J = 4.9 Hz, 3H), 2.87-2.71 (m, 2H), 2.50-2.33 (m, 2H), 2.28 (d, J = 4.6 Hz, 3H), 1.97-1.78 (m, 2H), 1.22-1.10 (m, 2H), 1.10-0.97 (m, 1H), 0.77-0.53 (m, 1H). | D then C |
| 206 | 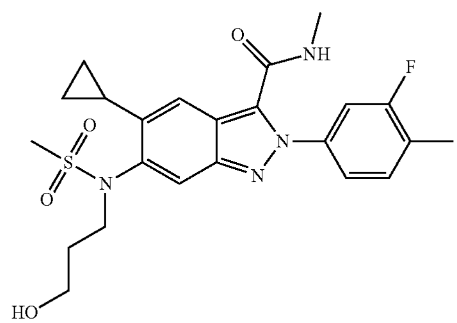 | [M + H]+: 475.1/(400 MHz, Acetone) δ 7.88 (d, J = 0.5 Hz, 1H), 7.80 (brs, 1H), 7.49-7.38 (m, 4H), 4.00-3.86 (m, 2H), 3.71-3.61 (m, 2H), 3.19 (s, 3H), 2.98 (d, J = 4.7 Hz, 3H), 2.51-2.42 (m, 1H), 2.38 (d, J = 1.9 Hz, 3H), 1.93-1.73 (m, 2H), 1.12-0.97 (m, 3H), 0.63-0.55 (m, 1H). | A |
| 207 | 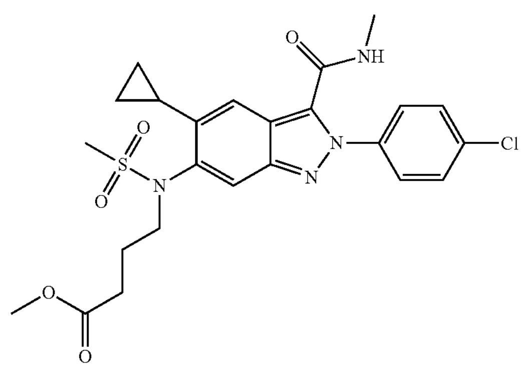 [SMILES: CNC(=O)c1c2cc(C3CC3)c(N(CCCC(=O)OC)S(C)(=O)=O)cc2nn1-c1ccc(Cl)cc1] | [M + H]+: 519.0/(400 MHz, Acetone) δ 7.88 (d, J = 0.6 Hz, 1H), 7.80 (brs, 1H), 7.71-7.65 (m, 2H), 7.61-7.55 (m, 2H), 7.40 (d, J = 0.5 Hz, 1H), 3.88-3.81 (m, 2H), 3.59 (s, 3H), 3.16 (s, 3H), 2.98-2.93 (m, 3H), 2.50-2.39 (m, 3H), 1.94-1.82 (m, 2H), 1.08-0.96 (m, 3H), 0.61-0.51 (m, 1H). | A then M |
| 208 | 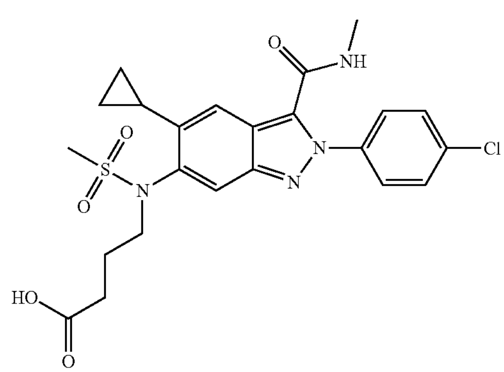 [SMILES: CNC(=O)c1c2cc(C3CC3)c(N(CCCC(=O)O)S(C)(=O)=O)cc2nn1-c1ccc(Cl)cc1] | [M + H]+: 505.0/(400 MHz, MeOD) δ 7.86 (s, 1H), 7.64-7.55 (m, 4H), 7.38 (s, 1H), 3.86-3.78 (m, 2H), 3.19 (s, 3H), 2.97 (s, 3H), 2.46-2.38 (m, 1H), 2.27-2.19 (m, 2H), 2.00-1.83 (m, 2H), 1.18-0.96 (m, 3H), 0.77-0.66 (m, 1H). | M |

TABLE 1-continued

Compounds and their general method(s) of synthesis

| No. | Structure | Observed LCMS m/z [M + H]+/1H NMR | Method |
|---|---|---|---|
| 209 | 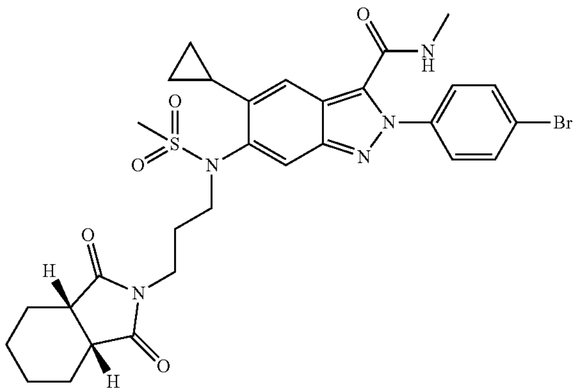 [SMILES: CNC(=O)c1c2cc(C3CC3)c(N(CCCN3C(=O)[C@H]4CCCC[C@H]4C3=O)S(C)(=O)=O)cc2nn1-c1ccc(Br)cc1] | [M + H]+: 655.90/657.91/(400 MHz, CDCl3) δ 7.78 (s, 1H), 7.74-7.67 (m, 2H), 7.55-7.48 (m, 2H), 7.41 (s, 1H), 5.83 (brd, J = 4.5 Hz, 2H), 3.91-3.67 (m, 2H), 3.58 (td, J = 6.8, 2.4 Hz, 2H), 3.11 (s, 3H), 3.06 (d, J = 4.9 Hz, 3H), 2.93-2.79 (m, 2H), 2.53-2.33 (m, 1H), 2.07-1.66 (m, 6H), 1.50-1.31 (m, 4H), 1.21-1.07 (m, 2H), 1.07-0.93 (m, 1H), 0.70-0.54 (m, 1H). | D |
| 210 | 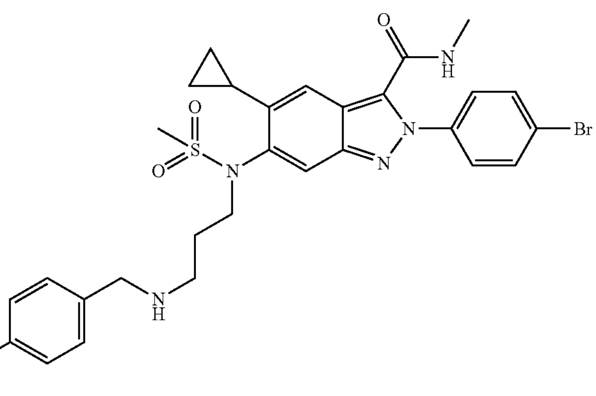 | [M + H]+: 640.14/642.04/(400 MHz, CDCl3) δ 8.36 (s, 1H), 7.74 (s, 1H), 7.73-7.65 (m, 2H), 7.54-7.46 (m, 2H), 7.37 (s, 1H), 7.27 (d, J = 8.7 Hz, 2H), 6.88 (d, J = 8.7 Hz, 2H), 6.04 (brd, J = 4.9 Hz, 1H), 3.95-3.83 (m, 2H), 3.82 (s, 3H), 3.80 (s, 2H), 3.08 (s, 3H), 3.04 (d, J = 4.9 Hz, 3H), 2.92-2.70 (m, 2H), 2.38-2.31 (m, 1H), 1.98-1.76 (m, 2H), 1.25-0.90 (m, 3H), 0.72-0.52 (m, 1H). | D |
| 211 | 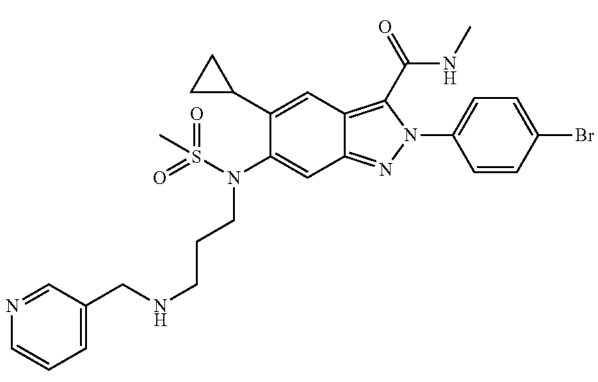 [SMILES: CNC(=O)c1c2cc(C3CC3)c(N(CCCNCc3cccnc3)S(C)(=O)=O)cc2nn1-c1ccc(Br)cc1] | [M + H]+: 611.04/613.03/(400 MHz, CDCl3) δ 8.51 (dd, J = 4.8, 1.6 Hz, 1H), 8.26 (d, J = 1.6 Hz, 1H), 7.77 (s, 1H), 7.71-7.67 (m, 3H), 7.52 (d, J = 8.8 Hz, 2H), 7.35-7.28 (m, 2H), 6.65 (brd, J = 4.1 Hz, 1H), 4.03-3.83 (m, 2H), 3.76 (q, J = 13.8 Hz, 2H), 3.09 (s, 6H), 2.78-2.62 (m, 2H), 2.47-2.32 (m, 1H), 1.97-1.79 (m, 2H), 1.22-0.88 (m, 3H), 0.60-0.43 (m, 1H). | D |

TABLE 1-continued

Compounds and their general method(s) of synthesis

| No. | Structure | Observed LCMS m/z [M + H]+/1H NMR | Method |
|---|---|---|---|
| 212 | 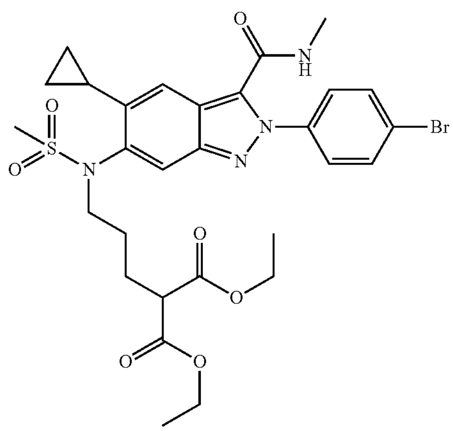 [SMILES: CCOC(=O)C(CCCN(c1cc2nn(-c3ccc(Br)cc3)c(C(=O)NC)c2cc1C1CC1)S(C)(=O)=O)C(=O)OCC] | [M + H]+: 662.9/664.9/(400 MHz, CDCl3) δ 7.74-7.70 (m, 1H), 7.70-7.64 (m, 2H), 7.51-7.45 (m, 2H), 7.36 (s, 1H), 5.86-5.78 (m, 1H), 4.24-4.09 (m, 4H), 3.84-3.69 (m, 2H), 3.30 (t, J = 7.4 Hz, 1H), 3.07 (s, 3H), 3.02 (d, J = 4.9 Hz, 3H), 2.45-2.35 (m, 1H), 2.00-1.89 (m, 2H), 1.80-1.59 (m, 2H), 1.28-1.19 (m, 6H), 1.14-1.05 (m, 2H), 1.05-0.96 (m, 1H), 0.64-0.54 (m, 1H). | M |
| 213 | 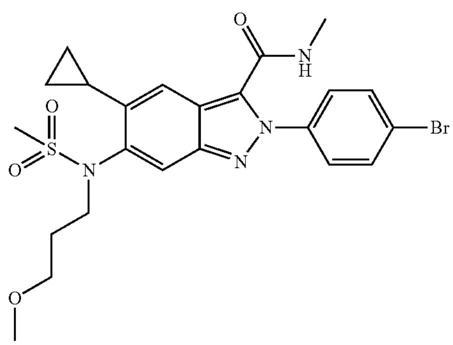 [SMILES: CNC(=O)c1c2cc(C3CC3)c(N(CCCOC)S(C)(=O)=O)cc2nn1-c1ccc(Br)cc1] | [M + H]+: 534.9/536.9/(400 MHz, CDCl3) δ 7.69 (s, 1H), 7.68-7.59 (m, 2H), 7.49-7.41 (m, 2H), 7.33 (s, 1H), 5.91 (brd, J = 4.6 Hz, 1H), 3.93-3.69 (m, 2H), 3.42 (t, J = 6.0 Hz, 2H), 3.28 (s, 3H), 3.06 (s, 3H), 2.99 (d, J = 4.9 Hz, 3H), 2.40 (tt, J = 8.4, 5.4 Hz, 1H), 1.95-1.76 (m, 2H), 1.14-0.91 (m, 3H), 0.63-0.48 (m, 1H). | O |
| 214 | 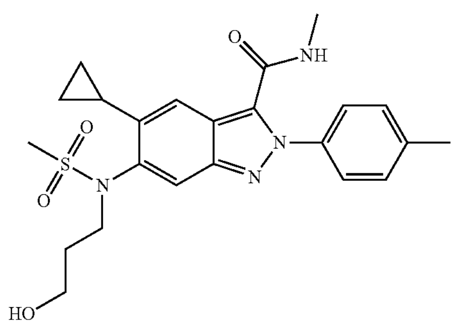 [SMILES: CNC(=O)c1c2cc(C3CC3)c(N(CCCO)S(C)(=O)=O)cc2nn1-c1ccc(C)cc1] | [M + H]+: 457.1/(400 MHz, Acetone) δ 7.87 (s, 1H), 7.69 (brs, 1H), 7.58-7.52 (m, 2H), 7.41 (s, 1H), 7.40-7.34 (m, 2H), 3.98-3.88 (m, 2H), 3.70-3.62 (m, 2H), 3.18 (s, 3H), 2.96 (d, J = 4.7 Hz, 3H), 2.51-2.42 (m, 4H), 1.90-1.73 (m, 2H), 1.10-0.96 (m, 3H), 0.63-0.54 (m, 1H). | C |
| 215 | 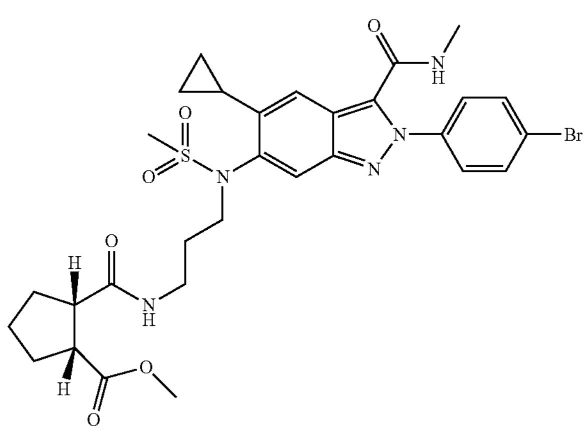 [SMILES: CNC(=O)c1c2cc(C3CC3)c(N(CCCNC(=O)[C@H]3CCC[C@H]3C(=O)OC)S(C)(=O)=O)cc2nn1-c1ccc(Br)cc1] | [M + H]+: 673.96/675.93/(400 MHz, CDCl3) δ 7.79 (d, J = 1.5 Hz, 1H), 7.75-7.66 (m, 2H), 7.56-7.47 (m, 2H), 7.41 (s, 1H), 6.35-6.14 (m, 1H), 5.94-5.74 (m, 1H), 3.97-3.78 (m, 2H), 3.74 (d, J = 4.3 Hz, 3H), 3.56-3.28 (m, 2H), 3.11 (d, J = 3.0 Hz, 3H), 3.09-3.03 (m, 1H), 3.05 (d, J = 4.9 Hz, 3H), 2.95-2.78 (m, 1H), 2.55-2.34 (m, 1H), 2.20-2.04 (m, 1H), 2.04-1.69 (m, 7H), 1.22-0.94 (m, 3H), 0.75-0.56 (m, 1H). | D |

TABLE 1-continued
Compounds and their general method(s) of synthesis
| No. | Structure | Observed LCMS m/z [M + H]+/1H NMR | Method |
|---|---|---|---|
| 216 | 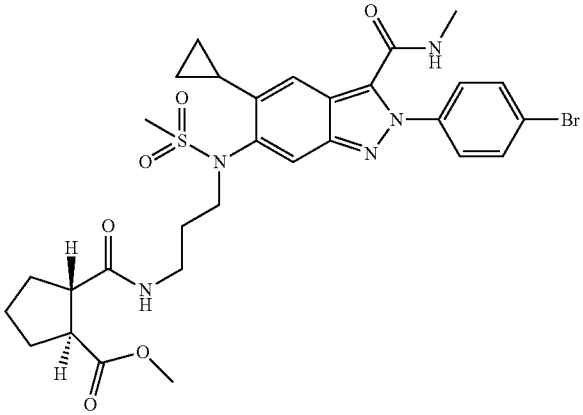 [SMILES: CNC(=O)c1c2cc(C3CC3)c(N(CCCNC(=O)[C@H]3CCC[C@@H]3C(=O)OC)S(C)(=O)=O)cc2nn1-c1ccc(Br)cc1] | [M + H]+: 673.96/675.96/(400 MHz, CDCl3) δ 7.81 (s, 1H), 7.71 (d, J = 8.8 Hz, 2H), 7.51 (d, J = 8.7 Hz, 2H), 7.41 (s, 1H), 6.07 (brd, J = 4.8 Hz, 1H), 5.84 (d, J = 4.0 Hz, 1H), 4.03-3.74 (m, 2H), 3.67 (s, 3H), 3.54-3.30 (m, 2H), 3.12 (s, 3H), 3.08-3.05 (m, 1H), 3.05 (d, J = 4.9 Hz, 3H), 2.98-2.85 (m, 1H), 2.56-2.33 (m, 1H), 2.21-1.88 (m, 5H), 1.86-1.66 (m, 3H), 1.26-1.00 (m, 3H), 0.76-0.57 (m, 1H). | D |
| 217 | 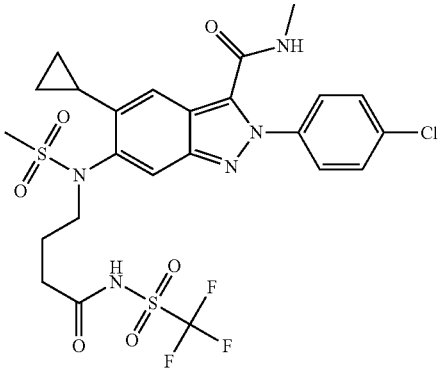 [SMILES: CNC(=O)c1c2cc(C3CC3)c(N(CCCC(=O)NS(=O)(=O)C(F)(F)F)S(C)(=O)=O)cc2nn1-c1ccc(Cl)cc1] | [M + H]+: 636.0/(400 MHz, MeOD) δ 7.86 (s, 1H), 7.65-7.57 (m, 4H), 7.39 (s, 1H), 3.82 (t, J = 7.7 Hz, 2H), 3.19 (s, 3H), 2.97 (s, 3H), 2.46-2.37 (m, 1H), 2.37-2.29 (m, 2H), 1.96-1.85 (m, 2H), 1.18-0.97 (m, 3H), 0.75-0.66 (m, 1H). | M |
| 218 | 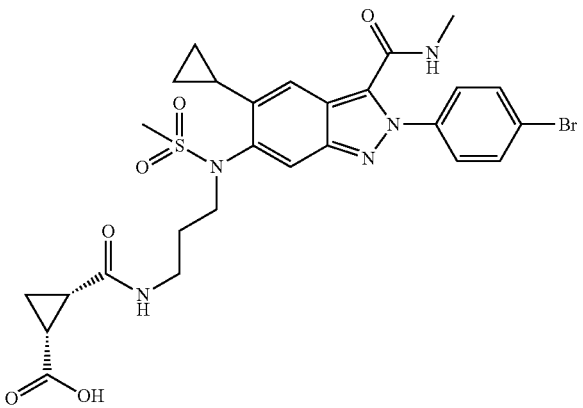 [SMILES: CNC(=O)c1c2cc(C3CC3)c(N(CCCNC(=O)[C@H]3C[C@H]3C(=O)O)S(C)(=O)=O)cc2nn1-c1ccc(Br)cc1] | [M + H]+: 631.98/633.94/(400 MHz, CDCl3) δ 7.88 (s, 0.5H), 7.80 (s, 0.5H), 7.72 (d, J = 8.8 Hz, 2H), 7.52 (d, J = 8.7 Hz, 2H), 7.42 (d, J = 3.3 Hz, 1H), 6.90 (t, J = 6.3 Hz, 1H), 5.99 (brs, 2H), 4.05-3.73 (m, 2H), 3.74-3.41 (m, 2H), 3.13 (d, J = 1.9 Hz, 3H), 3.06 (d, J = 4.1 Hz, 3H), 2.54-2.27 (m, 1H), 2.25-2.08 (m, 1H), 1.97-1.65 (m, 5H), 1.24-0.95 (m, 3H), 0.73-0.52 (m, 1H). | D |

TABLE 1-continued

Compounds and their general method(s) of synthesis

| No. | Structure | Observed LCMS m/z [M + H]+/1H NMR | Method |
|---|---|---|---|
| 219 | 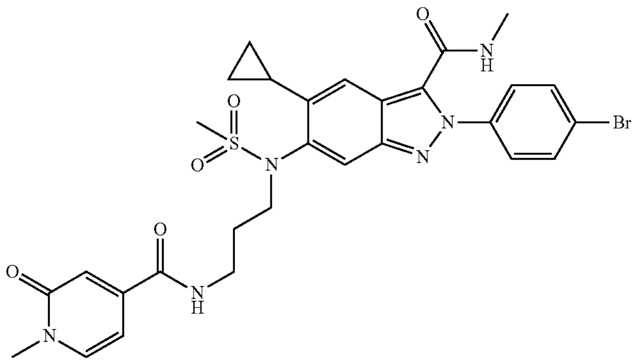 [SMILES: CNC(=O)c1c2cc(C3CC3)c(N(CCCNC(=O)c3ccn(C)c(=O)c3)S(C)(=O)=O)cc2nn1-c1ccc(Br)cc1] | [M + H]+: 654.99/656.96/(400 MHz, CDCl₃) δ 7.86 (s, 1H), 7.70 (d, J = 8.8 Hz, 2H), 7.53 (d, J = 8.8 Hz, 2H), 7.41 (s, 1H), 7.37 (d, J = 7.1 Hz, 1H), 6.70 (br dd, J = 8.7, 4.3 Hz, 1H), 6.63 (br t, J = 6.2 Hz, 1H), 6.58 (dd, J = 7.0, 1.9 Hz, 1H), 6.45 (d, J = 1.6 Hz, 1H), 4.03-3.79 (m, 2H), 3.78-3.50 (m, 2H), 3.58 (s, 3H), 3.11 (s, 3H), 3.07 (d, J = 4.8 Hz, 3H), 2.47-2.25 (m, 1H), 2.08-1.86 (m, 2H), 1.24-0.97 (m, 3H), 0.76-0.58 (m, 1H). | D |
| 220 | 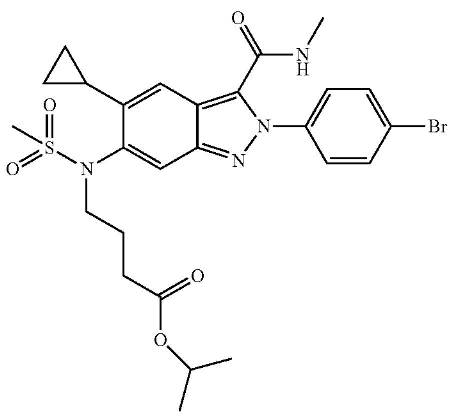 [SMILES: CNC(=O)c1c2cc(C3CC3)c(N(CCCC(=O)OC(C)C)S(C)(=O)=O)cc2nn1-c1ccc(Br)cc1] | [M + H]+: 590.8592.8/(400 MHz, CDCl₃) δ 7.74 (d, J = 7.80 Hz, 1H), 7.73-7.66 (m, 2H), 7.51 (t, J = 8.2 Hz, 2H), 7.39 (s, 1H), 5.93 (s, 1H), 5.08-4.96 (m, 1H), 3.82 (t, J = 7.5 Hz, 2H), 3.10 (s, 3H), 3.05 (t, J = 6.8 Hz, 3H), 2.51-2.32 (m, 3H), 2.06-1.85 (m, 2H), 1.25 (t, J = 5.5 Hz, 6H), 1.12 (ddd, J = 10.7, 5.9, 4.7 Hz, 2H), 1.08-1.00 (m, 1H), 0.66-0.58 (m, 1H). | M |
| 221 | 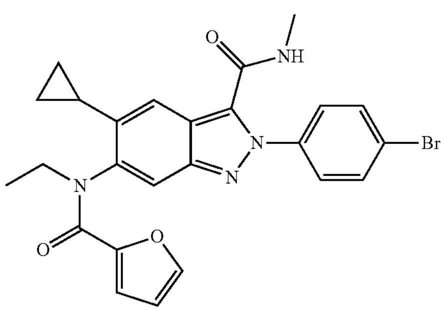 [SMILES: CCN(C(=O)c1ccco1)c1cc2nn(-c3ccc(Br)cc3)c(C(=O)NC)c2cc1C1CC1] | [M + H]+: 507.0/509.0/(400 MHz, CDCl₃) δ 7.68-7.64 (m, 2H), 7.60 (d, J = 0.5 Hz, 1H), 7.52-7.47 (m, 2H), 7.46 (s, 1H), 7.27 (d, J = 0.9 Hz, 1H), 6.15 (dd, J = 3.5, 1.7 Hz, 1H), 5.94 (d, J = 3.4 Hz, 1H), 5.91-5.84 (m, 1H), 4.42 (dq, J = 14.1, 7.1 Hz, 1H), 3.43 (dq, J = 14.1, 7.1 Hz, 1H), 3.02 (d, J = 4.9 Hz, 3H), 1.98-1.85 (m, 1H), 1.31 (t, J = 7.1 Hz, 3H), 1.06-0.94 (m, 1H), 0.92-0.83 (m, 1H), 0.77-0.66 (m, 1H), 0.65-0.54 (m, 1H). | A |
| 222 | 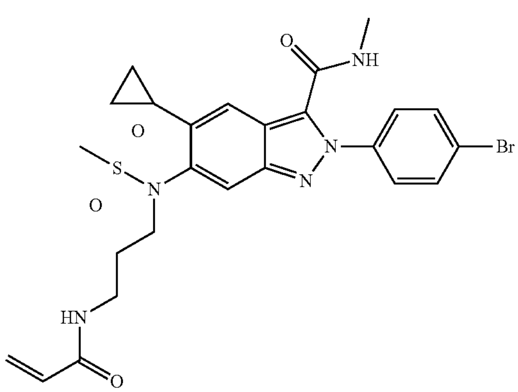 | [M + H]+: 573.9/575.9/(400 MHz, CD₃CN) δ 7.81 (s, 1H), 7.72-7.63 (m, 2H), 7.56-7.44 (m, 2H), 7.36 (s, 1H), 6.99 (br s, 1H), 6.57 (br s, 1H), 6.19-6.00 (m, 2H), 5.55 (dd, J = 7.5, 4.6 Hz, 1H), 3.84-3.66 (m, 2H), 3.36-3.19 (m, 2H), 3.08 (s, 3H), 2.89 (d, J = 4.8 Hz, 3H), 2.42-2.28 (m, 1H), 1.83-1.67 (m, 2H), 1.15-0.90 (m, 3H), 0.62 (dd, J = 13.9, 5.9 Hz, 1H). | D |

TABLE 1-continued

Compounds and their general method(s) of synthesis

| No. | Structure | Observed LCMS m/z [M + H]⁺/¹H NMR | Method |
|---|---|---|---|
| 223 | 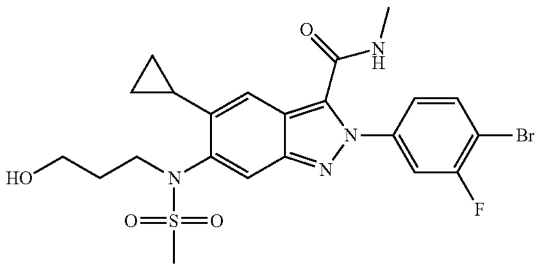 [SMILES: CNC(=O)c1c2cc(C3CC3)c(N(CCCO)S(C)(=O)=O)cc2nn1-c1ccc(Br)c(F)c1] | [M + H]+: 539.1/541.1/(400 MHz, CDCl₃) δ 7.79-7.64 (m, 2H), 7.49-7.38 (m, 1H), 7.32-7.22 (m, 2H), 5.92 (brs, 1H), 4.00-3.68 (m, 4H), 3.14-2.97 (m, 6H), 2.47-2.35 (m, 1H), 1.94-1.73 (m, 3H), 1.07-0.95 (m, 3H), 0.67-0.54 (m, 1H). | A then C |
| 224 | 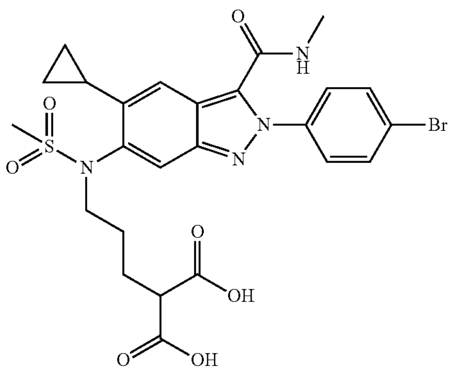 [SMILES: CNC(=O)c1c2cc(C3CC3)c(N(CCCC(C(=O)O)C(=O)O)S(C)(=O)=O)cc2nn1-c1ccc(Br)cc1] | [M + H]+: 606.9/608.9/(400 MHz, MeOD) δ 7.82 (s, 1H), 7.75-7.68 (m, 2H), 7.57-7.48 (m, 2H), 7.34 (s, 1H), 3.84-3.68 (m, 2H), 3.13 (s, 3H), 3.04 (t, J = 6.1 Hz, 1H), 2.94 (s, 3H), 2.42-2.31 (m, 1H), 2.02-1.85 (m, 2H), 1.76-1.52 (m, 2H), 1.16-0.94 (m, 3H), 0.70-1.61 (m, 1H). | M |
| 225 | 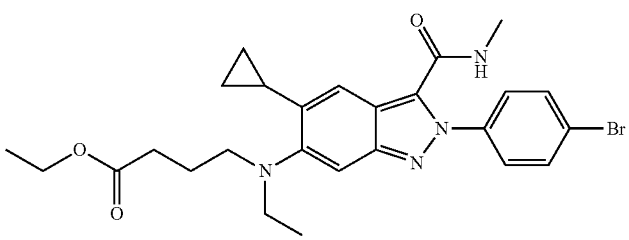 [SMILES: CCOC(=O)CCCN(CC)c1cc2nn(-c3ccc(Br)cc3)c(C(=O)NC)c2cc1C1CC1] | [M + H]+: 527.1/529.1/(400 MHz, CDCl₃) δ 7.71-7.58 (m, 2H), 7.51-7.42 (m, 2H), 7.33 (brs, 1H), 7.21 (brs, 1H), 5.76 (brd, J = 4.3 Hz, 1H), 4.10 (q, J = 7.1 Hz, 2H), 3.34 (brs, 1H), 3.27-3.08 (m, 3H), 3.08-2.92 (m, 3H), 2.33 (t, J = 6.9 Hz, 3H), 1.96-1.72 (m, 2H), 1.23 (t, J = 7.1 Hz, 3H), 1.14-0.93 (m, 5H), 0.83-0.65 (m, 2H). | A |
| 226 | 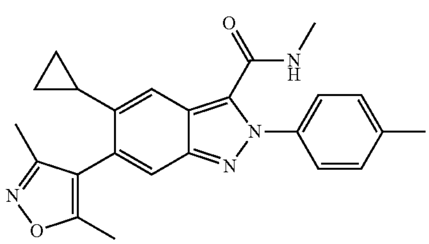 [SMILES: CNC(=O)c1c2cc(C3CC3)c(-c3c(C)noc3C)cc2nn1-c1ccc(C)cc1] | [M + H]+: 401.2/(400 MHz, CDCl₃) δ 7.61 (s, 1H), 7.55 (d, J = 0.7 Hz, 1H), 7.50-7.45 (m, 2H), 7.35 (d, J = 8.0 Hz, 2H), 5.61 (brs, 1H), 2.94 (d, J = 4.9 Hz, 3H), 2.47 (s, 3H), 2.31 (s, 3H), 2.17 (s, 3H), 1.73-1.62 (m, 1H), 0.90-0.86 (m, 2H), 0.78-0.67 (m, 2H). | K |
| 227 | 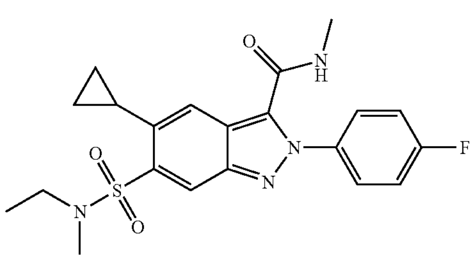 [SMILES: CCN(C)S(=O)(=O)c1cc2nn(-c3ccc(F)cc3)c(C(=O)NC)c2cc1C1CC1] | [M + H]+: 431.2/(400 MHz, CDCl₃) δ 8.71 (brs, 1H), 8.25 (s, 1H), 7.76-7.58 (m, 2H), 7.53-7.35 (m, 3H), 2.90 (s, 3H), 2.86-2.76 (m, 3H), 2.30-2.11 (m, 1H), 1.40-1.30 (m, 1H), 1.18-1.09 (m, 2H), 1.08-0.96 (m, 2H), 0.93-0.78 (m, 4H). | L |

| No. | Structure | Observed LCMS m/z [M + H]+/1H NMR | Method |
|---|---|---|---|
| 228 | 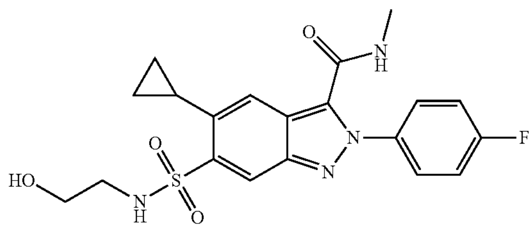 [SMILES: CNC(=O)c1c2cc(C3CC3)c(S(=O)(=O)NCCO)cc2nn1-c1ccc(F)cc1] | [M + H]+: 433.2/(400 MHz, CDCl3) δ 8.70 (brs, 1H), 8.31 (s, 1H), 7.73-7.58 (m, 3H), 7.51-7.34 (m, 3H), 5.75 (s, 1H), 4.76-4.66 (m, 1H), 3.50-3.36 (m, 2H), 2.99-2.92 (m, 1H), 2.90-2.76 (m, 3H), 2.68-2.55 (m, 1H), 1.05-1.00 (m, 2H), 0.94-0.79 (m, 2H). | L |
| 229 | 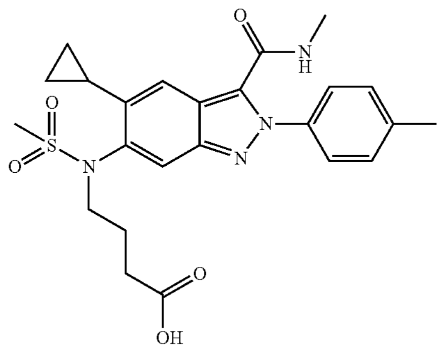 [SMILES: CNC(=O)c1c2cc(C3CC3)c(N(CCCC(=O)O)S(C)(=O)=O)cc2nn1-c1ccc(C)cc1] | [M + H]+: 485.1/(400 MHz, CDCl3) δ 8.71 (q, J = 4.6 Hz, 1H), 7.91 (s, 1H), 7.46 (d, J = 8.6 Hz, 2H), 7.36 (d, J = 8.2 Hz, 2H), 7.26 (s, 1H), 3.66 (t, J = 7.9 Hz, 2H), 3.17 (s, 3H), 2.82 (d, J = 5.1 Hz, 3H), 2.55-2.51 (m, 1H), 2.41 (s, 3H), 2.38-2.29 (m, 1H), 2.00-1.92 (brm, 2H), 1.71-1.54 (m, 2H), 1.05-0.90 (m, 3H), 0.64-0.54 (m, 1H). | M |
| 230 | 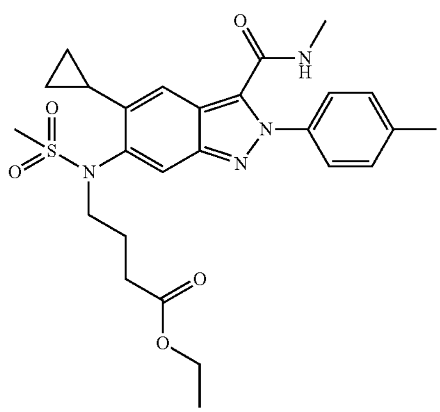 [SMILES: CCOC(=O)CCCN(c1cc2nn(-c3ccc(C)cc3)c(C(=O)NC)c2cc1C1CC1)S(C)(=O)=O] | [M + H]+: 513.2/(400 MHz, CDCl3) δ 7.77 (s, 1H), 7.56 (s, 1H), 7.50 (d, J = 8.4 Hz, 2H), 7.39 (d, J = 8.0 Hz, 2H), 5.70-5.61 (brm, 1H), 4.15 (q, J = 7.0 Hz, 2H), 3.83 (t, J = 7.5 Hz, 2H), 3.10 (s, 3H), 2.98 (d, J = 5.1 Hz, 3H), 2.51 (s, 3H), 2.48-2.40 (m, 3H), 2.05-1.90 (m, 2H), 1.27 (t, J = 7.0 Hz, 3H), 1.18-1.03 (m, 3H), 0.70-0.60 (m, 1H). | M |
| 231 | 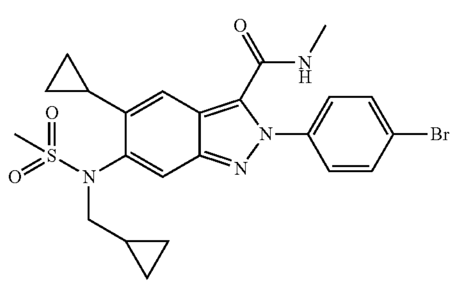 [SMILES: CNC(=O)c1c2cc(C3CC3)c(N(CC3CC3)S(C)(=O)=O)cc2nn1-c1ccc(Br)cc1] | [M + H]+: 517.0/519.0/(400 MHz, CDCl3) δ 7.84 (d, J = 0.5 Hz, 1H), 7.75-7.63 (m, 2H), 7.58-7.46 (m, 2H), 7.42 (s, 1H), 5.86 (s, 1H), 3.66 (ddd, J = 20.9, 14.2, 7.2 Hz, 2H), 3.16 (s, 3H), 3.06 (d, J = 4.9 Hz, 3H), 2.58-2.41 (m, 1H), 1.22-1.06 (m, 3H), 1.05-0.94 (m, 1H), 0.73-0.61 (m, 1H), 0.57 (d, J = 7.9 Hz, 2H), 0.32-0.16 (m, 2H). | C |

TABLE 1-continued

Compounds and their general method(s) of synthesis

| No. | Structure | Observed LCMS m/z [M + H]+/1H NMR | Method |
|---|---|---|---|
| 232 | 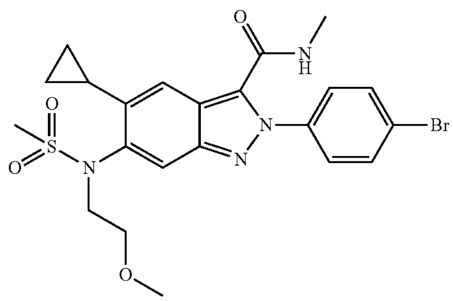 [SMILES: CNC(=O)c1c2cc(C3CC3)c(N(CCOC)S(C)(=O)=O)cc2nn1-c1ccc(Br)cc1] | [M + H]+: 521.0/523.0/(400 MHz, CDCl$_3$) δ 7.79 (s, 1H), 7.71 (d, J = 8.8 Hz, 2H), 7.52 (d, J = 8.8 Hz, 2H), 7.45 (s, 1H), 5.86 (s, 1H), 4.49-4.22 (m, 1H), 3.73-3.48 (m, 3H), 3.45 (s, 3H), 3.24 (s, 3H), 3.06 (d, J = 4.9 Hz, 3H), 2.39 (d, J = 41.8 Hz, 1H), 1.23-0.91 (m, 3H), 0.67-0.45 (m, 1H). | C |
| 233 | 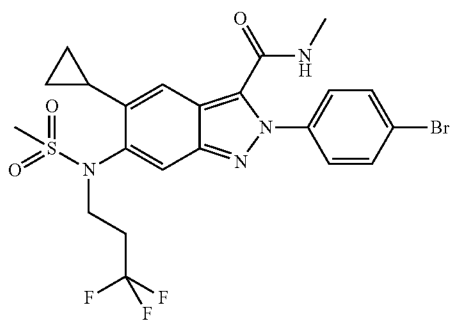 [SMILES: CNC(=O)c1c2cc(C3CC3)c(N(CCC(F)(F)F)S(C)(=O)=O)cc2nn1-c1ccc(Br)cc1] | [M + H]+: 559.0/561.0/(400 MHz, CDCl$_3$) δ 7.80 (s, 1H), 7.76-7.66 (m, 2H), 7.61-7.51 (m, 2H), 7.48 (s, 1H), 5.80 (brs, 1H), 4.16-3.94 (m, 2H), 3.13 (s, 3H), 3.05 (d, J = 4.9 Hz, 3H), 2.66-2.43 (m, 2H), 2.43-2.30 (m, 1H), 1.21-1.02 (m, 3H), 0.71-0.55 (m, 1H). | C |
| 234 | 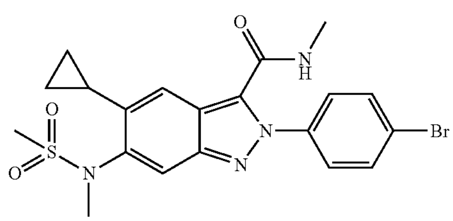 [SMILES: CNC(=O)c1c2cc(C3CC3)c(N(C)S(C)(=O)=O)cc2nn1-c1ccc(Br)cc1] | [M + H]+: 477.0/479.0/(400 MHz, CDCl$_3$) δ 7.77 (s, 1H), 7.75-7.64 (m, 2H), 7.59-7.44 (m, 3H), 5.89 (brs, 1H), 3.41 (s, 3H), 3.13 (s, 3H), 3.06 (d, J = 4.9 Hz, 3H), 2.54-2.32 (m, 1H), 1.23-0.79 (m, 3H), 0.63 (brs, 1H). | C |
| 235 | 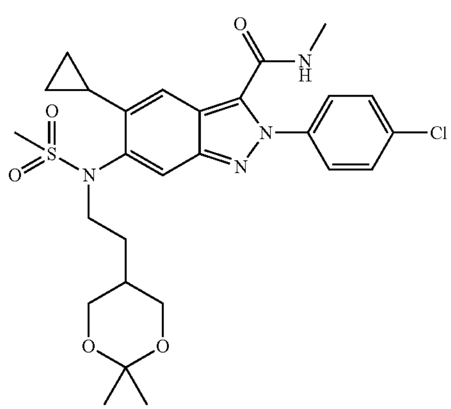 [SMILES: CNC(=O)c1c2cc(C3CC3)c(N(CCC3COC(C)(C)OC3)S(C)(=O)=O)cc2nn1-c1ccc(Cl)cc1] | [M + H]+: 560.9/(400 MHz, CDCl$_3$) δ 7.72 (s, 1H), 7.60-7.47 (m, 4H), 7.37 (s, 1H), 5.88-5.79 (m, 1H), 3.93-3.82 (m, 2H), 3.81-3.71 (m, 2H), 3.56 (td, J = 12.3, 8.2 Hz, 2H), 3.05 (s, 3H), 3.01 (d, J = 4.8 Hz, 3H), 2.46-2.33 (m, 1H), 1.96-1.71 (m, 1H), 1.67-1.55 (m, 2H), 1.39 (d, J = 4.6 Hz, 6H), 1.16-1.05 (m, 2H), 1.04-0.95 (m, 1H), 0.65-0.57 (m, 1H). | C |
| 236 | 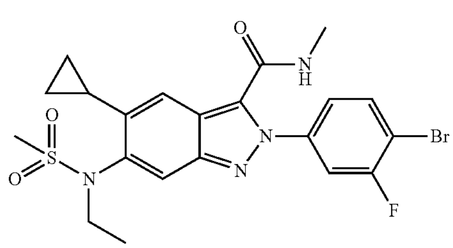 [SMILES: CCN(c1cc2nn(-c3ccc(Br)c(F)c3)c(C(=O)NC)c2cc1C1CC1)S(C)(=O)=O] | [M + H]+: 509.0/511.0/(400 MHz, CDCl$_3$) δ 7.83-7.67 (m, 2H), 7.48 (dd, J = 8.7, 2.3 Hz, 1H), 7.40-7.31 (m, 2H), 6.04 (brs, 1H), 3.95-3.77 (m, 2H), 3.11 (s, 3H), 3.09 (d, J = 4.9 Hz, 3H), 2.53-2.38 (m, 1H), 1.36-1.20 (m, 3H), 1.21-1.07 (m, 2H), 1.02 (m, 1H), 0.61 (brs, 1H). | C |

TABLE 1-continued

Compounds and their general method(s) of synthesis

| No. | Structure | Observed LCMS m/z [M + H]⁺/¹H NMR | Method |
|---|---|---|---|
| 237 | 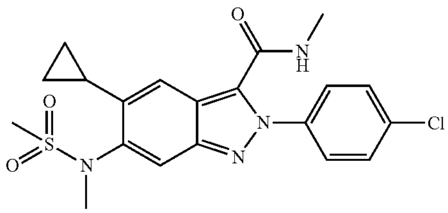 | [M + H]+: 433.0/(400 MHz, CDCl₃) δ 7.78 (d, J = 0.5 Hz, 1H), 7.60-7.52 (m, 4H), 7.50 (s, 1H), 5.87 (brs, 1H), 3.42 (s, 3H), 3.13 (s, 3H), 3.06 (d, J = 4.9 Hz, 3H), 2.54-2.33 (m, 1H), 1.17-1.03 (m, 2H), 0.99 (brs, 1H), 0.61 (brs, 1H). | C |
| 238 | 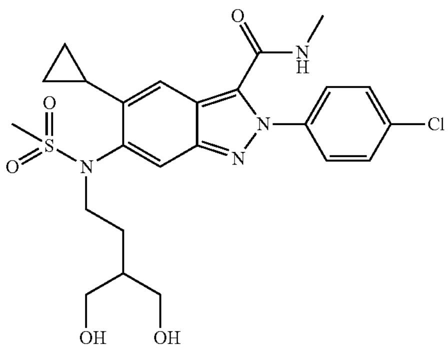 [SMILES: CNC(=O)c1c2cc(C3CC3)c(N(CCC(CO)CO)S(C)(=O)=O)cc2nn1-c1ccc(Cl)cc1] | [M + H]+: 520.9/(400 MHz, CDCl₃) δ 7.68 (s, 1H), 7.48 (s, 4H), 7.28 (s, 1H), 6.31-6.22 (m, 1H), 3.84-3.64 (m, 4H), 3.64-3.51 (m, 2H), 3.03 (s, 3H), 2.96 (d, J = 4.9 Hz, 3H), 2.76-2.64 (m, 2H), 2.37-2.27 (m, 1H), 1.77-1.69 (m, 1H), 1.69-1.52 (m, 2H), 1.10-0.97 (m, 2H), 0.97-0.86 (m, 1H), 0.62-0.53 (m, 1H). | N |
| 239 | 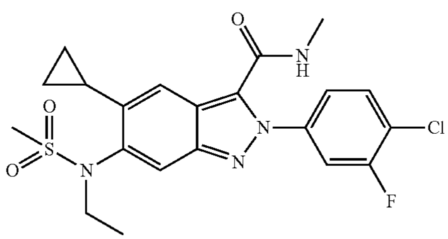 [SMILES: CCN(c1cc2nn(-c3ccc(Cl)c(F)c3)c(C(=O)NC)c2cc1C1CC1)S(C)(=O)=O] | [M + H]+: 465.0/(400 MHz, CDCl₃) δ 7.76 (s, 1H), 7.63-7.54 (m, 1H), 7.51 (dd, J = 9.1, 2.4 Hz, 1H), 7.39 (ddd, J = 8.6, 2.3, 1.2 Hz, 1H), 7.36 (s, 1H), 5.99 (brd, J = 4.0 Hz, 1H), 3.86 (qd, J = 7.1, 4.0 Hz, 2H), 3.11 (s, 3H), 3.10 (d, J = 4.9 Hz, 3H), 2.47 (dq, J = 8.4, 5.6 Hz, 1H), 1.28 (t, J = 7.2 Hz, 3H), 1.17-1.08 (m, 2H), 1.02 (dd, J = 14.3, 8.8 Hz, 1H), 0.61 (d, J = 5.0 Hz, 1H). | C |
| 240 | AND Enantiomer | [M + H]+: 430.1/(400 MHz, CDCl₃) δ 8.03 (s, 1H), 7.72 (s, 1H), 7.61-7.55 (m, 2H), 7.25-7.19 (m, 2H), 5.85-5.76 (m, 1H), 5.03 (dd, J = 11.5, 3.7 Hz, 1H), 3.00 (d, J = 4.9 Hz, 3H), 2.74 (s, 3H), 2.58 (dqd, J = 14.7, 7.4, 3.8 Hz, 1H), 2.31-2.17 (m, 1H), 2.16-2.07 (m, 1H), 1.11-1.05 (m, 2H), 1.02-0.94 (m, 1H), 0.97 (t, J = 7.4 Hz, 3H), 0.56-0.49 (m, 1H). | K |
| 241 | 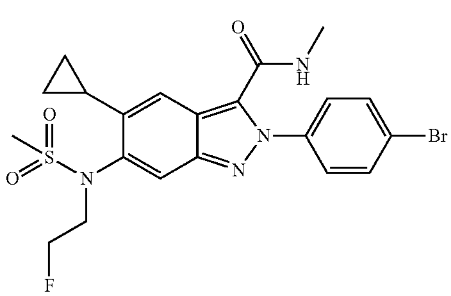 [SMILES: CNC(=O)c1c2cc(C3CC3)c(N(CCF)S(C)(=O)=O)cc2nn1-c1ccc(Br)cc1] | [M + H]+: 509.0/511.0/(400 MHz, CDCl₃) δ 7.78 (s, 1H), 7.70-7.63 (m, 2H), 7.50-7.45 (m, 2H), 7.43 (s, 1H), 5.81 (brd, J = 4.1 Hz, 1H), 4.62 (dd, J = 5.7, 3.7 Hz, 1H), 4.50 (dd, J = 7.6, 2.7 Hz, 1H), 4.48-4.31 (m, 1H), 3.74 (ddt, J = 33.8, 15.5, 3.0 Hz, 1H), 3.17 (s, 3H), 3.01 (d, J = 4.9 Hz, 3H), 2.47-2.27 (m, 1H), 1.12-0.98 (m, 3H), 0.59-0.50 (m, 1H). | C |

TABLE 1-continued

Compounds and their general method(s) of synthesis

| No. | Structure | Observed LCMS m/z [M + H]+/1H NMR | Method |
|---|---|---|---|
| 242 | 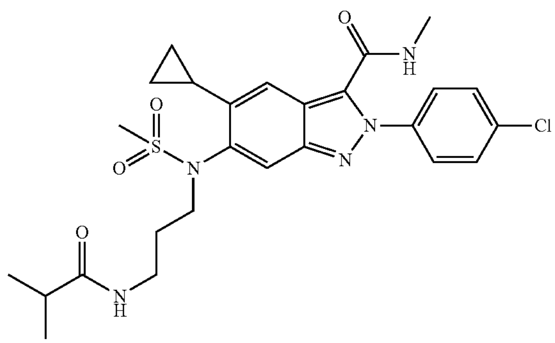 [SMILES: CNC(=O)c1c2cc(C3CC3)c(N(CCCNC(=O)C(C)C)S(C)(=O)=O)cc2nn1-c1ccc(Cl)cc1] | [M + H]+: 545.9/(400 MHz, CDCl3) δ 7.75 (s, 1H), 7.60-7.46 (m, 4H), 7.37 (s, 1H), 5.93 (t, J = 5.8 Hz, 1H), 5.79 (brd, J = 4.4 Hz, 1H), 3.95-3.65 (m, 2H), 3.57-3.26 (m, 2H), 3.06 (s, 3H), 3.00 (d, J = 4.9 Hz, 3H), 2.55-2.23 (m, 2H), 1.78 (p, J = 6.5 Hz, 2H), 1.16 (d, J = 6.9 Hz, 6H), 1.13-1.00 (m, 3H), 0.69-0.56 (m, 1H). | D then C |
| 243 | 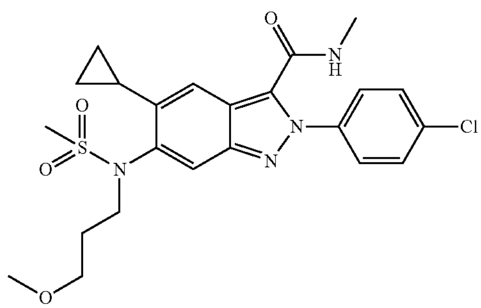 [SMILES: CNC(=O)c1c2cc(C3CC3)c(N(CCCOC)S(C)(=O)=O)cc2nn1-c1ccc(Cl)cc1] | [M + H]+: 491.0/(400 MHz, CDCl3) δ 7.77 (s, 1H), 7.62-7.50 (m, 4H), 7.40 (s, 1H), 5.85 (brd, J = 4.1 Hz, 1H), 3.88 (ddd, J = 8.3, 6.4, 4.6 Hz, 2H), 3.48 (t, J = 6.0 Hz, 2H), 3.33 (s, 3H), 3.11 (s, 3H), 3.05 (d, J = 4.9 Hz, 3H), 2.46 (tt, J = 8.4, 5.5 Hz, 1H), 2.03-1.80 (m, 2H), 1.20-0.96 (m, 3H), 0.82-0.58 (m, 1H). | C |
| 244 | 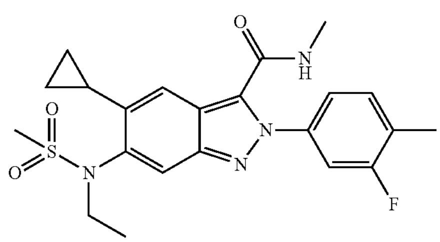 [SMILES: CCN(c1cc2nn(-c3ccc(C)c(F)c3)c(C(=O)NC)c2cc1C1CC1)S(C)(=O)=O] | [M + H]+: 445.0/(400 MHz, CDCl3) δ 7.75 (s, 1H), 7.67-7.48 (m, 1H), 7.48-7.31 (m, 3H), 5.88 (brs, 1H), 3.92-3.78 (m, 2H), 3.11 (s, 3H), 3.04 (d, J = 4.8 Hz, 3H), 2.50-2.33 (m, 1H), 2.41 (s, 3H), 1.28 (t, J = 7.1 Hz, 3H), 1.16-0.97 (m, 3H), 0.69-0.55 (m, 1H). | C (buchwald) |
| 245 | 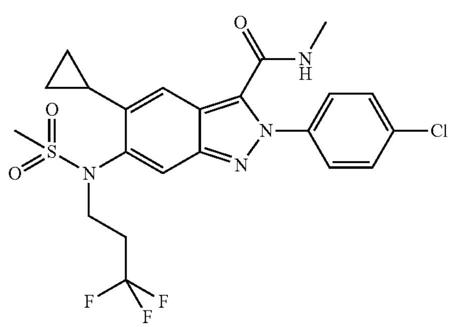 [SMILES: CNC(=O)c1c2cc(C3CC3)c(N(CCC(F)(F)F)S(C)(=O)=O)cc2nn1-c1ccc(Cl)cc1] | [M + H]+: 515.1/(400 MHz, CDCl3) δ 7.81 (s, 1H), 7.61-7.54 (m, 4H), 7.48 (s, 1H), 5.80 (brs, 1H), 4.13-4.00 (m, 2H), 3.13 (s, 3H), 3.05 (d, J = 4.9 Hz, 3H), 2.70-2.43 (m, 2H), 2.43-2.31 (m, 1H), 1.21-1.05 (m, 3H), 0.72-0.58 (m, 1H). | C |
| 246 | 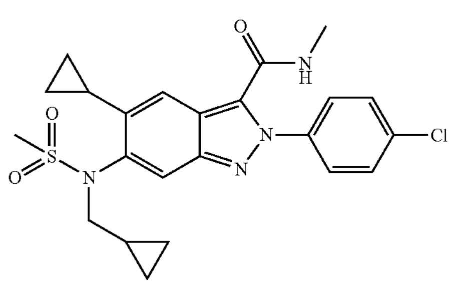 | [M + H]+: 473.1/(400 MHz, CDCl3) δ 7.84 (s, 1H), 7.64-7.51 (m, 4H), 7.42 (s, 1H), 5.86 (brs, 1H), 3.66 (ddd, J = 20.9, 14.2, 7.2 Hz, 2H), 3.16 (s, 3H), 3.06 (d, J = 4.9 Hz, 3H), 2.56-2.44 (m, 1H), 1.20-1.06 (m, 3H), 1.04-0.96 (m, 1H), 0.72-0.61 (m, 1H), 0.57 (d, J = 7.9 Hz, 2H), 0.30-0.21 (m, 2H). | C |

TABLE 1-continued

Compounds and their general method(s) of synthesis

| No. | Structure | Observed LCMS m/z [M + H]+/1H NMR | Method |
|---|---|---|---|
| 247 | 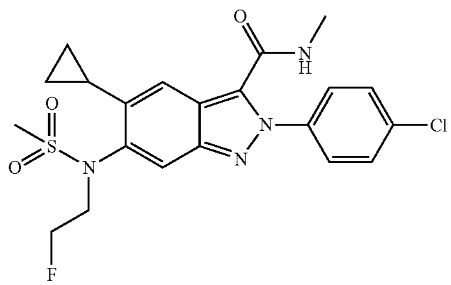 [SMILES: CNC(=O)c1c2cc(C3CC3)c(N(CCF)S(C)(=O)=O)cc2nn1-c1ccc(Cl)cc1] | [M + H]+: 465.1/(400 MHz, CDCl3) δ 7.78 (s, 1H), 7.57-7.46 (m, 4H), 7.44 (s, 1H), 5.81 (brd, J = 3.8 Hz, 1H), 4.62 (dd, J = 5.7, 3.7 Hz, 1H), 4.55-4.30 (m, 2H), 3.74 (ddt, J = 33.9, 15.4, 3.0 Hz, 1H), 3.17 (s, 3H), 3.01 (d, J = 4.9 Hz, 3H), 2.48-2.25 (m, 1H), 1.21-0.86 (m, 3H), 0.63-0.48 (m, 1H). | C |
| 248 | 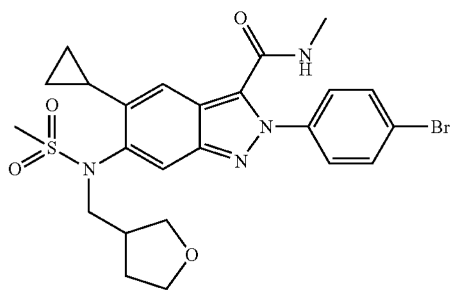 | [M + H]+: 559.0/561.0/(400 MHz, CDCl3) δ 7.81 (s, 0.5H), 7.77 (s, 0.5H), 7.74-7.69 (m, 2H), 7.54-7.50 (m, 2H), 7.39 (s, 1H), 5.81 (brs, 1H), 3.96-3.67 (m, 6H), 3.47 (dd, J = 8.9, 5.3 Hz, 0.5H), 3.09 (s, 3H), 3.05 (d, J = 4.9 Hz, 3H), 2.57-2.36 (m, 2H), 2.14-1.96 (m, 1H), 1.94-1.82 (m, 0.5H), 1.26-1.08 (m, 2H), 1.08-0.97 (m, 1H), 0.77-0.64 (m, 1H). | C |
| 249 | 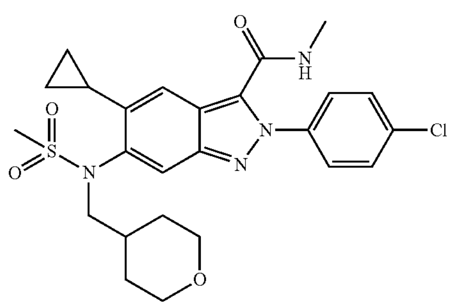 [SMILES: CNC(=O)c1c2cc(C3CC3)c(N(CC3CCOCC3)S(C)(=O)=O)cc2nn1-c1ccc(Cl)cc1] | [M + H]+: 517.1/(400 MHz, CDCl3) δ 7.79 (s, 1H), 7.64-7.51 (m, 4H), 7.39 (s, 1H), 5.84 (brd, J = 4.5 Hz, 1H), 4.10-3.90 (m, 2H), 3.79-3.60 (m, 2H), 3.39-3.28 (m, 2H), 3.07 (s, 3H), 3.04 (d, J = 4.9 Hz, 3H), 2.54-2.44 (m, 1H), 1.95-1.85 (m, 1H), 1.84-1.73 (m, 1H), 1.71-1.63 (m, 1H), 1.50-1.29 (m, 2H), 1.22-1.04 (m, 3H), 0.70-0.63 (m, 1H). | C |
| 250 | 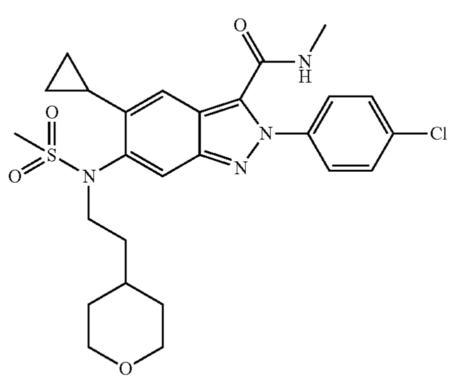 [SMILES: CNC(=O)c1c2cc(C3CC3)c(N(CCC3CCOCC3)S(C)(=O)=O)cc2nn1-c1ccc(Cl)cc1] | [M + H]+: 531.1/(400 MHz, CDCl3) δ 7.75 (s, 1H), 7.63-7.51 (m, 4H), 7.40 (s, 1H), 5.88 (brd, J = 4.5 Hz, 1H), 4.00-3.89 (m, 2H), 3.87-3.76 (m, 2H), 3.46-3.30 (m, 2H), 3.09 (s, 3H), 3.04 (d, J = 4.9 Hz, 3H), 2.52-2.39 (m, 1H), 1.71-1.49 (m, 5H), 1.39-1.20 (m, 2H), 1.20-0.99 (m, 3H), 0.70-0.58 (m, 1H). | C |

TABLE 1-continued

Compounds and their general method(s) of synthesis

| No. | Structure | Observed LCMS m/z [M + H]+/1H NMR | Method |
|---|---|---|---|
| 251 | 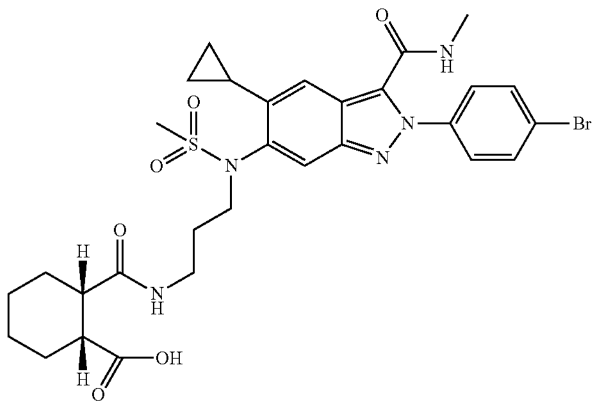 [SMILES: CNC(=O)c1c2cc(C3CC3)c(N(CCCNC(=O)[C@H]3CCCC[C@H]3C(=O)O)S(C)(=O)=O)cc2nn1-c1ccc(Br)cc1] | [M + H]+: 674.0/676.0/(400 MHz, CDCl3) δ 7.88 (s, 0.5H), 7.79 (s, 0.5H), 7.70 (d, J = 8.1 Hz, 2H), 7.53-7.48 (m, 2H), 7.38 (s, 1H), 6.36 (brd, J = 6.1 Hz, 1H), 6.08 (brs, 1H), 3.92-3.73 (m, 2H), 3.57-3.32 (m, 2H), 3.12 (d, J = 2.5 Hz, 3H), 3.04 (d, J = 4.8 Hz, 3H), 2.98-2.82 (m, 1H), 2.72-2.53 (m, 1H), 2.46-2.34 (m, 1H), 2.29-1.38 (m, 10H), 1.19-0.98 (m, 3H), 0.67-0.56 (m, 1H). | D |
| 252 | 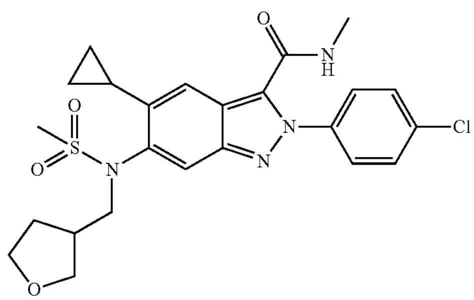 [SMILES: CNC(=O)c1c2cc(C3CC3)c(N(CC3CCOC3)S(C)(=O)=O)cc2nn1-c1ccc(Cl)cc1] | [M + H]+: 503.0/(400 MHz, CDCl3) δ 7.79 (d, J = 14.6 Hz, 1H), 7.64-7.50 (m, 4H), 7.39 (s, 1H), 5.82 (brs, 1H), 3.98-3.68 (m, 5H), 3.47 (dd, J = 8.9, 5.3 Hz, 1H), 3.09 (s, 3H), 3.05 (d, J = 4.9 Hz, 3H), 2.56-2.39 (m, 2H), 2.14-1.98 (m, 1H), 1.89 (dt, J = 20.1, 6.4 Hz, 1H), 1.24-1.09 (m, 2H), 1.09-1.00 (m, 1H), 0.74-0.67 (m, 1H). | C |
| 253 | 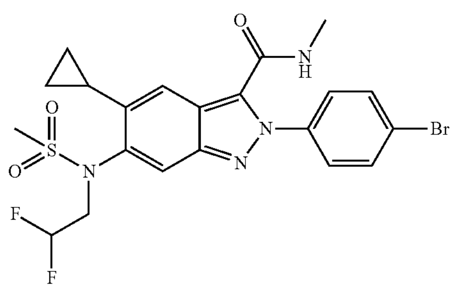 [SMILES: CNC(=O)c1c2cc(C3CC3)c(N(CC(F)F)S(C)(=O)=O)cc2nn1-c1ccc(Br)cc1] | [M + H]+: 527.0/529.0/(400 MHz, CDCl3) δ 7.79 (s, 1H), 7.71-7.60 (m, 2H), 7.52-7.39 (m, 3H), 6.18-5.81 (m, 1H), 5.78 (brd, J = 4.8 Hz, 1H), 4.36 (ddd, J = 18.8, 16.2, 5.2 Hz, 1H), 4.02-3.75 (m, 1H), 3.18 (s, 3H), 3.01 (d, J = 4.9 Hz, 3H), 2.40-2.07 (m, 1H), 1.22-0.93 (m, 3H), 0.69-0.42 (m, 1H). | C |
| 254 | 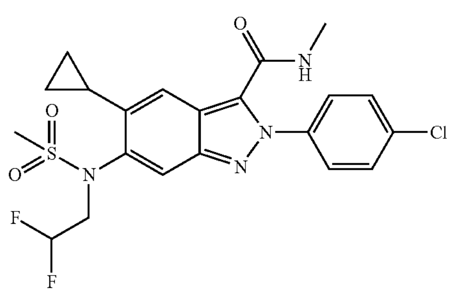 [SMILES: CNC(=O)c1c2cc(C3CC3)c(N(CC(F)F)S(C)(=O)=O)cc2nn1-c1ccc(Cl)cc1] | [M + H]+: 483.0/(400 MHz, CDCl3) δ 7.78 (s, 1H), 7.57-7.47 (m, 4H), 7.44 (s, 1H), 6.04 (dt, J = 55.5, 4.1 Hz, 1H), 5.87-5.75 (m, 1H), 4.54-4.17 (m, 1H), 4.03-3.75 (m, 1H), 3.18 (s, 3H), 3.00 (d, J = 4.9 Hz, 3H), 2.44-2.17 (m, 1H), 1.19-0.96 (m, 3H), 0.72-0.43 (m, 1H). | C |
| 255 | 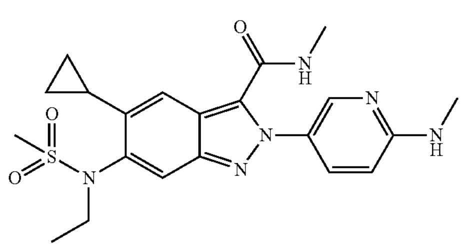 [SMILES: CCN(c1cc2nn(-c3ccc(NC)nc3)c(C(=O)NC)c2cc1C1CC1)S(C)(=O)=O] | [M + H]+: 443.1/(400 MHz, CDCl3) δ 8.16 (d, J = 2.2 Hz, 1H), 7.87 (dd, J = 9.3, 2.4 Hz, 1H), 7.69 (s, 1H), 7.34 (s, 1H), 6.75-6.51 (m, 2H), 6.10 (brs, 1H), 3.89-3.72 (m, 2H), 3.08 (s, 3H), 3.06-3.00 (m, 6H), 2.46-2.35 (m, 1H), 1.23 (t, J = 7.1 Hz, 3H), 1.12-0.95 (m, 3H), 0.63-0.53 (m, 1H). | R |

TABLE 1-continued

Compounds and their general method(s) of synthesis

| No. | Structure | Observed LCMS m/z [M + H]+/1H NMR | Method |
|---|---|---|---|
| 256 | 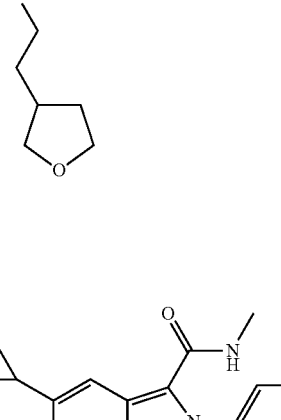 | [M + H]+: 560.9/562.9/(400 MHz, CDCl3) δ 7.67 (d, J = 3.1 Hz, 1H), 7.60 (d, J = 8.8 Hz, 2H), 7.41 (d, J = 8.8 Hz, 2H), 7.31 (s, 1H), 5.75-5.65 (brm, 1H), 3.84-3.59 (m, 5H), 3.28-3.18 (m, 1H), 2.98 (s, 3H), 2.94 (d, J = 4.7 Hz, 3H), 2.40-2.29 (m, 1H), 2.22-2.10 (m, 1H), 2.06-1.91 (m, 1H), 1.77-1.54 (m, 2H), 1.45-1.34 (m, 1H), 1.07-0.98 (m, 2H), 0.97-0.90 (m, 1H), 0.58-0.49 (m, 1H). | C |
| 257 | 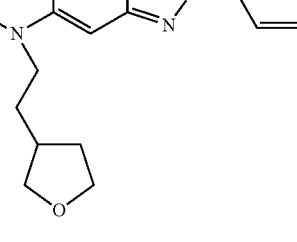 | [M + H]+: 517.0/(400 MHz, CDCl3) δ 7.76 (d, J = 3.5 Hz, 1H), 7.62-7.52 (m, 4H), 7.41 (s, 1H), 5.94-5.80 (brm, 1H), 3.95-3.69 (m, 5H), 3.39-3.30 (m, 1H), 3.09 (s, 3H), 3.04 (d, J = 4.9 Hz, 3H), 2.51-2.40 (m, 1H), 2.33-2.21 (m, 1H), 2.17-2.02 (m, 1H), 1.88-1.64 (m, 2H), 1.58-1.46 (m, 1H), 1.19-1.09 (m, 2H), 1.07-0.99 (m, 1H), 0.68-0.60 (m, 1H). | C |
| 258 | 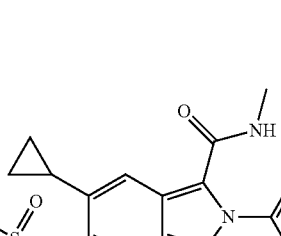 | [M + H]+: 545.0/547.0/(400 MHz, CDCl3) δ 7.75 (s, 1H), 7.69-7.65 (m, 2H), 7.51-7.46 (m, 2H), 7.44 (s, 1H), 5.76 (br s, 1H), 4.06 (dq, J = 14.4, 7.2 Hz, 1H), 3.84 (dq, J = 14.3, 7.3 Hz, 1H), 3.01 (d, J = 4.9 Hz, 3H), 2.24-2.13 (m, 1H), 1.30-1.21 (m, 3H), 1.19-1.06 (m, 2H), 1.04-0.95 (m, 1H), 0.73-0.64 (m, 1H). | A then C |
| 259 | 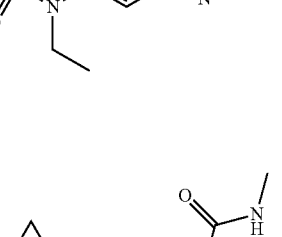 | [M + H]+: 501.1/503.1/(400 MHz, CDCl3) δ 7.75 (s, 1H), 7.59-7.48 (m, 4H), 7.44 (s, 1H), 5.75 (br s, 1H), 4.06 (dq, J = 14.3, 7.2 Hz, 1H), 3.84 (dq, J = 14.4, 7.3 Hz, 1H), 3.00 (d, J = 4.9 Hz, 3H), 2.24-2.13 (m, 1H), 1.31-1.22 (m, 3H), 1.19-1.06 (m, 2H), 1.04-0.95 (m, 1H), 0.74-0.65 (m, 1H). | A then C |

TABLE 1-continued

Compounds and their general method(s) of synthesis

| No. | Structure | Observed LCMS m/z [M + H]+/1H NMR | Method |
|---|---|---|---|
| 260 | (structure) | [M + H]+: 527.0/529.0 | A then C |

[1] Using o-fluorophenol in step a;
[2] using 2-bromoethanol in step a and p-fluoroaniline in step b;
[3] using bromoethane in step a;
[4] using p-fluoroaniline in step b;
[5] using bromoethane in step a and p-fluoroaniline or o-fluorophenol in step b;
[6] using bromoethane in step a and p-fluorophenol in step b;
[7] using 2-bromoethanol in step a and aniline in step b;
[8] using o-fluorophenol or p-fluorophenol in step b;
[9] using 5-cyclopropyl-6-{[2-(1,3-dioxo-1,3-dihydro-2H-isoindol-2-yl)ethyl](methylsulfonyl)amino}-2-{4-[(4-fluorophenyl)amino]phenyl}-N-methyl-2H-indazole-3-carboxamide as starting material in step b;
[10] using 2-(4-fluorophenyl)-N-methyl-6-[(methylsulfonyl)amino]-2H-indazole-3-carboxamide as starting material;
[11] using 2-bromoethanol in step a and 3-benzyloxyaniline in step b followed by benzyl deprotection;
[12] using 2-bromoethanol in step a and 3-benzyloxyaniline in step b;
[13] using 2-bromoethanol in step a and phenol in step b;
[14] from step b, using 6-[2-acetamidoethyl(methylsulfonyl)amino]-2-(4-bromophenyl)-5-cyclopropyl-N-methyl-indazole-3-carboxamide as starting material;
[15] using acetic acid in step c;
[16] using bromoethane in step a and isopropylamine in step b;
[17] using iodomethane in step b;
[18] using 4-bromobutyronitrile in step b Biological Data
HCV Polymerase Inhibition Assay HCV polymerase reactions were carried out using a modified method of Howe et al., *Antimicrobial Agents and Chemotherapy* 2004 48(12): 4813-4821. Reactions contained a final concentration of, 0.5% DMSO, 50 nM, 1b (BK) NS5bΔ21, 20 mM Tris-HCl pH 7.5, 5 mM MgCl$_2$, 5 mM MnCl$_2$, 3 mM DTT, 0.05% BSA, 0.2 U/μL RNasin, 10 μg/mL Poly(rC) template, GTP (at Km) and 0.05 μCi/μL $^{33}$P-GTP in a total reaction volume of 50 μL. Compounds were tested in a three fold dilution series, for example starting from 50 μM. Reactions were initiated with the addition of GTP and terminated after 1 hour with 50 μL ice cold 0.2 M EDTA. Terminated reactions were transferred to DEAE 96-well filter plates, unincorporated nucleotides washed from the filters and 50 μL scintillation fluid added prior to reading on a scintillation counter. Similarly, a genotype 3a (VRL-69) NS5bΔ21 polymerase enzyme assay was conducted using essentially the same method.

The compound concentration that reduced $^{33}$P-GTP incorporation by 50% (IC$_{50}$) was calculated using non-linear regression.

Representative 1b polymerase IC$_{50}$ (μM) values for selected compounds of the invention in the HCV polymerase inhibition assay are listed as follows where IC$_{50}$ (μM) values lie in the ranges:

| A: <0.99 μM | | | | | | | | | | | |
|---|---|---|---|---|---|---|---|---|---|---|---|
| 4 | 5 | 8 | 9 | 19 | 20 | 21 | 22 | 23 | 24 | 25 | 26 |
| 27 | 28 | 29 | 30 | 31 | 52 | 54 | 56 | 57 | 58 | 59 | 61 |
| 62 | 63 | 64 | 65 | 66 | 67 | 68 | 69 | 70 | 88 | 89 | 90 |
| 92 | 93 | 94 | 95 | 96 | 97 | 98 | 99 | 100 | 101 | 102 | 108 |
| 110 | 112 | 113 | 115 | 116 | 117 | 118 | 119 | 120 | 131 | 133 | 134 |
| 135 | 138 | 140 | 143 | 146 | 147 | 148 | 149 | 150 | 151 | 152 | 153 |
| 154 | 155 | 156 | 160 | 161 | 164 | 166 | 167 | 168 | 169 | 170 | 171 |
| 172 | 173 | 174 | 175 | 176 | 177 | 178 | 179 | 180 | 181 | 182 | 183 |
| 184 | 186 | 187 | 188 | 189 | 190 | 191 | 193 | 194 | 196 | 197 | 198 |
| 200 | 201 | 202 | 204 | 205 | 206 | 207 | 208 | 209 | 211 | 212 | 213 |
| 214 | 215 | 216 | 217 | 218 | 219 | 220 | 222 | 223 | 224 | 229 | 230 |
| 231 | 233 | 234 | 235 | 236 | 237 | 238 | 239 | 241 | 242 | 243 | 244 |
| 245 | 246 | 247 | 248 | 249 | 250 | 251 | 252 | 253 | 254 | 255 | 256 |

-continued

| B: 1.0-9.99 μM | | | | | | | | | | | |
|---|---|---|---|---|---|---|---|---|---|---|---|
| 3 | 15 | 18 | 35 | 36 | 37 | 38 | 50 | 53 | 55 | 60 | 71 |
| 72 | 75 | 79 | 91 | 103 | 106 | 107 | 111 | 114 | 121 | 122 | 123 |
| 124 | 126 | 128 | 132 | 136 | 139 | 141 | 144 | 145 | 157 | 162 | 165 |
| 185 | 192 | 195 | 199 | 210 | 225 | 232 | 257 | 258 | | | |
| C: 10.0-49.99 | | | | | | | | | | | |
| 1 | 14 | 33 | 105 | 125 | 127 | 48 | 129 | 104 | 137 | 78 | 142 |
| 77 | 158 | 73 | 163 | 76 | 74 | 51 | 203 | 83 | 221 | 226 | 240 |
| 85 | 86 | | | | | | | | | | |

HCV Replicon Assays

A genotype 1b (Con 1) subgenomic replicon cell line based on Blight et al., Science 2000 290: 1972-1974, modified to express a Renilla luciferase reporter gene was used to assess antiviral activity of test compounds. Cell cultures were maintained in a sub-confluent state in DMEM with glutamine, 10% heat-inactivated foetal bovine serum (FBS) and G418 (Geneticin®).

For assay, cells were seeded at a density of 7000 cells/well into 96 well tissue culture trays in culture media lacking G418. Compounds were tested in a three fold dilution series, for example starting from 50 uM. After 72 hours incubation at 37° C. and 5% $CO_2$, Renilla luciferase activity was quantified via the Promega Renilla Luciferase or Renilla-Glo™ Luciferase Assay Systems (Promega corporation. The same method was employed for replicon assays using subgenomic genotype 1a and 2a replicon cell lines with a seeding cell density of 5000 cells/well for the 2a cell lines.

The compound concentration that reduced luciferase activity by 50% ($EC_{50}$) was calculated using non-linear regression. Representative genotype 1b $EC_{50}$ values for selected compounds of the invention are listed as follows where $EC_{50}$ (μM) values lie in the ranges:

Cytotoxicity Analysis

Cytotoxicity of compounds against genotype 1b replicon cells was determined via metabolism of the vital dye 3-(4,5-dimethylthiaxol-2-yl)-2,5-diphenyltetrazolium bromide (MTT, for example see Watanabe et al., Journal of Virological Methods 1994 48:257-265). Plates were prepared as described for the HCV Replicon assay and cytotoxicity of the test article was evaluated after three days. MTT was added to assay plates followed by three hour incubation at 37° C. Wells were aspirated to dryness and the formazan dye dissolved by the addition of isopropanol. Absorbance values were read at 540/690 nm). The compound concentration that reduced cell viability by 50% ($CC_{50}$) was calculated using non-linear regression. In general, compounds of the invention displayed low cytotoxicity with $CC_{50}$ values of >50 μM.

Cross-Genotype HCV Activity

Compounds of the invention were tested in HCV replicon assays for genotype 1b, 1a and 2a and in HCV polymerase assays for genotype 1b and 3a as previously described. Results obtained for representative compounds of the invention across four major HCV genotypes are provided in Table 2.

| A: <0.99 μM | | | | | | | | | | | |
|---|---|---|---|---|---|---|---|---|---|---|---|
| 3 | 4 | 5 | 9 | 19 | 20 | 21 | 22 | 23 | 24 | 25 | 26 |
| 27 | 28 | 29 | 30 | 35 | 38 | 52 | 53 | 54 | 56 | 57 | 59 |
| 62 | 63 | 64 | 65 | 66 | 69 | 88 | 92 | 95 | 96 | 98 | 99 |
| 100 | 110 | 111 | 112 | 113 | 116 | 117 | 118 | 119 | 120 | 122 | 123 |
| 131 | 134 | 135 | 136 | 138 | 140 | 156 | 160 | 161 | 164 | 166 | 167 |
| 168 | 169 | 170 | 171 | 172 | 173 | 174 | 175 | 177 | 179 | 180 | 181 |
| 183 | 186 | 188 | 189 | 190 | 191 | 192 | 194 | 197 | 199 | 200 | 201 |
| 202 | 204 | 205 | 206 | 209 | 212 | 213 | 214 | 215 | 216 | 220 | 222 |
| 223 | 225 | 230 | 231 | 232 | 233 | 234 | 235 | 236 | 237 | 239 | 241 |
| 242 | 243 | 244 | 245 | 246 | 247 | 248 | 249 | 250 | 251 | 252 | 253 |
| 254 | 255 | 256 | 257 | | | | | | | | |
| B: 1.0-9.99 μM | | | | | | | | | | | |
| 1 | 14 | 18 | 36 | 37 | 48 | 50 | 51 | 55 | 60 | 61 | 67 |
| 70 | 71 | 72 | 73 | 74 | 76 | 77 | 78 | 79 | 80 | 83 | 86 |
| 91 | 93 | 94 | 97 | 101 | 102 | 104 | 105 | 106 | 107 | 108 | 114 |
| 115 | 124 | 125 | 126 | 127 | 128 | 129 | 133 | 142 | 143 | 144 | 145 |
| 146 | 147 | 148 | 151 | 155 | 162 | 163 | 165 | 176 | 178 | 182 | 184 |
| 185 | 187 | 193 | 196 | 198 | 207 | 210 | 211 | 217 | 218 | 219 | 221 |
| 224 | 226 | 238 | 258 | | | | | | | | |
| C: 10.0-49.99 μM | | | | | | | | | | | |
| 8 | 12 | 58 | 68 | 75 | 84 | 85 | 89 | 90 | 130 | 132 | 139 |
| 141 | 149 | 150 | 152 | 153 | 154 | 157 | 159 | 195 | 203 | 208 | 227 |
| 229 | 240 | | | | | | | | | | |

TABLE 2

Cross-genotype HCV assay results for representative compounds of the invention

| Compound Example No. | 1b NS5b polymerase IC$_{50}$ (µM) | Replicon 1b EC$_{50}$ (µM) | Replicon 2a EC$_{50}$ (µM) | Replicon 1a EC$_{50}$ (µM) | 3a NS5b polymerase IC$_{50}$ (µM) |
|---|---|---|---|---|---|
| 4 | 0.17 | 0.09 | 0.94 | 0.21 | 0.01 |
| 5 | 0.07 | 0.13 | 0.32 | 0.05 | 0.04 |
| 21 | 0.04 | 0.46 | 0.34 | 0.29 | 0.04 |
| 22 | 0.11 | 0.07 | 0.34 | 0.38 | 0.02 |
| 28 | 0.12 | 0.10 | 0.20 | 0.74 | 0.02 |
| 54 | 0.36 | 0.10 | 1.03 | 0.30 | 0.02 |
| 59 | 0.26 | 0.67 | 1.43 | 0.30 | 0.05 |
| 62 | 0.18 | 0.17 | 2.86 | 0.08 | 0.05 |
| 66 | 0.32 | 0.12 | 0.36 | 0.02 | 0.08 |
| 95 | 0.07 | 0.05 | 0.18 | 0.07 | 0.04 |
| 98 | 0.10 | 0.08 | 0.46 | 0.16 | 0.03 |
| 99 | 0.09 | 0.07 | 1.08 | 0.43 | 0.02 |
| 111 | 1.17 | 0.34 | 2.05 | 2.92 | 0.26 |
| 112 | 0.41 | 0.13 | 2.73 | 1.90 | 0.04 |
| 117 | 0.43 | 0.07 | 0.15 | 0.34 | 0.07 |
| 119 | 0.13 | 0.24 | 2.70 | 1.20 | 0.03 |
| 120 | 0.11 | 0.09 | 14.38 | 3.69 | 0.08 |
| 131 | 0.37 | 0.14 | 3.79 | 0.45 | 0.47 |
| 134 | 0.09 | 0.11 | 5.02 | 0.54 | 0.03 |
| 136 | 1.55 | 0.27 | 1.80 | 1.53 | 0.82 |
| 156 | 0.25 | 0.21 | 1.51 | 0.21 | 0.07 |
| 160 | 0.07 | 0.09 | 0.78 | 0.34 | 0.04 |
| 164 | 0.52 | 0.21 | 0.62 | 0.01 | 0.04 |
| 166 | 0.16 | 0.02 | 0.34 | 0.02 | 0.03 |
| 171 | 0.31 | 0.21 | 4.26 | 0.28 | 0.04 |
| 172 | 0.11 | 0.06 | 1.83 | 0.06 | 0.04 |
| 174 | 0.13 | 0.11 | 1.73 | 0.06 | 0.03 |
| 175 | 0.10 | 0.06 | 0.08 | 0.26 | 0.03 |
| 177 | 0.28 | 0.07 | 0.31 | 0.11 | 0.06 |
| 179 | 0.26 | 0.07 | 0.52 | 0.18 | 0.03 |
| 180 | 0.37 | 0.14 | 1.11 | 0.57 | 0.05 |
| 189 | 0.13 | 0.03 | 0.23 | 0.08 | 0.05 |
| 190 | 0.83 | 0.07 | 0.43 | 0.09 | 0.04 |
| 191 | 0.43 | 0.19 | 2.59 | 0.40 | 0.02 |
| 200 | 0.22 | 0.17 | 1.05 | 0.65 | 0.04 |
| 216 | 0.18 | 0.04 | 0.68 | 0.13 | 0.02 |
| 234 | 0.14 | 0.08 | 0.42 | 0.24 | 0.02 |
| 235 | 0.09 | 0.04 | 0.14 | 0.28 | 0.03 |

Combination Studies in Replicon Cells

A genotype 1b (Con 1) subgenomic replicon cell line based on Blight et al., *Science* 2000 290: 1972-1974, modified to express a Renilla luciferase reporter gene was used to assess synergy of test compounds. Cell cultures were maintained in a sub-confluent state in DMEM with glutamine, 10% heat-inactivated foetal bovine serum (FBS) and G418 (Geneticin®).

For assay, cells were seeded at a density of 7000 cells/well into 96 well tissue culture trays in culture media lacking G418. The compound concentration that reduced luciferase activity by 50% (EC$_{50}$) was determined independently for each compound and used to set the range of concentrations for the combination experiments. Each compound was tested singly and in combination using 3-fold serial dilutions above and below the EC$_{50}$. The ratio of the 2 compounds tested remained fixed across the titration range. Cytotoxicity of individual compounds was assessed independently and the titration range was below the compound concentration that reduced cell viability by 50% (CC$_{50}$). After 72 hours incubation at 37° C. and 5% CO$_2$, Renilla luciferase activity was quantified via the Promega Renilla Luciferase Assay System.

Figure 2:
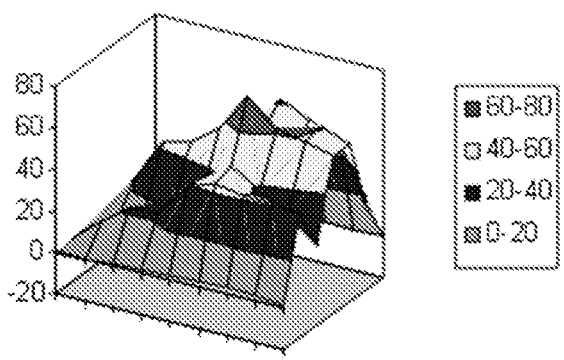
FIG. 2 is a 3D synergy plot which shows the synergistic activity of Compound 175 in combination with a NS3/4a protease inhibitor (VX-950, telaprevir) in accordance with an embodiment of the invention where the Z axis represents the percentage replicon inhibition for the combination with the compounds being represented on the X and Y axis.
Figure 3:
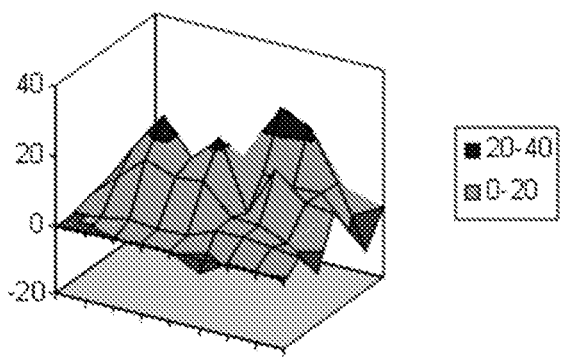
FIG. 3 is a 3D synergy plot which shows the synergistic activity of Compound 175 in combination with a NS5a inhibitor (BMS-790052, daclatasvir) in accordance with an embodiment of the invention where the Z axis represents the percentage replicon inhibition for the combination with the compounds being represented on the X and Y axis.

Results were analysed and levels of synergy assessed via generation of 3D synergy plots using MacSynergy™ II (Prichard, M. N., K. R. Aseltine, and C. Shipman, Jr. 1993. MacSynergy II. Version 1.0. User's manual. University of Michigan, Ann Arbor.). Combinations of an inhibitor of the invention and an HCV inhibitor targeting a different viral protein, or with a different mechanism of inhibiting the NS5b polymerase, were demonstrated to be strongly synergistic. Compound 175 was selected as a representative example of the compounds of the invention for synergistic studies. The 3D synergy plots shown in FIGS. 1, 2 and 3 represent statistically significant synergy (95% confidence intervals) for different binary combinations of Compound 175 and a nucleoside NS5b inhibitor (FIG. 1), a NS3/4a protease inhibitor (FIG. 2) and an NS5a inhibitor (FIG. 3). None of the compounds showed cytotoxicity in the concentration range tested in the combination experiments.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication, or information derived from it, or to any matter which is know, is not, and should not be taken as an acknowledgement or admission or any form of suggestion that that prior publication, or information derived from it, or known matter forms part of the common general knowledge in the field of endeavour to which this specification relates.

The invention claimed is:

1. A compound of formula (I), salts, N-oxides, solvates, hydrates, racemates, or enantiomers thereof:

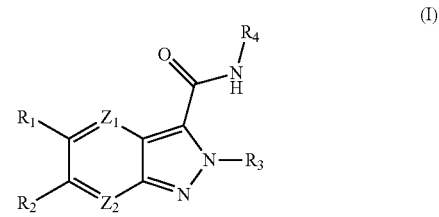

(I)

$Z_1$ and $Z_2$ are each independently selected from C—H, C-halo, C—C$_{1-4}$alkyl, C—C$_{1-4}$alkylhalo, C—C$_{1-4}$alkoxy, C—C$_{1-4}$alkoxyhalo and N;

$R_1$ is selected from H, C$_{1-6}$alkyl, C$_{2-6}$alkenyl, C$_{2-6}$alkynyl, C$_{1-6}$alkoxy, halo, C$_{1-4}$alkylhalo, C$_{1-4}$alkoxyhalo, C$_{3-7}$cycloalkyl, C$_{3-7}$cycloalkenyl, 5-6-membered heterocyclyl and 5-6 membered heteroaryl and wherein alkyl, alkenyl, alkynyl, alkoxy, cycloalkyl, heterocyclyl and heteroaryl in each occurrence may be optionally substituted;

$R_2$ is selected from halo, C$_{1-6}$alkyl, C$_{2-6}$alkenyl, NO$_2$, N(R$_5$)$_2$, NR$_5$R$_6$, NR$_6$(SO$_2$R$_5$), SO$_2$N(R$_8$)$_2$, SR$_8$, C(R$_5$)$_2$SO$_2$R$_8$, and NR$_5$C(=O)R$_8$;

$R_3$ is selected from aryl, aryl-X-aryl, aryl-X-heteroaryl, heteroaryl, heteroaryl-X-heteroaryl, and heteroaryl-X-aryl wherein X is [C(R$_5$)$_2$]$_p$, O, S, S(=O), SO$_2$, NR$_5$, C=O, CF$_2$, C(=O)NR$_5$ or NR$_5$C(=O) wherein p is 1, 2 or 3 and wherein aryl and heteroaryl in each occurrence may be optionally substituted;

$R_4$ is H, C$_{1-4}$alkyl, C$_{2-4}$alkenyl, C$_{2-4}$alkynyl, or C$_{3-7}$cycloalkyl;

$R_5$ in each occurrence is independently H or optionally substituted C$_{1-6}$alkyl;

$R_6$ is selected from H, C$_{1-6}$alkyl, C$_{2-6}$alkenyl, C$_{2-6}$alkynyl, C$_{1-6}$alkoxy, C$_{1-6}$alkylhalo, C$_{1-6}$alkoxyhalo, R$_8$, C$_{1-6}$alkyl-R$_8$, C$_{1-6}$alkyl-OR$_8$, C$_{1-6}$alkyl-SR$_8$, C$_{1-6}$alkyl-S(=O)R$_8$, C$_{1-6}$alkyl-SO$_2$R$_8$, C$_{1-6}$alkyl-N(R$_8$)$_2$, $C_{1-6}$alkyl-C(=O)-$R_8$, $C_{1-6}$alkyl-O(C=O)—$R_8$, $C_{1-6}$alkyl-C(=O)O—$R_8$, $C_{1-6}$alkyl-C(=O)N($R_8$)$_2$, $C_{1-6}$alkyl-NR$_5$C(=O)—$R_8$, $C_{1-6}$alkyl-NR$_5$SO$_2$—$R_8$, $C_{1-6}$alkyl-SO$_2$NR$_5$—$R_8$ and $C_{1-6}$alkyl-C(=O)NR$_5$SO$_2$R$_8$ and wherein alkyl, alkenyl, alkynyl, alkoxy, aryl, cycloalkyl, heterocyclyl and heteroaryl in each occurrence of $R_6$ may be optionally substituted;

$R_8$ in each occurrence is independently H, an optionally substituted $C_{1-6}$alkyl, an optionally substituted $C_{2-6}$alkenyl, an optionally substituted ($C_{1-6}$alkyl)$_q$-aryl, an optionally substituted ($C_{1-6}$alkyl)$_q$-$C_{3-7}$cycloalkyl, an optionally substituted ($C_{1-6}$alkyl)$_q$-5-6-membered heterocyclyl or an optionally substituted ($C_{1-6}$alkyl)$_q$-5-6-membered heteroaryl; and q is 0 or 1.

2. A compound according to claim 1, wherein $Z_1$ and $Z_2$ are each C—H.

3. A compound according to claim 1, wherein $R_1$ is H.

4. A compound according to claim 1, wherein $R_1$ is selected from optionally substituted $C_{1-6}$alkyl, optionally substituted $C_{2-3}$alkenyl, optionally substituted $C_{2-3}$alkynyl, optionally substituted $C_{1-3}$alkoxy, halo, $C_{1-3}$alkylhalo, $C_{1-3}$alkoxyhalo, optionally substituted 5-6-membered heterocyclyl, optionally substituted 5-6 membered heteroaryl, $C_{5-6}$cycloalkenyl and $C_{3-6}$cycloalkyl.

5. A compound according to claim 4, wherein $R_1$ is cyclopropyl.

6. A compound according to claim 1, wherein $R_2$ is selected from NR$_6$(SO$_2$R$_5$), SO$_2$N(R$_8$)$_2$, C(R$_5$)$_2$SO$_2$R$_8$ and NR$_5$C(=O)R$_8$.

7. A compound according to claim 6, wherein $R_2$ is NR$_6$(SO$_2$R$_5$) and $R_5$ is $C_{1-6}$alkyl or $C_{1-3}$alkyl substituted with halo.

8. A compound according to claim 6 wherein $R_6$ is optionally substituted $C_{1-6}$alkyl.

9. A compound according to claim 8, wherein $R_6$ is —(CH$_2$)$_n$—$R_{10}$ wherein n is an integer selected from 0, 1, 2 or 3 and $R_{10}$ is selected from H, $C_{1-3}$alkyl, $C_{2-3}$alkenyl, $C_{1-3}$alkoxy, halo, $C_{1-3}$haloalkyl, $C_{1-3}$haloalkoxy, OH, OR$_{11}$, $C_{1-3}$alkylOH, CH($C_{1-3}$alkylOH)$_2$, CO$_2$H, CH(CO$_2$H)$_2$, CO$_2$R$_{11}$, CH(CO$_2$C$_{1-3}$alkyl)$_2$, OC(=O)H, OC(=O)R$_{11}$, SR$_{11}$, S(=O)R$_{11}$, SO$_2$R$_{11}$, SO$_2$NH$_2$, SO$_2$NHR$_{11}$, SO$_2$N(R$_{11}$)$_2$, NHSO$_2$R$_{11}$, NR$_{11}$SO$_2$R$_{11}$, CN, NH$_2$, NHR$_{11}$, N(R$_{11}$)$_2$, NHC(=O)H, NHC(=O)R$_{11}$, NR$_{11}$C(=O)R$_{11}$, C(=O)NH$_2$, C(=O)NHR$_{11}$, C(=O)N(R$_{11}$)$_2$, C(=O)NHSO$_2$R$_{11}$, C(=O)NR$_{11}$SO$_2$R$_{11}$, $C_{3-7}$cycloalkyl, aryl, heterocyclyl and heteroaryl; wherein each $R_{11}$ is independently selected from $C_{1-3}$alkyl, $C_{3-6}$cycloalkyl, $C_{3-6}$cycloalkenyl, phenyl, $C_{1-3}$alkylphenyl, 5-6-membered heterocyclyl, 5-6 membered heteroaryl and $C_{1-3}$alkyl 5-6-membered heteroaryl; and wherein each alkyl, cycloalkyl, aryl, heterocyclyl, heteroaryl or —(CH$_2$)— moiety when present may be further optionally substituted.

10. A compound according to claim 1, wherein $R_3$ is optionally substituted and is selected from phenyl, phenyl-X-phenyl, phenyl-X-heteroaryl, heteroaryl, heteroaryl-X-heteroaryl, and heteroaryl-X-phenyl wherein heteroaryl is a 6-membered heteroaryl.

11. A compound according to claim 1, wherein X is O, S or NR$_5$.

12. A compound according to claim 1, wherein $R_4$ is $C_{1-3}$alkyl.

13. A compound according to claim 1, which is a compound of formula (Ia), salts, N-oxides, solvates, hydrates, racemates, or enantiomers thereof

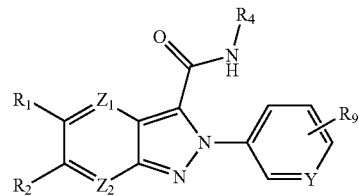

(Ia)

wherein
$Z_1$ and $Z_2$ are each CH;
Y is CH or N;
$R_1$ is H, $C_{3-6}$cycloalkyl, $C_{1-6}$alkyl, halo or $C_{1-6}$alkoxy;
$R_2$ is NR$_6$(SO$_2$R$_5$), SO$_2$N(R$_8$)$_2$, C(R$_5$)$_2$SO$_2$, or NR$_5$C(=O)R$_8$;
$R_6$ is selected from H, optionally substituted $C_{1-6}$alkyl and optionally substituted 5-6-membered heterocyclyl;
$R_5$ is H or optionally substituted $C_{1-6}$alkyl;
$R_8$ is H or optionally substituted $C_{1-6}$alkyl;
$R_9$ is H or one or more substituents independently selected from halo, $C_{1-6}$alkyl, $C_{2-6}$alkenyl, $C_{1-3}$alkylhalo, $C_{1-6}$alkoxy, $C_{1-6}$alkylamino, $C_{3-6}$cycloalkyl and X-optionally substituted phenyl; and
X is O or NR$_5$.

14. A compound according to claim 1 selected from the group consisting of:
1) 2-(4-bromophenyl)-5-cyclopropyl-N-methyl-6-[(methylsulfonyl)amino]-2H-indazole-3-carboxamide;
2) 5-cyclopropyl-2-[4-(4-fluorophenoxy)phenyl]-N-methyl-6-[(methylsulfonyl)amino]-2H-indazole-3-carboxamide;
3) 5-cyclopropyl-2-[4-(4-fluorophenoxy)phenyl]-6-[(2-hydroxyethyl)(methylsulfonyl)amino]-N-methyl-2H-indazole-3-carboxamide;
4) 2-(4-bromophenyl)-5-cyclopropyl-6-[(3-hydroxypropyl)(methylsulfonyl)amino]-N-methyl-2H-indazole-3-carboxamide;
5) 5-cyclopropyl-2-{4-[(2-fluorophenyl)amino]phenyl}-6-[(3-hydroxypropyl)(methylsulfonyl)amino]-N-methyl-2H-indazole-3-carboxamide;
6) 2-(4-bromophenyl)-5-cyclopropyl-6-{[2-(1,3-dioxo-1,3-dihydro-2H-isoindol-2-yl)ethyl](methylsulfonyl)amino}-N-methyl-2H-indazole-3-carboxamide;
7) 6-[(2-aminoethyl)(methylsulfonyl)amino]-2-(4-bromophenyl)-5-cyclopropyl-N-methyl-2H-indazole-3-carboxamide;
8) 2-(4-bromophenyl)-5-cyclopropyl-N-methyl-6-[(methylsulfonyl){2-[(2H-tetrazol-5-ylacetyl)amino]ethyl}amino]-2H-indazole-3-carboxamide;
9) 2-(4-bromophenyl)-5-cyclopropyl-6-[(2-{[(4-fluorobenzyl)sulfonyl]amino}ethyl)(methylsulfonyl)amino]-N-methyl-2H-indazole-3-carboxamide;
10) 2-(4-fluorophenyl)-5-methoxy-N-methyl-6-[(methylsulfonyl)amino]-2H-indazole-3-carboxamide;
11) 6-[(2-{[(tert-butyl)dimethyl)silyl]oxy}ethyl)(methylsulfonyl)amino]-2-(4-fluorophenyl)-5-methoxy-N-methyl-2H-indazole-3-carboxamide;
12) 2-(4-fluorophenyl)-6-[2-hydroxyethyl(methylsulfonyl)amino]-5-methoxy-N-methyl-indazole-3-carboxamide;
13) 5-cyclopropyl-2-(4-fluorophenyl)-N-methyl-6-[(methylsulfonyl)amino]-2H-indazole-3-carboxamide;
14) 5-cyclopropyl-2-(4-fluorophenyl)-6-[(2-hydroxyethyl)(methylsulfonyl)amino]-N-methyl-2H-indazole-3-carboxamide;

15) 2-[(2-{[5-cyclopropyl-2-(4-fluorophenyl)-3-(methylcarbamoyl)-2H-indazol-6-yl](methylsulfonyl)amino}ethoxy)carbonyl]benzoic acid;
18) 5-cyclopropyl-2-[4-(2-fluorophenoxy)phenyl]-6-[(2-hydroxyethyl)(methylsulfonyl)amino]-N-methyl-2H-indazole-3-carboxamide;
19) 5-cyclopropyl-2-{4-[(4-fluorophenyl)amino]phenyl}-6-[(2-hydroxyethyl)(methylsulfonyl)amino]-N-methyl-2H-indazole-3-carboxamide;
20) 2-(4-bromophenyl)-5-cyclopropyl-6-[ethyl(methylsulfonyl)amino]-N-methyl-2H-indazole-3-carboxamide;
21) 5-cyclopropyl-2-{4-[(4-fluorophenyl)amino]phenyl}-6-[(3-hydroxypropyl)(methylsulfonyl)amino]-N-methyl-2H-indazole-3-carboxamide;
22) 5-cyclopropyl-6-[ethyl(methylsulfonyl)amino]-2-{4-[(4-fluorophenyl)amino]phenyl}-N-methyl-2H-indazole-3-carboxamide;
23) 5-cyclopropyl-6-[ethyl(methylsulfonyl)amino]-2-[4-(4-fluorophenoxy)phenyl]-N-methyl-2H-indazole-3-carboxamide;
24) 2-(4-bromophenyl)-5-cyclopropyl-6-[(2-hydroxyethyl)(methylsulfonyl)amino]-N-methyl-2H-indazole-3-carboxamide;
25) 5-cyclopropyl-6-[ethyl(methylsulfonyl)amino]-2-{4-[(2-fluorophenyl)amino]phenyl}-N-methyl-2H-indazole-3-carboxamide;
26) 5-cyclopropyl-2-{4-[(2-fluorophenyl)amino]phenyl}-6-[(2-hydroxyethyl)(methylsulfonyl)amino]-N-methyl-2H-indazole-3-carboxamide;
27) 5-cyclopropyl-6-[(2-hydroxyethyl)(methylsulfonyl)amino]-N-methyl-2-[4-(phenylamino)phenyl]-2H-indazole-3-carboxamide;
28) 5-cyclopropyl-6-[ethyl(methylsulfonyl)amino]-2-[4-(2-fluorophenoxy)phenyl]-N-methyl-2H-indazole-3-carboxamide;
29) 5-cyclopropyl-2-[4-(2-fluorophenoxy)phenyl]-6-[(3-hydroxypropyl)(methylsulfonyl)amino]-N-methyl-2H-indazole-3-carboxamide;
30) 5-cyclopropyl-2-[4-(4-fluorophenoxy)phenyl]-6-[(3-hydroxypropyl)(methylsulfonyl)amino]-N-methyl-2H-indazole-3-carboxamide;
31) 5-cyclopropyl-2-{4-[(4-fluorophenyl)amino]phenyl}N-methyl-6-[(methylsulfonyl){2-[(2H-tetrazol-5-ylacetyl)amino]ethyl}amino]-2H-indazole-3-carboxamide;
32) 2-(4-fluorophenyl)-6-[(2-hydroxyethyl)(methylsulfonyl)amino]-N-methyl-2H-indazole-3-carboxamide;
33) 5-cyclopropyl-2-[4-(3-hydroxyanilino)phenyl]-6-[2-hydroxyethyl(methylsulfonyl)amino]-N-methyl-indazole-3-carboxamide;
34) 2-[4-(3-benzyloxyanilino)phenyl]-5-cyclopropyl-6-[2-hydroxyethyl(methylsulfonyl)amino]-N-methyl-indazole-3-carboxamide;
35) 5-cyclopropyl-6-[2-hydroxyethyl(methylsulfonyl)amino]-N-methyl-2-(4-phenoxyphenyl)indazole-3-carboxamide;
36) 6-[2-acetamidoethyl(methylsulfonyl)amino]-5-cyclopropyl-2-[4-(4-fluorophenoxy)phenyl]-N-methyl-indazole-3-carboxamide;
37) 6-[2-acetamidoethyl(methylsulfonyl)amino]-2-(4-bromophenyl)-5-cyclopropyl-N-methyl-indazole-3-carboxamide;
38) 5-cyclopropyl-6-[ethyl(methylsulfonyl)amino]-N-methyl-2-[4-(propan-2-ylamino)phenyl]-2H-indazole-3-carboxamide;
39) 5-cyclopropyl-2-[4-(4-fluorophenoxy)phenyl]-N-methyl-6-[methyl(methylsulfonyl)amino]-2H-indazole-3-carboxamide;
40) 6-[(3-cyanopropyl)(methylsulfonyl)amino]-5-cyclopropyl-2-[4-(4-fluorophenoxy)phenyl]-N-methyl-2H-indazole-3-carboxamide;
41) 2-(4-bromophenyl)-5-methoxy-N-methyl-6-[(methylsulfonyl)amino]-2H-indazole-3-carboxamide;
42) 5-bromo-2-(4-fluorophenyl)-N-methyl-6-[(methylsulfonyl)amino]-2H-indazole-3-carboxamide;
43) 5-cyclopropyl-2-[6-(4-fluorophenoxy)pyridin-3-yl]-N-methyl-6-[(methylsulfonyl)amino]-2H-indazole-3-carboxamide;
44) 2-(4-chlorophenyl)-5-cyclopropyl-N-methyl-6-[(methylsulfonyl)amino]-2H-indazole-3-carboxamide;
45) 5-cyclopropyl-2-(3-fluoro-4-methylphenyl)-N-methyl-6-[(methylsulfonyl)amino]-2H-indazole-3-carboxamide;
46) 2-(4-bromo-3-fluorophenyl)-5-cyclopropyl-N-methyl-6-[(methylsulfonyl)amino]-2H-indazole-3-carboxamide;
47) 2-(4-Bromophenyl)-5-cyclopropyl-6-{[(difluoromethyl)sulfonyl]amino}-N-methyl-2H-indazole-3-carboxamide
48) 6-[acetyl(ethyl)amino]-2-(4-bromophenyl)-5-cyclopropyl-N-methyl-2H-indazole-3-carboxamide;
49) 5-cyclopropyl-2-(4-fluorophenyl)-6-iodo-N-methyl-2H-indazole-3-carboxamide;
50) 5-cyclopropyl-6-[(3-hydroxypropyl)(methylsulfonyl)amino]-N-methyl-2-[4-(propan-2-yl)phenyl]-2H-indazole-3-carboxamide;
51) 2-(4-bromophenyl)-5-cyclopropyl-6-{[2]-dihydroxypropyl](methylsulfonyl)amino}-N-methyl-2H-indazole-3-carboxamide;
52) 2-(4-bromophenyl)-5-cyclopropyl-N-methyl-6-{(methylsulfonyl)[1-(methylsulfonyl)pyrrolidin-3-yl]amino}-2H-indazole-3-carboxamide;
53) 5-cyclopropyl-2-(4-cyclopropylphenyl)-6-[(3-hydroxypropyl)(methylsulfonyl)amino]-N-methyl-2H-indazole-3-carboxamide;
54) 2-(4-chlorophenyl)-5-cyclopropyl-6-[(3-hydroxypropyl)(methylsulfonyl)amino]-N-methyl-2H-indazole-3-carboxamide;
55) 5-cyclopropyl-6-[(3-hydroxypropyl)(methylsulfonyl)amino]-2-(4-methoxyphenyl)-N-methyl-2H-indazole-3-carboxamide;
56) 2-(4-chlorophenyl)-5-cyclopropyl-6-[(3,3-difluoropropyl)(methylsulfonyl)amino]-N-methyl-2H-indazole-3-carboxamide;
57) 2-(4-chlorophenyl)-5-cyclopropyl-6-[(3-fluoropropyl)(methylsulfonyl)amino]-N-methyl-2H-indazole-3-carboxamide;
58) 4-(3-{[5-cyclopropyl-2-{4-[(4-fluorophenyl)amino]phenyl}-3-(methylcarbamoyl)-2H-indazol-6-yl](methylsulfonyl)amino}propyl)amino]-4-oxobutanoic acid;
59) 6-{[3-(acetylamino)propyl](methylsulfonyl)amino}-2-(4-bromophenyl)-5-cyclopropyl-N-methyl-2H-indazole-3-carboxamide;
60) 6-{[3-(acetylamino)propyl](methylsulfonyl)amino}-5-cyclopropyl-N-methyl-2-{4-[(2-methylpropyl)amino]phenyl}-2H-indazole-3-carboxamide;
61) 6-{[3-(beta-alanylamino)propyl](methylsulfonyl)amino}-2-(4-bromophenyl)-5-cyclopropyl-N-methyl-2H-indazole-3-carboxamide;
62) 2-(4-bromophenyl)-6-[{3-[(cyclobutylcarbonyl)amino]propyl}(methylsulfonyl)amino]-5-cyclopropyl-N-methyl-2H-indazole-3-carboxamide;

63) (1R,2S)-2-[(3-{[2-(4-bromophenyl)-5-cyclopropyl-3-(methylcarbamoyl)-2H-indazol-6-yl](methylsulfonyl)amino}propyl)carbamoyl]cyclopentanecarboxylic acid;
64) 2-(4-bromophenyl)-5-cyclopropyl-N-methyl-6-{[3-({[4-methylmorpholin-3-yl]carbonyl}amino)propyl](methylsulfonyl)amino}-2H-indazole-3-carboxamide;
65) 2-(4-bromophenyl)-5-cyclopropyl-6-{[3-(dimethylamino)propyl](methylsulfonyl)amino}-N-methyl-2H-indazole-3-carboxamide;
66) methyl 4-[(3-{[2-(4-bromophenyl)-5-cyclopropyl-3-(methylcarbamoyl)-2H-indazol-6-yl](methylsulfonyl)amino}propyl)amino]-4-oxobutanoate;
67) N-(3-{[2-(4-bromophenyl)-5-cyclopropyl-3-(methylcarbamoyl)-2H-indazol-6-yl](methylsulfonyl)amino}propyl)-N'-(propan-2-yl)butanediamide;
68) 4-{[3-[2-(4-bromophenyl)-5-cyclopropyl-3-(methylcarbamoyl)-2H-indazol-6-yl](methylsulfonyl)amino}propyl)amino]-4-oxobutanoic acid;
69) 2-(4-bromophenyl)-5-cyclopropyl-6-{[3-(2,5-dioxopyrrolidin-1-yl)propyl](methylsulfonyl)amino}-N-methyl-2H-indazole-3-carboxamide;
70) 2-(4-bromophenyl)-5-cyclopropyl-N-methyl-6-{(methylsulfonyl)[3-(2-oxoimidazolidin-1-yl)propyl]amino}-2H-indazole-3-carboxamide;
71) 5-ethenyl-6-[ethyl(methylsulfonyl)amino]-2-(4-fluorophenyl)-N-methyl-2H-indazole-3-carboxamide;
72) 5-ethyl-6-[ethyl(methylsulfonyl)amino]-2-(4-fluorophenyl)-N-methyl-2H-indazole-3-carboxamide;
73) 5-(cyclopent-1-en-1-yl)-6-[ethyl(methylsulfonyl)amino]-2-(4-fluorophenyl)-N-methyl-2H-indazole-3-carboxamide;
74) 5-cyclopentyl-6-[ethyl(methylsulfonyl)amino]-2-(4-fluorophenyl)-N-methyl-2H-indazole-3-carboxamide;
75) 6-[ethyl(methylsulfonyl)amino]-2-(4-fluorophenyl)-5-(3-hydroxyprop-1-yn-1-yl)-N-methyl-2H-indazole-3-carboxamide;
76) 6-[ethyl(methylsulfonyl)amino]-2-(4-fluorophenyl)-5-[(1Z)-3-hydroxyprop-1-en-1-yl]-N-methyl-2H-indazole-3-carboxamide;
77) 6-[ethyl(methylsulfonyl)amino]-5-ethynyl-2-(4-fluorophenyl)-N-methyl-2H-indazole-3-carboxamide;
78) 5-(difluoromethoxy)-6-[ethyl(methylsulfonyl)amino]-2-(4-fluorophenyl)-N-methyl-2H-indazole-3-carboxamide;
79) 5-cyclopropyl-6-[(3-hydroxypropyl)(methylsulfonyl)amino]-N-methyl-2-{4-[(propan-2-yloxy)methyl]phenyl}-2H-indazole-3-carboxamide;
81) 2-(4-bromophenyl)-5-cyclopropyl-6-[(2E)-4-hydroxybut-2-en-2-yl]-N-methyl-2H-indazole-3-carboxamide;
82) 2-(4-bromophenyl)-5-cyclopropyl-6-[(2Z)-4-hydroxybut-2-en-2-yl]-N-methyl-2H-indazole-3-carboxamide;
85) ethyl 5-[5-cyclopropyl-3-(methylcarbamoyl)-2-(4-methylphenyl)-2H-indazol-6-yl]-5-(methylsulfonyl)pentanoate;
86) 5-cyclopropyl-N-methyl-2-(4-methylphenyl)-6-[1-(methylsulfonyl)propyl]-2H-indazole-3-carboxamide;
87) 5-cyclopropyl-6-(ethylsulfamoyl)-2-(4-fluorophenyl)-N-methyl-2H-indazole-3-carboxamide;
88) ethyl 4-{[2-(4-bromophenyl)-5-cyclopropyl-3-(methylcarbamoyl)-2H-indazol-6-yl](methylsulfonyl)amino}butanoate;
89) 4-{[2-(4-bromophenyl)-5-cyclopropyl-3-(methylcarbamoyl)-2H-indazol-6-yl](methylsulfonyl)amino}butanoic acid;
90) N-[2-(4-bromophenyl)-5-cyclopropyl-3-(methylcarbamoyl)-2H-indazol-6-yl]-N-(methylsulfonyl)-beta-alanine;
91) 2-(4-bromophenyl)-5-cyclopropyl-N-methyl-6-{(methylsulfonyl)[3-oxo-3-(propan-2-ylamino)propyl]amino}-2H-indazole-3-carboxamide;
92) butan-2-yl 4-{[2-(4-bromophenyl)-5-cyclopropyl-3-(methylcarbamoyl)-2H-indazol-6-yl](methylsulfonyl)amino}butanoate;
93) phenyl 4-{[2-(4-bromophenyl)-5-cyclopropyl-3-(methylcarbamoyl)-2H-indazol-6-yl](methylsulfonyl)amino}butanoate;
94) [(2,2-dimethylpropanoyl)oxy]methyl 4-{[2-(4-bromophenyl)-5-cyclopropyl-3-(methylcarbamoyl)-2H-indazol-6-yl] (methylsulfonyl)amino}butanoate;
95) 2-(4-bromophenyl)-5-cyclopropyl-6-{[2-(2,2-dimethyl-1,3-dioxan-5-yl)ethyl](methylsulfonyl)amino}-N-methyl-2H-indazole-3-carboxamide;
96) 2-(4-bromophenyl)-5-cyclopropyl-6-{[4-hydroxy-3-(hydroxymethyl)butyl] (methylsulfonyl)amino}-N-methyl-2H-indazole-3-carboxamide;
97) 2-(4-bromophenyl)-5-cyclopropyl-N-methyl-6-{(methylsulfonyl)[2-(2-oxo-1,3-dioxan-5-yl)ethyl]amino}-2H-indazole-3-carboxamide;
98) 2-(4-bromophenyl)-5-cyclopropyl-N-methyl-6-[(methylsulfonyl)(prop-2-en-1-yl)amino]-2H-indazole-3-carboxamide;
99) 2-(4-bromophenyl)-5-cyclopropyl-N-methyl-6-{[3-(methylsulfanyl)propyl] (methylsulfonyl)amino}-2H-indazole-3-carboxamide;
100) 2-(4-bromophenyl)-5-cyclopropyl-N-methyl-6-{(methylsulfonyl)[3-(methylsulfonyl)propyl]amino}-2H-indazole-3-carboxamide;
101) 2-(4-bromophenyl)-5-cyclopropyl-N-methyl-6-{[3-(methylsulfinyl)propyl](methylsulfonyl)amino}-2H-indazole-3-carboxamide;
102) 2-(4-bromophenyl)-5-cyclopropyl-N-methyl-6-[(methylsulfonyl)(3-sulfamoylpropyl)amino]-2H-indazole-3-carboxamide;
106) 2-(4-bromophenyl)-5-cyclopropyl-6-{[2-hydroxypropyl](methylsulfonyl)amino}-N-methyl-2H-indazole-3-carboxamide;
107) 2-(4-bromophenyl)-5-cyclopropyl-N-methyl-6-[(methylsulfonyl)(piperidin-4-yl)amino]-2H-indazole-3-carboxamide;
108) 2-(4-bromophenyl)-5-cyclopropyl-N-methyl-6-{(methylsulfonyl)[1-(methylsulfonyl)piperidin-4-yl]amino}-2H-indazole-3-carboxamide;
109) 2-(6-benzyloxy-3-pyridyl)-5-cyclopropyl-6-(methanesulfonamido)-N-methyl-indazole-3-carboxamide;
110) 5-cyclopropyl-6-[ethyl(methylsulfonyl)amino]-2-[6-(isobutylamino)-3-pyridyl]-N-methyl-indazole-3-carboxamide;
111) 5-cyclopropyl-2-[4-(4-fluorophenoxy)phenyl]-N-methyl-6-{(methylsulfonyl) [3-(piperidin-1-yl)propyl]amino}-2H-indazole-3-carboxamide;
112) 5-cyclopropyl-2-[4-(4-fluorophenoxy)phenyl]-N-methyl-6-{(methylsulfonyl)[2-(morpholin-4-yl)ethyl]amino}-2H-indazole-3-carboxamide;
113) 5-cyclopropyl-2-[4-(4-fluorophenoxy)phenyl]-N-methyl-6-[(methylsulfonyl)(propyl)amino]-2H-indazole-3-carboxamide;
114) 5-cyclopropyl-2-[4-(4-fluorophenoxy)phenyl]-N-methyl-6-{(methylsulfonyl)[2-(piperidin-1-yl)ethyl]amino}-2H-indazole-3-carboxamide;

115) 2-({3-[{5-cyclopropyl-2-[4-(4-fluorophenoxy)phenyl]-3-(methylcarbamoyl)-2H-indazol-6-yl}(methylsulfonyl)amino]propoxy}carbonyl)benzoic acid;
116) 3-{[5-cyclopropyl-2-{4-[(4-fluorophenyl)amino]phenyl}-3-(methylcarbamoyl)-2H-indazol-6-yl}(methylsulfonyl)amino]propyl acetate;
117) 5-cyclopropyl-6-[ethyl(methylsulfonyl)amino]-N-methyl-2-{4-[(2-methylpropyl)amino]phenyl}-2H-indazole-3-carboxamide;
118) 3-[{5-cyclopropyl-2-[4-(4-fluorophenoxy)phenyl]-3-(methylcarbamoyl)-2H-indazol-6-yl}(methylsulfonyl)amino]propyl pyrazine-2-carboxylate;
119) 6-{[3-(acetylamino)propyl](methylsulfonyl)amino}-5-cyclopropyl-2-{4-[(4-fluorophenyl)amino]phenyl}-N-methyl-2H-indazole-3-carboxamide;
120) 5-cyclopropyl-2-{4-[(4-fluorophenyl)amino]phenyl}-6-[{3-[(furan-3-ylcarbonyl)amino]propyl}(methylsulfonyl)amino]-N-methyl-2H-indazole-3-carboxamide;
121) 5-cyclopropyl-6-[ethyl(methylsulfonyl)amino]-N-methyl-2-[4-(2-methylpropoxy)phenyl]-2H-indazole-3-carboxamide;
122) 5-cyclopropyl-6-[(3-hydroxypropyl)(methylsulfonyl)amino]-N-methyl-2-{4-[(2-methylpropyl)amino]phenyl}-2H-indazole-3-carboxamide;
123) 6-[ethyl(methylsulfonyl)amino]-2-{4-[(2-fluorophenyl)amino]phenyl}-5-methoxy-N-methyl-2H-indazole-3-carboxamide;
124) 6-[ethyl(methylsulfonyl)amino]-5-methoxy-N-methyl-2-{4-[(2-methylpropyl)amino]phenyl}-2H-indazole-3-carboxamide;
125) 6-[ethyl(methylsulfonyl)amino]-5-methoxy-N-methyl-2-phenyl-2H-indazole-3-carboxamide;
126) 2-{4-[(2-fluorophenyl)amino]phenyl}-6-[(3-hydroxypropyl)(methylsulfonyl)amino]-5-methoxy-N-methyl-2H-indazole-3-carboxamide;
129) 6-[ethyl(methylsulfonyl)amino]-2-(4-fluorophenyl)-N-methyl-5-(prop-1-en-2-yl)-2H-indazole-3-carboxamide;
130) 6-[ethyl(methylsulfonyl)amino]-2-(4-fluorophenyl)-N-methyl-5-(propan-2-yl)-2H-indazole-3-carboxamide;
131) ethyl N-[2-(4-bromophenyl)-5-cyclopropyl-3-(methylcarbamoyl)-2H-indazol-6-yl]-N-(methylsulfonyl)-beta-alaninate;
132) 5-bromo-6-[ethyl(methylsulfonyl)amino]-2-(4-fluorophenyl)-N-methyl-2H-indazole-3-carboxamide;
133) 2-(4-bromophenyl)-5-cyclopropyl-6-{[3-(glycylamino)propyl](methylsulfonyl)amino}-N-methyl-2H-indazole-3-carboxamide;
134) 2-(4-bromophenyl)-5-cyclopropyl-N-methyl-6-[(methylsulfonyl){3-[(methylsulfonyl)amino]propyl}amino]-2H-indazole-3-carboxamide;
135) 2-(4-bromophenyl)-5-cyclopropyl-N-methyl-6-[{3-[methyl(methylsulfonyl)amino]propyl}(methylsulfonyl)amino]-2H-indazole-3-carboxamide;
136) 5-cyclopropyl-6-[ethyl(methylsulfonyl)amino]-2-[6-(4-fluorophenoxy)pyridin-3-yl]-N-methyl-2H-indazole-3-carboxamide;
137) 6-[ethyl(methylsulfonyl)amino]-2-(4-fluorophenyl)-N-methy-2H-indazole-3-carboxamide;
138) 5-cyclopropyl-6-[ethyl(methylsulfonyl)amino]-2-(4-fluorophenyl)-N-methyl-2H-indazole-3-carboxamide;
139) 6-[ethyl(methylsulfonyl)amino]-2-(4-fluorophenyl)-N,5-dimethyl-2H-indazole-3-carboxamide;
140) 2-(4-bromophenyl)-5-cyclopropyl-N-methyl-6-[(methylsulfonyl)(pyridin-4-ylmethyl)amino]-2H-indazole-3-carboxamide;
141) ethyl N-[2-(4-bromophenyl)-5-cyclopropyl-3-(methylcarbamoyl)-2H-indazol-6-yl]-N-(methylsulfonyl)glycinate;
142) 5-(3,6-dihydro-2H-pyran-4-yl)-6-[ethyl(methylsulfonyl)amino]-2-(4-fluorophenyl)-N-methyl-2H-indazole-3-carboxamide;
143) 2-(4-bromophenyl)-5-cyclopropyl-N-methyl-6-{[4-(methylamino)-4-oxobutyl](methylsulfonyl)amino}-2H-indazole-3-carboxamide;
144) 6-[ethyl(methylsulfonyl)amino]-2-(4-fluorophenyl)-N-methyl-5-(prop-1-en-1-yl)-2H-indazole-3-carboxamide;
145) 6-[ethyl(methylsulfonyl)amino]-2-(4-fluorophenyl)-N-methyl-5-propyl-2H-indazole-3-carboxamide;
146) 2-[(3-{[5-cyclopropyl-3-(methylcarbamoyl)-2-{4-[(2-methylpropyl)amino]phenyl}-2H-indazol-6-yl](methylsulfonyl)amino}propyl)carbamoyl]benzoic acid;
147) 2-[(3-{[2-(4-bromophenyl)-5-cyclopropyl-3-(methylcarbamoyl)-2H-indazol-6-yl](methylsulfonyl)amino}propyl)carbamoyl]benzoic acid;
148) 2-(4-bromophenyl)-5-cyclopropyl-N-methyl-6-{[3-(methylamino)-3-oxopropyl](methylsulfonyl)amino}-2H-indazole-3-carboxamide;
149) 6-[ethyl(methylsulfonyl)amino]-2-(4-fluorophenyl)-5-(3-hydroxy-3-methylbut-1-yn-1-yl)-N-methyl-2H-indazole-3-carboxamide;
150) 2-(4-bromophenyl)-5-cyclopropyl-N-methyl-6-[(methylsulfonyl){3-oxo-3-[(phenylsulfonyl)amino]propyl}amino]-2H-indazole-3-carboxamide;
151) N-(3-{[2-(4-bromophenyl)-5-cyclopropyl-3-(methylcarbamoyl)-2H-indazol-6-yl](methylsulfonyl)amino}propyl)-N'-methylbenzene-1,2-dicarboxamide;
152) N-(3-{[2-(4-bromophenyl)-5-cyclopropyl-3-(methylcarbamoyl)-2H-indazol-6-yl](methylsulfonyl)amino}propyl)-N-methylbutanediamide;
153) 2-(4-bromophenyl)-5-cyclopropyl-N-methyl-6-[(methylsulfonyl){3-oxo-3-[(thiophen-2-ylsulfonyl)amino]propyl}amino]-2H-indazole-3-carboxamide;
154) 2-(4-bromophenyl)-5-cyclopropyl-6-[(3-{[(4-fluorophenyl)sulfonyl]amino}-3-oxopropyl)(methylsulfonyl)amino]-N-methyl-2H-indazole-3-carboxamide;
155) 2-(4-bromophenyl)-5-cyclopropyl-6-{[3-(dimethylamino)-3-oxopropyl](methylsulfonyl)amino}-N-methyl-2H-indazole-3-carboxamide;
156) 2-(4-bromophenyl)-5-cyclopropyl-N-methyl-6-[{3-[(2-methylpropanoyl)amino]propyl}(methylsulfonyl)amino]-2H-indazole-3-carboxamide;
160) 2-(4-bromophenyl)-5-cyclopropyl-6-[{3-[(furan-3-ylcarbonyl)amino]propyl}(methylsulfonyl)amino]-N-methyl-2H-indazole-3-carboxamide;
161) 2-(4-bromophenyl)-5-cyclopropyl-6-[{3-[(3-methoxypropanoyl)amino]propyl}(methylsulfonyl)amino]-N-methyl-2H-indazole-3-carboxamide;
162) 2-(4-bromophenyl)-5-cyclopropyl-6-{[3-(ethylamino)-3-oxopropyl](methylsulfonyl)amino}-N-methyl-2H-indazole-3-carboxamide;
163) 6-[ethyl(methylsulfonyl)amino]-2-(4-fluorophenyl)-N-methyl-5-(2-methyl-1,3-thiazol-4-yl)-2H-indazole-3-carboxamide;
164) ethyl 4-[(3-{[2-(4-bromophenyl)-5-cyclopropyl-3-(methylcarbamoyl)-2H-indazol-6-yl](methylsulfonyl)amino}propyl)amino]-4-oxobutanoate;

165) 2-(4-bromophenyl)-5-cyclopropyl-N-methyl-6-(methylsulfonyl)[3-oxo-3-(propylamino)propyl]amino 1-2H-indazole-3-carboxamide;
166) 6-{[3-(benzoylamino)propyl](methylsulfonyl)amino}-2-(4-bromophenyl)-5-cyclopropyl-N-methyl-2H-indazole-3-carboxamide;
167) 2-(4-bromophenyl)-5-cyclopropyl-N-methyl-6-[(3-{[(1-methyl-1H-imidazol-4-yl)carbonyl]amino}propyl)(methylsulfonyl)amino]-2H-indazole-3-carboxamide;
168) 2-(4-bromophenyl)-5-cyclopropyl-N-methyl-6-[(methylsulfonyl){3-[(1,2-oxazol-4-ylcarbonyl)amino]propyl}amino]-2H-indazole-3-carboxamide;
169) 2-(4-bromophenyl)-5-cyclopropyl-6-{[3-(1,3-dioxo-1,3-dihydro-2H-isoindol-2-yl)propyl](methylsulfonyl)amino}-N-methyl-2H-indazole-3-carboxamide;
170) 5-(cyanomethoxy)-6-[ethyl(methylsulfonyl)amino]-2-(4-fluorophenyl)-N-methyl-2H-indazole-3-carboxamide;
171) 2-(4-bromophenyl)-6-{[3-(butanoylamino)propyl](methylsulfonyl)amino}-5-cyclopropyl-N-methyl-2H-indazole-3-carboxamide;
172) 2-(4-bromophenyl)-5-cyclopropyl-N-methyl-6-[(methylsulfonyl){3-[(trifluoroacetyl)amino]propyl}amino]-2H-indazole-3-carboxamide
173) 2-(4-bromophenyl)-5-cyclopropyl-N-methyl-6-[(3-{[(5-methyl-1,2-oxazol-4-yl)carbonyl]amino}propyl)(methylsulfonyl)amino]-2H-indazole-3-carboxamide;
174) 2-(4-bromophenyl)-5-cyclopropyl-N-methyl-6-[(3-{[(5-methyl-1,3-oxazol-4-yl)carbonyl]amino}propyl)(methylsulfonyl)amino]-2H-indazole-3-carboxamide;
175) 2-(4-chlorophenyl)-5-cyclopropyl-6-[ethyl(methylsulfonyl)amino]-N-methyl-2H-indazole-3-carboxamide;
176) 2-(4-bromophenyl)-5-cyclopropyl-N-methyl-6-[(methylsulfonyl)(3-{[(1-oxidopyridin-3-yl)carbonyl]amino}propyl)amino]-2H-indazole-3-carboxamide;
177) 2-(4-bromophenyl)-5-cyclopropyl-6-[(3-{[(2-methoxypyridin-4-yl)carbonyl]amino}propyl)(methylsulfonyl)amino]-N-methyl-2H-indazole-3-carboxamide;
178) 2-(4-bromophenyl)-5-cyclopropyl-N-methyl-6-[(methylsulfonyl){3-[(pyridazin-4-yl-carbonyl)amino]propyl}amino]-2H-indazole-3-carboxamide;
179) 2-(4-bromophenyl)-5-cyclopropyl-N-methyl-6-[(3-{[(4-methyl-1,2,5-oxadiazol-3-yl)carbonyl]amino}propyl)(methylsulfonyl)amino]-2H-indazole-3-carboxamide;
180) 2-(4-bromophenyl)-5-cyclopropyl-6-[(3-{[(1,5-dimethyl-1H-pyrazol-4-yl)carbonyl]amino}propyl)(methylsulfonyl)amino]-N-methyl-2H-indazole-3-carboxamide;
181) 2-(4-bromophenyl)-5-cyclopropyl-6-[{3-[(furan-2-ylcarbony)amino]propyl}(methylsulfonyl)amino]-N-methyl-2H-indazole-3-carboxamide;
182) 2-(4-bromophenyl)-5-cyclopropyl-N-methyl-6-{[3-({[1-methyl-5-oxopyrrolidin-3-yl]carbonyl}amino)propyl](methylsulfonyl)amino}-2H-indazole-3-carboxamide;
183) 2-(4-bromophenyl)-5-cyclopropyl-6-[{3-[(cyclopropylcarbonyl)amino]propyl}(methylsulfonyl)amino]-N-methyl-2H-indazole-3-carboxamide;
184) 2-(4-bromophenyl)-5-cyclopropyl-6-{[4-(ethylamino)-4-oxobutyl](methylsulfonyl)amino}-N-methyl-2H-indazole-3-carboxamide;
185) 2-(4-bromophenyl)-5-cyclopropyl-6-[3-[(N,N-dimethyl-beta-alanyl)amino]propyl}(methylsulfonyl)amino]-N-methyl-2H-indazole-3-carboxamide;
186) 2-(4-bromophenyl)-5-cyclopropyl-N-methyl-6-{(methylsulfonyl)[3-({[6-(morpholin-4-yl)pyridin-3-yl]carbonyl}amino)propyl]amino}-2H-indazole-3-carboxamide;
187) (1S,2S)-2-[(3-{[2-(4-bromophenyl)-5-cyclopropyl-3-(methylcarbamoyl)-2H-indazol-6-yl](methylsulfonyl)amino}propyl)carbamoyl]cyclohexanecarboxylic acid;
188) (1R,6S)-6-[(3-{[2-(4-bromophenyl)-5-cyclopropyl-3-(methylcarbamoyl)-2H-indazol-6-yl](methylsulfonyl)amino}propyl)carbamoyl]cyclohex-3-ene-1-carboxylic acid;
189) 2-(4-bromophenyl)-5-cyclopropyl-6-[{3-[(2-fluoro-3-methoxybenzoyl)amino]propyl}(methylsulfonyl)amino]-N-methyl-2H-indazole-3-carboxamide;
190) 2-(4-bromophenyl)-5-cyclopropyl-6-[(3-{[(2-methoxypyridin-3-yl)carbonyl]amino}propyl)(methylsulfonyl)amino]-N-methyl-2H-indazole-3-carboxamide;
191) 2-(4-bromophenyl)-5-cyclopropyl-N-methyl-6-[(methylsulfonyl){3-[(pyridin-3-ylcarbonyl)amino]propyl}amino]-2H-indazole-3-carboxamide;
192) 5-cyclopropyl-6-[ethyl(methylsulfonyl)amino]-N-methyl-2-[4-(prop-1-en-2-yl)phenyl]-2H-indazole-3-carboxamide;
193) 2-(4-bromophenyl)-5-cyclopropyl-6-[{4-[(ethylsulfonyl)amino]-4-oxobutyl}(methylsulfonyl)amino]-N-methyl-2H-indazole-3-carboxamide;
194) 2-(4-bromophenyl)-5-cyclopropyl-N-methyl-6-{(methylsulfonyl)[3-(2-oxopyrrolidin-1-yl)propyl]amino}-2H-indazole-3-carboxamide;
195) 2-(4-bromophenyl)-5-cyclopropyl-N-methyl-6-{(methylsulfonyl)[pyrrolidin-3-yl]amino}-2H-indazole-3-carboxamide;
196) 2-(4-bromophenyl)-5-cyclopropyl-N-methyl-6-[(methylsulfonyl)(4-oxo-4-{[(trifluoromethyl)sulfonyl]amino}butyl)amino]-2H-indazole-3-carboxamide;
197) 6-{[3-(benzoylamino)propyl](methylsulfonyl)amino}-2-(4-chlorophenyl)-5-cyclopropyl-N-methyl-2H-indazole-3-carboxamide;
198) 2-(4-bromophenyl)-5-cyclopropyl-6-[{4-[(dimethylsulfamoyl)amino]-4-oxobutyl}(methylsulfonyl)amino]-N-methyl-2H-indazole-3-carboxamide;
199) 2-(4-chlorophenyl)-5-cyclopropyl-6-{[3-(dimethylamino)propyl] (methylsulfonyl)amino}-N-methyl-2H-indazole-3-carboxamide;
200) 2-(4-bromophenyl)-5-cyclopropyl-N-methyl-6-{(methylsulfonyl)[3-(morpholin-4-yl)propyl]amino}-2H-indazole-3-carboxamide;
201) 2-(4-chlorophenyl)-5-cyclopropyl-N-methyl-6-{(methylsulfonyl)[3-(morpholin-4-yl)propyl]amino}-2H-indazole-3-carboxamide;
202) 2-(4-bromophenyl)-5-cyclopropyl-6-{[(2,2-dimethl-1,3-dioxan-5-yl)methyl](methylsulfonyl)amino}-N-methyl-2H-indazole-3-carboxamide;
203) 2-(4-bromophenyl)-5-cyclopropyl-6-{[3-hydroxy-2-(hydroxymethyl)propyl](methylsulfonyl)amino}-N-methyl-2H-indazole-3-carboxamide;
204) methyl (1R,2S)-2-[(3-{[2-(4-bromophenyl)-5-cyclopropyl-3-(methylcarbamoyl)-2H-indazol-6-yl](methylsulfonyl)amino}propyl)carbamoyl]cyclopropanecarboxylate;
205) 2-(4-chlorophenyl)-5-cyclopropyl-N-methyl-6-{[3-({[4-methylmorpholin-3-yl]carbonyl}amino)propyl](methylsulfonyl)amino}-2H-indazole-3-carboxamide;
206) 5-cyclopropyl-2-(3-fluoro-4-methylphenyl)-6-[(3-hydroxypropyl)(methylsulfonyl)amino]-N-methyl-2H-indazole-3-carboxamide;

207) methyl 4-{[2-(4-chlorophenyl)-5-cyclopropyl-3-(methylcarbamoyl)-2H-indazol-6-yl](methylsulfonyl)amino}butanoate;
208) 4-{[2-(4-chlorophenyl)-5-cyclopropyl-3-(methylcarbamoyl)-2H-indazol-6-yl](methylsulfonyl)amino}butanoic acid;
209) 2-(4-bromophenyl)-5-cyclopropyl-6-[{3-[(3aR,7aS)-1,3-dioxooctahydro-2H-isoindol-2-yl]propyl}(methylsulfonyl)amino]-N-methyl-2H-indazole-3-carboxamide;
210) 2-(4-bromophenyl)-5-cyclopropyl-6-[{3-[(4-methoxybenzyl)amino]propyl}(methylsulfonyl)amino]-N-methyl-2H-indazole-3-carboxamide;
211) 2-(4-bromophenyl)-5-cyclopropyl-N-methyl-6-[(methylsulfonyl) {3-[(pyridin-3-ylmethy)amino]propyl}amino]-2H-indazole-3-carboxamide;
212) diethyl (3-{[2-(4-bromophenyl)-5-cyclopropyl-3-(methylcarbamoyl)-2H-indazol-6-yl](methylsulfonyl)amino}propyl)propanedioate;
213) 2-(4-bromophenyl)-5-cyclopropyl-6-[(3-methoxypropyl)(methylsulfonyl)amino]-N-methyl-2H-indazole-3-carboxamide;
214) 5-cyclopropyl-6-[(3-hydroxypropyl)(methylsulfonyl)amino]-N-methyl-2-(4-methylphenyl)-2H-indazole-3-carboxamide;
215) methyl (1R,2S)-2-[(3-{[2-(4-bromophenyl)-5-cyclopropyl-3-(methylcarbamoyl)-2H-indazol-6-yl](methylsulfonyl)amino}propyl)carbamoyl]cyclopentanecarboxylate;
216) methyl (1S,2S)-2-[(3-{[2-(4-bromophenyl)-5-cyclopropyl-3-(methylcarbamoyl)-2H-indazol-6-yl](methylsulfonyl)amino}propyl)carbamoyl]cyclopentanecarboxylate;
217) 2-(4-chlorophenyl)-5-cyclopropyl-N-methyl-6-[(methylsulfonyl)(4-oxo-4-{[(trifluoromethyl)sulfonyl]amino}butyl)amino]-2H-indazole-3-carboxamide;
218) (1R,2S)-2-[(3-{[2-(4-bromophenyl)-5-cyclopropyl-3-(methylcarbamoyl)-2H-indazol-6-yl](methylsulfonyl)amino}propyl)carbamoyl]cyclopropanecarboxylic acid;
219) 2-(4-bromophenyl)-5-cyclopropyl-N-methyl-6-[(3-{[(1-methyl-2-oxo-1,2-dihydropyridin-4-yl)carbonyl]amino}propyl)(methylsulfonyl)amino]-2H-indazole-3-carboxamide;
220) propan-2-yl 4-{[2-(4-bromophenyl)-5-cyclopropyl-3-(methylcarbamoyl)-2H-indazol-6-yl](methylsulfonyl)amino}butanoate;
221) 2-(4-bromophenyl)-5-cyclopropyl-6-[ethyl(furan-2-ylcarbonyl)amino]-N-methyl-2H-indazole-3-carboxamide;
222) 6-[3-(acryloylamino)propyl] (methylsulfonyl)amino-2-(4-bromophenyl)-5-cyclopropyl-N-methyl-2H-indazole-3-carboxamide;
223) 2-(4-bromo-3-fluorophenyl)-5-cyclopropyl-6-[(3-hydroxypropyl)(methylsulfonyl)amino]-N-methyl-2H-indazole-3-carboxamide
224) (3-{[2-(4-bromophenyl)-5-cyclopropyl-3-(methylcarbamoyl)-2H-indazol-6-yl](methylsulfonyl)amino}propyl)propanedioic acid;
225) ethyl 4-{[2-(4-bromophenyl)-5-cyclopropyl-3-(methylcarbamoyl)-2H-indazol-6-yl](ethyl)amino}butanoate
227) 5-cyclopropyl-6-[ethyl(methyl)sulfamoyl]-2-(4-fluorophenyl)-N-methyl-2H-indazole-3-carboxamide;
228) 5-cyclopropyl-2-(4-fluorophenyl)-6-[(2-hydroxyethyl)sulfamoyl]-N-methyl-2H-indazole-3-carboxamide;
229) 4-{[5-cyclopropyl-3-(methylcarbamoyl)-2-(4-methylphenyl)-2H-indazol-6-yl](methylsulfonyl)amino}butanoic acid;
230) ethyl 4-{[5-cyclopropyl-3-(methylcarbamoyl)-2-(4-methylphenyl)-2H-indazol-6-yl](methylsulfonyl)amino}butanoate;
231) 2-(4-bromophenyl)-5-cyclopropyl-6-[(cyclopropylmethyl)(methylsulfonyl)amino]-N-methyl-2H-indazole-3-carboxamide
232) 2-(4-bromophenyl)-5-cyclopropyl-6-[(2-methoxyethyl)(methylsulfonyl)amino]-N-methyl-2H-indazole-3-carboxamide;
233) 2-(4-bromophenyl)-5-cyclopropyl-N-methyl-6-[(methylsulfonyl)(3,3,3-trifluoropropyl)amino]-2H-indazole-3-carboxamide;
234) 2-(4-bromophenyl)-5-cyclopropyl-N-methyl-6-[methyl(methylsulfonyl)amino]-2H-indazole-3-carboxamide;
235) 2-(4-chlorophenyl)-5-cyclopropyl-6-{[2-(2,2-dimethyl-1,3-dioxan-5-yl)ethyl](methylsulfonyl)amino}-N-methyl-2H-indazole-3-carboxamide;
236) 2-(4-bromo-3-fluorophenyl)-5-cyclopropyl-6-[ethyl(methylsulfonyl)amino]-N-methyl-2H-indazole-3-carboxamide;
237) 2-(4-chlorophenyl)-5-cyclopropyl-N-methyl-6-[methyl(methylsulfonyl)amino]-2H-indazole-3-carboxamide;
238) 2-(4-chlorophenyl)-5-cyclopropyl-6-{[4-hydroxy-3-(hydroxymethyl)butyl](methylsulfonyl)amino}-N-methyl-2H-indazole-3-carboxamide
239) 2-(4-chloro-3-fluorophenyl)-5-cyclopropyl-6-[ethyl(methylsulfonyl)amino]-N-methyl-2H-indazole-3-carboxamide;
240) 5-cyclopropyl-2-(4-fluorophenyl)-N-methyl-6-[1-(methylsulfonyl)propyl]-2H-indazole-3-carboxamide;
241) 2-(4-bromophenyl)-5-cyclopropyl-6-[(2-fluoroethyl)(methylsulfonyl)amino]-N-methyl-2H-indazole-3-carboxamide;
242) 2-(4-chlorophenyl)-5-cyclopropyl-N-methyl-6-[{3-[(2-methylpropanoyl)amino]propyl}(methylsulfonyl)amino]-2H-indazole-3-carboxamide
243) 2-(4-chlorophenyl)-5-cyclopropyl-6-[(3-methoxypropyl)(methylsulfonyl)amino]-N-methyl-2H-indazole-3-carboxamide
244) 5-cyclopropyl-6-[ethyl(methylsulfonyl)amino]-2-(3-fluoro-4-methylphenyl)-N-methyl-2H-indazole-3-carboxamide;
245) 2-(4-chlorophenyl)-5-cyclopropyl-N-methyl-6-[(methylsulfonyl)(3,3,3-trifluoropropyl)amino]-2H-indazole-3-carboxamide;
246) 2-(4-chlorophenyl)-5-cyclopropyl-6-[(cyclopropylmethyl)(methylsulfonyl)amino]-N-methyl-2H-indazole-3-carboxamide
247) 2-(4-chlorophenyl)-5-cyclopropyl-6-[(2-fluoroethyl)(methylsulfonyl)amino]-N-methyl-2H-indazole-3-carboxamide;
248) 2-(4-bromophenyl)-5-cyclopropyl-N-methyl-6-[(methylsulfonyl)(tetrahydrofuran-3-ylmethyl)amino]-2H-indazole-3-carboxamide;
249) 2-(4-chlorophenyl)-5-cyclopropyl-N-methyl-6-[(methylsulfonyl)(tetrahydro-2H-pyran-4-ylmethyl)amino]-2H-indazole-3-carboxamide;
250) 2-(4-chlorophenyl)-5-cyclopropyl-N-methyl-6-{(methylsulfonyl)[2-(tetrahydro-2H-pyran-4-yl)ethyl]amino}-2H-indazole-3-carboxamide;

251) (1R,2S)-2-[(3-{[2-(4-bromophenyl)-5-cyclopropyl-3-(methylcarbamoyl)-2H-indazol-6-yl](methylsulfonyl)amino}propyl)carbamoyl]cyclohexanecarboxylic acid;

252) 2-(4-chlorophenyl)-5-cyclopropyl-N-methyl-6-[(methylsulfonyl)(tetrahydrofuran-3-ylmethyl)amino]-2H-indazole-3-carboxamide;

253) 2-(4-bromophenyl)-5-cyclopropyl-6-[(2,2-difluoroethyl)(methylsulfonyl)amino]-N-methyl-2H-indazole-3-carboxamide;

254) 2-(4-chlorophenyl)-5-cyclopropyl-6-[(2,2-difluoroethyl)(methylsulfonyl)amino]-N-methyl-2H-indazole-3-carboxamide;

255) 5-cyclopropyl-6-[ethyl(methylsulfonyl)amino]-N-methyl-2-[6-(methylamino)-3-pyridyl]indazole-3-carboxamide;

256) 2-(4-bromophenyl)-5-cyclopropyl-N-methyl-6-{(methylsulfonyl)[2-(tetrahydrofuran-3-yl)ethyl]amino}-2H-indazole-3-carboxamide;

257) 2-(4-chlorophenyl)-5-cyclopropyl-N-methyl-6-{(methylsulfonyl)[2-(tetrahydrofuran-3-yl)ethyl]amino}-2H-indazole-3-carboxamide;

258) 2-(4-bromophenyl)-5-cyclopropyl-6-{ethyl[(trifluoromethyl)sulfonyl]amino}-N-methyl-2H-indazole-3-carboxamide;

259) 2-(4-chlorophenyl)-5-cyclopropyl-6-{ethyl[(trifluoromethyl)sulfonyl]amino}-N-methyl-2H-indazole-3-carboxamide; and 260) 2-(4-bromophenyl)-5-cyclopropyl-6-{[(difluoromethyl)sulfonyl](ethyl)amino}-N-methyl-2H-indazole-3-carboxamide.

15. A method for making the compounds of formula (I) according to claim 1 wherein $R_2$ is $NR_6(SO_2R_5)$ comprising reacting a compound of formula (II) with a halogenated-$R_6$ reagent (provided that $R_6$ is not H):

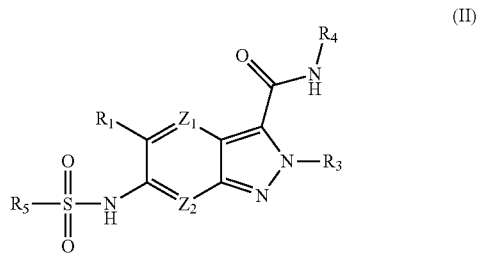

wherein
$Z_1$, $Z_2$, $R_1$, $R_3$, $R_4$ and $R_5$ are as defined in claim 1.

16. A pharmaceutical agent comprising the compound according to claim 1 or pharmaceutically acceptable salts, N-oxides, solvates, hydrates, racemates, or enantiomers thereof.

17. A HCV viral polymerase inhibitor comprising the compound according claim 1 or pharmaceutically acceptable salts, N-oxides, solvates, hydrates, racemates, or enantiomers thereof.

18. A pharmaceutical composition comprising the compound according to claim 1 or pharmaceutically acceptable salts, N-oxides, solvates, hydrates, racemates, or enantiomers thereof, a pharmaceutically acceptable carrier and optionally one or more antiviral agents.

19. A method for the treatment of a Hepatitis C virus (HCV) infection, which comprises administering an effective amount of the compound according to claim 1 or pharmaceutically acceptable salts, N-oxides, solvates, hydrates, racemates, or enantiomers thereof, to a subject suffering from HCV.

20. A method of inhibiting the RNA-dependent RNA polymerase activity of the enzyme NS5B, encoded by HCV, comprising exposing the enzyme NS5B to an effective amount of the compound according to claim 1 or pharmaceutically acceptable salts, N-oxides, solvates, hydrates, racemates, or enantiomers thereof.

21. A method of inhibiting HCV replication comprising exposing a cell infected with HCV to an effective amount of the compound according to claim 1 or pharmaceutically acceptable salts, N-oxides, solvates, hydrates, racemates, or enantiomers thereof.

22. A pharmaceutical composition according to claim 18 wherein the one or more antiviral agents is independently selected from an NS5b inhibitor; an NS3/4a protease inhibitor; an NS5a inhibitor; and Ribavarin optionally in combination with peg/IFN.

23. A pharmaceutical composition according to claim 18 wherein the antiviral agent is an NS5b inhibitor.

24. A pharmaceutical composition according to claim 23 wherein the NS5b inhibitor is a nucleoside inhibitor.

25. A pharmaceutical composition according to claim 23 wherein the NS5b inhibitor is a non-nucleoside inhibitor.

26. A pharmaceutical composition according to claim 18 wherein the antiviral agent is an NS3/4a protease inhibitor.

27. A pharmaceutical composition according to claim 18 wherein the antiviral agent is an NS5a inhibitor.

28. A pharmaceutical composition according to claim 18 formulated for oral delivery.

29. A pharmaceutical composition comprising a compound of formula (I) or pharmaceutically acceptable salts, N-oxides, solvates, hydrates, racemates, or enantiomers thereof, a pharmaceutically acceptable carrier and one or more other antiviral agents wherein
$Z_1$ and $Z_2$ are each independently selected from C—H, C-halo, C—$C_{1-4}$alkyl, C—$C_{1-4}$alkylhalo, C—$C_{1-4}$alkoxy, C—$C_{1-4}$alkoxyhalo and N;

$R_1$ is selected from H, $C_{1-6}$alkyl, $C_{2-6}$alkenyl, $C_{2-6}$alkynyl, $C_{1-6}$alkoxy, halo, $C_{1-4}$alkylhalo, $C_{1-4}$alkoxyhalo, $C_{3-7}$cycloalkyl, $C_{3-7}$cycloalkenyl, 5-6-membered heterocyclyl and 5-6 membered heteroaryl and wherein alkyl, alkenyl, alkynyl, alkoxy, cycloalkyl, heterocyclyl and heteroaryl in each occurrence may be optionally substituted;

$R_2$ is selected from halo, $C_{1-6}$alkyl, $C_{2-6}$alkenyl, $NO_2$, $N(R_5)_2$, $NR_5R_6$, $NR_6(SO_2R_5)$, $SO_2N(R_8)_2$, $SR_8$, $C(R_5)_2SO_2R_8$ and $NR_5C(=O)R_8$;

$R_3$ is selected from aryl, aryl-X-aryl, aryl-X-heteroaryl, heteroaryl, heteroaryl-X-heteroaryl, and heteroaryl-X-aryl wherein X is $[C(R_5)_2]_p$, O, S, S(=O), $SO_2$, $NR_5$, C=O, $CF_2$, C(=O)$NR_5$ or $NR_5C(=O)$ wherein p is 1, 2 or 3 and wherein aryl and heteroaryl in each occurrence may be optionally substituted;

$R_4$ is H, $C_{1-4}$alkyl, $C_{2-4}$alkenyl, $C_{2-4}$alkynyl, or $C_{3-7}$cycloalkyl;

$R_5$ in each occurrence is independently H or optionally substituted $C_{1-6}$alkyl;

$R_6$ is selected from H, $C_{1-6}$alkyl, $C_{2-6}$alkenyl, $C_{2-6}$alkynyl, $C_{1-6}$alkoxy, $C_{1-6}$alkylhalo, $C_{1-6}$alkoxyhalo, $R_8$, $C_{1-6}$alkyl-$R_8$, $C_{1-6}$alkyl-$OR_8$, $C_{1-6}$alkyl-$SR_8$, $C_{1-6}$alkyl-$S(=O)R_8$, $C_{1-6}$alkyl-$SO_2R_8$, $C_{1-6}$alkyl-$N(R_8)_2$, $C_{1-6}$alkyl-$C(=O)$—$R_8$, $C_{1-6}$alkyl-$C(=O)O$—$R_8$, $C_{1-6}$alkyl-$C(=O)N(R_8)_2$, $C_{1-6}$alkyl-$NR_5C(=O)$—$R_8$, $C_{1-6}$alkyl-$NR_5SO_2$—$R_8$, $C_{1-6}$alkyl-$SO_2NR_5$—$R_8$ and $C_{1-6}$alkyl-$C(=O)NR_5SO_2R_8$ and wherein alkyl, alkenyl, alkynyl, alkoxy, aryl, cycloalkyl, heterocyclyl and heteroaryl in each occurrence of $R_6$ may be optionally substituted;

$R_8$ in each occurrence is independently H, an optionally substituted $C_{1-6}$alkyl, an optionally substituted $C_{2-6}$alkenyl, an optionally substituted $(C_{1-6}$alkyl$)_q$-aryl, an optionally substituted $(C_{1-6}$alkyl$)_q$-$C_{3-7}$cycloalkyl, an optionally substituted $(C_{1-6}$alkyl$)_q$-5-6-membered heterocyclyl or an optionally substituted $(C_{1-6}$alkyl$)_q$-5-6-membered heteroaryl; and q is 0 or 1.

30. A pharmaceutical composition according to claim 29 wherein the one or more other antiviral agents is independently selected from an NS5b inhibitor; an NS3/4a protease inhibitor; an NS5a inhibitor; and Ribavarin optionally in combination with peg/IFN.

31. A pharmaceutical composition according to claim 29 wherein the other antiviral agent is an NS5b inhibitor.

32. A pharmaceutical composition according to claim 31 wherein the NS5b inhibitor is a nucleoside inhibitor.

33. A pharmaceutical composition according to claim 31 wherein the NS5b inhibitor is a non-nucleoside inhibitor.

34. A pharmaceutical composition according to claim 29 wherein the other antiviral agent is an NS3/4a protease inhibitor.

35. A pharmaceutical composition according to claim 29 wherein the other antiviral agent is an NS5a inhibitor.

36. A pharmaceutical composition according to claim 29 formulated for oral delivery.

37. A method for the treatment of a Hepatitis C virus (HCV) infection, which comprises administering an effective amount of the pharmaceutical composition according to claim 18 to a subject suffering from HCV.

* * * * *